(12) United States Patent
Kang et al.

(10) Patent No.: US 9,859,507 B2
(45) Date of Patent: Jan. 2, 2018

(54) ORGANIC ELECTROLUMINESCENT COMPOUND AND ORGANIC ELECTROLUMINESCENT DEVICE COMPRISING THE SAME

(71) Applicant: Rohm and Haas Electronic Materials Korea Ltd., Cheonan (KR)

(72) Inventors: Hee-Ryong Kang, Seoul (KR); Hyun-Ju Kang, Gwangmyeong (KR); Young-Mook Lim, Cheonan (KR); Mi-Ja Lee, Cheonan (KR); Nam-Kyun Kim, Yongin (KR); Bitnari Kim, Cheonan (KR); Jin-Ri Hong, Cheonan (KR); Doo-Hyeon Moon, Hwaseong (KR); Su-Hyun Lee, Suwon (KR)

(73) Assignee: ROHM AND HAAS ELECTRONIC MATERIALS KOREA LTD., Cheonan (KR)

( * ) Notice: Subject to any disclaimer, the term of this patent is extended or adjusted under 35 U.S.C. 154(b) by 0 days.

(21) Appl. No.: 15/306,123

(22) PCT Filed: Apr. 30, 2015

(86) PCT No.: PCT/KR2015/004436
§ 371 (c)(1),
(2) Date: Oct. 24, 2016

(87) PCT Pub. No.: WO2015/167300
PCT Pub. Date: Nov. 5, 2015

(65) Prior Publication Data
US 2017/0047528 A1 Feb. 16, 2017

(30) Foreign Application Priority Data

May 2, 2014 (KR) .................. 10-2014-0053261
Sep. 4, 2014 (KR) .................. 10-2014-0117823
Apr. 23, 2015 (KR) .................. 10-2015-0057081

(51) Int. Cl.
| | | |
|---|---|---|
| *C07D 487/16* | (2006.01) |
| *C07D 471/16* | (2006.01) |
| *C09K 11/06* | (2006.01) |
| *H01L 51/54* | (2006.01) |
| *C07D 519/00* | (2006.01) |
| *H05B 33/14* | (2006.01) |
| *H01L 51/00* | (2006.01) |
| *C09K 11/02* | (2006.01) |
| *H01L 51/50* | (2006.01) |

(52) U.S. Cl.
CPC ........ *H01L 51/0072* (2013.01); *C07D 471/16* (2013.01); *C07D 487/16* (2013.01); *C07D 519/00* (2013.01); *C09K 11/025* (2013.01); *C09K 11/06* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *H01L 51/5016* (2013.01)

(58) Field of Classification Search
CPC .. C07D 487/04; C07D 487/16; C07D 471/16; C07D 519/00; C09K 11/06; H01L 51/50; H01L 51/5032; H01L 51/5064; H05B 33/00
USPC ................ 544/338, 339; 546/33, 38; 257/40
See application file for complete search history.

(56) References Cited

FOREIGN PATENT DOCUMENTS

| | | |
|---|---|---|
| EP | 2182040 A2 | 5/2010 |
| JP | 2014-073965 A | 4/2014 |
| KR | 20120095997 A | 8/2012 |
| WO | 2014104704 A1 | 7/2014 |
| WO | 2014185694 A1 | 11/2014 |

OTHER PUBLICATIONS

Atzrodt et al. Angew. Chem. Int. Ed. 2007, 46, 7744-7765.*

* cited by examiner

*Primary Examiner* — Venkataraman Balasubramanian
(74) *Attorney, Agent, or Firm* — Jae-Choon You; Andrew E. C. Merriam

(57) ABSTRACT

The present disclosure relates to an organic electroluminescent compound of Formula 1 (variables R1-R10 defined herein), and an organic electroluminescent device comprising the same. By using the organic electroluminescent compound according to the present disclosure, it is possible to produce an organic electroluminescent device which can be operated at a lowered driving voltage, shows excellence in luminous efficiency such as current efficiency and power efficiency, and has high color purity and improved lifespan.

8 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak in 1987, by using small aromatic diamine molecules and aluminum complexes as materials to form a light-emitting layer [Appl. Phys. Lett. 51, 913, 1987].

The most important factor determining luminous efficiency in the organic EL device is light-emitting materials. Until now, fluorescent materials have been widely used as light-emitting material. However, in view of electroluminescent mechanisms, since phosphorescent materials theoretically enhance luminous efficiency by four (4) times compared to fluorescent materials, phosphorescent light-emitting materials are widely being researched. Iridium(III) complexes have been widely known as phosphorescent materials, including bis(2-(2'-benzothienyl)-pyridinato-N, C3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red-, green-, and blue-emitting materials, respectively.

At present, 4,4'-N,N'-dicarbazol-biphenyl (CBP) is the most widely known host material for phosphorescent materials. Recently, Pioneer (Japan) et al., developed a high performance organic EL device using bathocuproine (BCP) and aluminum(III)bis(2-methyl-8-quinolinate)(4-phenylphenolate) (BAlq) etc., as host materials, which were known as hole blocking materials.

Although these materials provide good light-emitting characteristics, they have the following disadvantages: (1) Due to their low glass transition temperature and poor thermal stability, their degradation may occur during a high-temperature deposition process in a vacuum. (2) The power efficiency of the organic EL device is given by [(π/voltage)×current efficiency], and the power efficiency is inversely proportional to the voltage. Although the organic EL device comprising phosphorescent host materials provides higher current efficiency (cd/A) than one comprising fluorescent materials, a significantly high driving voltage is necessary. Thus, there is no merit in terms of power efficiency (lm/W). (3) Furthermore, the operational lifespan of the organic EL device is short, and luminous efficiency still needs to be improved.

Korean Patent Application Laying-open No. 10-2012-0095997 discloses a compound in which at least one carbon atom of a crosslinked triarylamine is replaced with a nitrogen atom. However, it fails to disclose a compound in which the nitrogen-containing moiety is a quinoline or quinoxaline.

DISCLOSURE OF THE INVENTION

Problems to be Solved

The first objective of the present disclosure is to provide an organic electroluminescent compound which can provide an organic electroluminescent device having a long lifespan and a lowered driving voltage and showing excellence in luminous efficiency such as current efficiency and power efficiency, and color purity. The second objective of the present disclosure is to provide an organic electroluminescent device comprising the organic electroluminescent compound.

Solution to Problems

The present inventors found that the above objective can be achieved by an organic electroluminescent compound represented by the following formula 1.

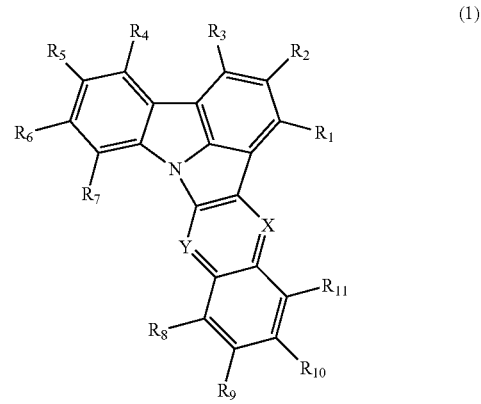

wherein X and Y, each independently, represent —CR$_{12}$— or —N—, with the proviso that X and Y are not be simultaneously —CR$_{12}$—, and R$_1$ to R$_{12}$, each independently, represent hydrogen, deuterium, a halogen, a cyano, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a substituted or unsubstituted 3- to 30-membered, mono- or polycyclic, alicyclic or aromatic ring, whose carbon atom(s) may be replaced with at least one hetero atom selected from the group consisting of nitrogen, oxygen, and sulfur, wherein the heteroaryl contains one or more hetero atoms selected from the group consisting of B, N, O, S, Si, and P.

Effects of the Invention

By using the organic electroluminescent compound according to the present disclosure, it is possible to produce an organic electroluminescent device which can be operated at a lowered driving voltage, shows excellence in luminous efficiency such as current efficiency and power efficiency, and has high color purity and improved lifespan.

EMBODIMENTS OF THE INVENTION

Hereinafter, the present disclosure will be described in detail. However, the following description is intended to explain the invention, and is not meant in any way to restrict the scope of the invention.

The present disclosure provides the organic electroluminescent compound of formula 1 above, an organic electroluminescent material comprising the same, and an organic electroluminescent device comprising the compound.

The details of the organic electroluminescent compound of formula 1 of the present disclosure are as follows.

Herein, "alkyl" includes methyl, ethyl, n-propyl, isopropyl, n-butyl, isobutyl, tert-butyl, etc. "Cycloalkyl" includes cyclopropyl, cyclobutyl, cyclopentyl, cyclohexyl, etc. "3- to 7-membered heterocycloalkyl" indicates a cycloalkyl having 3 to 7 ring backbone atoms including at least one hetero atom selected from the group consisting of B, N, O, S, Si, and P, preferably O, S, and N, and includes tetrahydrofuran, pyrrolidine, thiolan, tetrahydropyran, etc. Furthermore, "aryl(ene)" indicates a monocyclic or fused ring derived from an aromatic hydrocarbon; may be a spiro-type in which two rings are connected with each other via one atom; and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "3- to 30-membered heteroaryl(ene)" indicates an aryl group having 3 to 30 ring backbone atoms including at least one, preferably 1 to 4, hetero atom selected from the group consisting of B, N, O, S, Si, and P, and preferably O, S, and N; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidyl, pyridazinyl, etc., and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, dihydroacridinyl, etc. Furthermore, "halogen" includes F, Cl, Br, and I.

Herein, "substituted" in the expression, "substituted or unsubstituted," means that a hydrogen atom in a certain functional group is replaced with another atom or group, i.e. a substituent. In the present disclosure, the substituents for the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring in $R_1$ to $R_{12}$, $L_a$, $L_b$, $L_c$, $L_d$, $R_{13}$ to $R_{15}$, $R_{31}$ to $R_{37}$, $R_{21}$ to $R_{27}$, $L_4$, M, $Y_1$, $Y_2$, $R_{41}$ to $R_{43}$, L, $R_{100}$ to $R_{127}$, and $R_{201}$ to $R_{211}$, each independently, may be one or more selected from the group consisting of deuterium, a halogen, a cyano, a carboxy, a nitro, a hydroxy, a (C1-C30)alkyl, a halo(C1-C30)alkyl, a (C1-C30)alkoxy, a (C1-C30)alkylthio, a (C3-C30)cycloalkyl, a 3- to 7-membered heterocycloalkyl, a (C6-C30)aryloxy, a (C6-C30)arylthio, a 3- to 30-membered heteroaryl unsubstituted or substituted with a (C6-C30)aryl or a di(C6-C30)arylamino, a (C6-C30)aryl unsubstituted or substituted with a 3- to 30-membered heteroaryl or a di(C6-C30)arylamino, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl and a (C1-C30)alkyl(C6-C30)aryl; and, each independently, may be preferably, one or more selected from the group consisting of a (C1-C10)alkyl, a 5- to 18-membered heteroaryl, a 5- to 18-membered heteroaryl substituted with a (C6-C18)aryl, a 5- to 18-membered heteroaryl substituted with a di(C6-C12)arylamino, a (C6-C18)aryl, a (C6-C18)aryl substituted with a 5- to 18-membered heteroaryl, a (C6-C18)aryl substituted with a di(C6-C12)arylamino, a di(C6-C12)arylamino, and a (C1-C10)alkyl(C5-C18)aryl.

Specifically, the compound of formula 1 may be represented by any one of the following formulae 2 to 4.

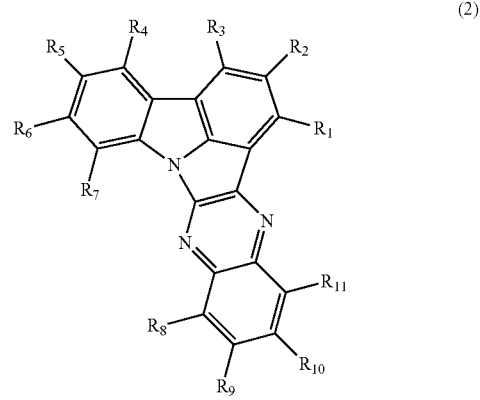

(2)

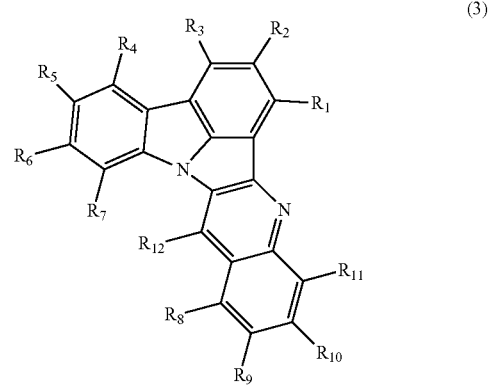

(3)

(4)

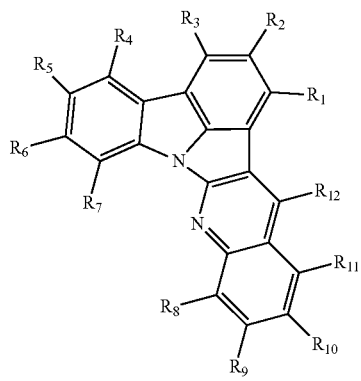

wherein $R_1$ to $R_{12}$ are as defined in formula 1 above.

In the present disclosure, specifically, $R_1$ to $R_{12}$, each independently, may represent hydrogen, a substituted or unsubstituted (C1-C20)alkyl, a substituted or unsubstituted (C6-C20)aryl, a substituted or unsubstituted 5- to 30-membered heteroaryl, or a substituted or unsubstituted di(C6-C20)arylamino; or may be linked to an adjacent substituent(s) to form a substituted or unsubstituted 5- to 15-membered mono- or polycyclic aromatic ring. More specifically, $R_1$ to $R_{12}$, each independently, may represent hydrogen, a substituted or unsubstituted (C1-C20)alkyl, or any one of the following formulae 5-1 to 5-9; or may be linked to an adjacent substituent(s) to form a substituted or unsubstituted benzene ring or a substituted or unsubstituted naphthalene ring.

(5-1)
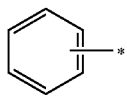

(5-2)
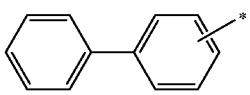

(5-3)
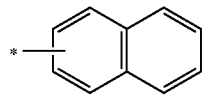

(5-4)
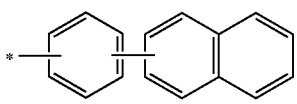

(5-5)
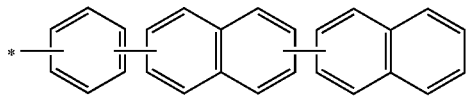

(5-6)
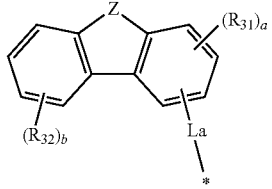

(5-7)
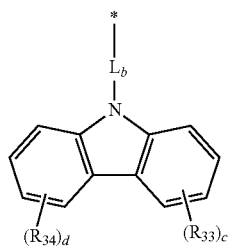

(5-8)
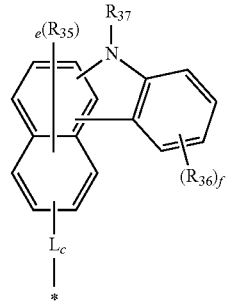

(5-9)
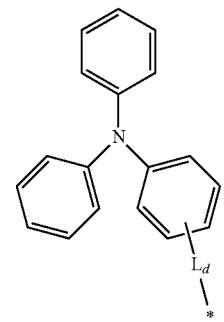

wherein $L_a$, $L_b$, $L_c$, and $L_d$, each independently, represent a single bond, a substituted or unsubstituted (C6-C30)arylene, or a substituted or unsubstituted 3- to 30-membered heteroarylene;

Z represents —S—, —O—, —NR$_{13}$—, or —CR$_{14}$R$_{15}$—;

$R_{13}$ to $R_{15}$, each independently, represent hydrogen, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, or a substituted or unsubstituted 3- to 7-membered heterocycloalkyl;

$R_{31}$ to $R_{37}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted 3- to 7-membered heterocycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a mono- or di-(C1-C30)alkylamino, a mono- or di-(C6-C30)arylamino, or a (C1-C30)alkyl(C6-C30)arylamino; or may be linked to an adjacent substituent(s) to form a substituted or unsubstituted 3- to 30-membered, mono- or polycyclic, alicyclic or aromatic ring, whose carbon atom(s) may be replaced with at least one hetero atom selected from the group consisting of nitrogen, oxygen, and sulfur;

a represents an integer of 1 to 3; b to d and f, each independently, represent an integer of 1 to 4; e represents an integer of 1 to 5; and where a, b, c, d, e, or f is an integer of 2 or more, each of $R_{31}$, $R_{32}$, $R_{33}$, $R_{34}$, $R_{35}$, or $R_{36}$ may be the same or different;

wherein the heteroaryl(ene) and heterocycloalkyl, each independently, contain one or more hetero atoms selected from the group consisting of B, N, O, S, Si, and P.

$L_a$ to $L_d$, each independently, may represent specifically, a single bond, or a substituted or unsubstituted (C6-C18) arylene, and more specifically, a single bond, or a substituted or unsubstituted phenylene.

Z may represent specifically —$NR_{13}$—.

$R_{13}$ to $R_{15}$, each independently, may represent specifically, hydrogen, a substituted or unsubstituted (C1-C10) alkyl, or a substituted or unsubstituted (C5-C18)aryl.

$R_{31}$ to $R_{36}$, each independently, may represent specifically, hydrogen, a substituted or unsubstituted (C1-C10) alkyl, a substituted or unsubstituted (C6-C18)aryl, or a substituted or unsubstituted 5- to 18-membered heteroaryl, or may be linked to an adjacent substituent(s) to form a substituted or unsubstituted 5- to 18-membered mono- or polycyclic, alicyclic or aromatic ring, whose carbon atom(s) may be replaced with one (1) to three (3) hetero atoms selected from the group consisting of nitrogen, oxygen, and sulfur; and more specifically, each independently, may represent hydrogen, a substituted or unsubstituted phenyl, a substituted or unsubstituted carbazolyl, a substituted or unsubstituted dibenzofuranyl, or a substituted or unsubstituted dibenzothiophenyl, or may be linked to an adjacent substituent(s) to form a substituted or unsubstituted phenyl ring or any one of the following formulae 6-1 to 6-7:

(6-1)
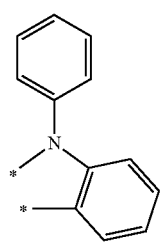

(6-2)
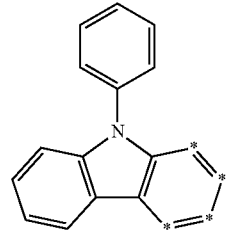

(6-3)
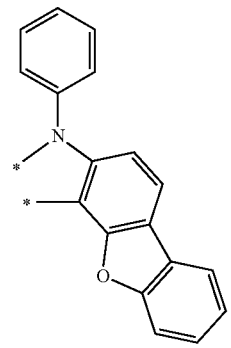

(6-4)
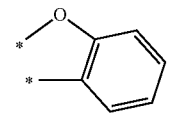

(6-5)
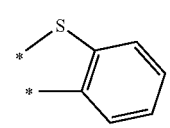

(6-6)
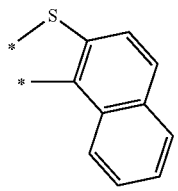

(6-7)
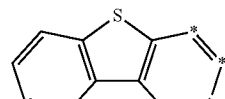

wherein * represents a bonding site.

$R_{37}$ may represent specifically, hydrogen or a substituted or unsubstituted (C6-C18)aryl; and more specifically, hydrogen or a substituted or unsubstituted phenyl.

According to one embodiment of the present disclosure, at least one of $R_1$ to $R_7$ may be any one of formulae 5-6 to 5-8, in which Z of formula 5-6 may represent —$NR_{13}$—.

More specifically, the organic electroluminescent compound of formula 1 of the present disclosure includes the following, but is not limited thereto:

A-1
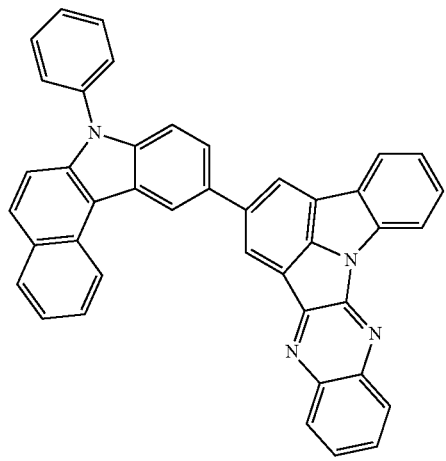
A-2
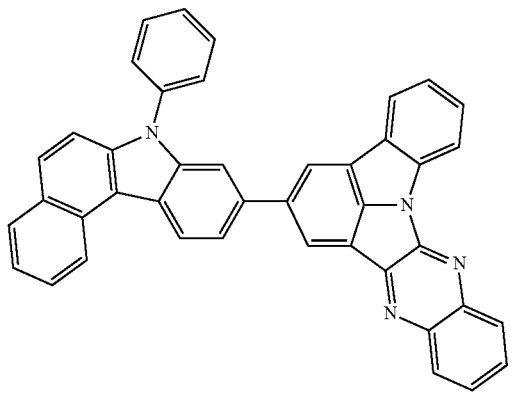
A-3
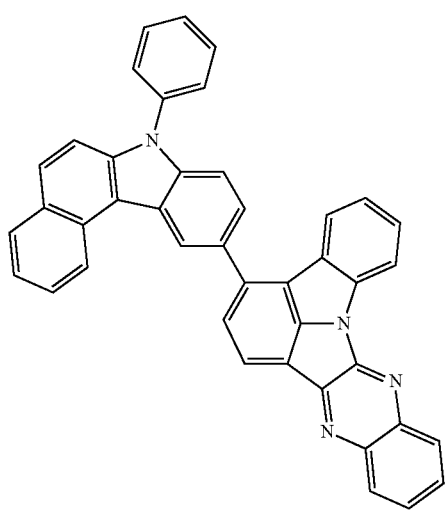
A-4
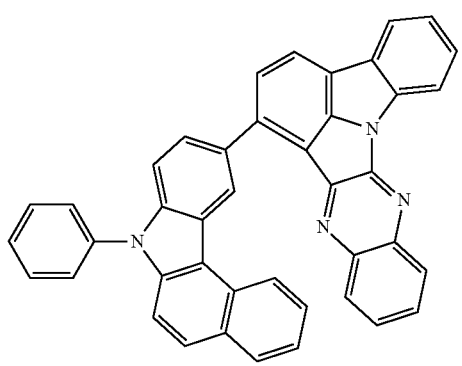
A-5
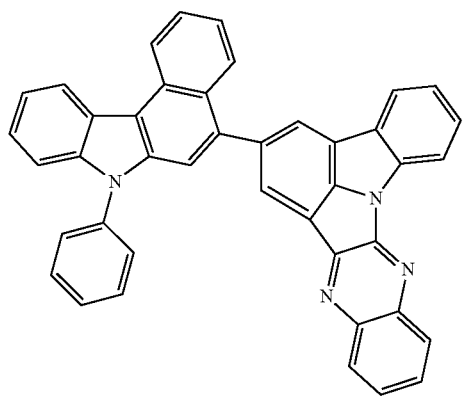
A-6
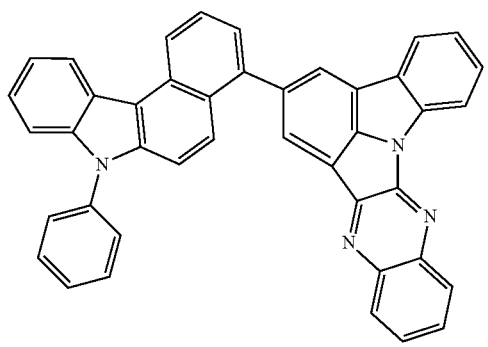

-continued
A-7
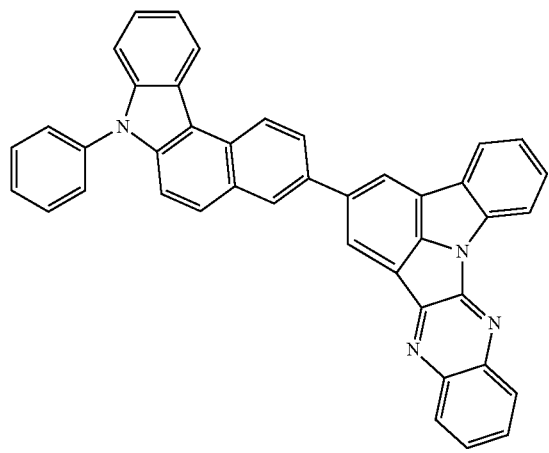
A-8
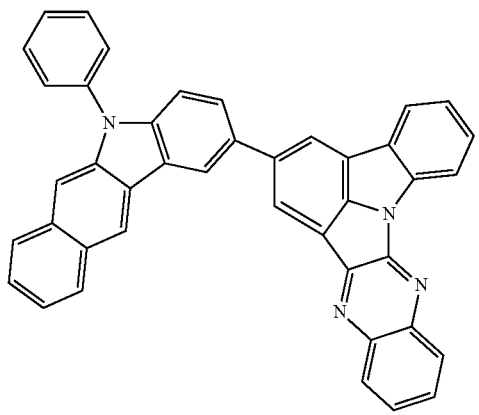
A-9
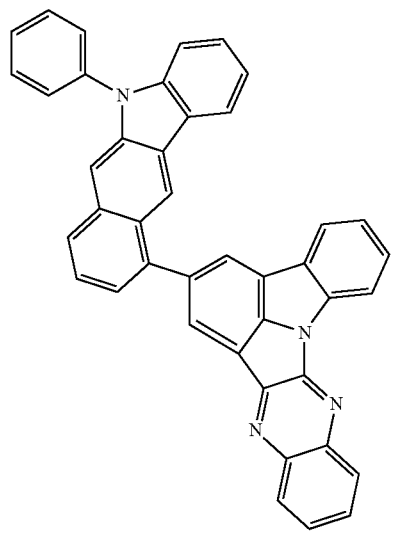
A-10
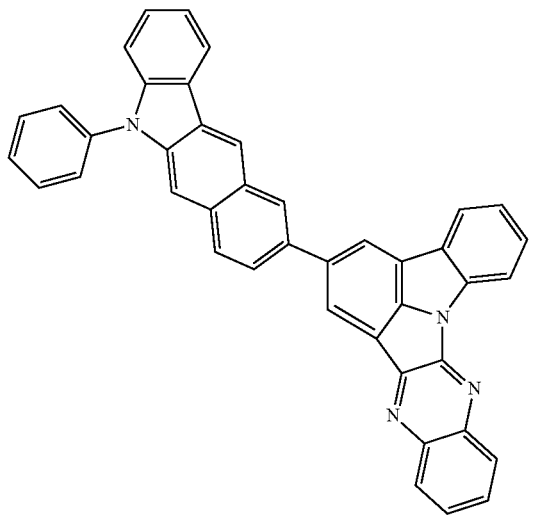
A-11
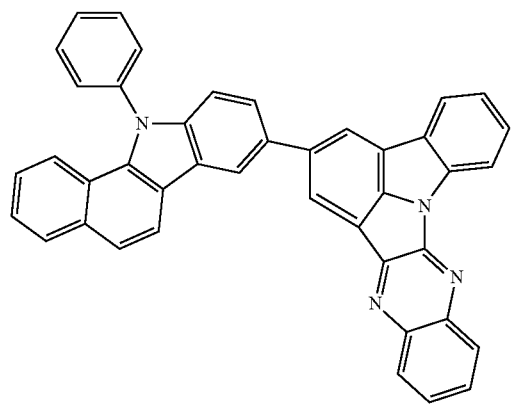
A-12
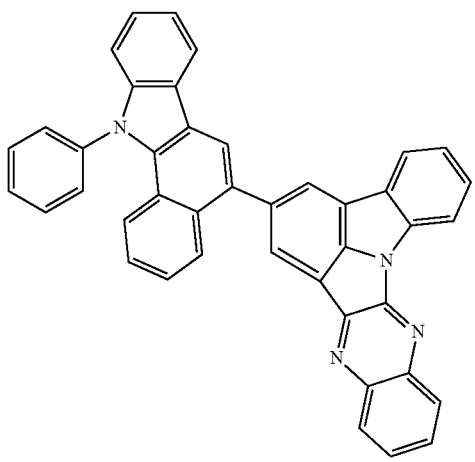

-continued
A-13
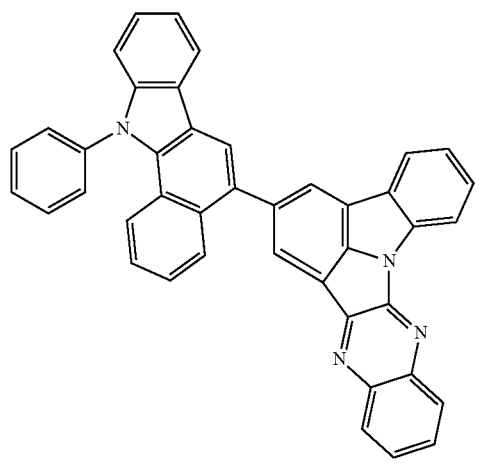
A-14
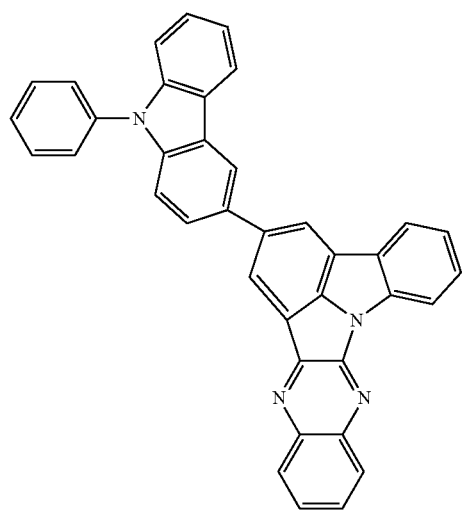
A-15
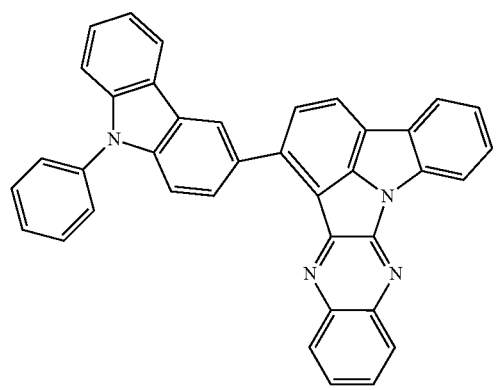
A-16
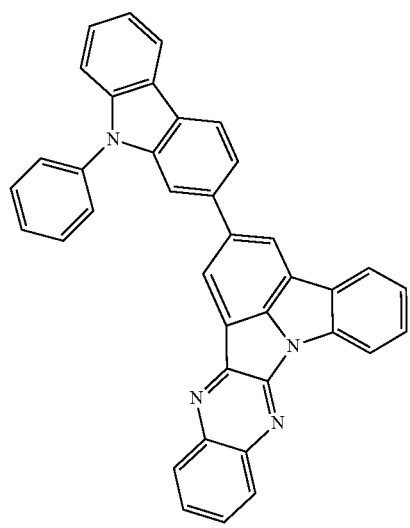
A-17
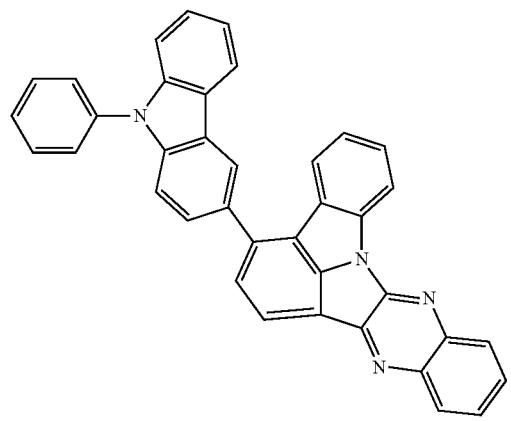
A-18
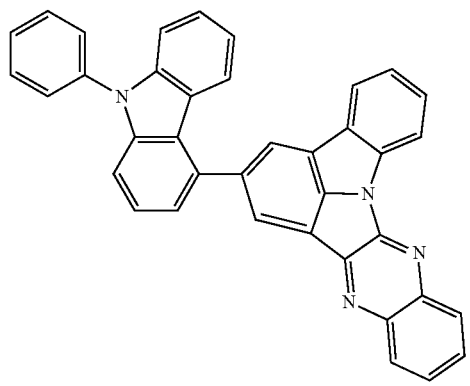

-continued
A-19
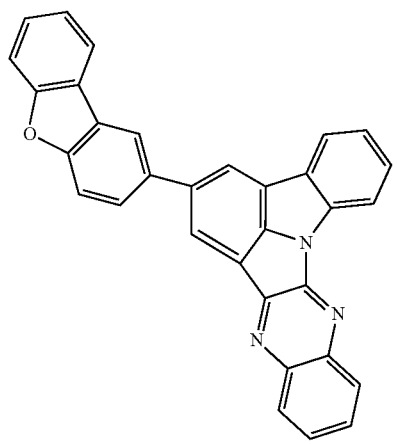
A-20
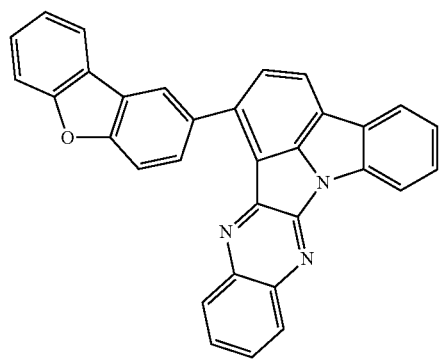
A-21
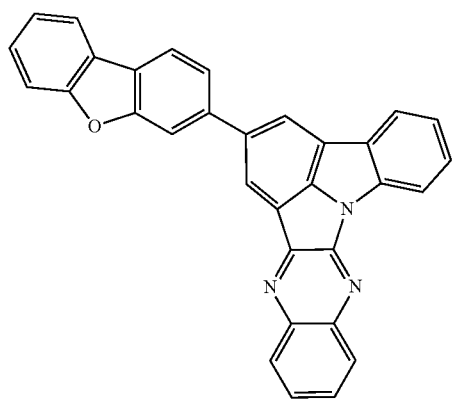
A-22
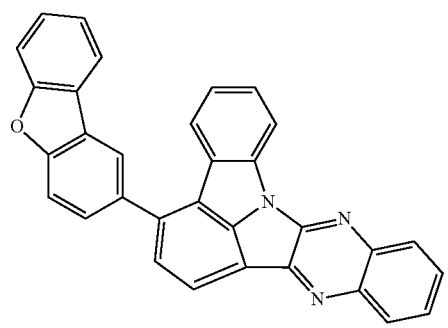
A-23
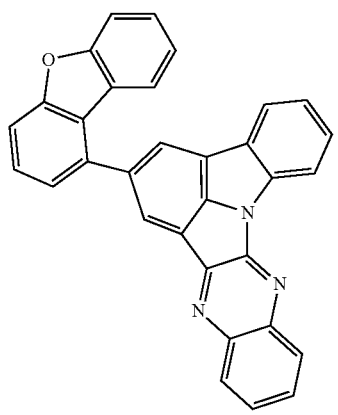
A-24
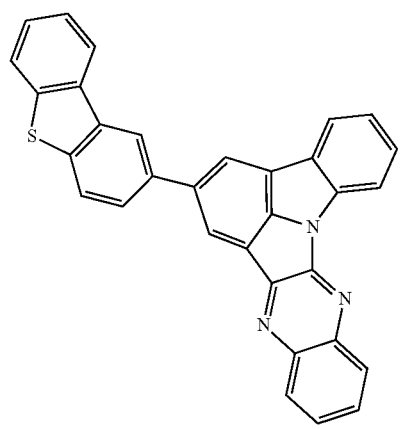

-continued
A-25
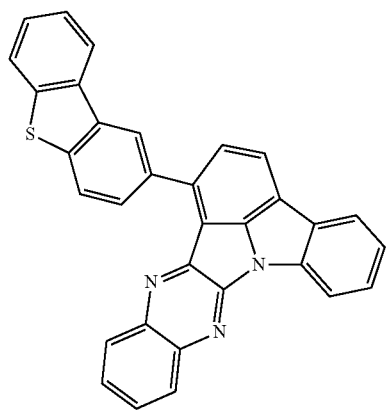
A-26
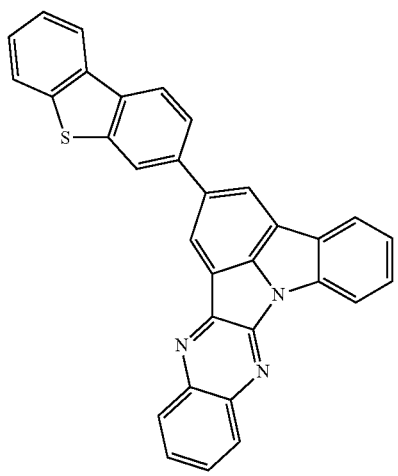
A-27
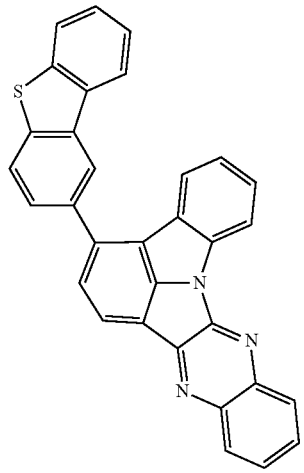
A-28
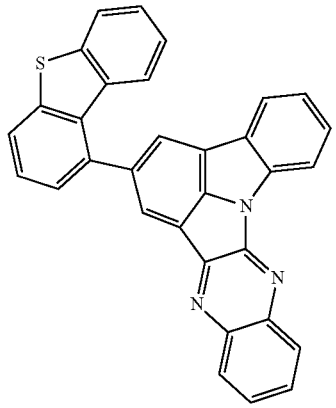
A-29
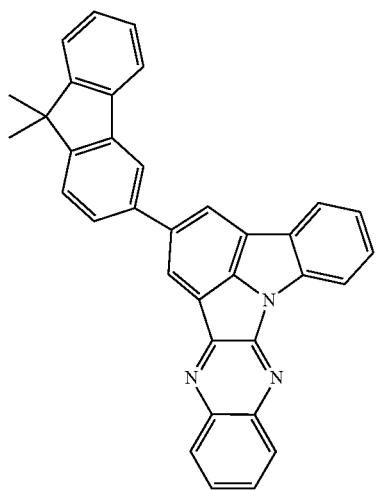
A-30
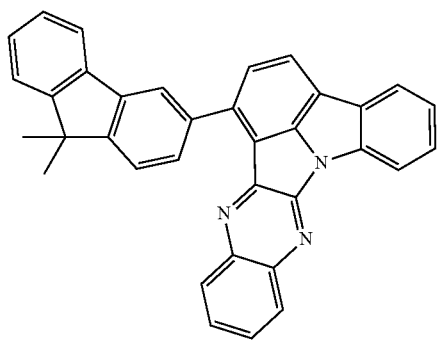

-continued
A-31
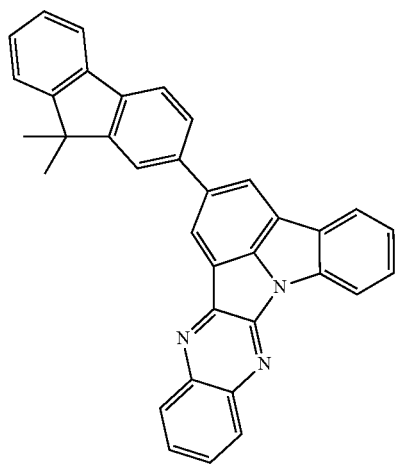
A-32
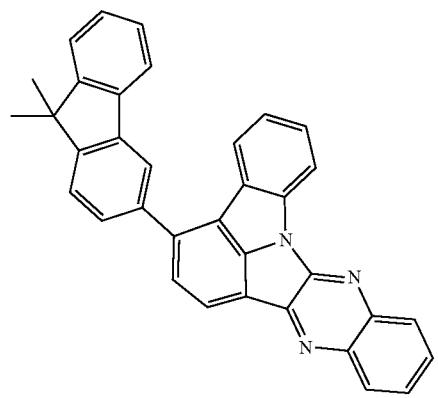
A-33
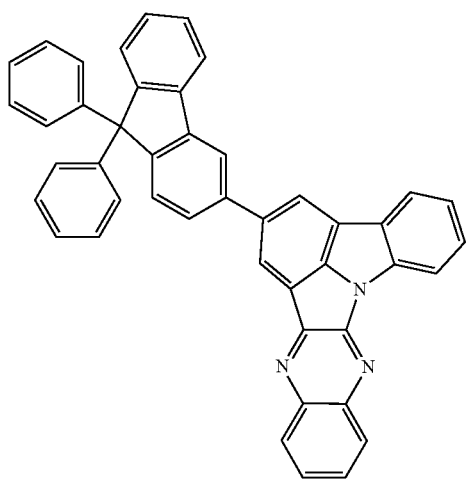
A-34
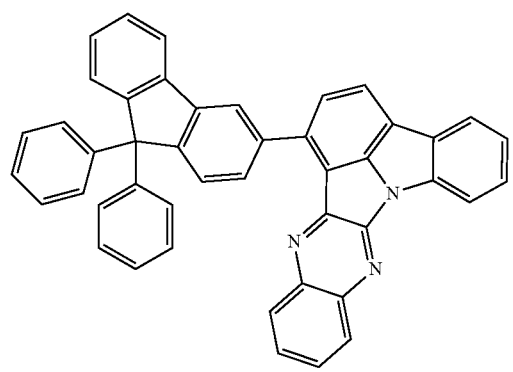
A-35
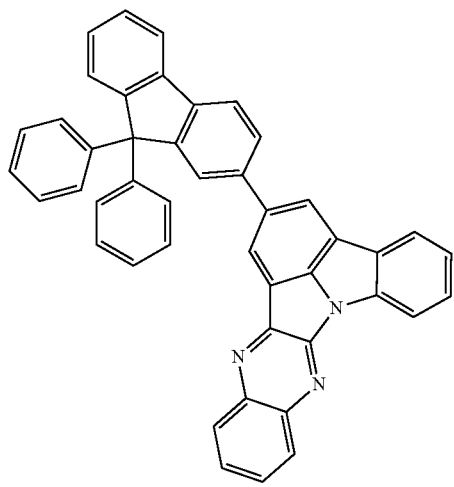
A-36
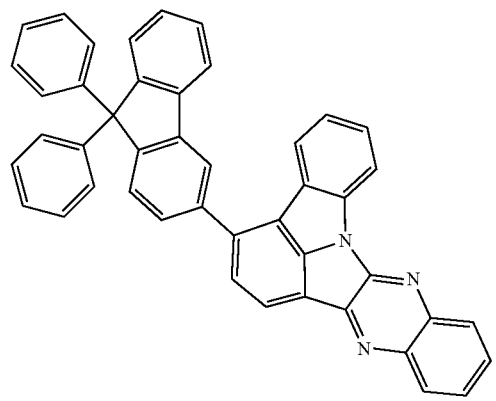

-continued
A-37
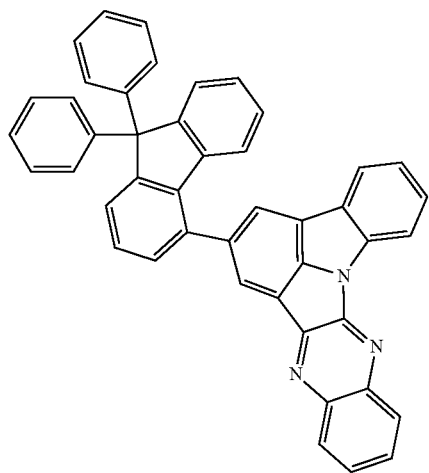
A-38
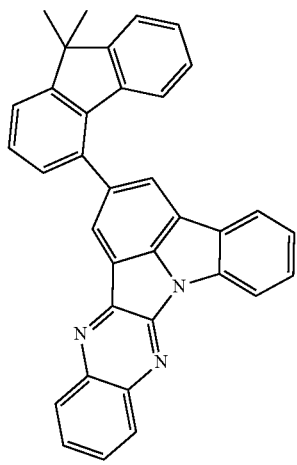
A-39
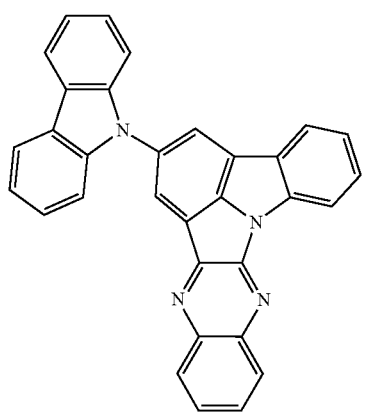
A-40
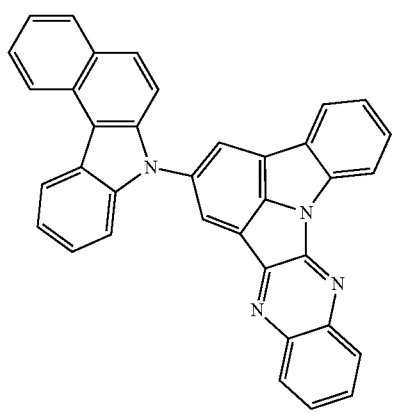
A-41
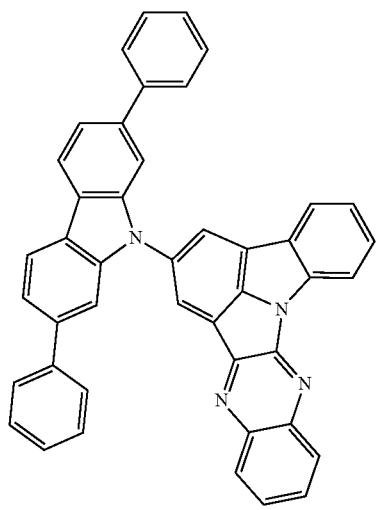
A-42
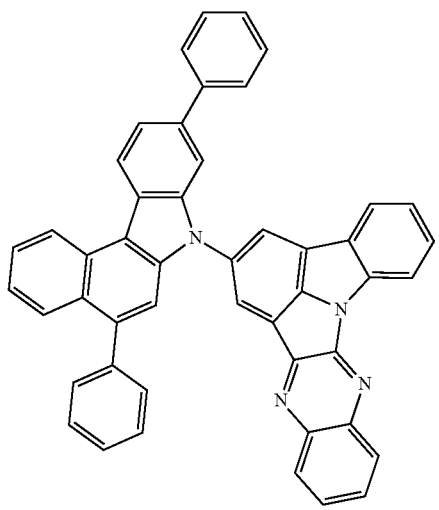

A-43
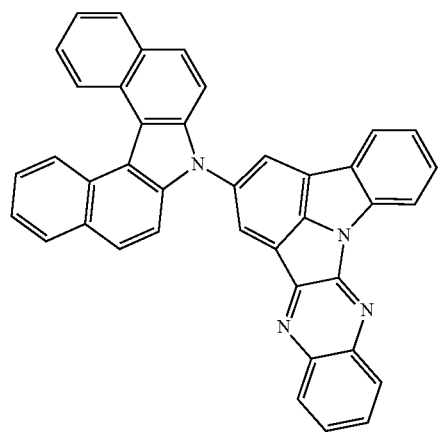
A-44
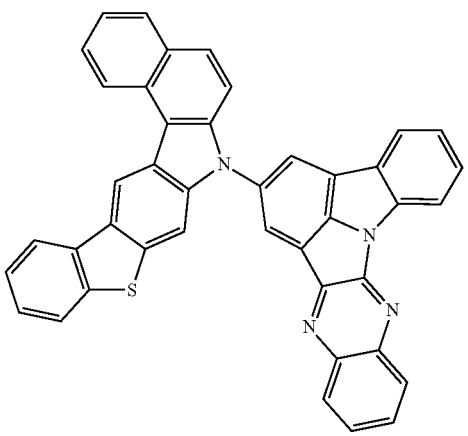
A-45
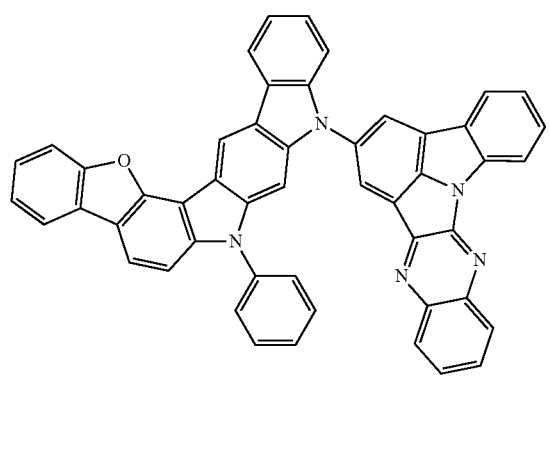
A-46
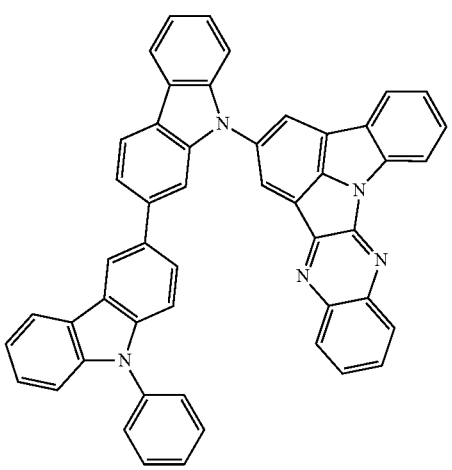
A-47
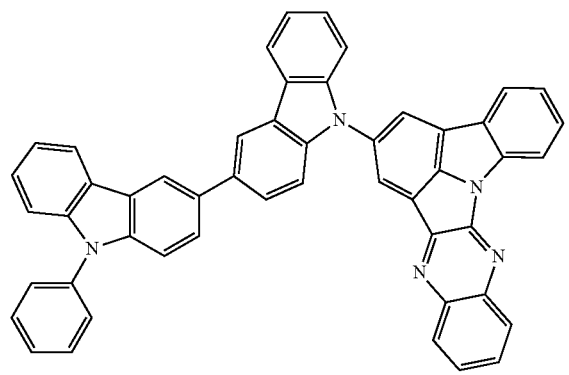
A-48
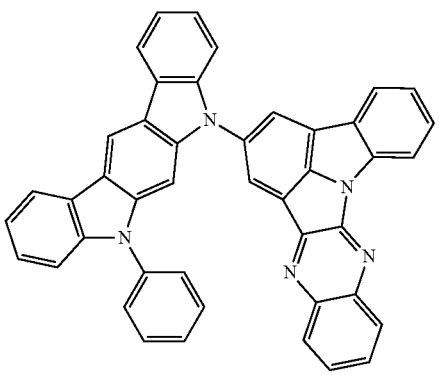

-continued
A-49
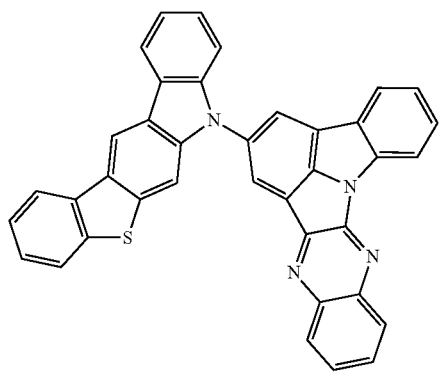
A-50
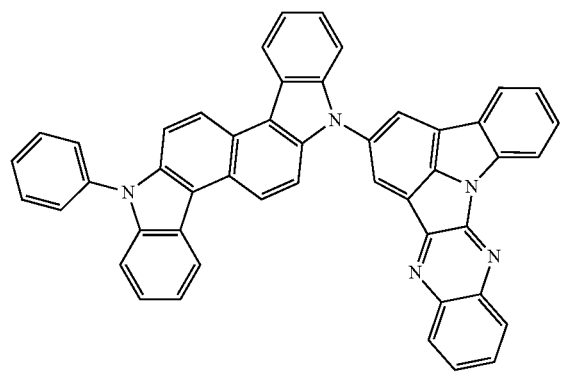
A-51
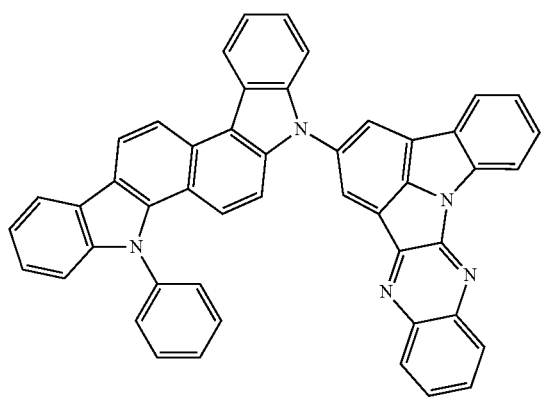
A-52
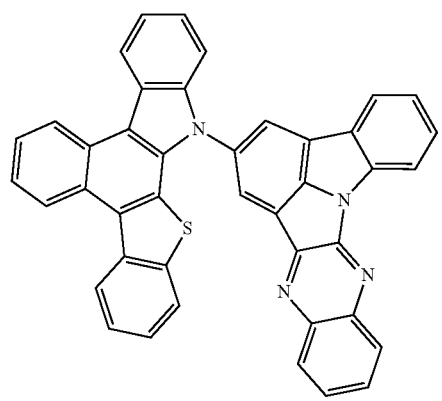
A-53
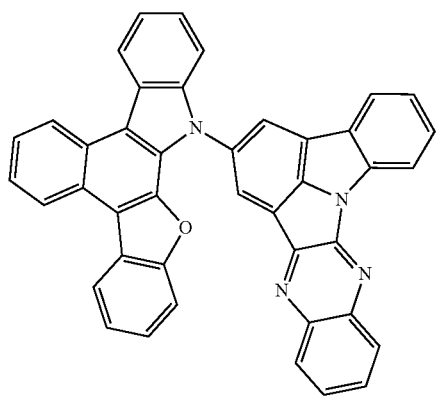
A-54
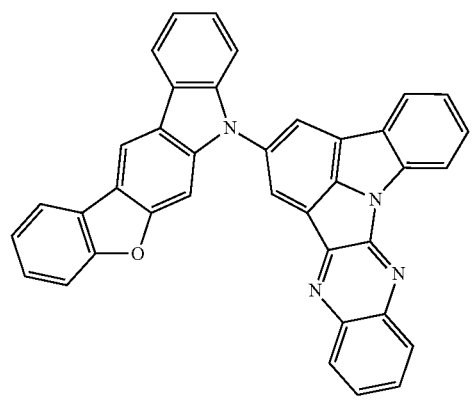
A-55
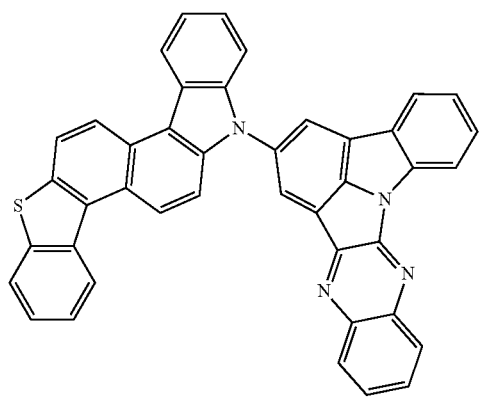
A-56
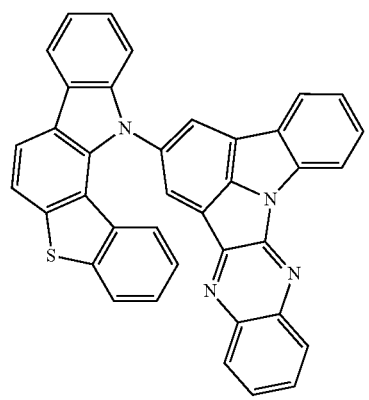

-continued
A-57
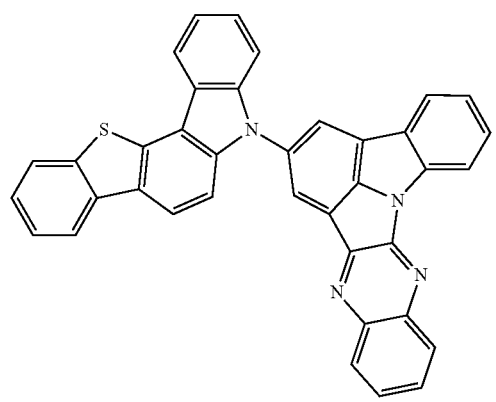
A-58
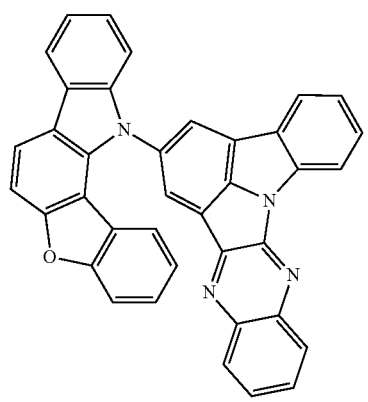
A-59
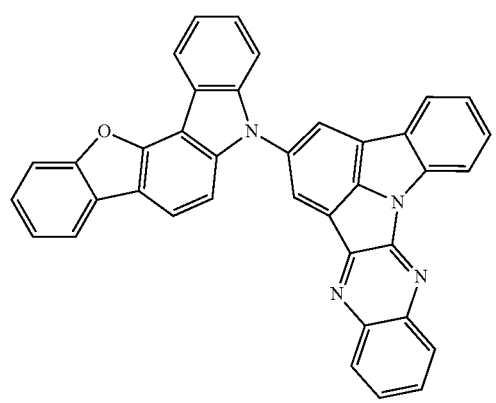
A-60
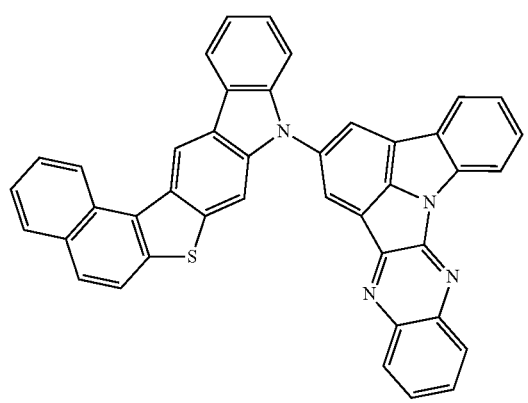
A-61
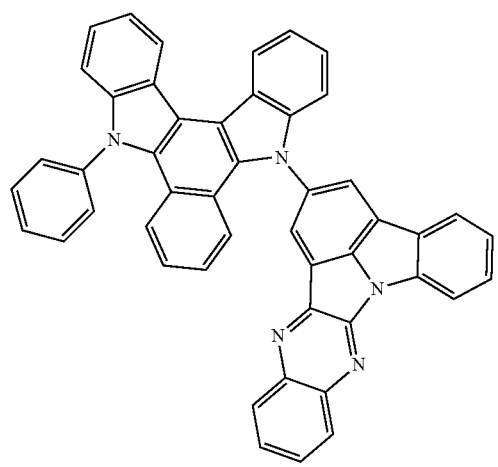
A-62
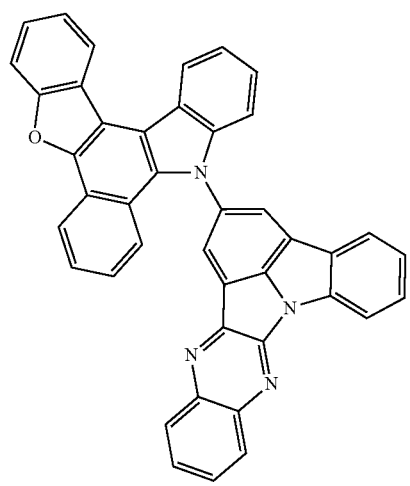

-continued
A-63
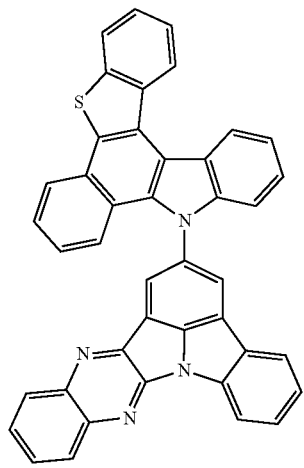
A-64
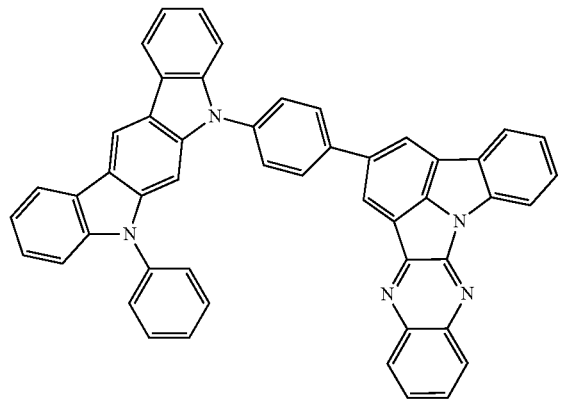
A-65
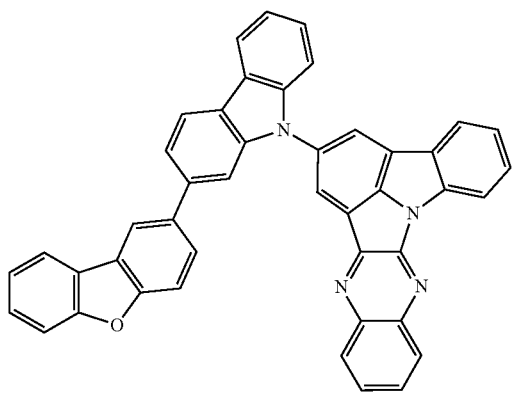
A-66
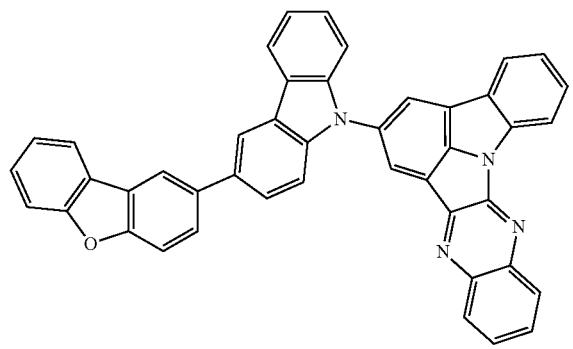
A-67
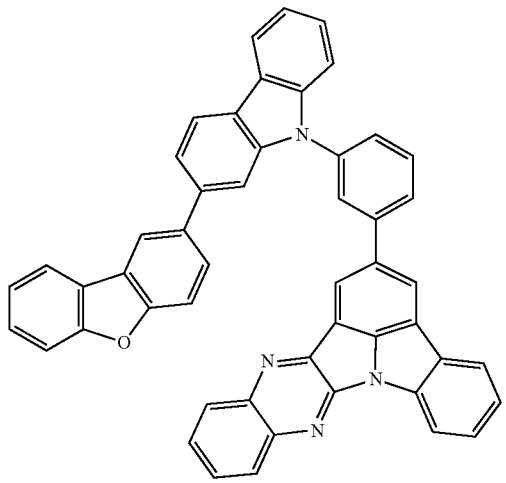
A-68
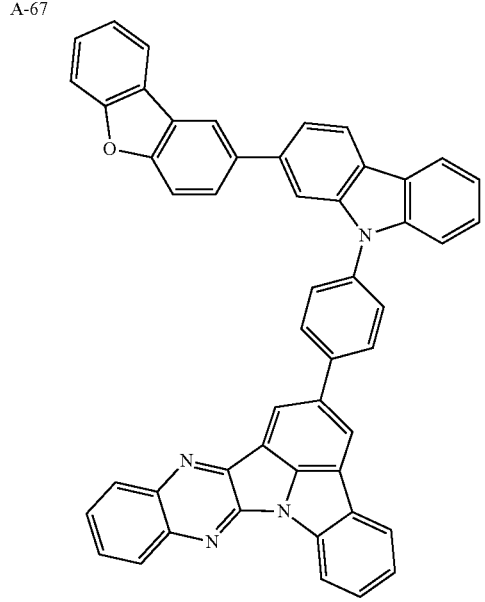

-continued
A-69
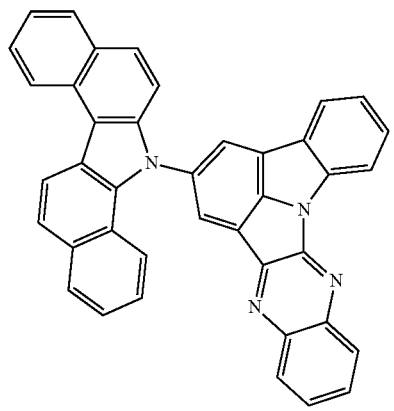
A-70
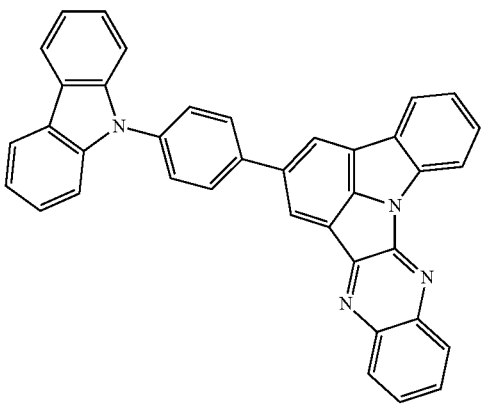
A-71
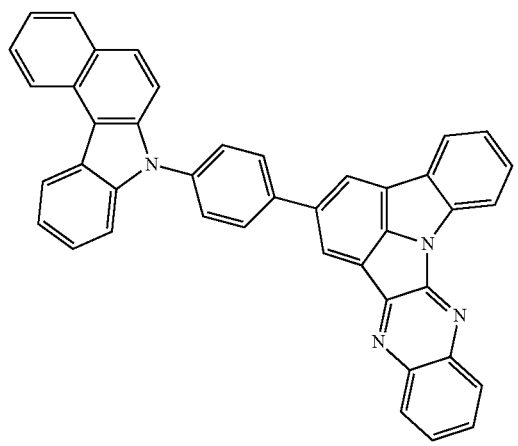
A-72
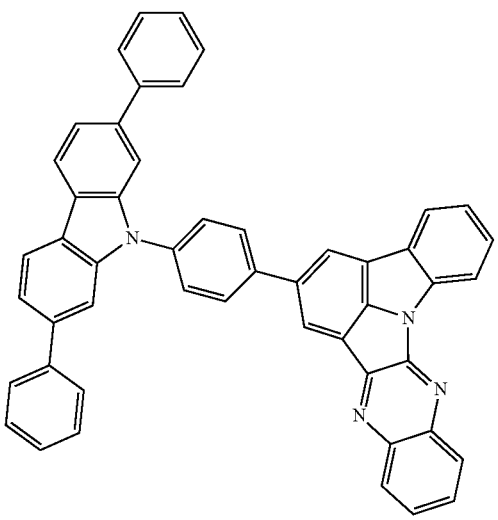
A-73
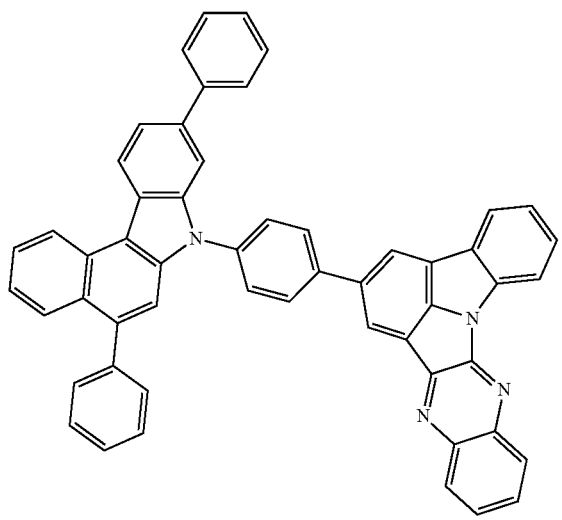
A-74
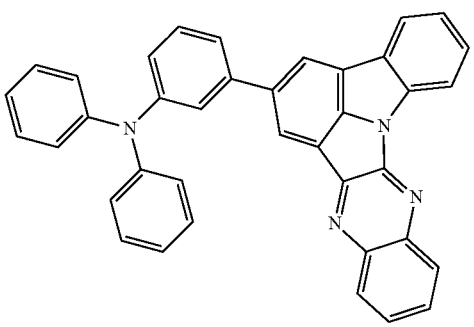

-continued
A-75
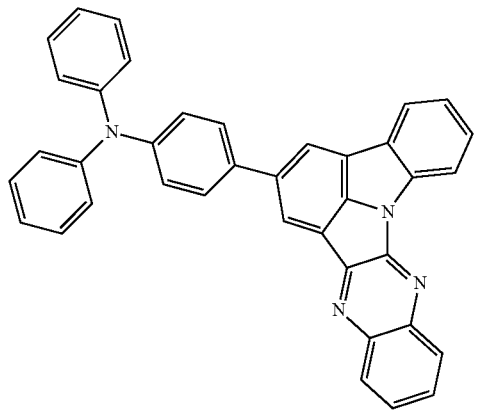
A-76
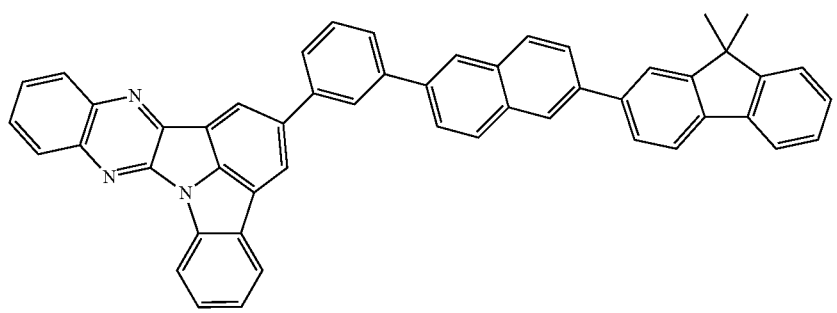
A-77
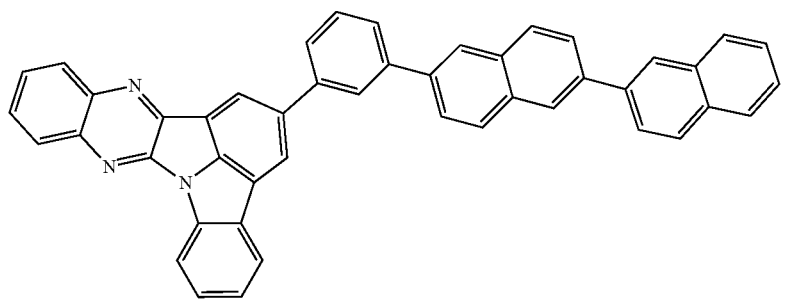
A-78
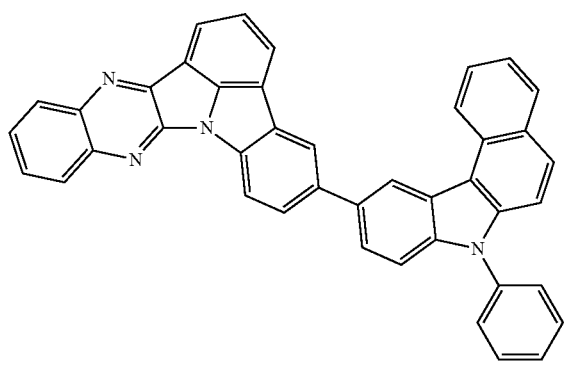
A-79
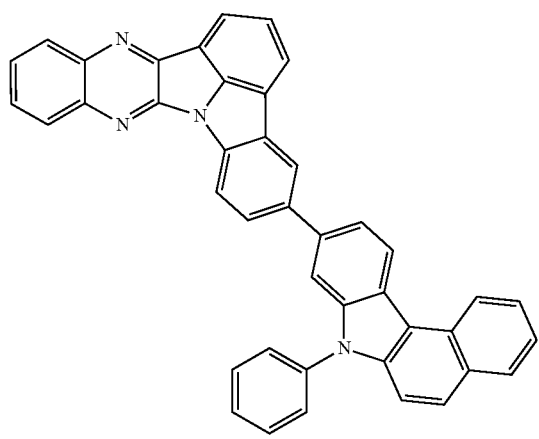

A-80
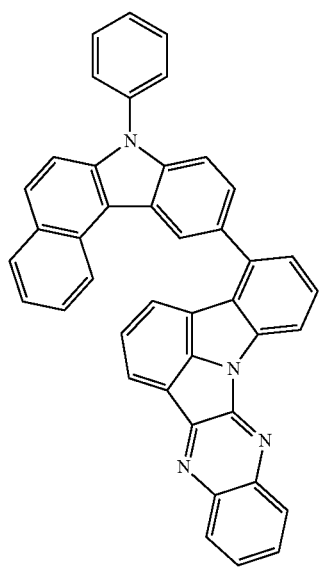
A-81
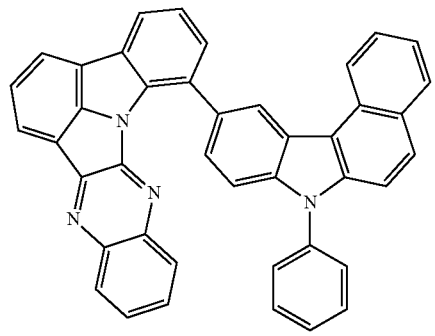
A-82
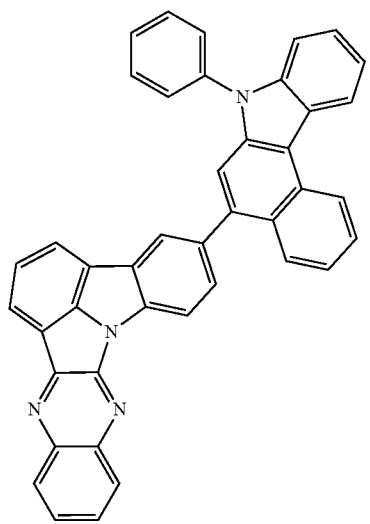
A-83
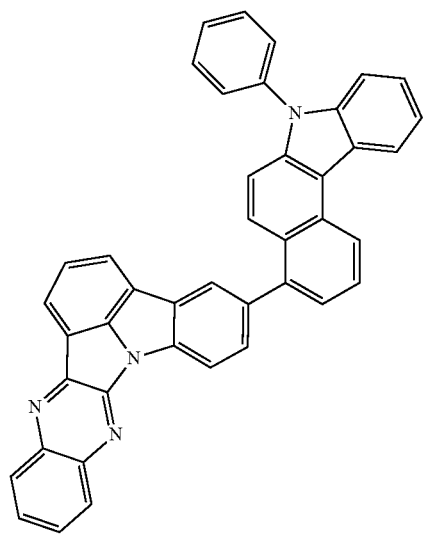

-continued
A-84
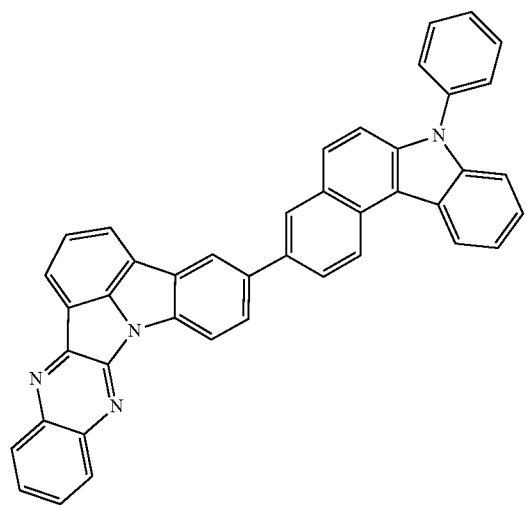
A-85
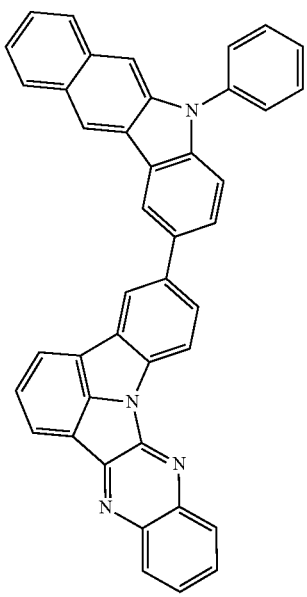
A-86
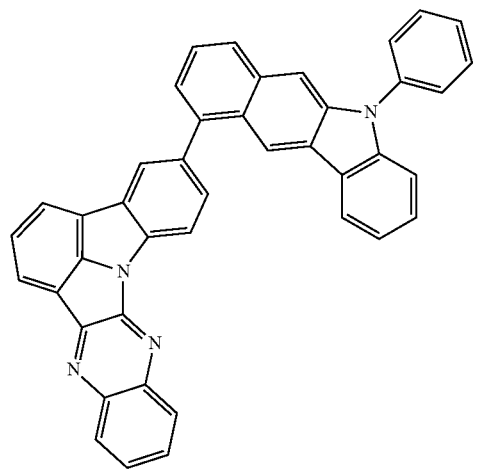
A-87
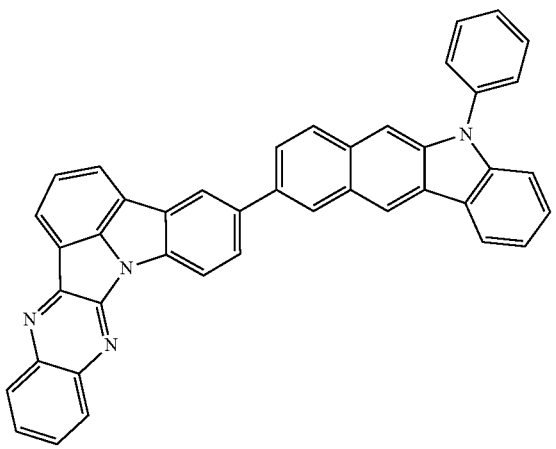

-continued
A-88
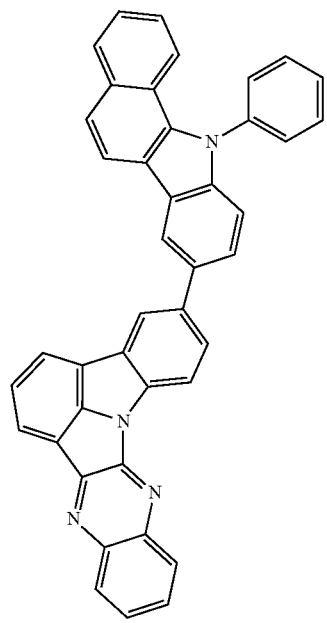
A-89
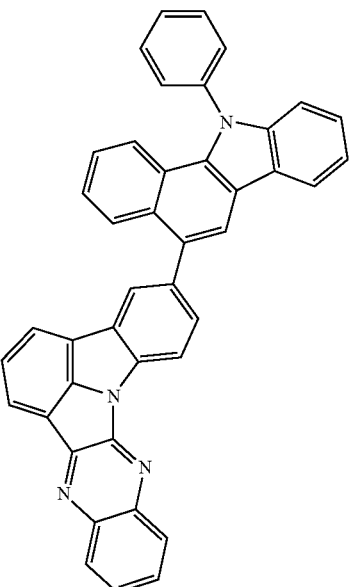
A-90
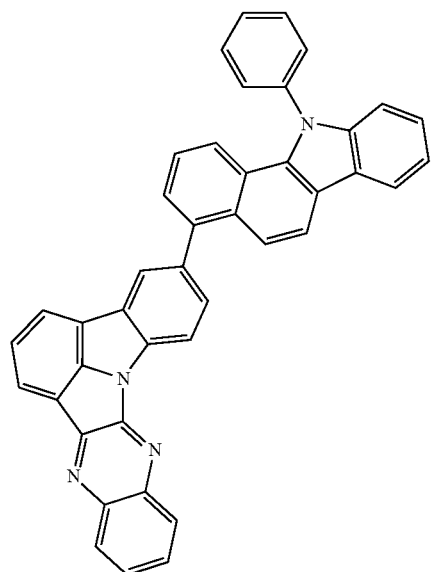
A-91
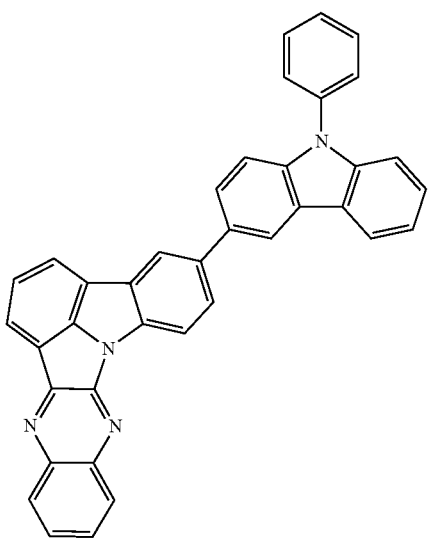

-continued
A-92
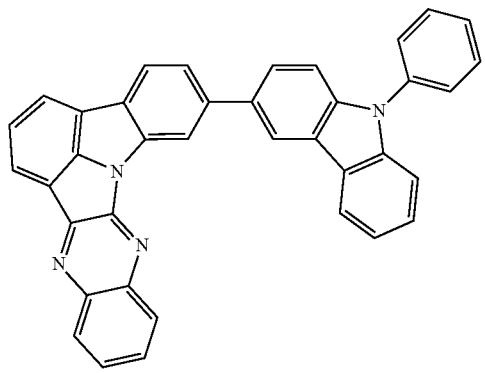
A-93
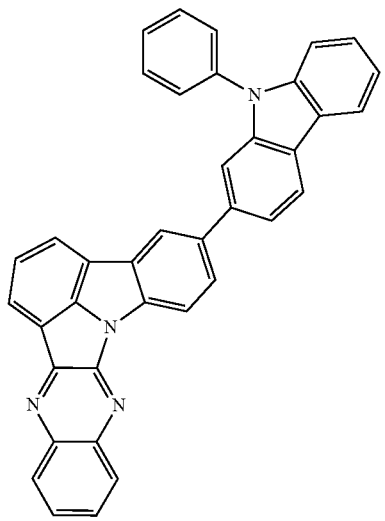
A-94
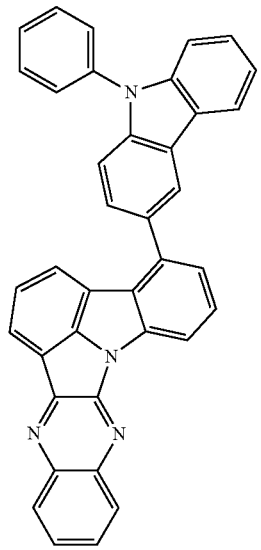
A-95
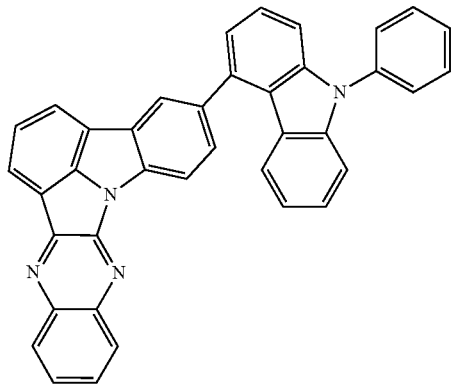

-continued
A-96
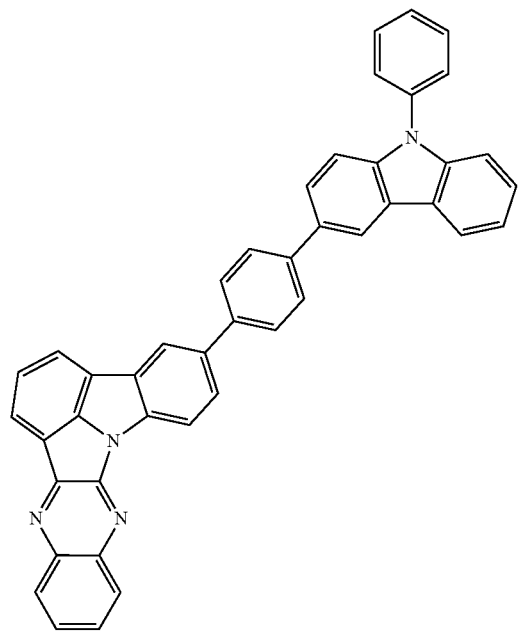
A-97
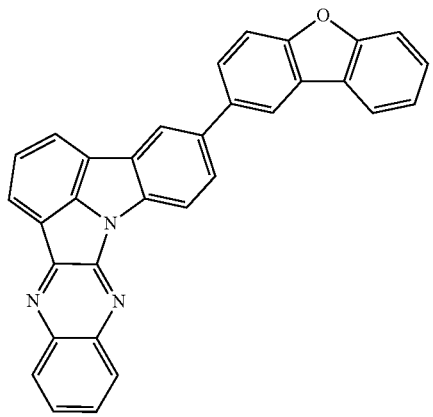
A-98
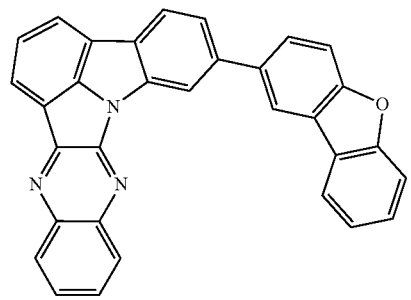
A-99
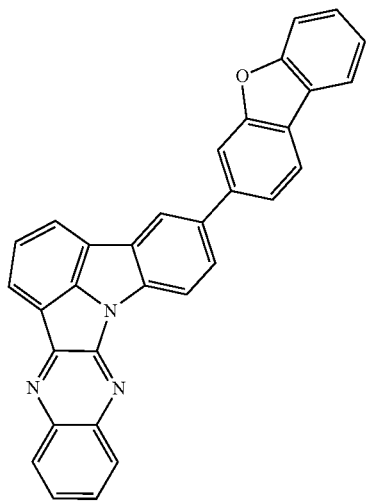
A-100
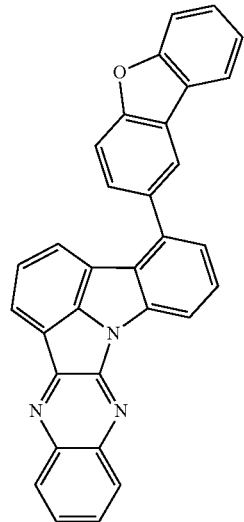
A-101
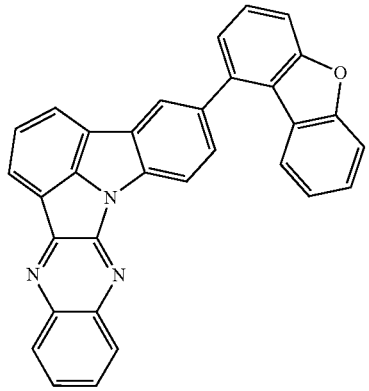

-continued
A-102
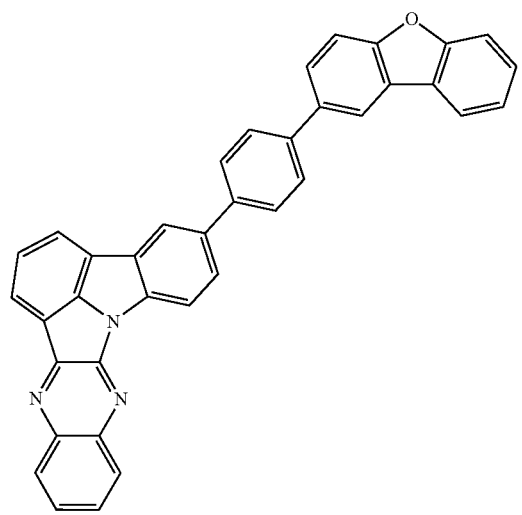
A-103
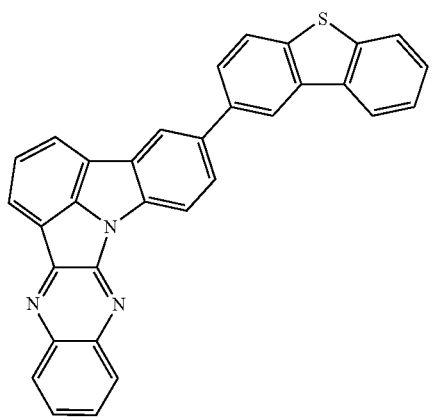
A-104
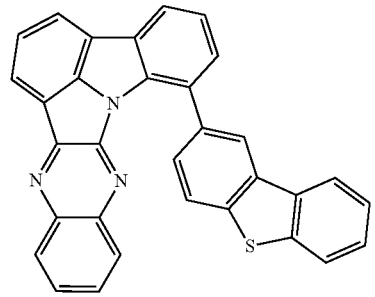
A-105
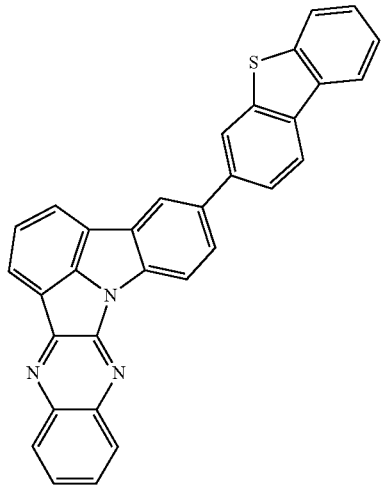
A-106
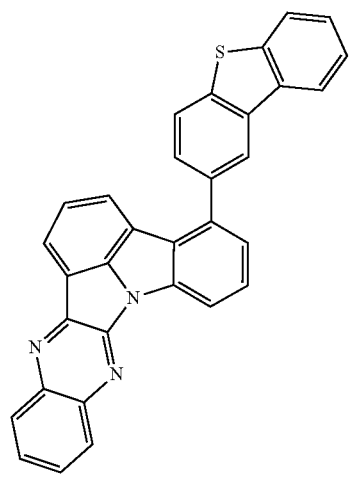
A-107
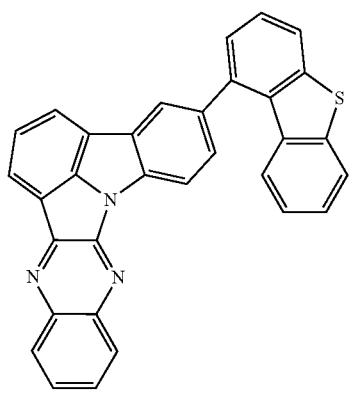

-continued
A-108
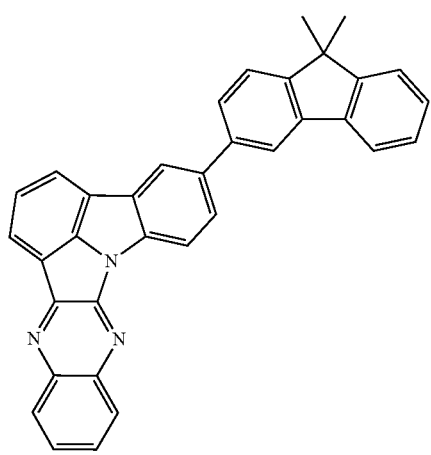
A-109
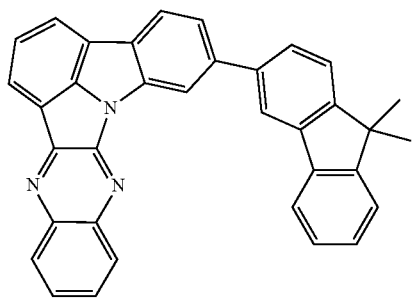
A-110
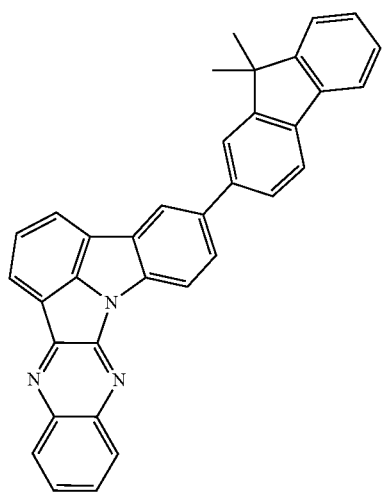
A-111
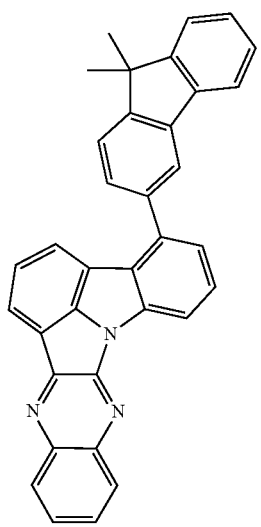
A-112
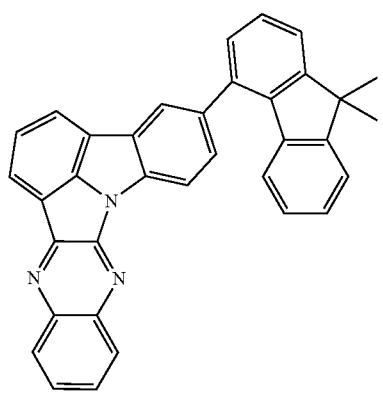
A-113
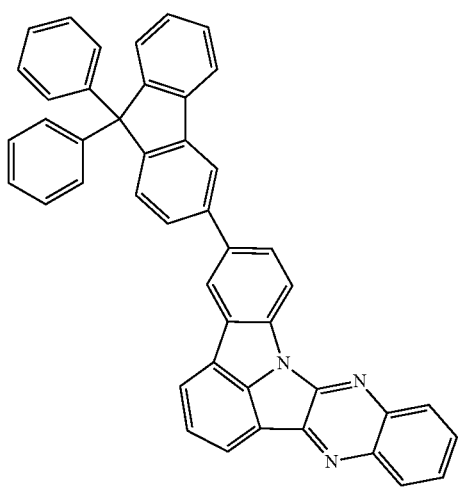

-continued
A-114
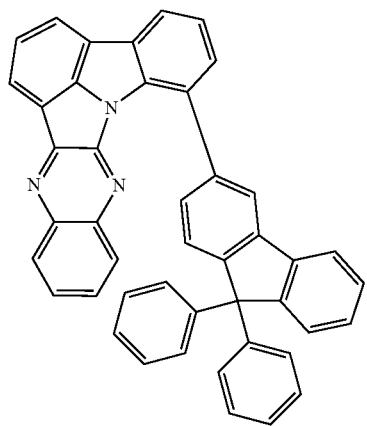
A-115
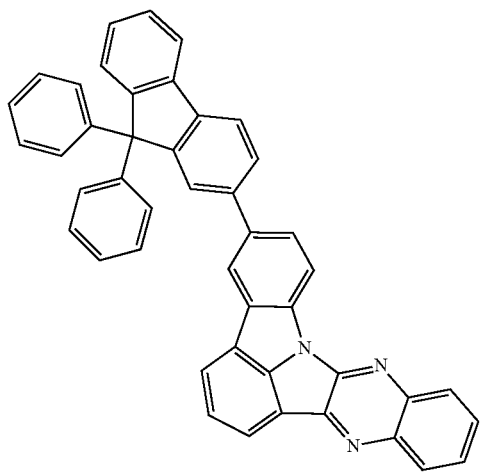
A-116
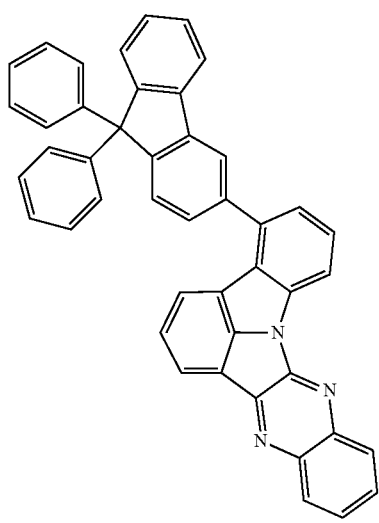
A-117
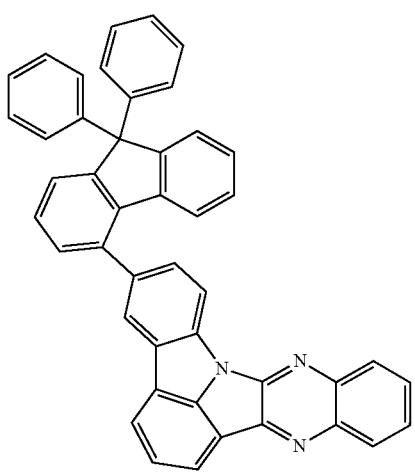
A-118
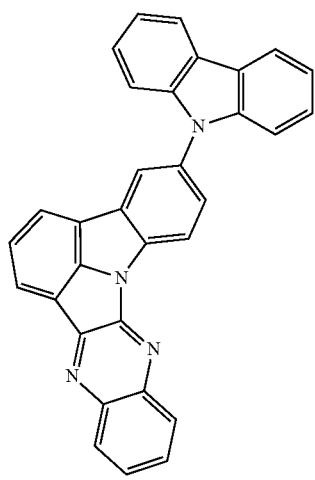
A-119
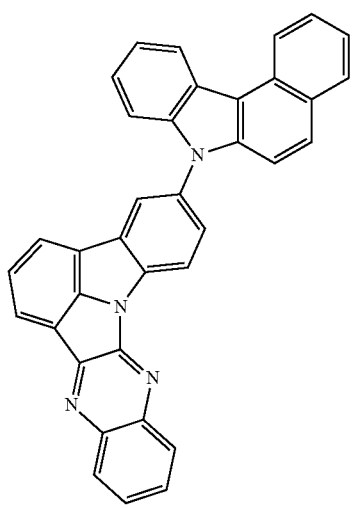

-continued
A-120
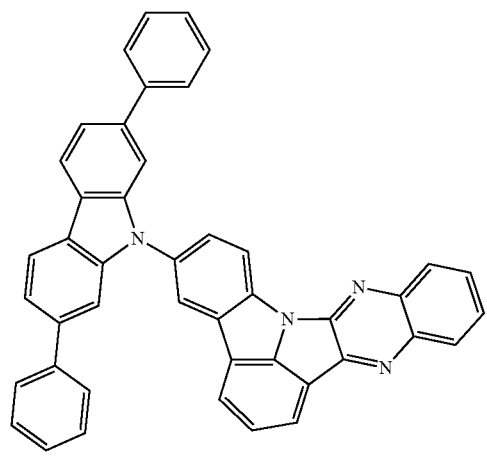
A-121
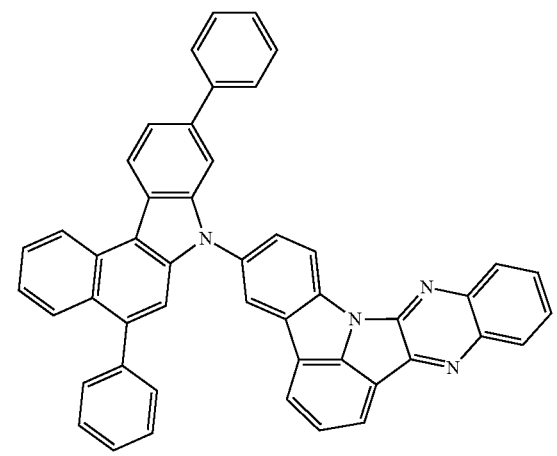
A-122
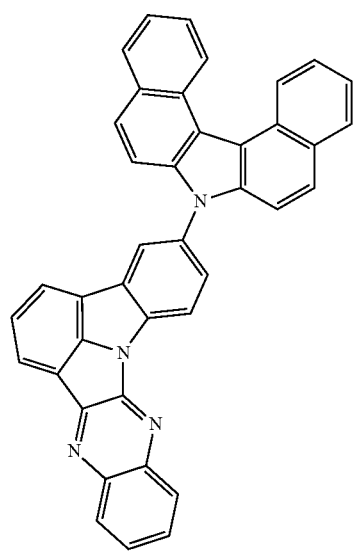
A-123
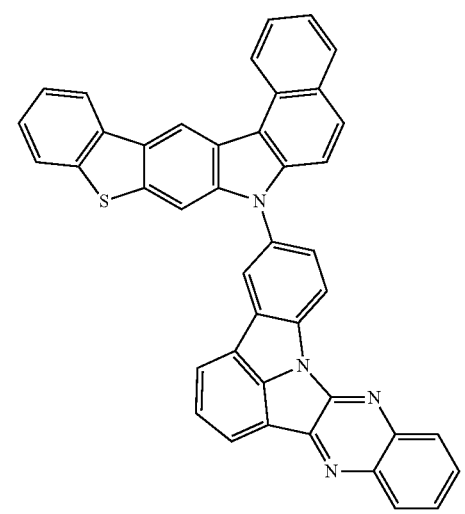
A-124
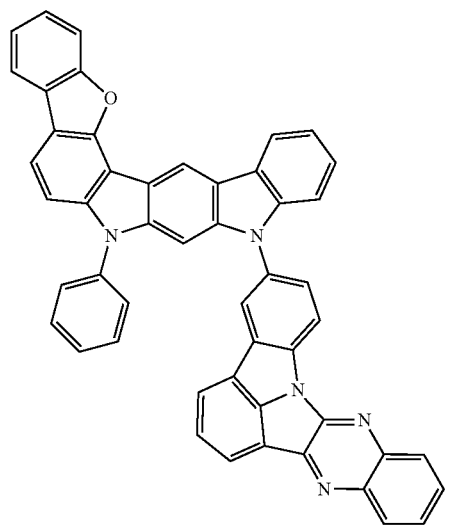
A-125
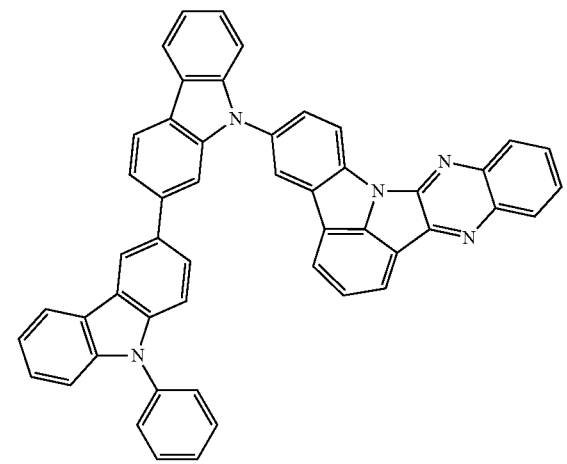

-continued
A-126
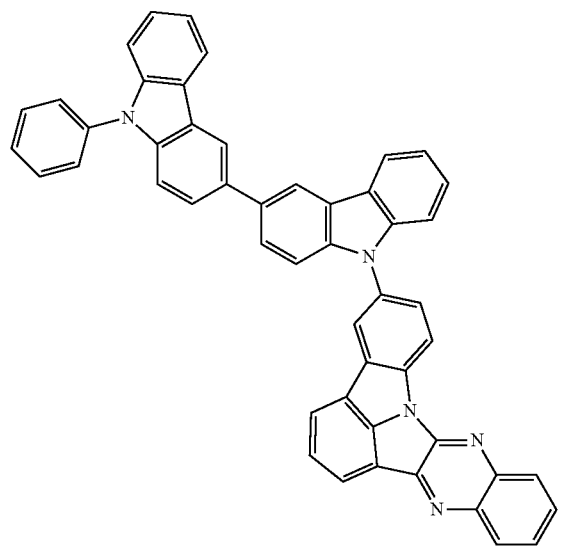
A-127
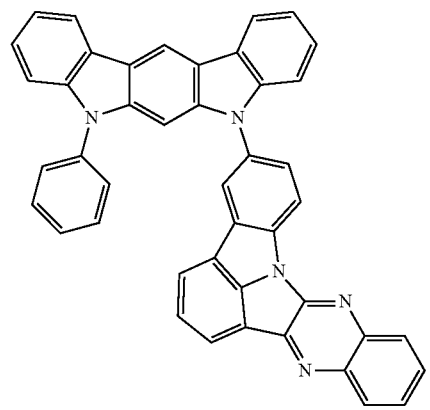
A-128
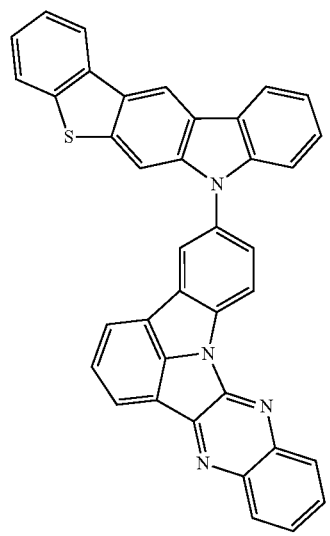
A-129
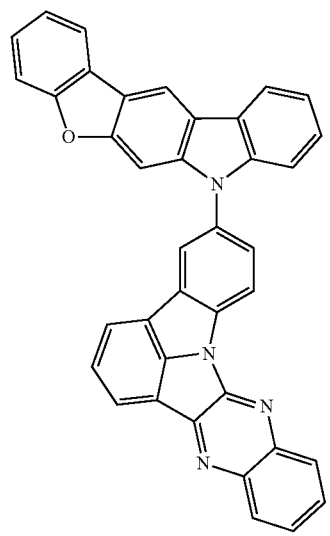
A-130
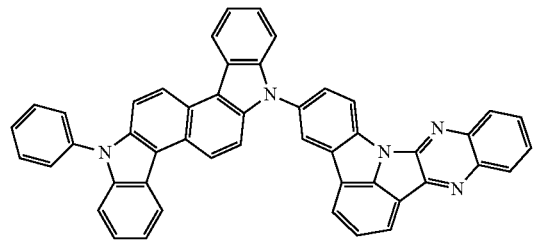
A-131
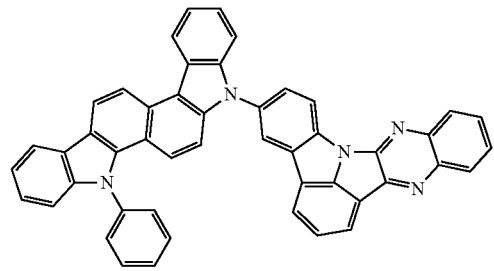

-continued
A-132
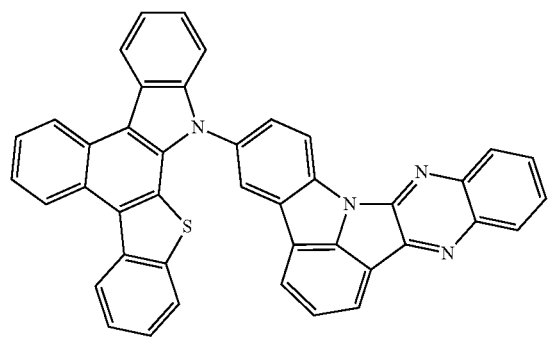
A-133
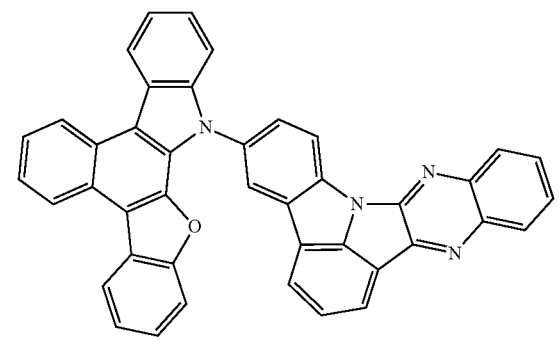
A-134
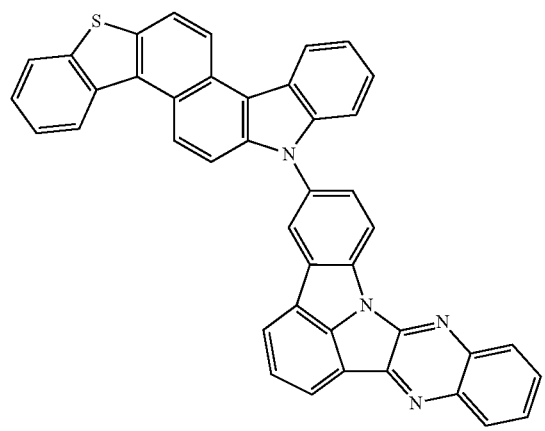
A-135
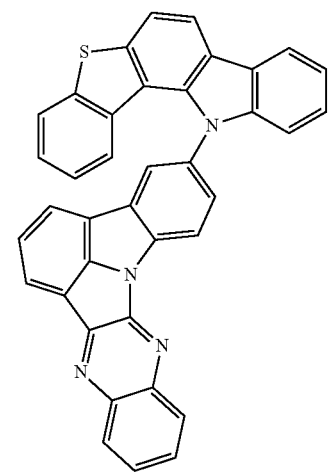
A-136
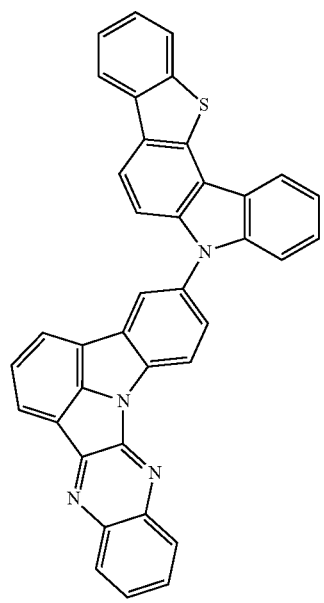
A-137
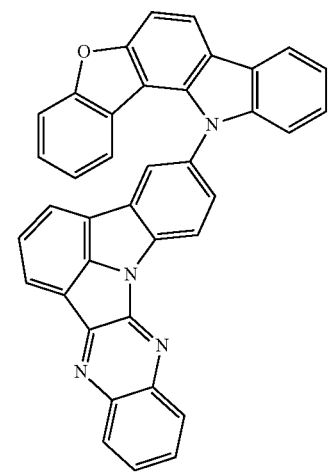

-continued
A-138
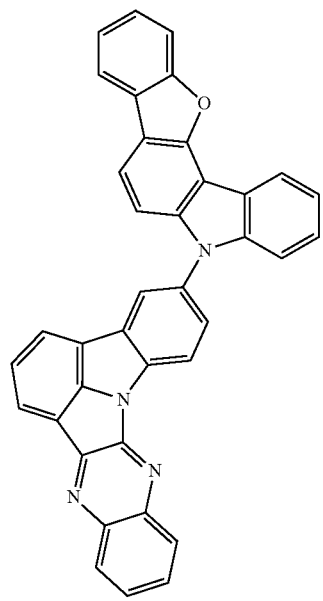
A-139
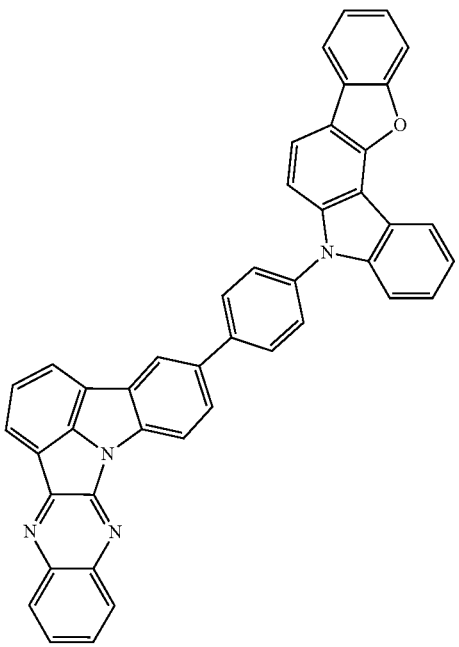
A-140
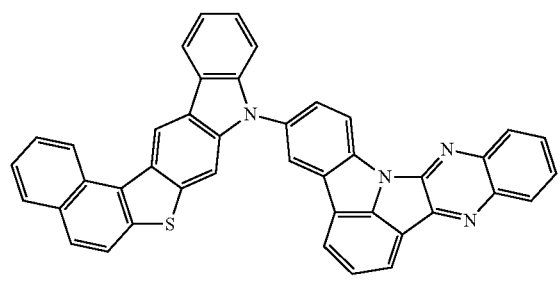
A-141
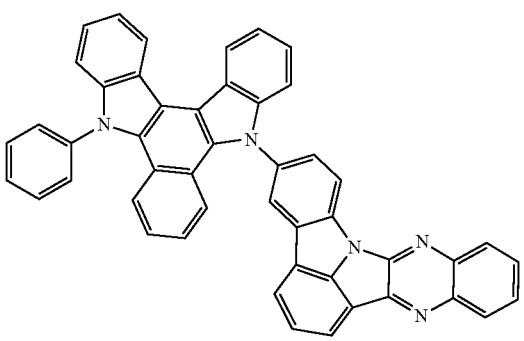
A-142
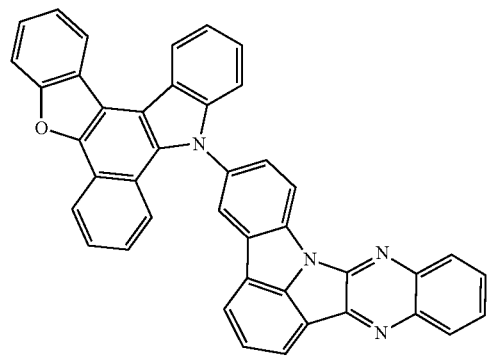
A-143
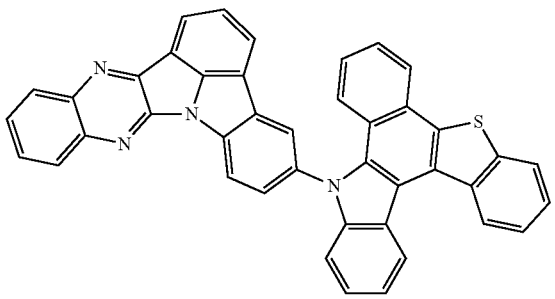

-continued
A-144
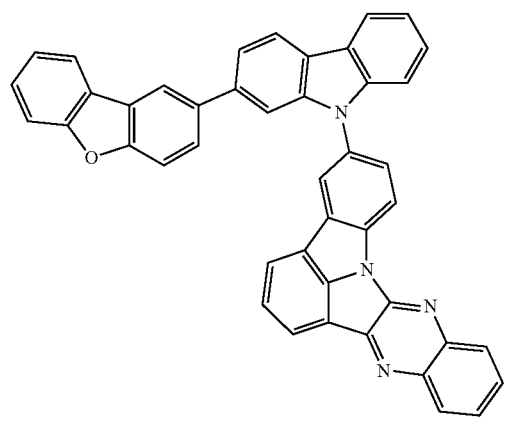
A-145
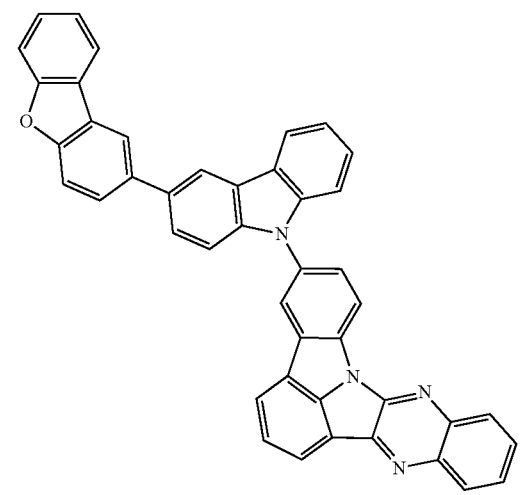
A-146
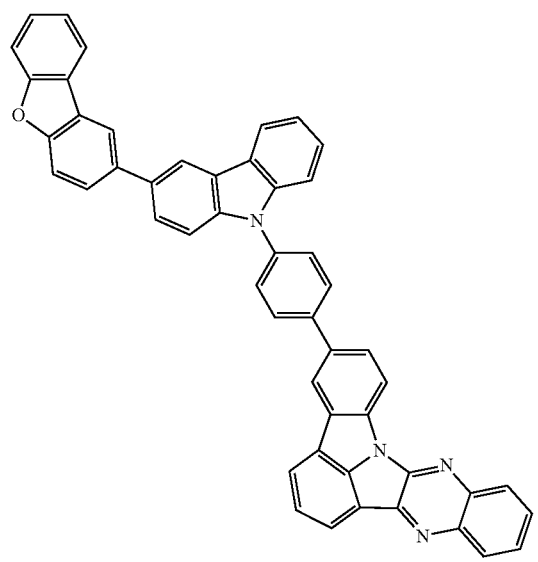
A-147
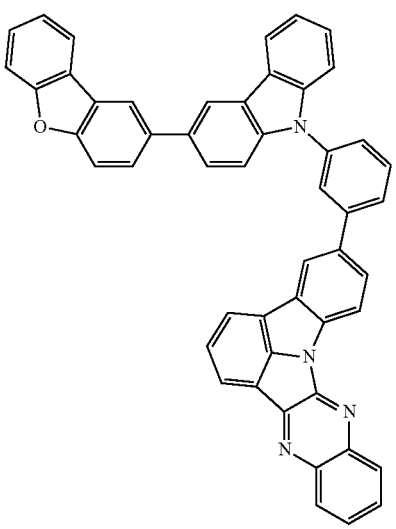

-continued
A-148
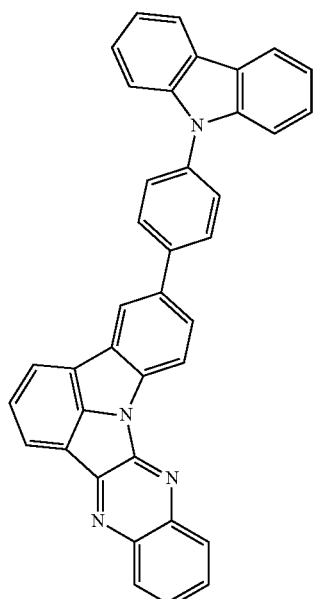
A-149
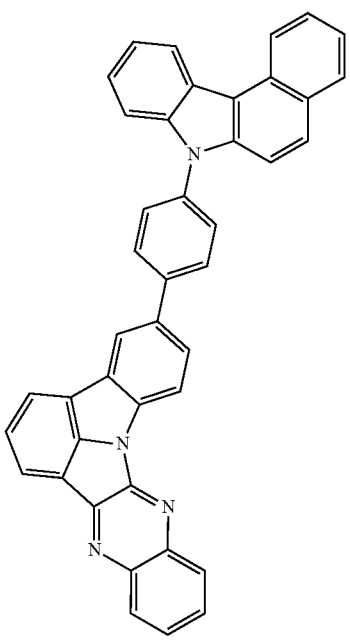
A-150
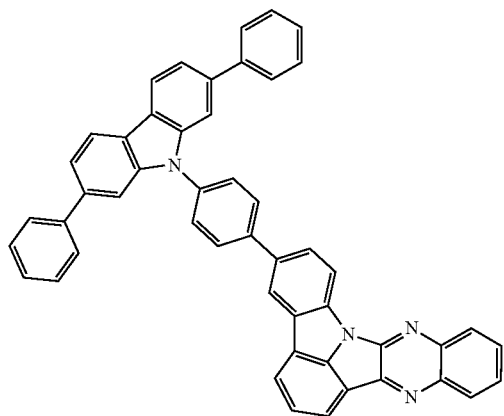
A-151
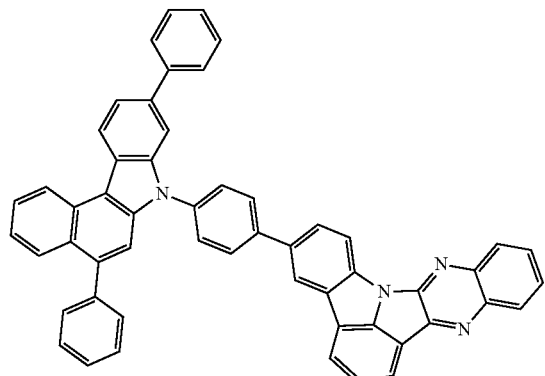
A-152
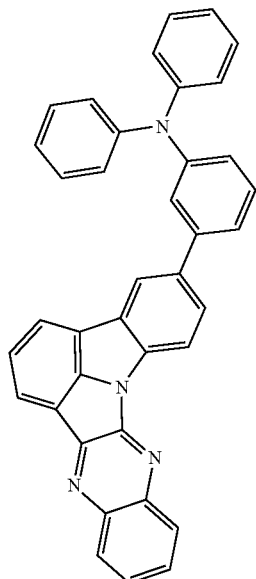
A-153
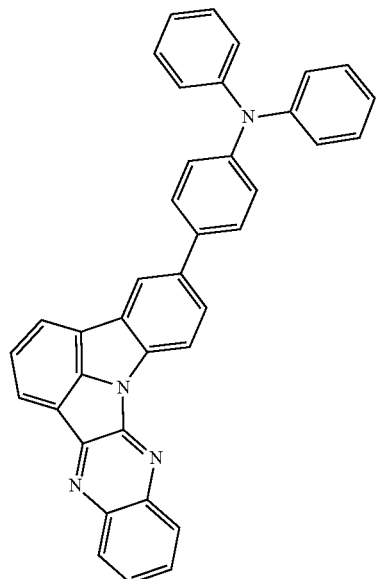

-continued
A-154
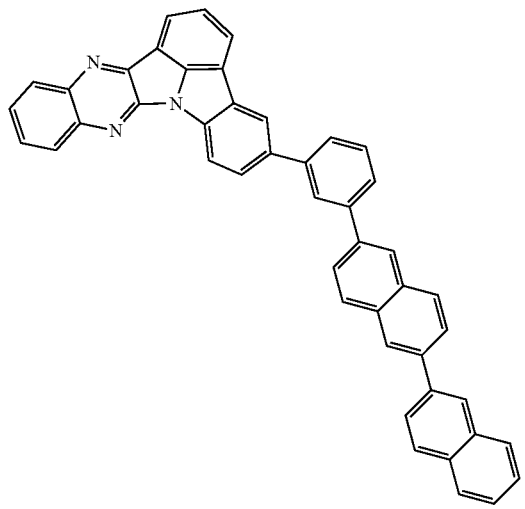
A-155
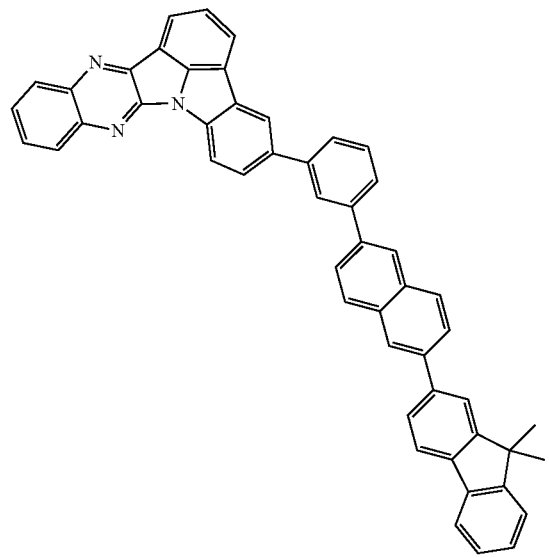
A-156
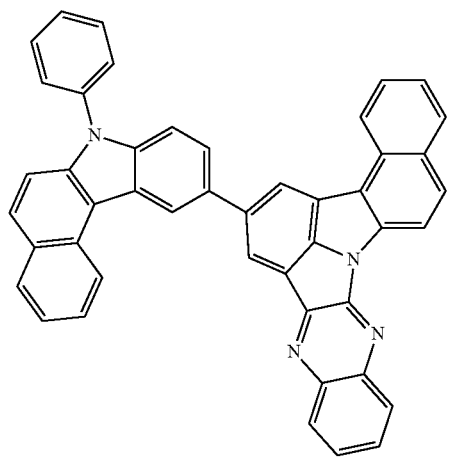
A-157
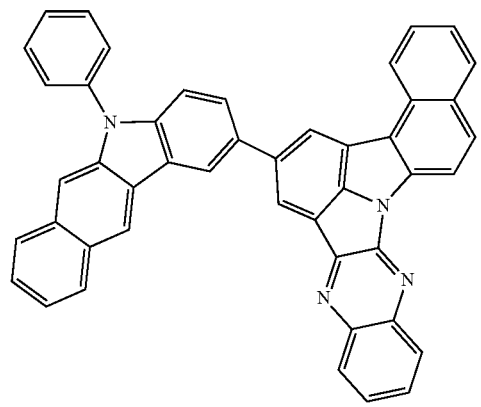
A-158
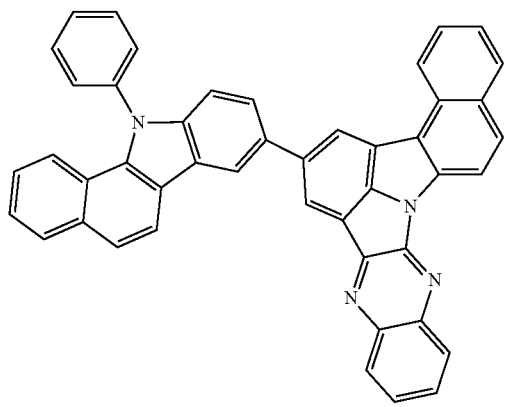
A-159
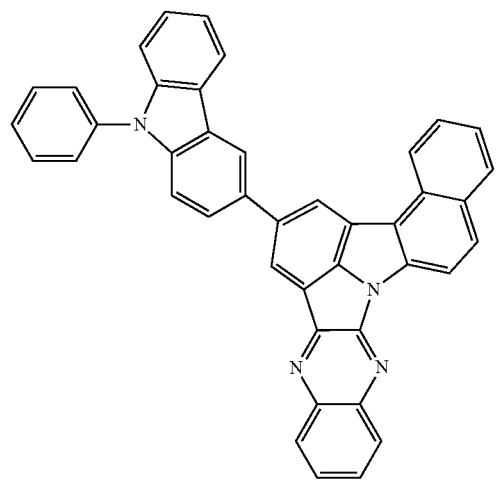

A-160
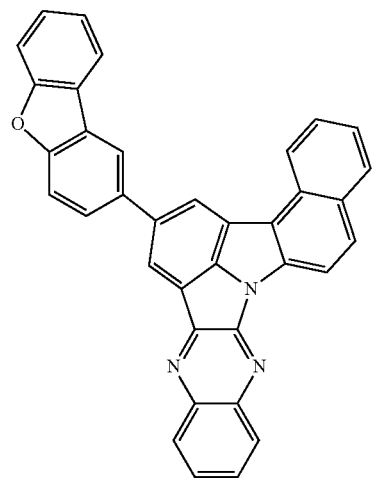
A-161
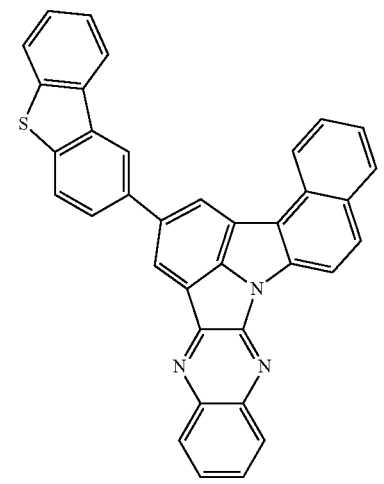
A-162
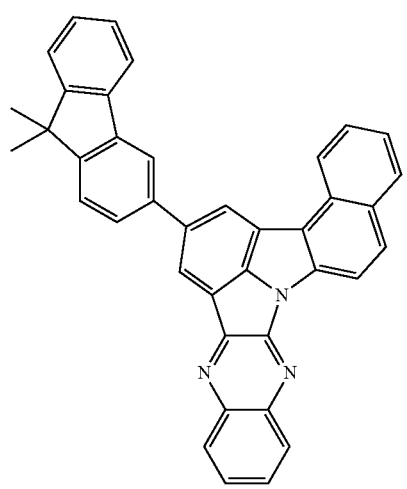
A-163
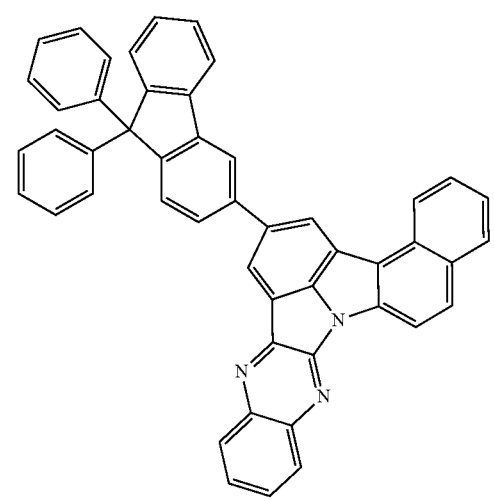
A-164
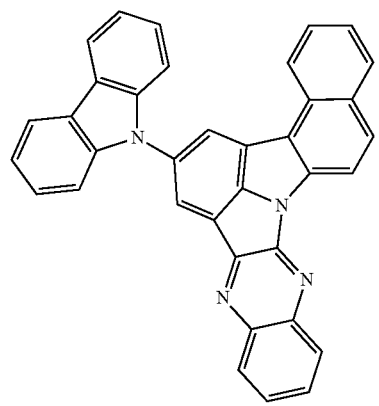
A-165
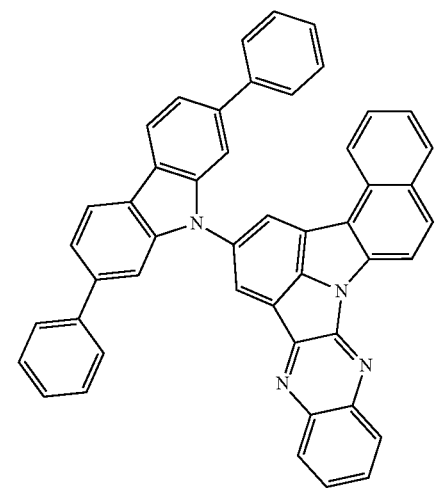

-continued
A-166
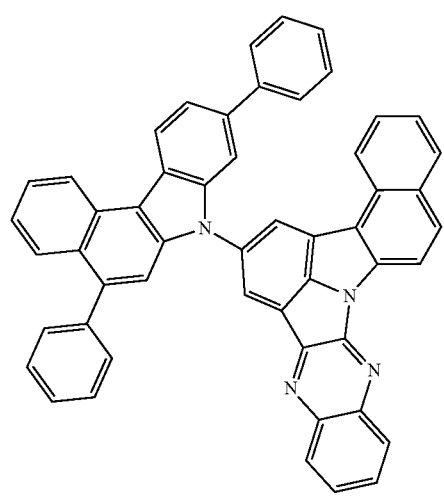
A-167
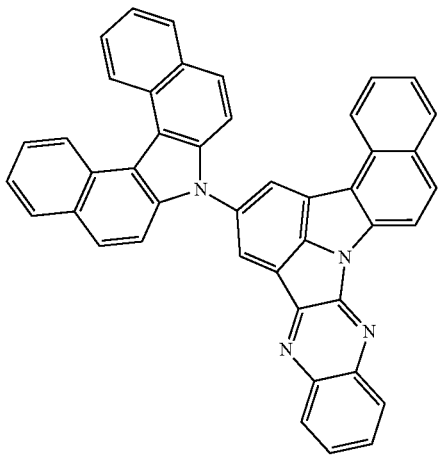
A-168
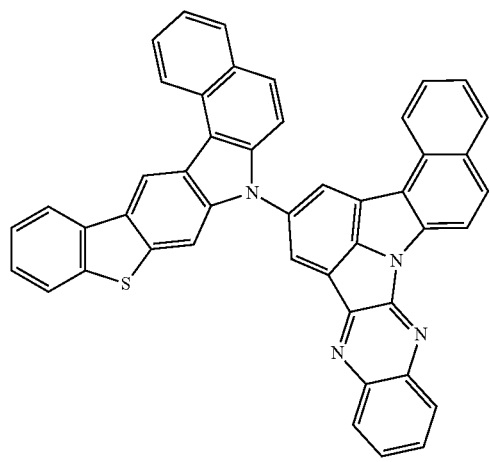
A-169
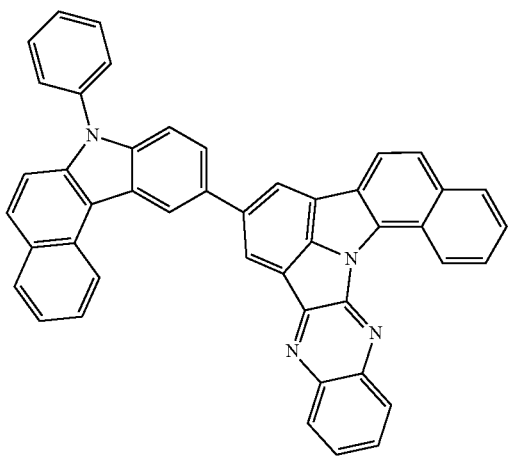
A-170
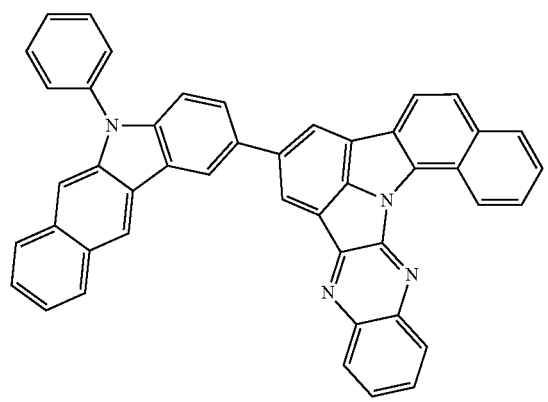
A-171
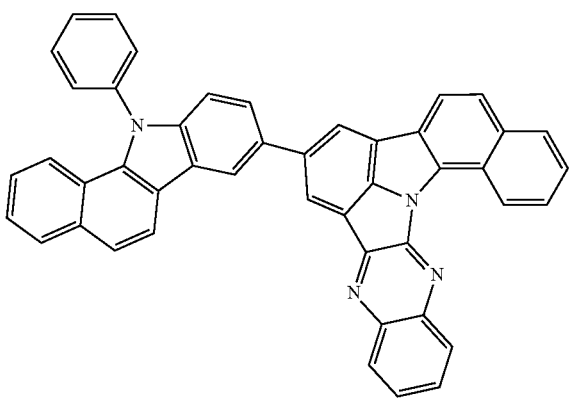

-continued
A-172
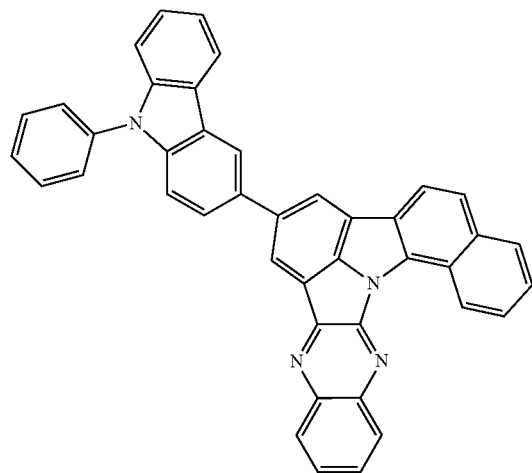
A-173
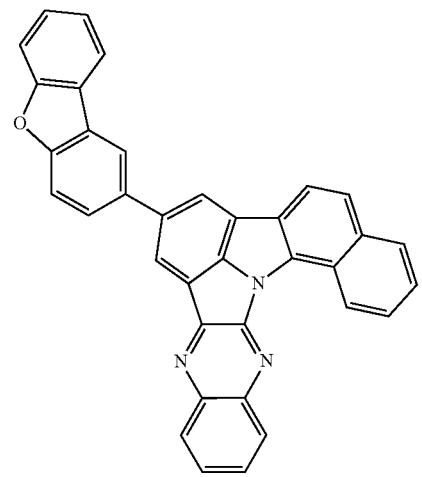
A-174
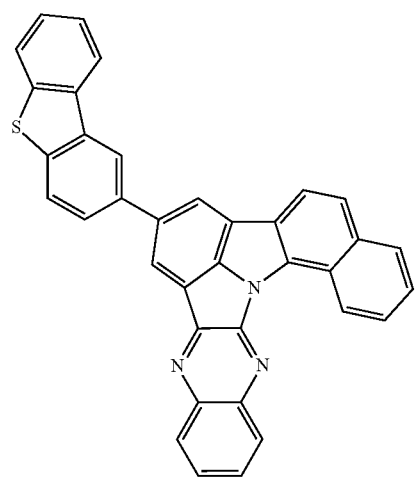
A-175
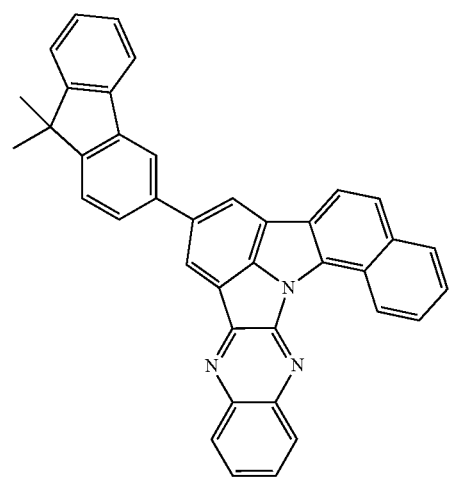
A-176
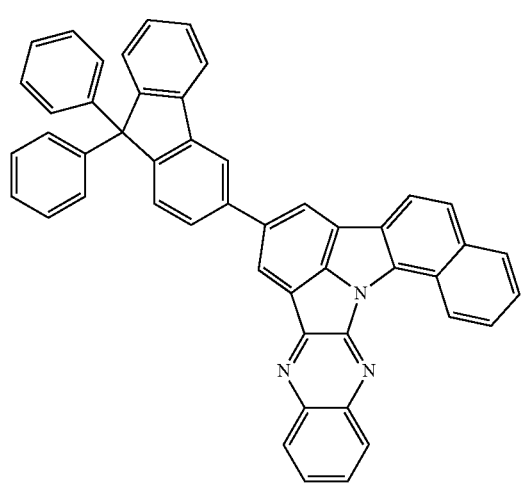
A-177
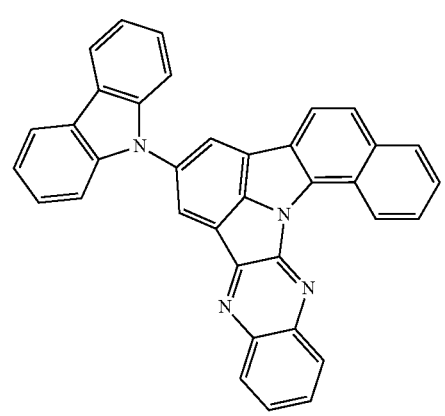

-continued
A-178
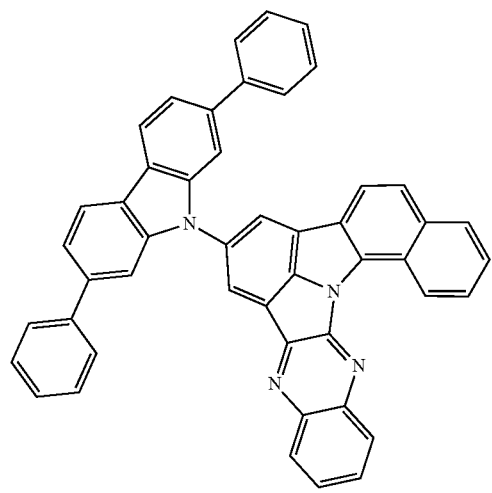
A-179
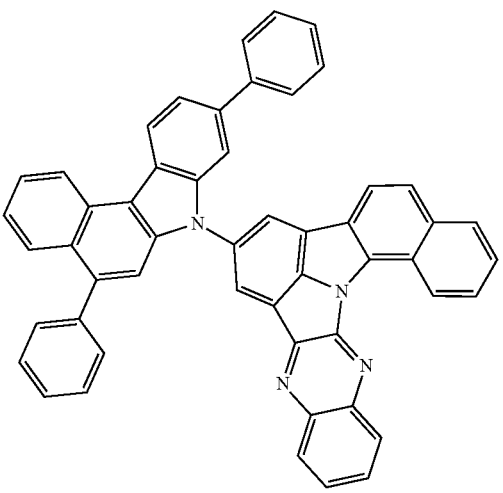
A-180
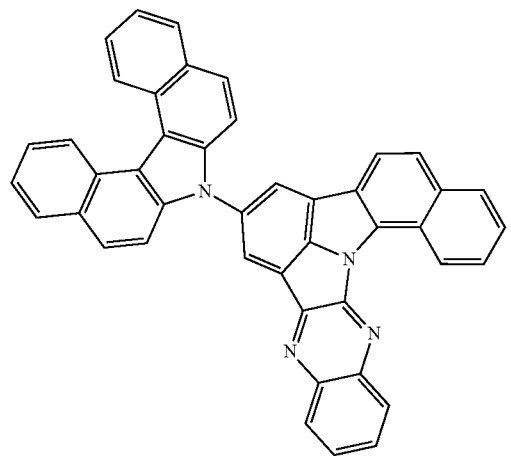
A-181
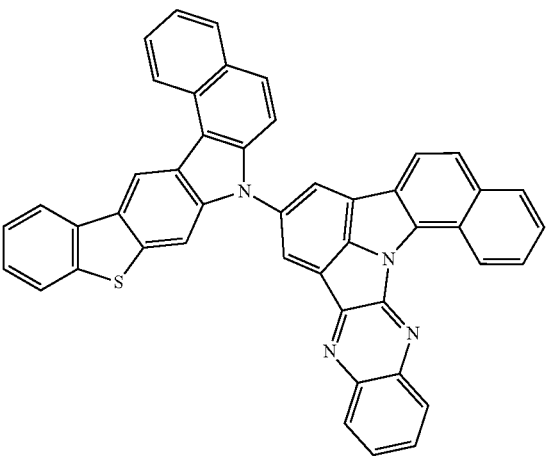
A-182
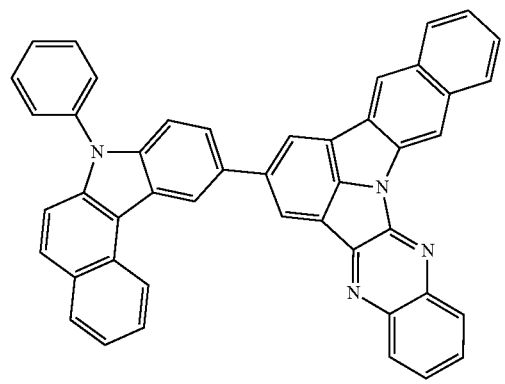
A-183
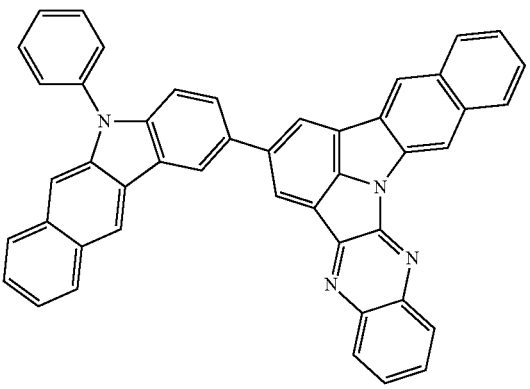

-continued
A-184
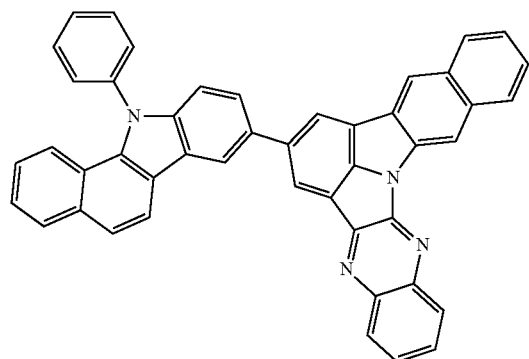
A-185
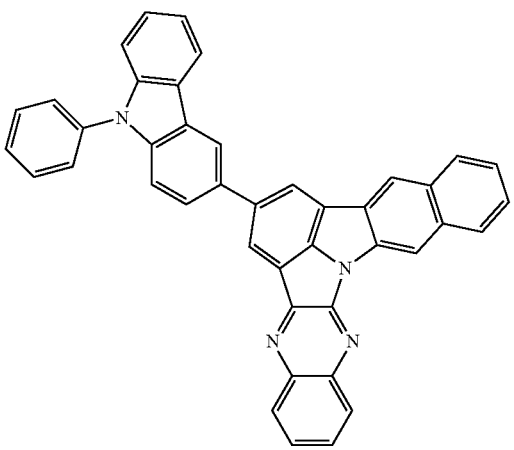
A-186
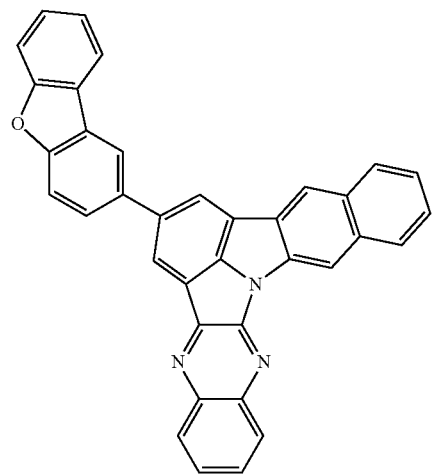
A-187
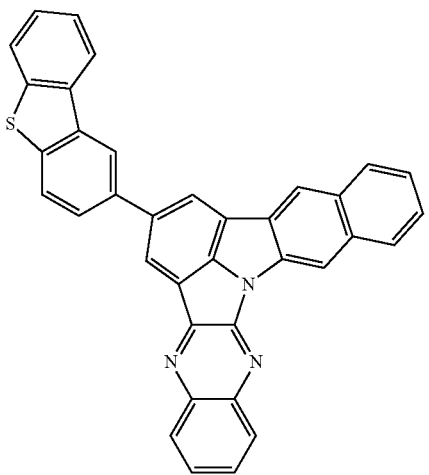
A-188
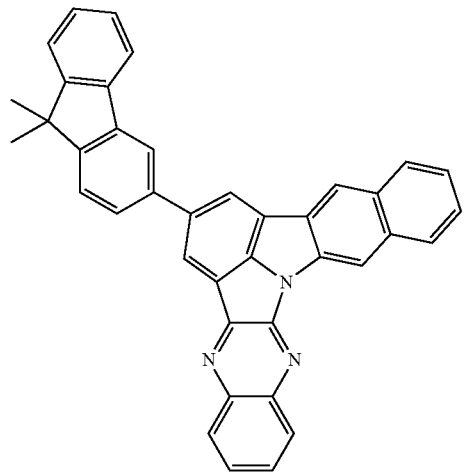
A-189
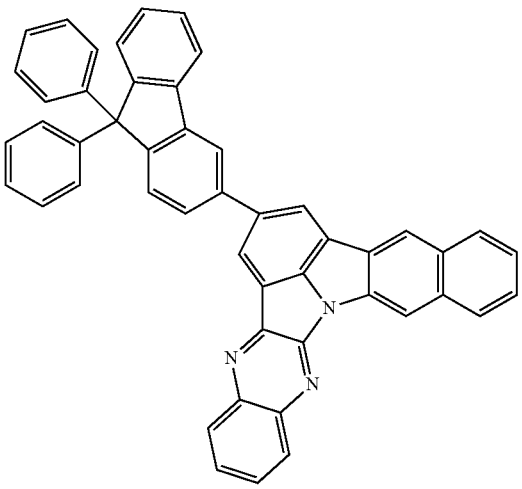

-continued
A-190
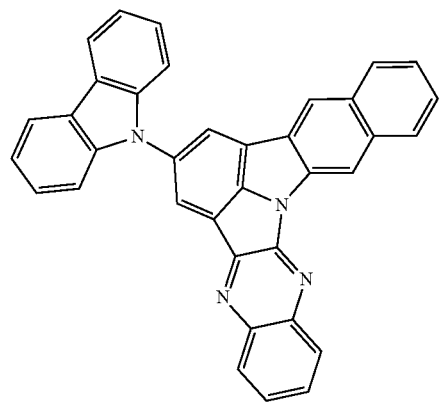
A-191
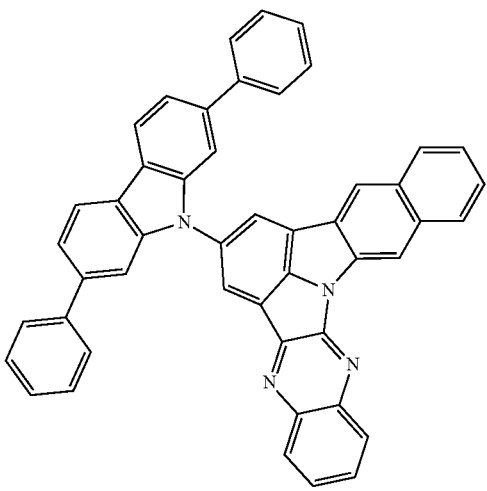
A-192
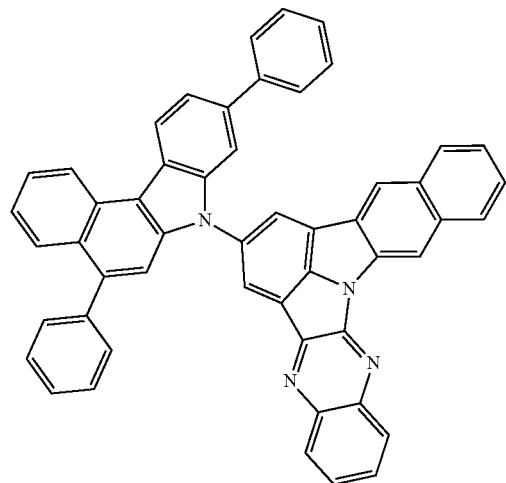
A-193
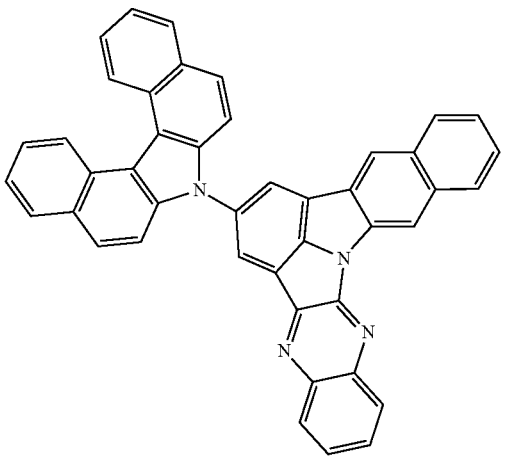
A-194
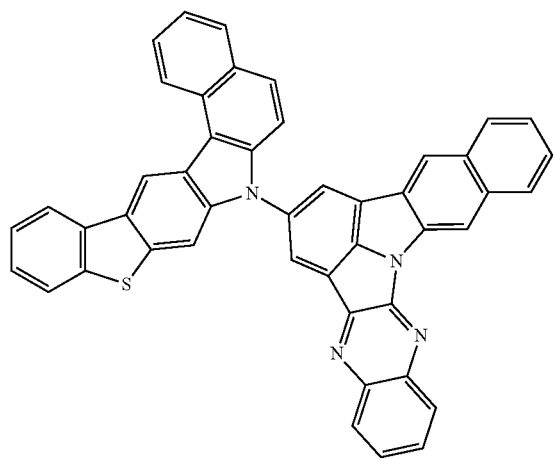
A-195
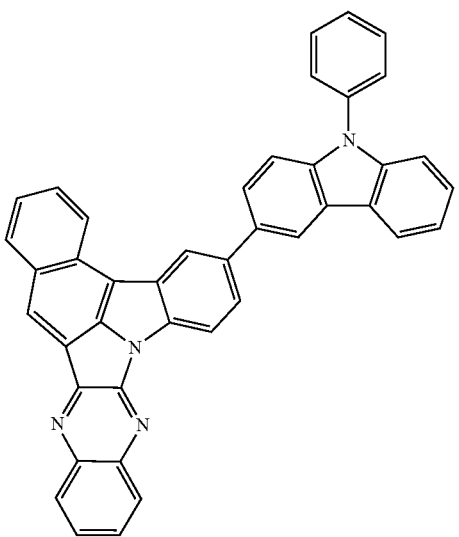

-continued
A-196
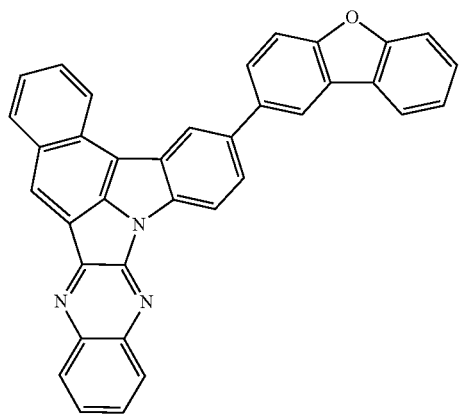
A-197
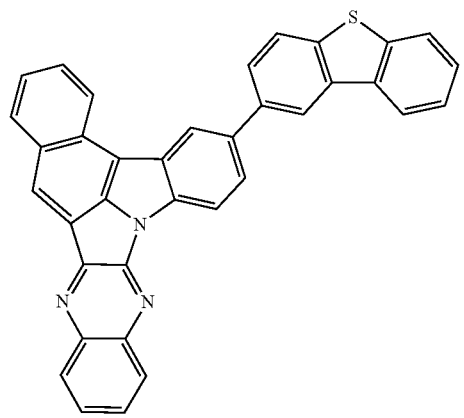
A-198
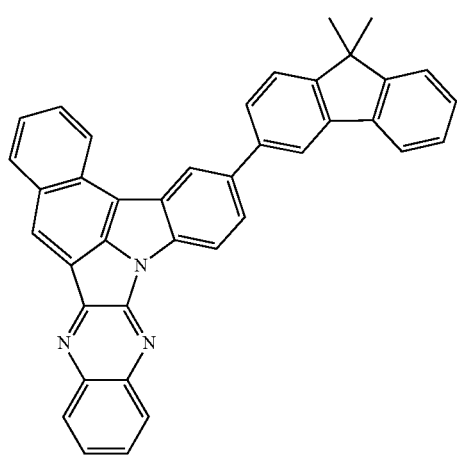
A-199
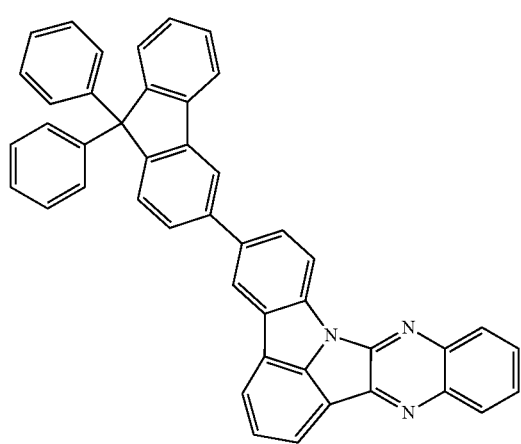
A-200
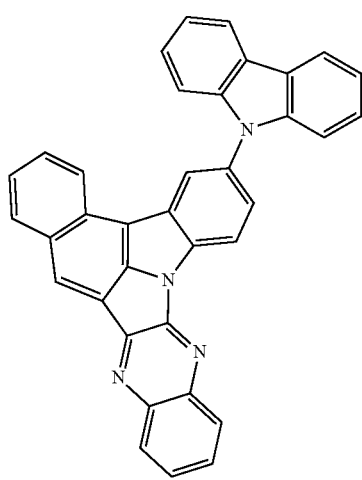
A-201
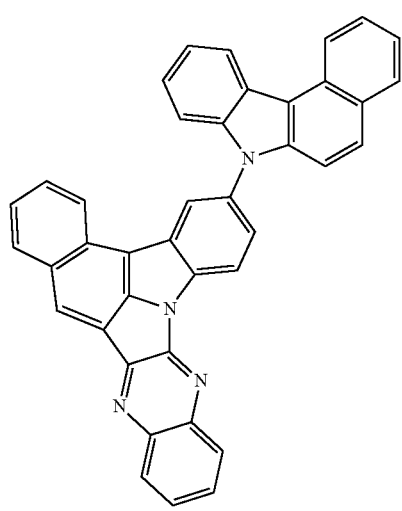

-continued
A-202
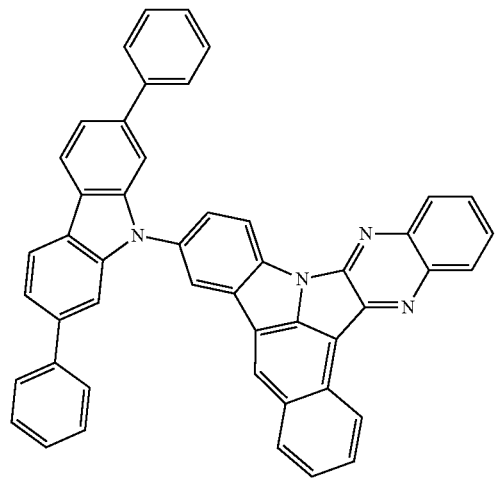
A-203
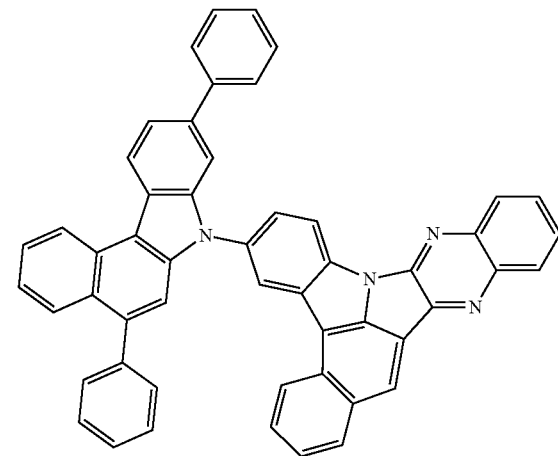
A-204
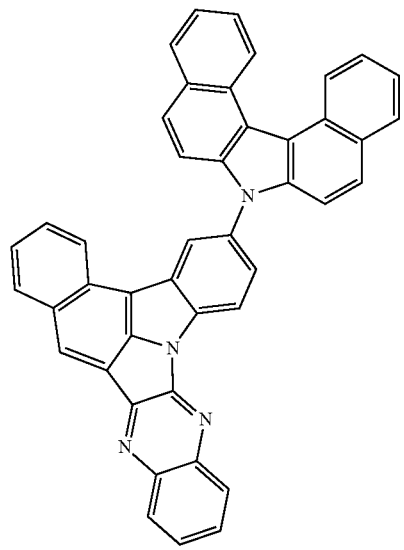
A-205
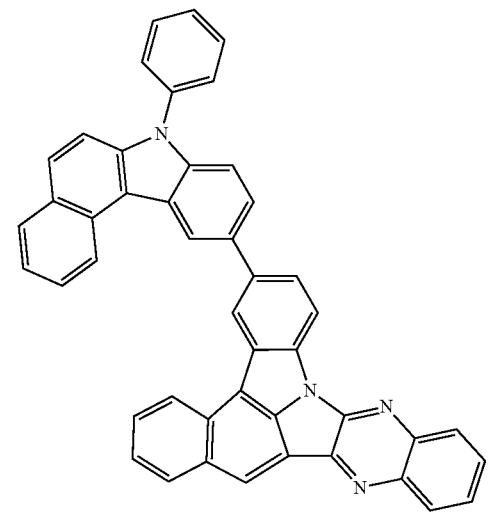
A-206
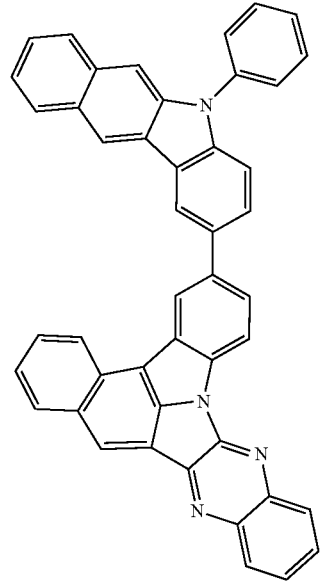
A-207
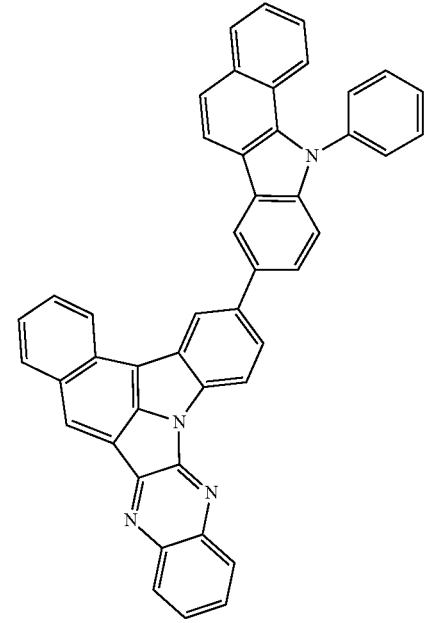

-continued
A-208
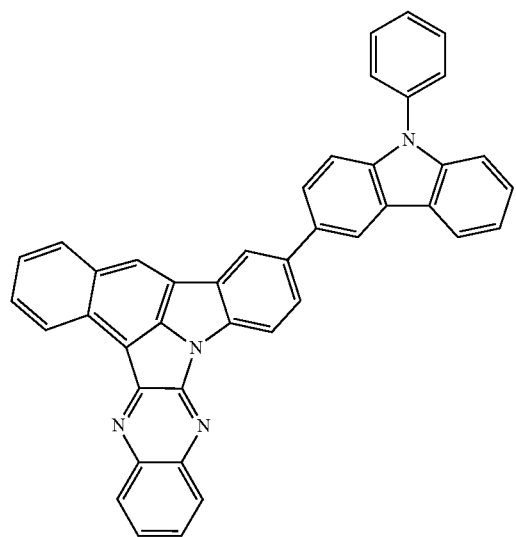
A-209
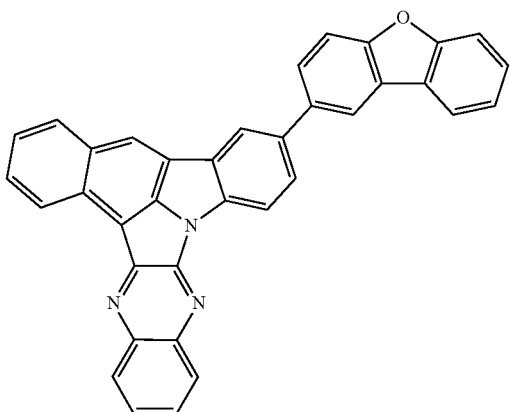
A-210
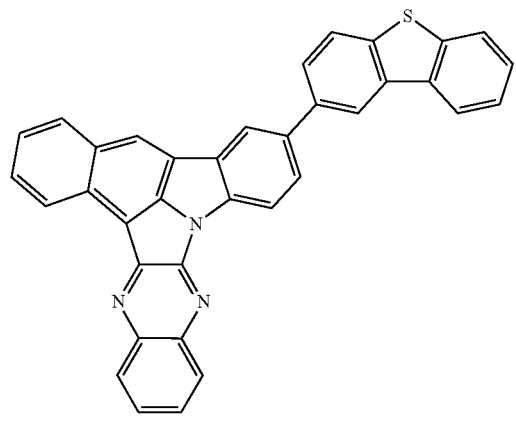
A-211
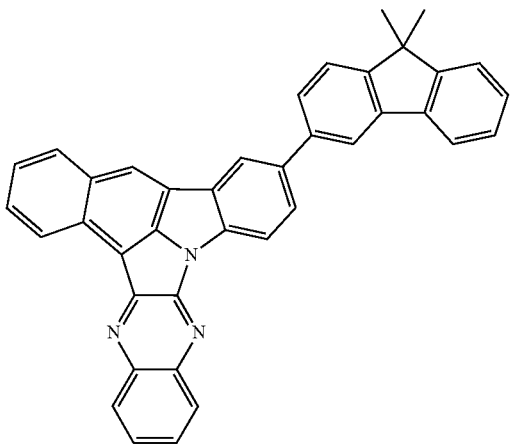
A-212
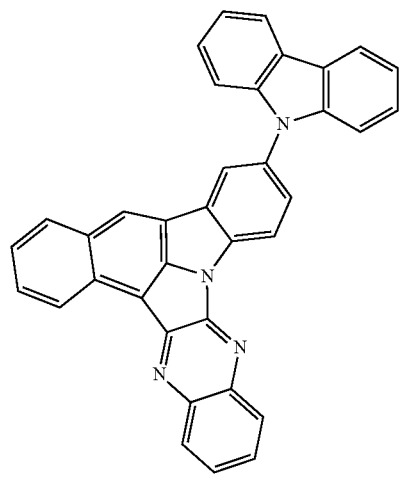
A-213
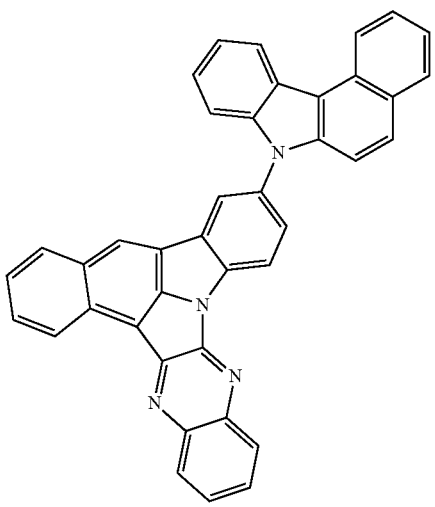

-continued
A-214
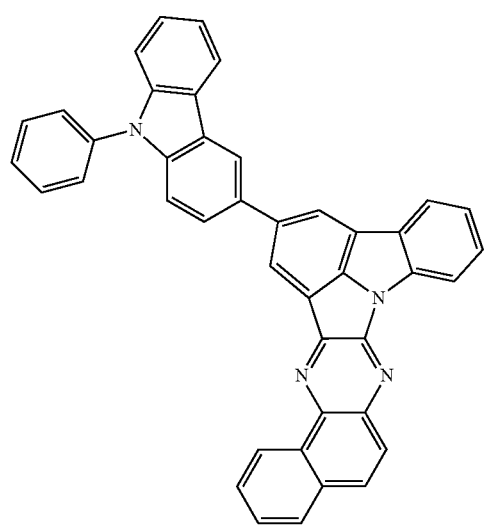
A-215
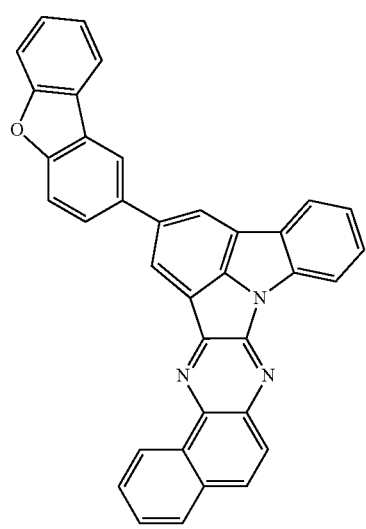
A-216
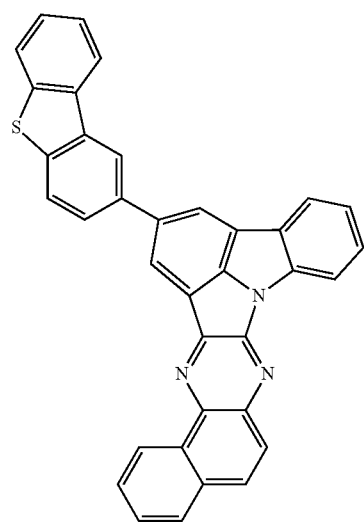
A-217
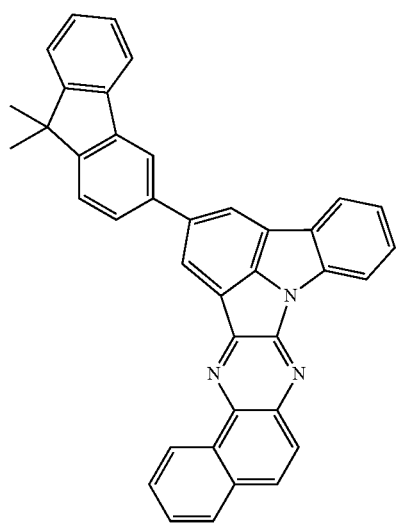
A-218
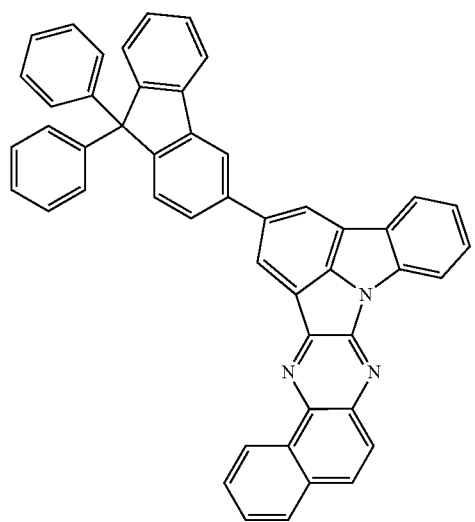
A-219
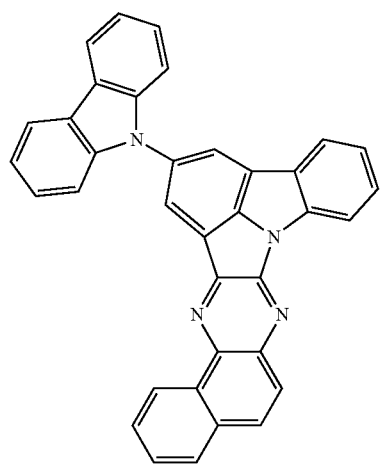

-continued
A-220
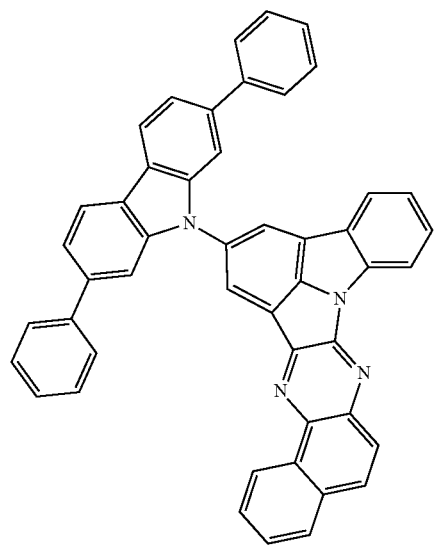
A-221
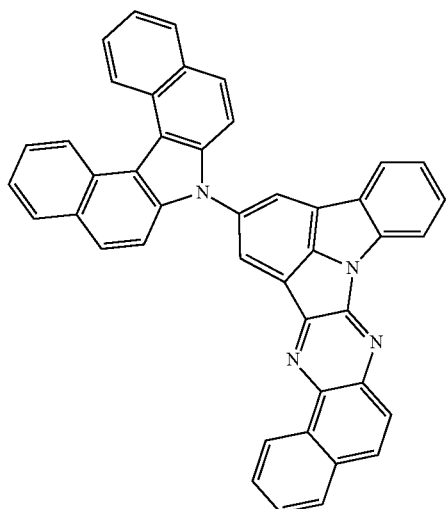
A-223
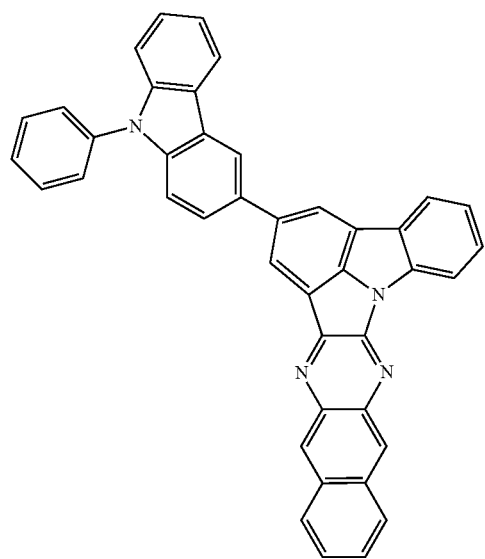
A-224
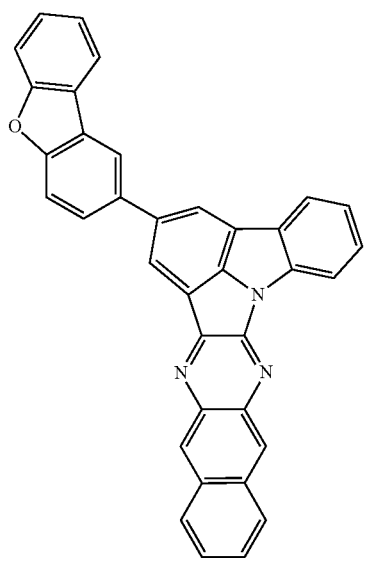
A-225
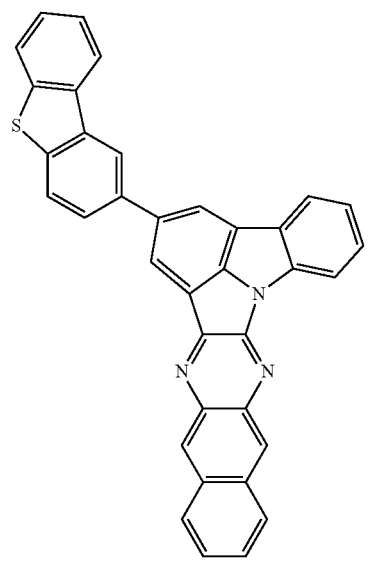
A-226
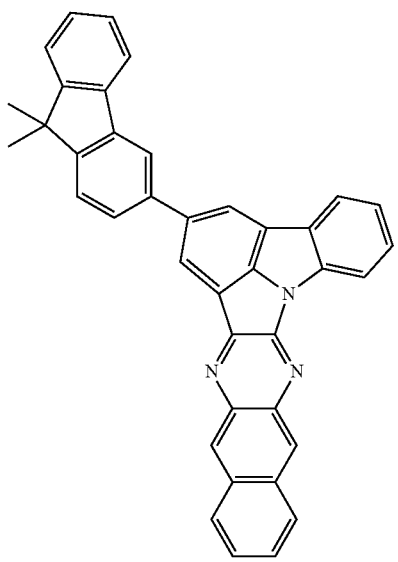

-continued
A-227
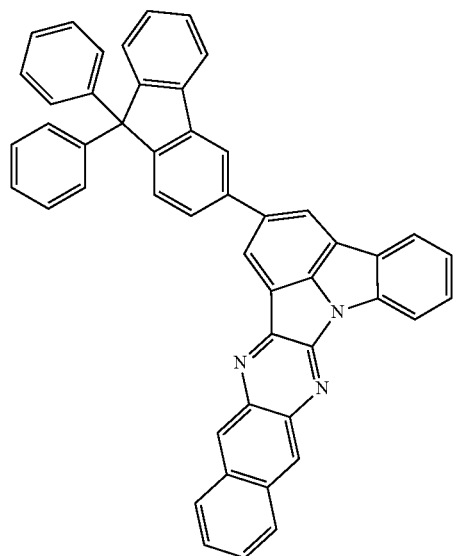
A-228
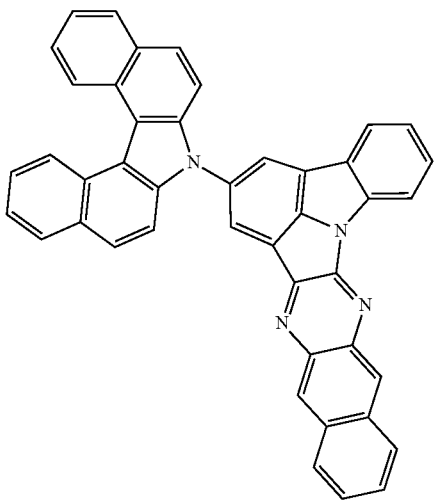
A-229
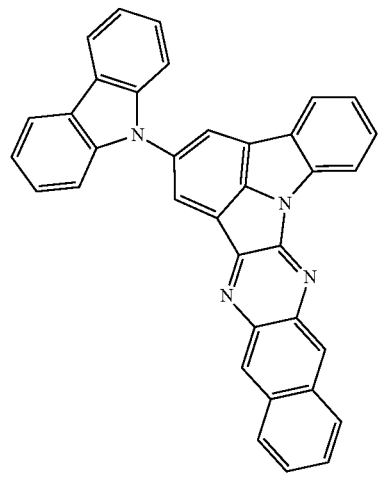
A-230
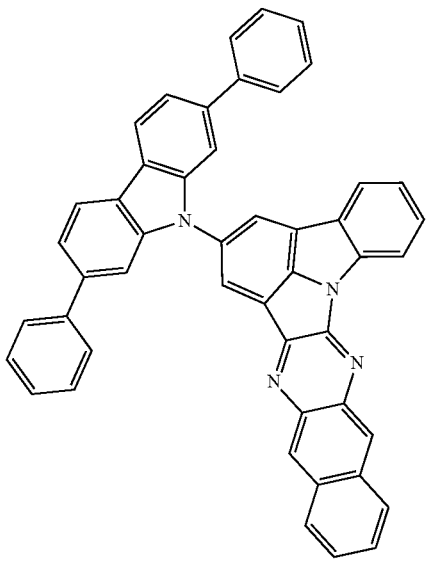
A-231
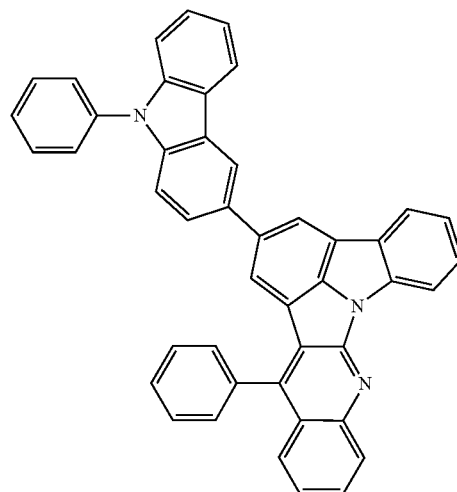
A-232
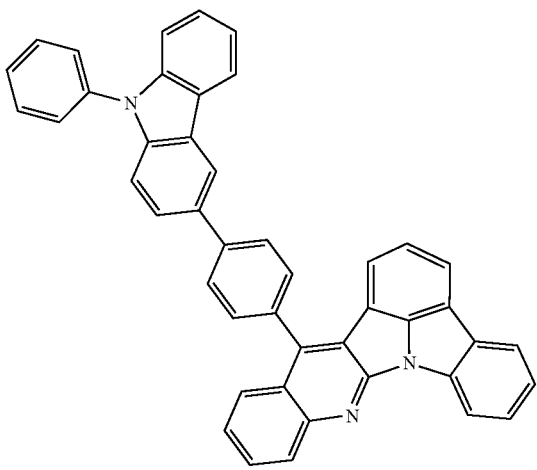

-continued
A-233
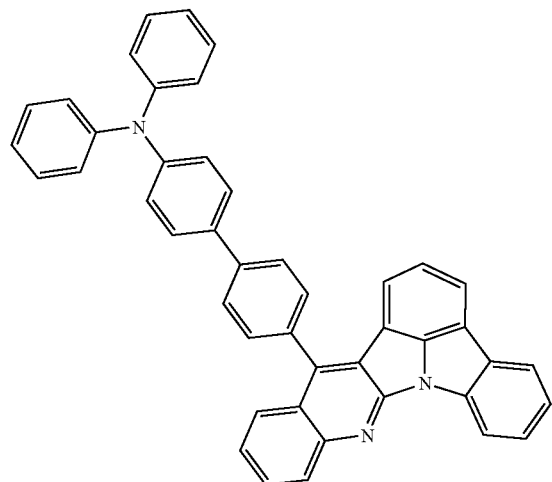
A-234
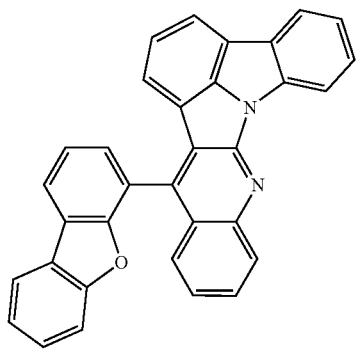
A-235
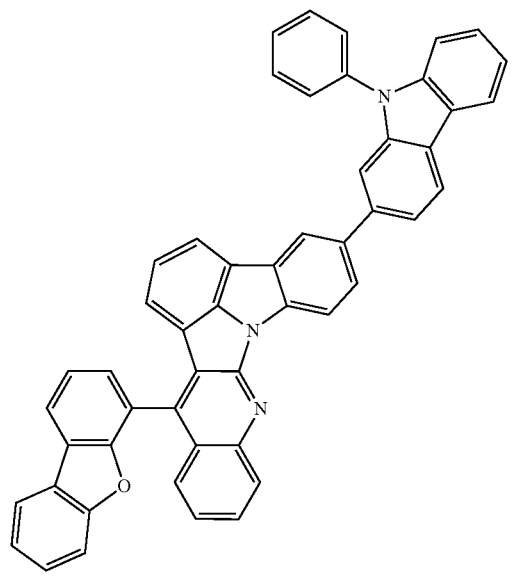
A-236
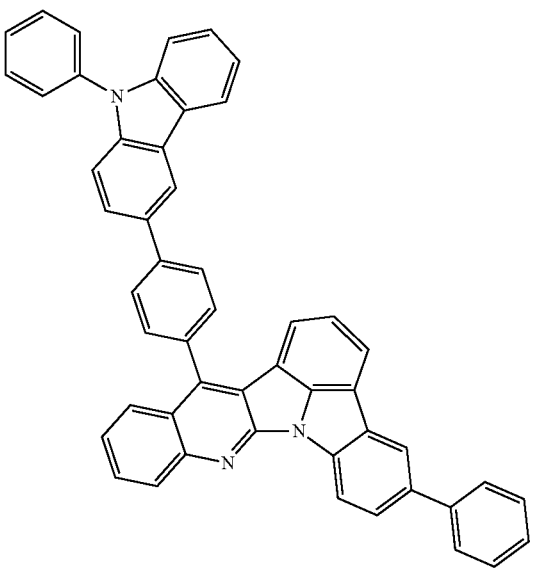
A-237
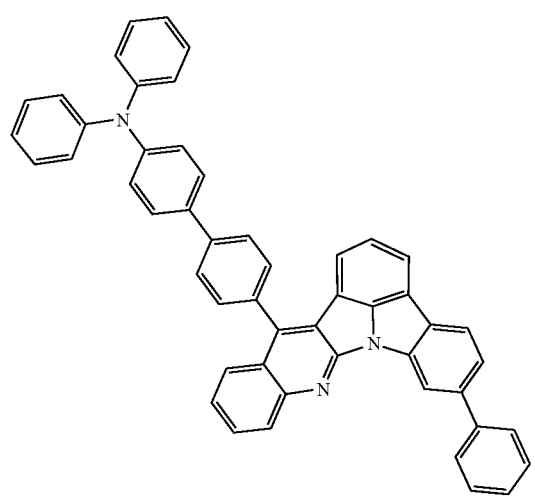
A-238
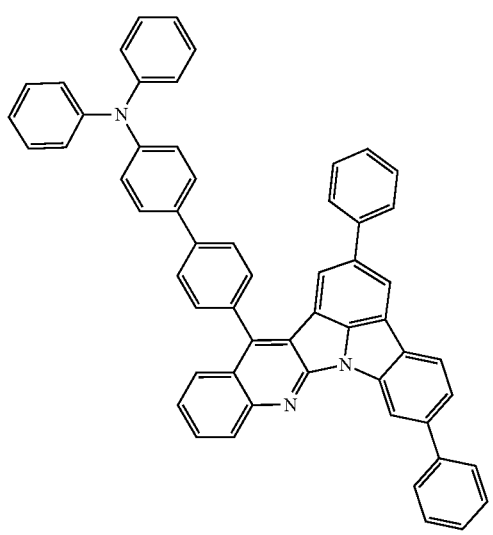

A-239
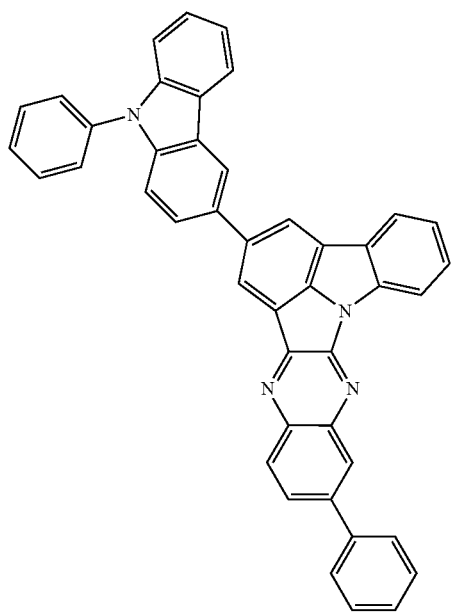
A-240
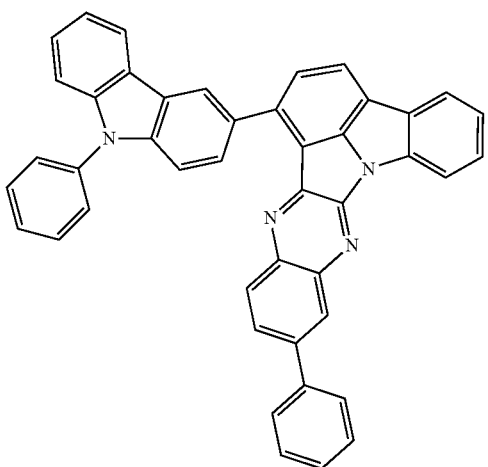
A-241
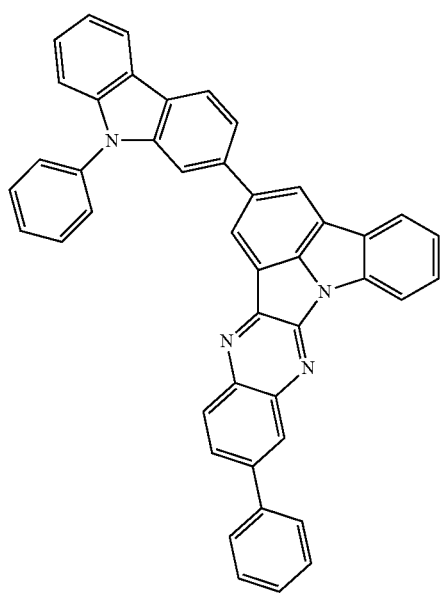
A-242
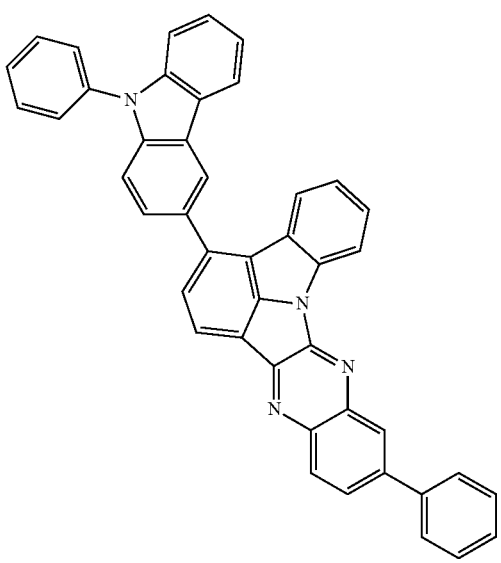

-continued
A-243
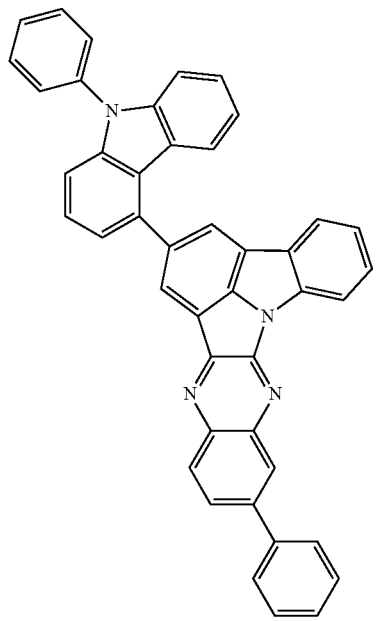
A-244
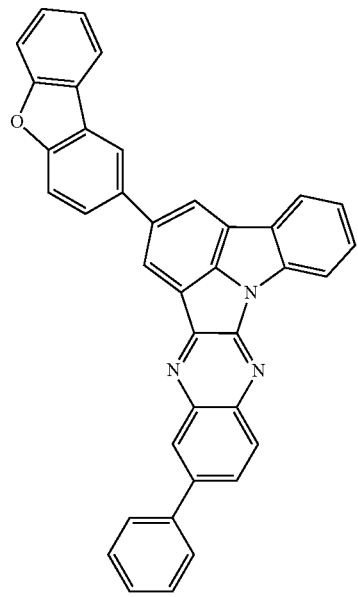
A-245
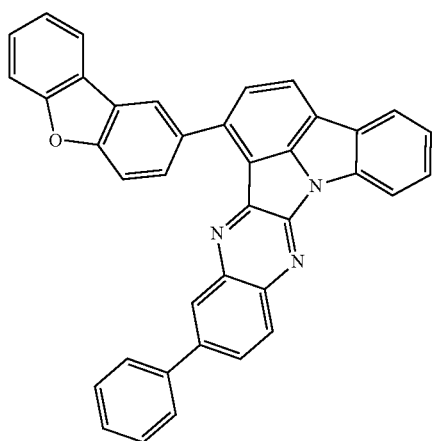
A-246
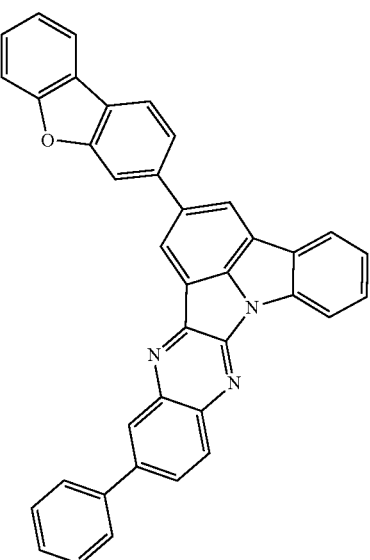

-continued
A-247
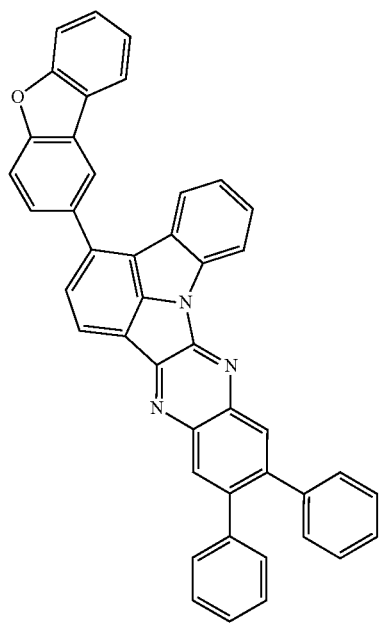
A-248
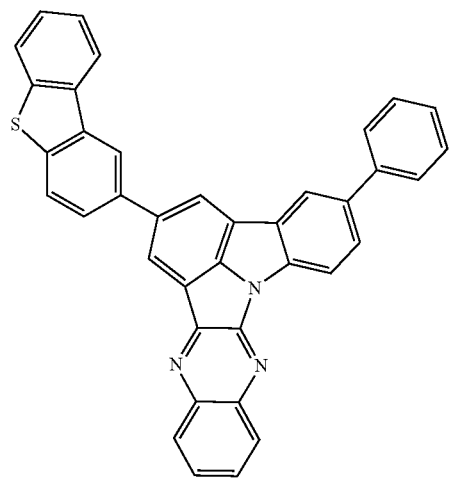
A-249
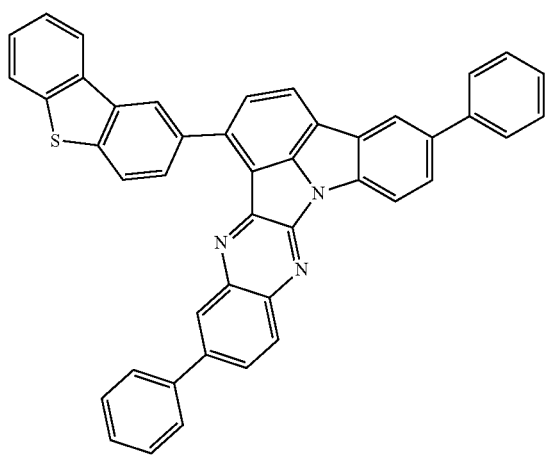
A-250
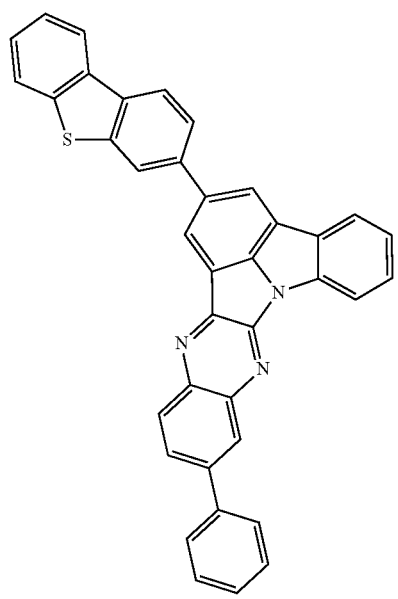

A-251
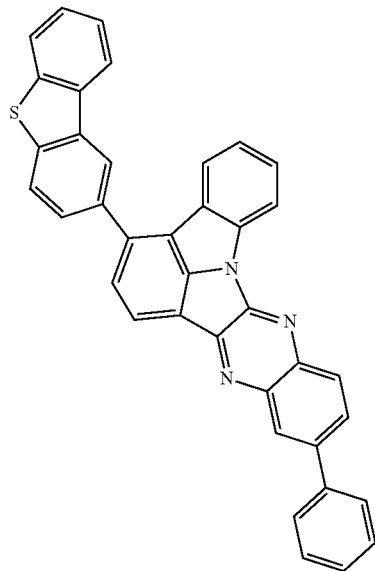
A-252
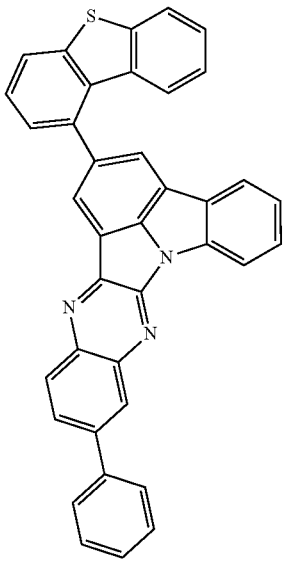
A-253
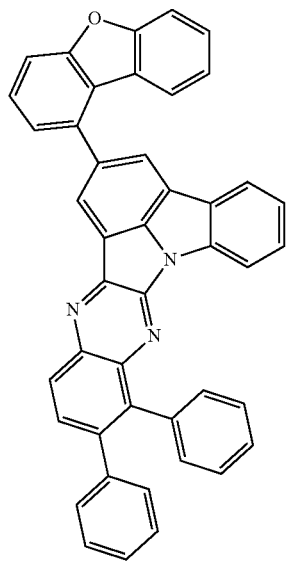
A-254
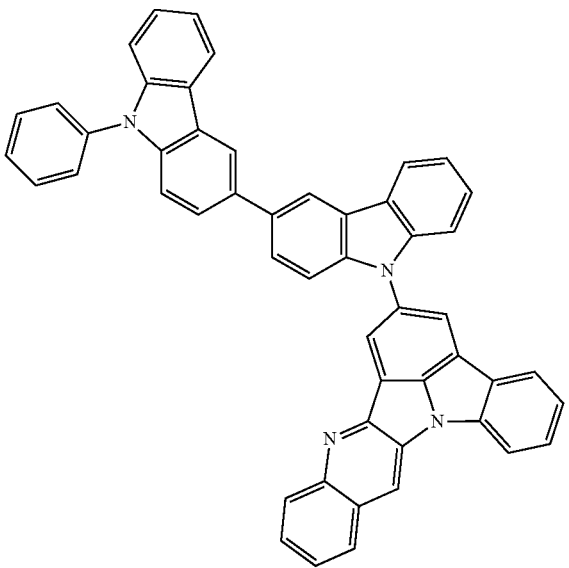

-continued
A-255
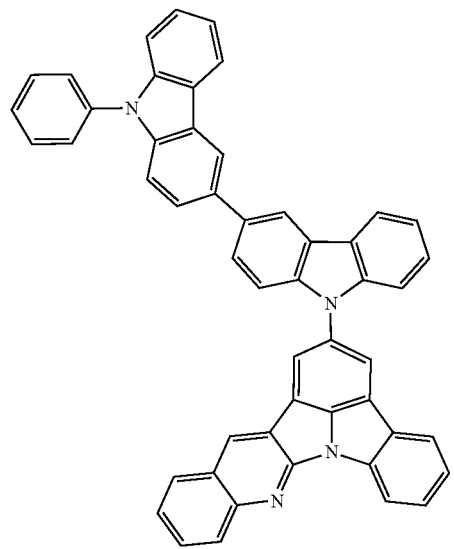
A-256
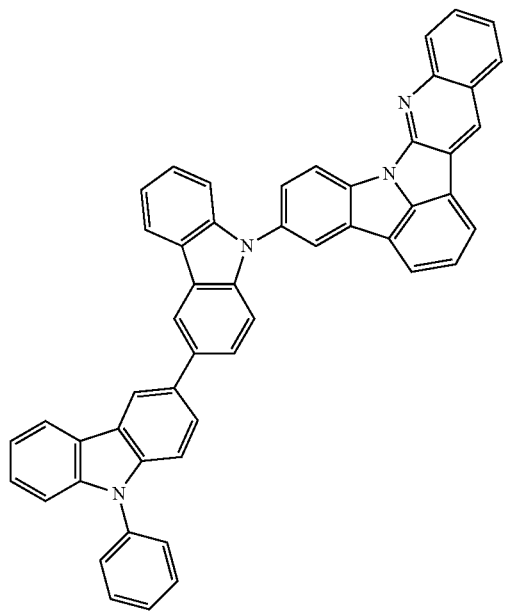
A-257
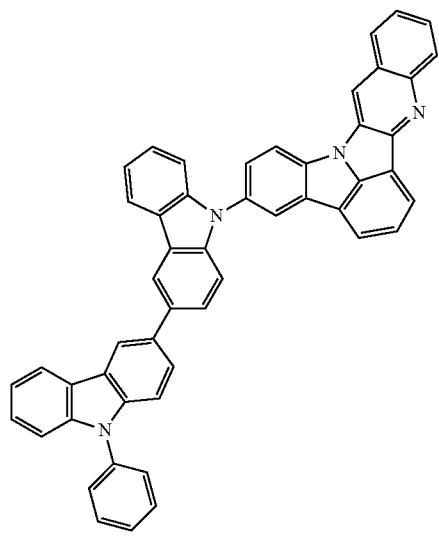
A-258
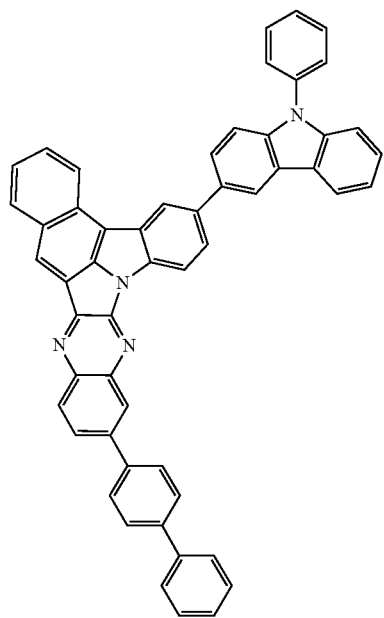

-continued
A-259
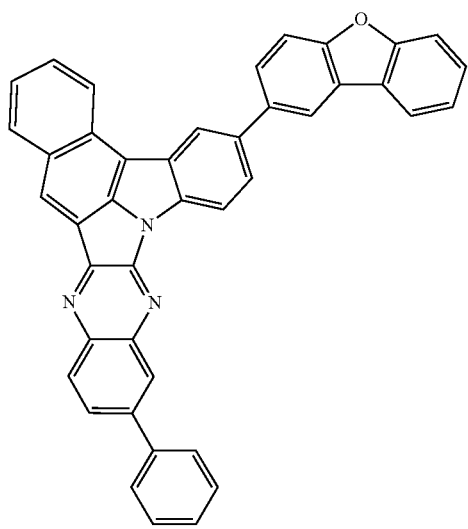
A-260
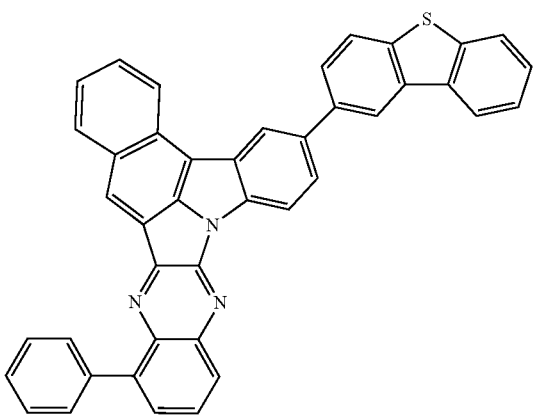
A-261
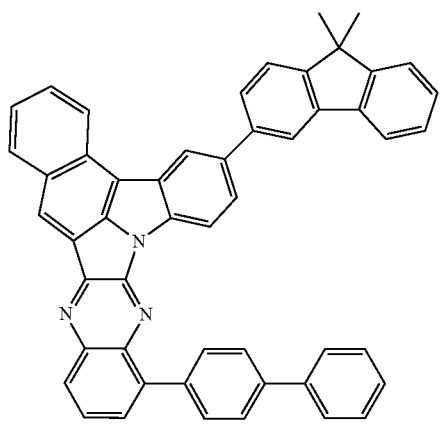
A-262
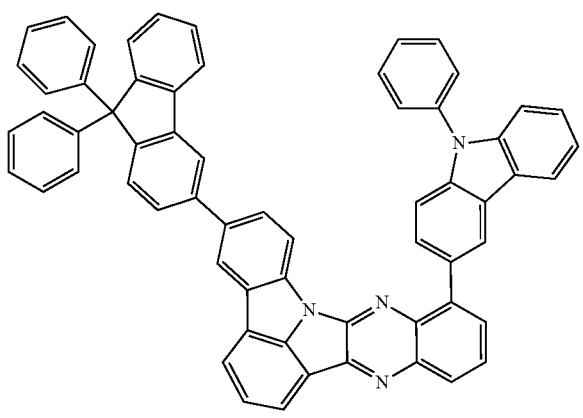
A-263
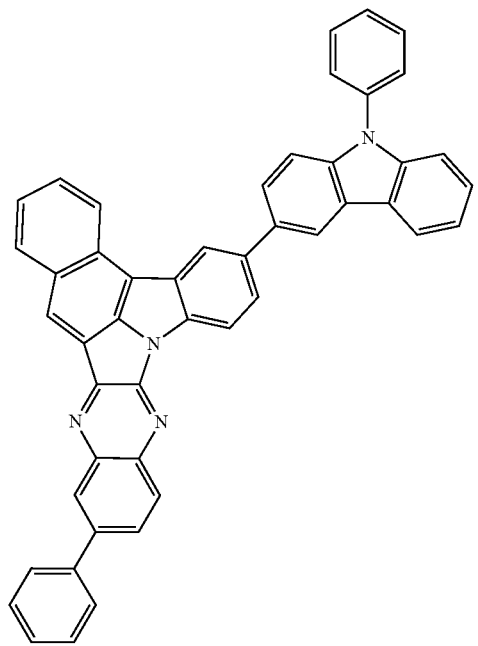
A-264
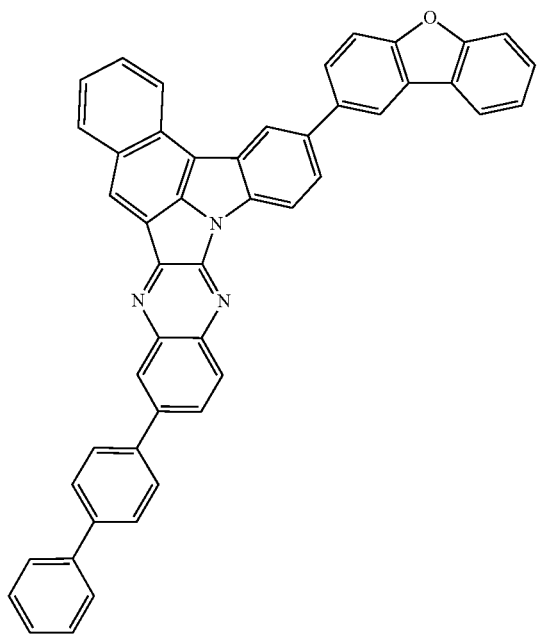

-continued
A-265
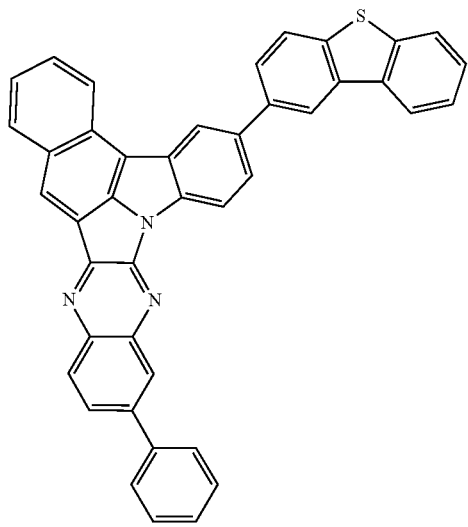
A-266
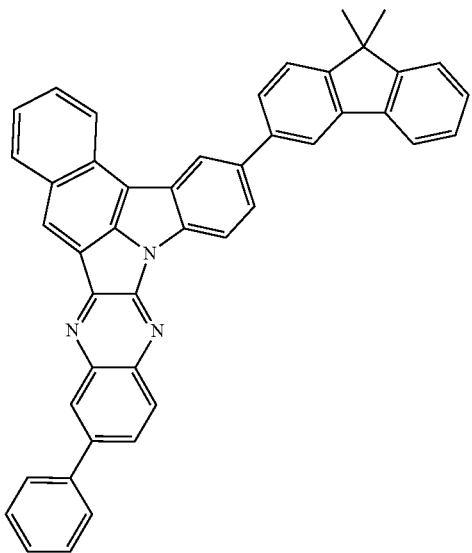
A-267
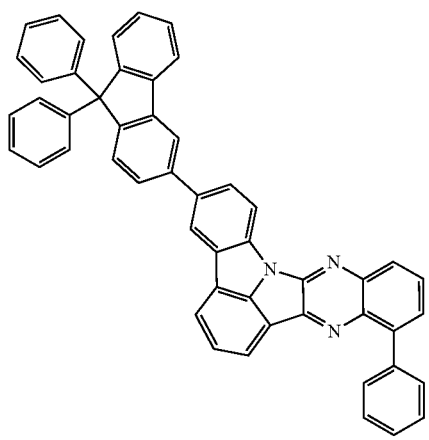
A-268
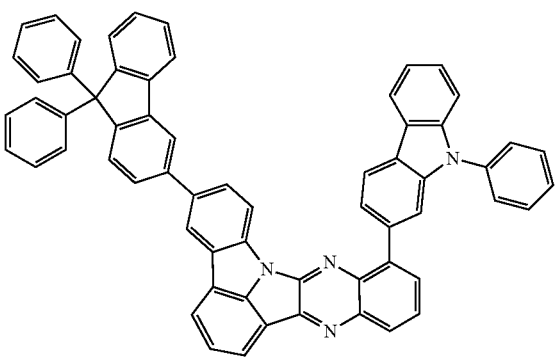
A-269
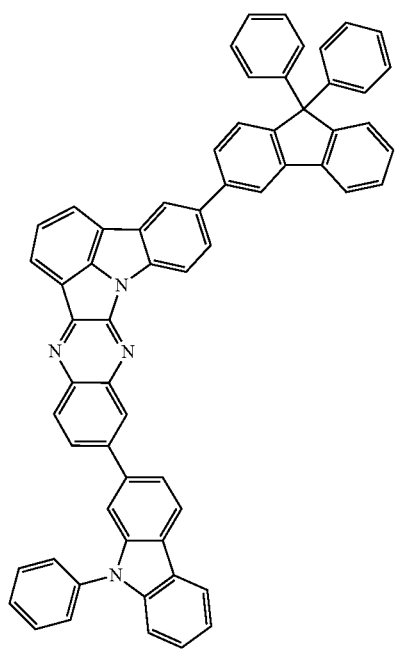
A-270
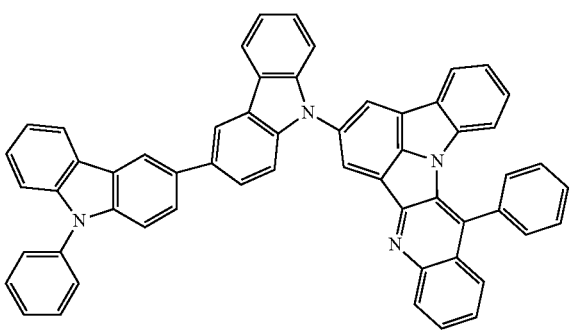

-continued
A-271
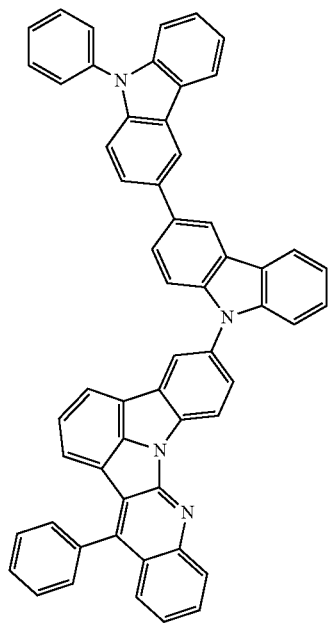
A-272
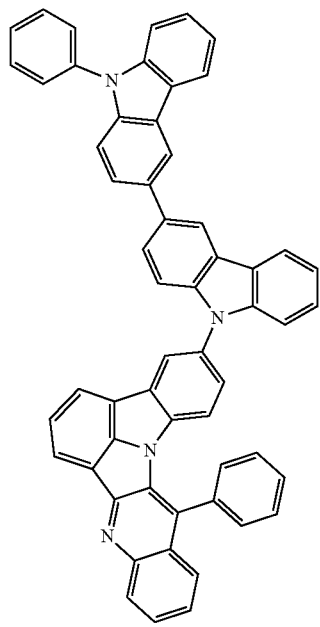
A-273
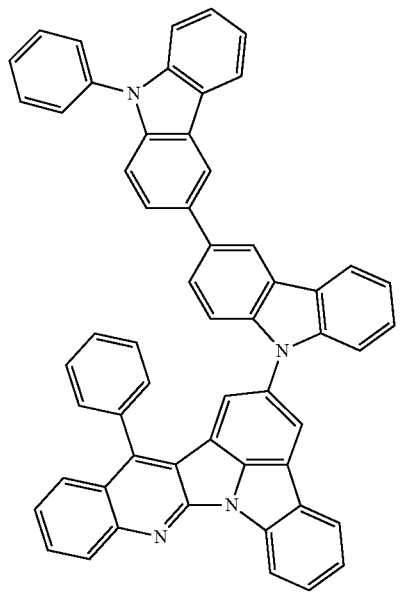
A-274
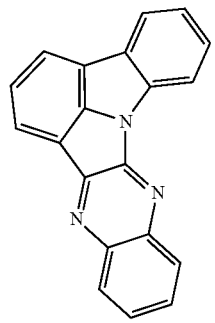
A-275
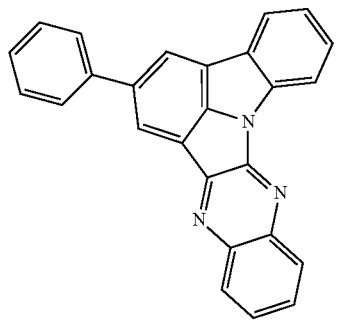
A-276
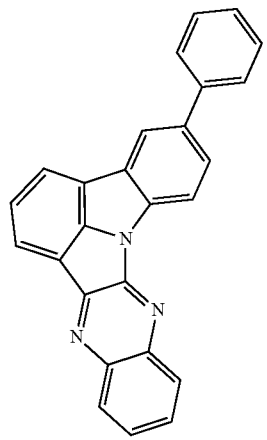

-continued
A-277
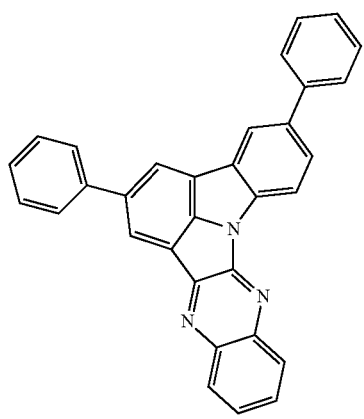
A-278
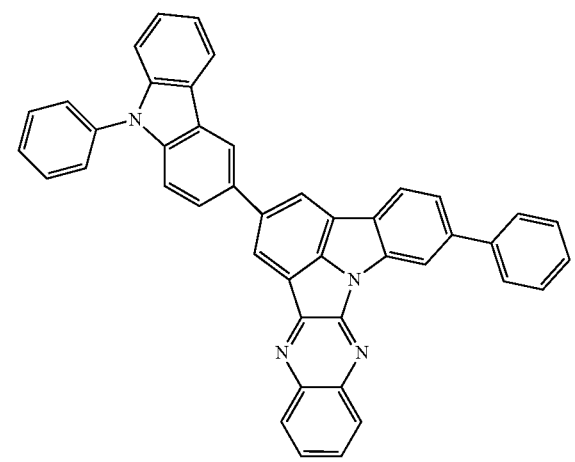
A-279
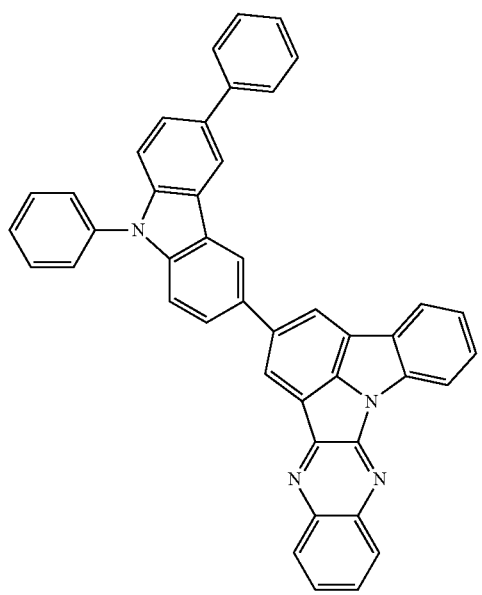
A-280
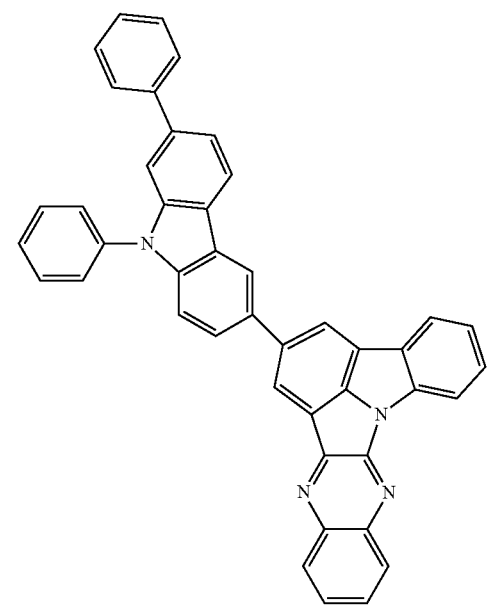
A-281
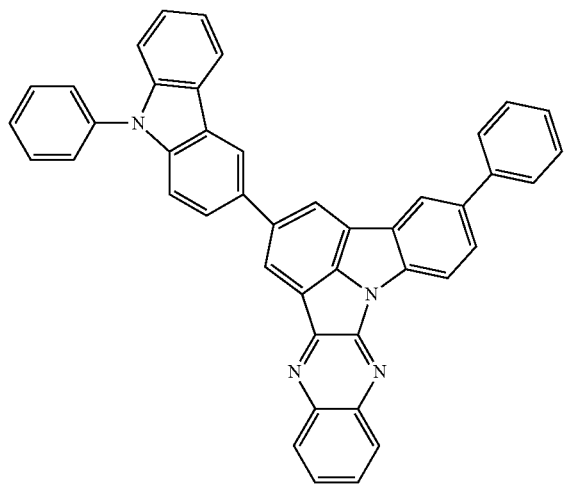
A-282
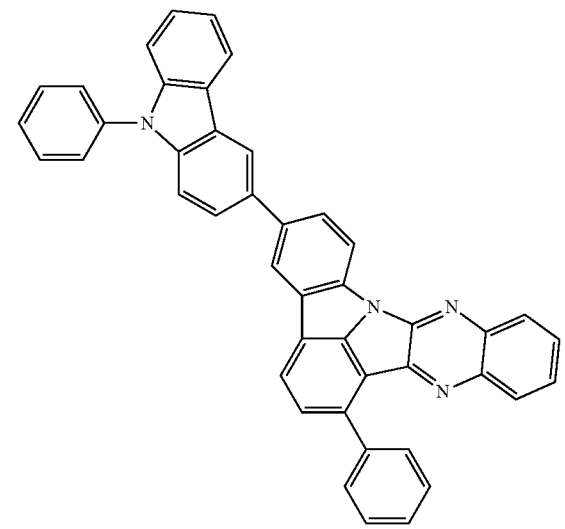

-continued
A-283
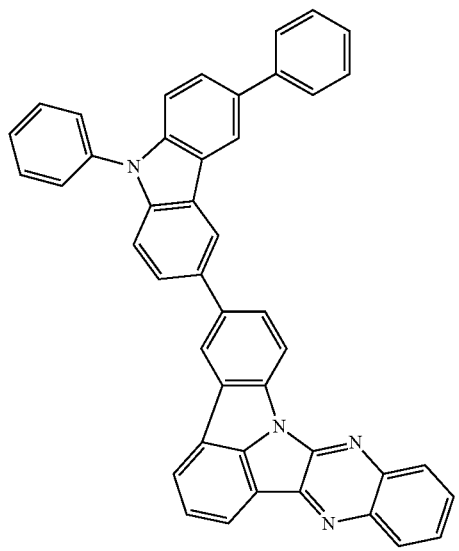
A-284
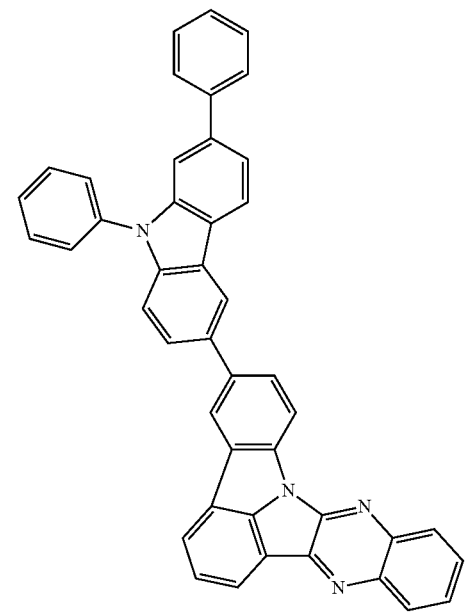
A-285
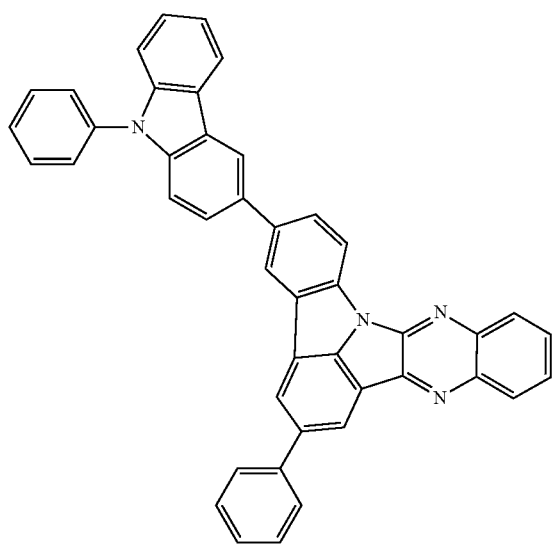
A-286
A-287
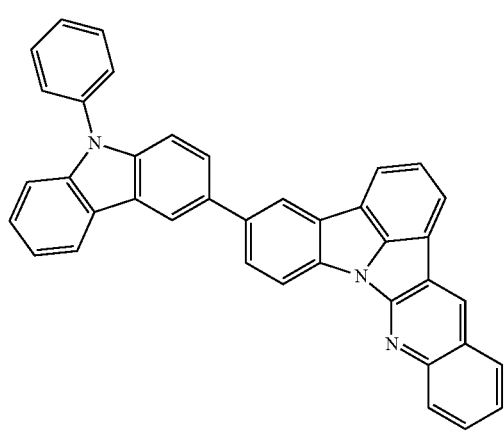
A-288
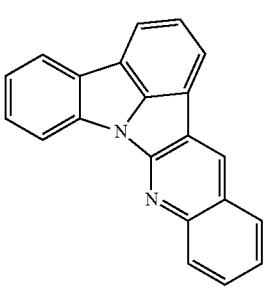

A-289

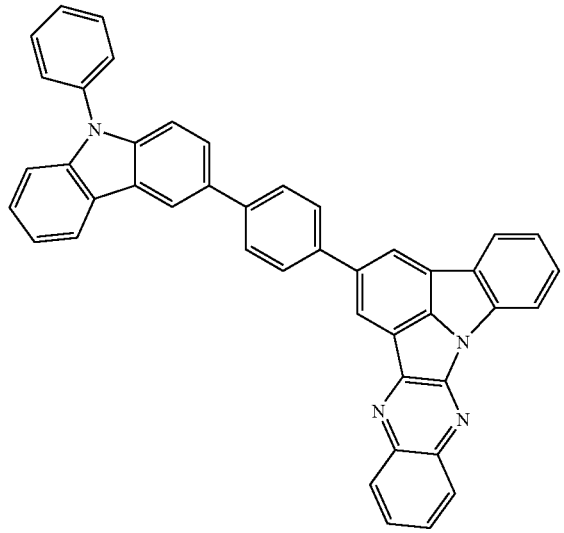

The organic electroluminescent compound of the present disclosure can be prepared by a synthetic method known to one skilled in the art. For example, it can be prepared according to the following reaction scheme 1.

[Reaction Scheme 1]

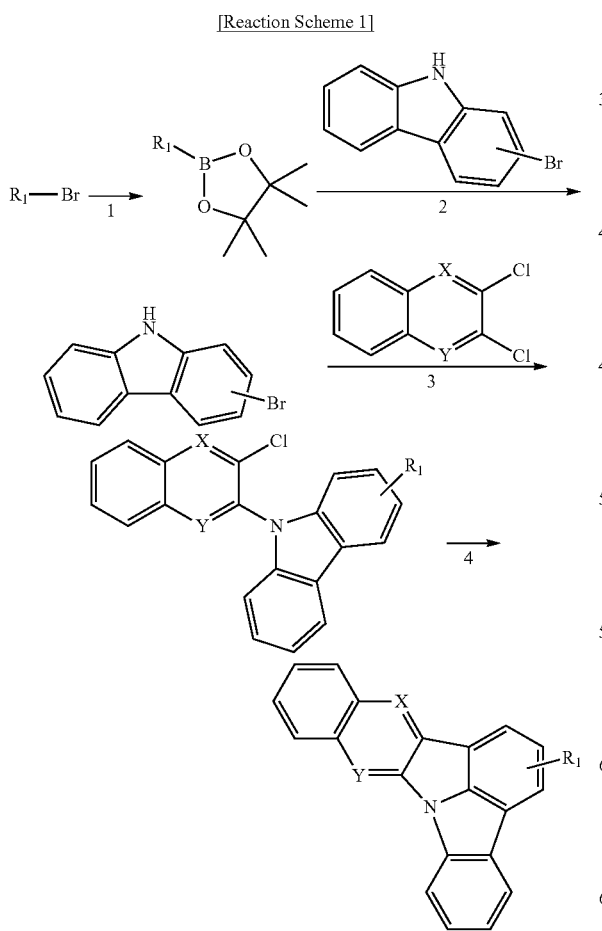

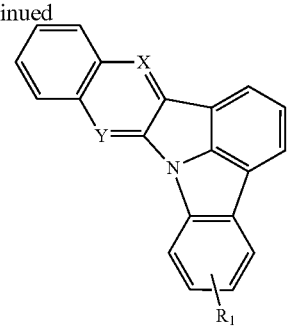

wherein $R_1$, X, and Y are as defined in formula 1 above.

In addition, the present disclosure provides an organic electroluminescent material comprising the organic electroluminescent compound of formula 1, and an organic electroluminescent device comprising the material.

The organic electroluminescent material may consist of the organic electroluminescent compound of the present disclosure. Otherwise, the material may further comprise a conventional compound(s) which has been comprised for an organic electroluminescent material.

The organic electroluminescent material may be preferably a host material, more preferably a phosphorescent host material, and even more preferably a red-emitting phosphorescent host material. When the organic electroluminescent material is used as a host material, it may further comprise a second host material described below, in addition to the compound of formula 1.

The organic electroluminescent device of the present disclosure may comprise a first electrode, a second electrode, and at least one organic layer disposed between the first and second electrodes, and the organic layer may comprise at least one compound of formula 1.

One of the first and second electrodes may be an anode, and the other may be a cathode. The organic layer may comprise a light-emitting layer. The organic layer may further comprise at least one layer selected from the group consisting of a hole injection layer, a hole transport layer, an electron transport layer, an electron injection layer, an interlayer, a hole blocking layer, an electron blocking layer, and an electron buffering layer, in addition to the light-emitting layer.

The compound of formula 1 of the present disclosure may be comprised in a light-emitting layer. When used in a light-emitting layer, the compound of formula 1 of the present disclosure may be comprised as a host material, preferably a phosphorescent host material, and more preferably a red-emitting phosphorescent host material. Preferably, the light-emitting layer may further comprise one or more dopants. If necessary, the light-emitting layer may further comprise a compound other than the compound of formula 1 of the present disclosure, as a second host material. It is preferable that a doping amount of the dopant compound is less than 20 wt % based on the total amount of the host compound and the dopant compound in a light-emitting layer. The weight ratio in the light-emitting layer between the first host material and the second host material is in the range of 1:99 to 99:1, and specifically 30:70 to 70:30 in view of driving voltage, luminous efficiency, and lifespan.

The second host material may be from any of the known phosphorescent host materials. The material selected from the group consisting of the compounds of formulae 7 to 11 below is preferable as the second host material in view of luminous efficiency.

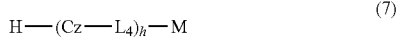
(7)

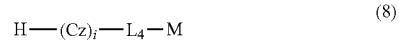
(8)

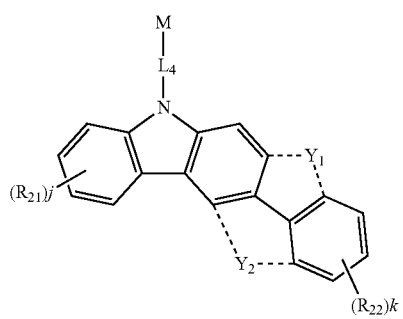
(9)

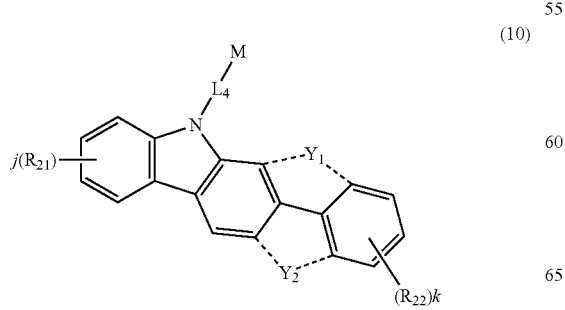
(10)

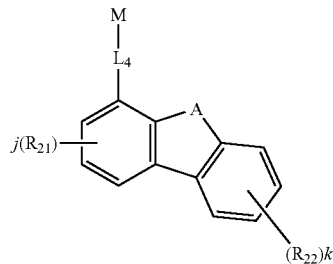
(11)

wherein Cz represents the following structure:

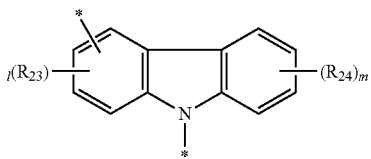

A represents —O— or —S—; $R_{21}$ to $R_{24}$, each independently, represent hydrogen, deuterium, a halogen, a substituted or unsubstituted (C1-C30)alkyl, a substituted or unsubstituted (C6-C30)aryl, a substituted or unsubstituted 5- to 30-membered heteroaryl or $R_{25}R_{26}R_{27}Si$—; $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted 5- to 30-membered heteroarylene; M represents a substituted or unsubstituted (C6-C30)aryl, or a substituted or unsubstituted 5- to 30-membered heteroaryl; $Y_1$ and $Y_2$, each independently, represent —O—, —S—, —N($R_{41}$)—, or —C($R_{42}$)($R_{43}$)—, and $Y_1$ and $Y_2$ are not present simultaneously; $R_{41}$ to $R_{43}$, each independently, represent a substituted or unsubstituted (C1-C30)alkyl, a substituted or unsubstituted (C6-C30)aryl, or a substituted or unsubstituted 5- to 30-membered heteroaryl, $R_{42}$ and $R_{43}$ may be the same or different; h and i, each independently, represent an integer of 1 to 3; j, k, l, and m, each independently, represent an integer of 0 to 4; and when h, i, j, k, l, or m is an integer of 2 or more, each of (Cz-$L_4$), (Cz), $R_{21}$, $R_{22}$, $R_{23}$ or $R_{24}$ may be the same or different.

Specifically, the second host material includes the following:

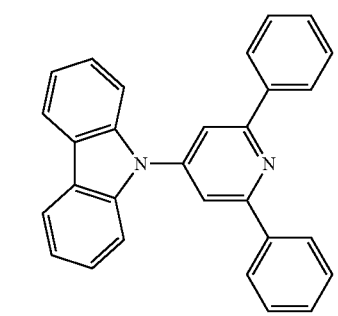

-continued
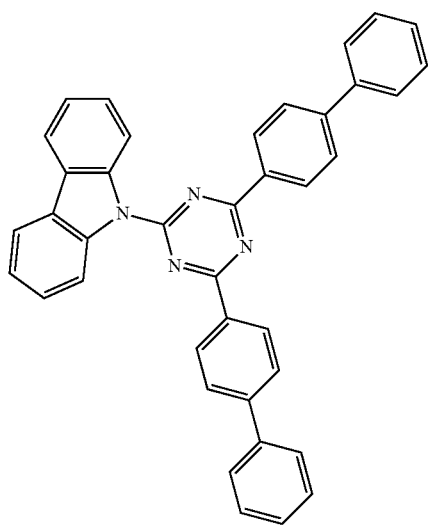
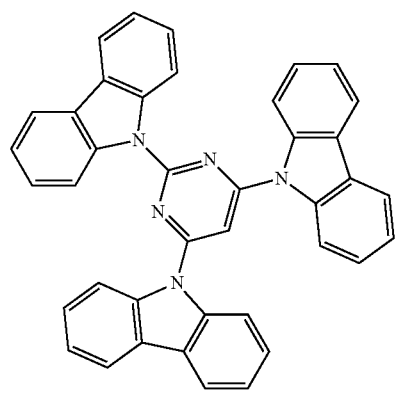
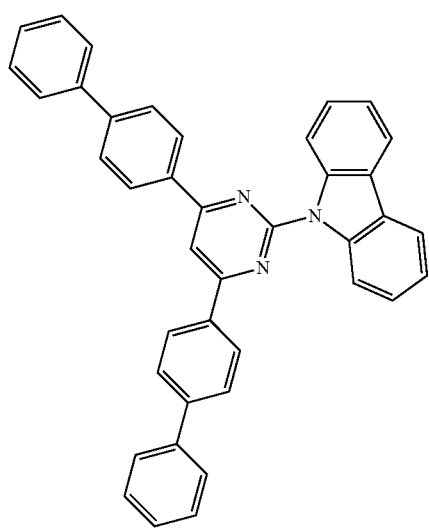
-continued
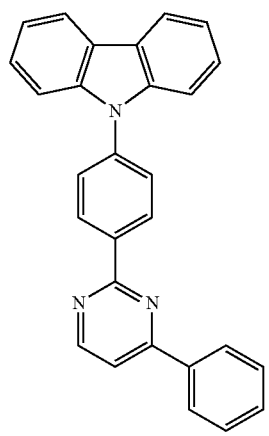
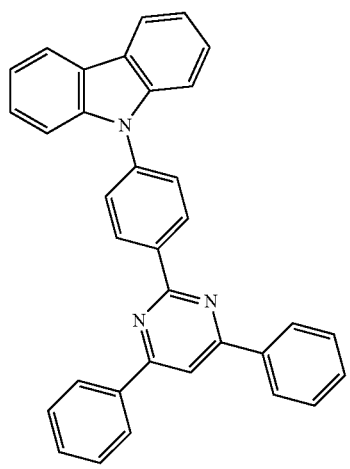
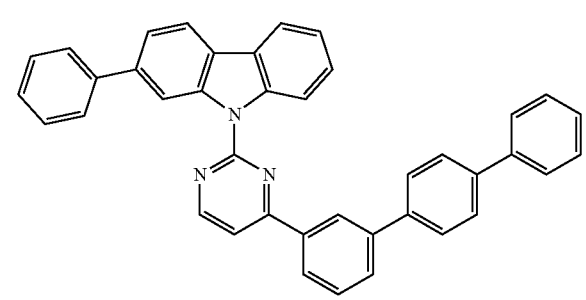
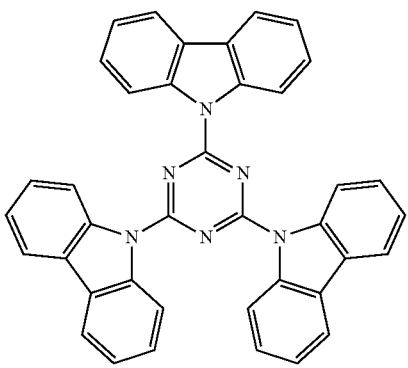

117
-continued
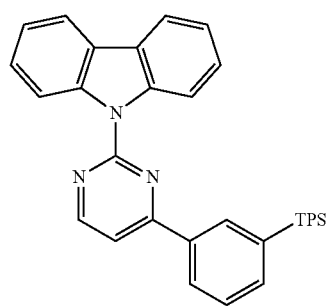
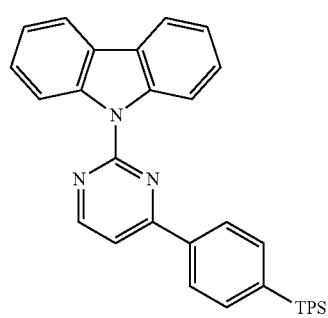
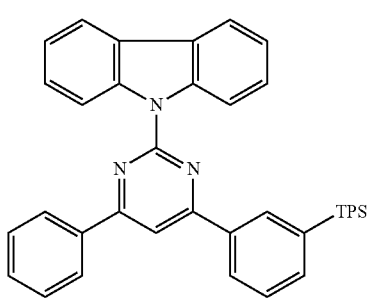
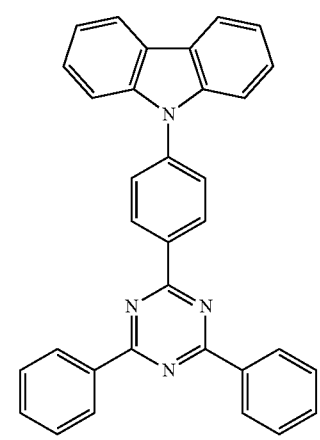
118
-continued
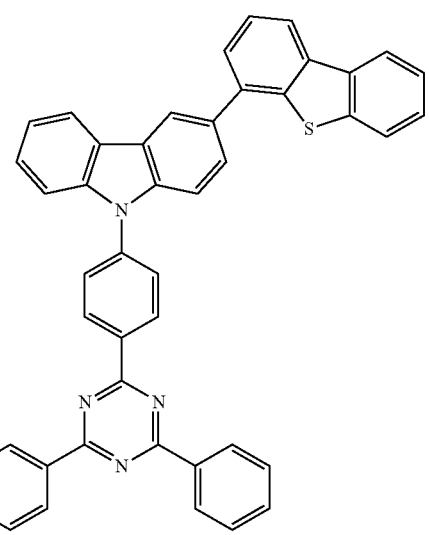
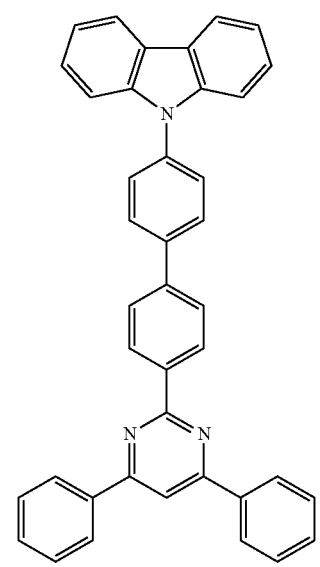
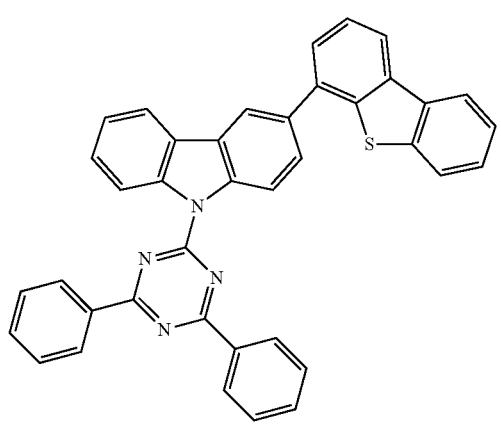

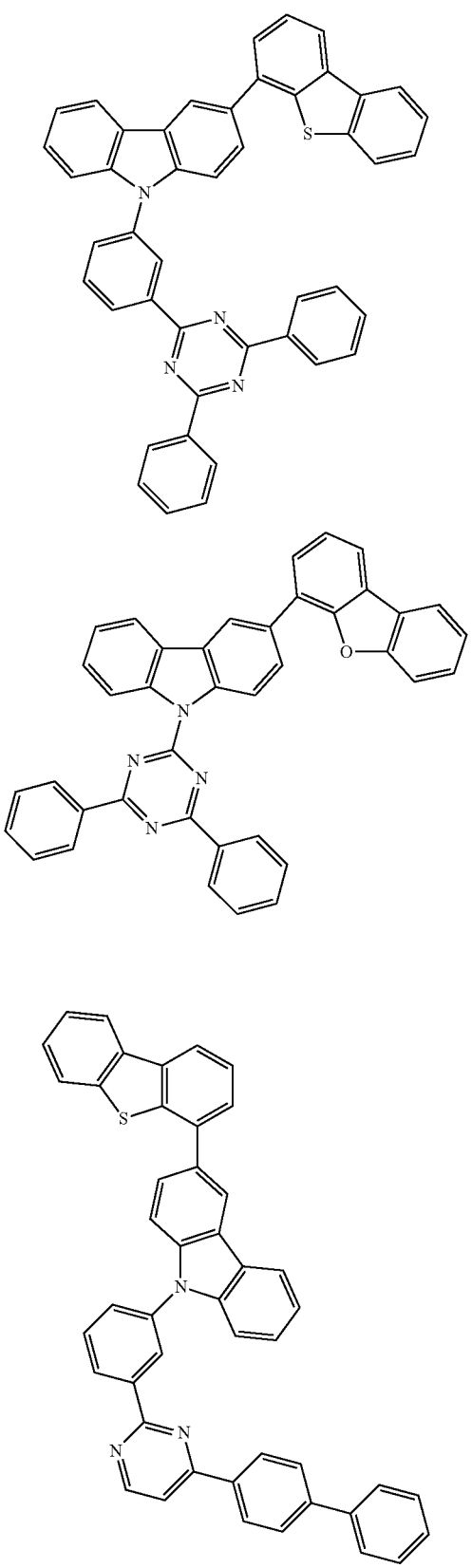
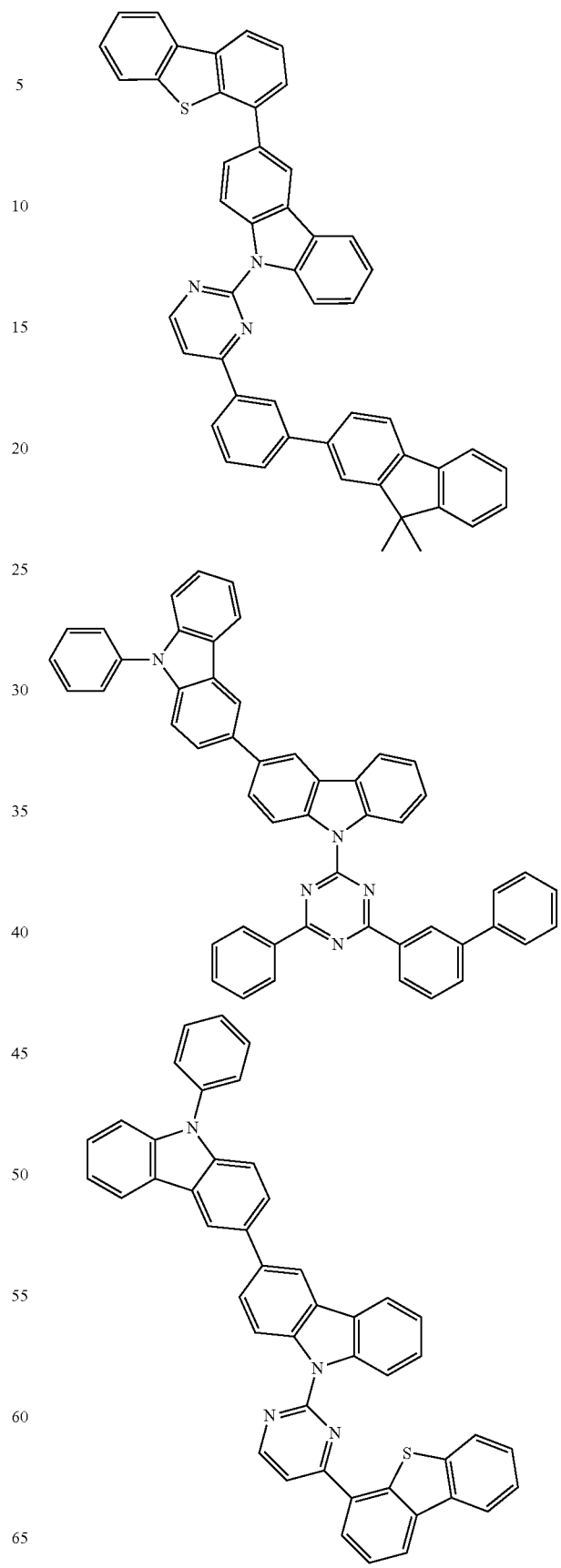

121
-continued
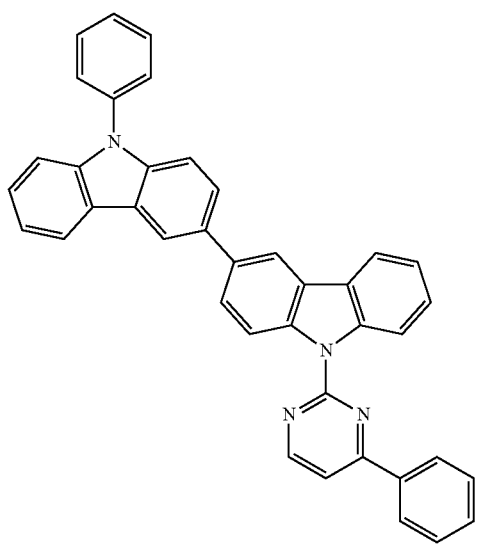
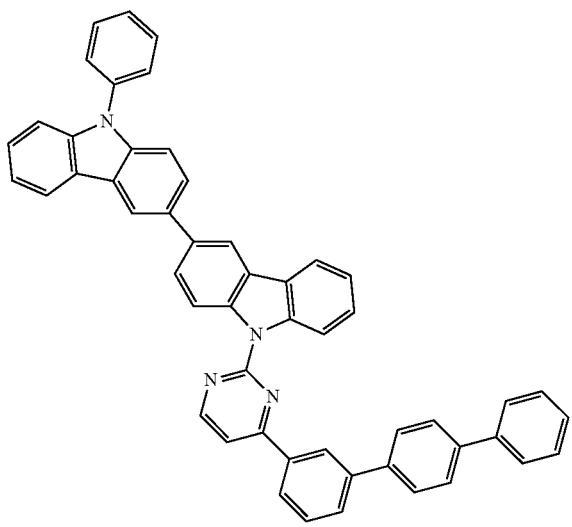
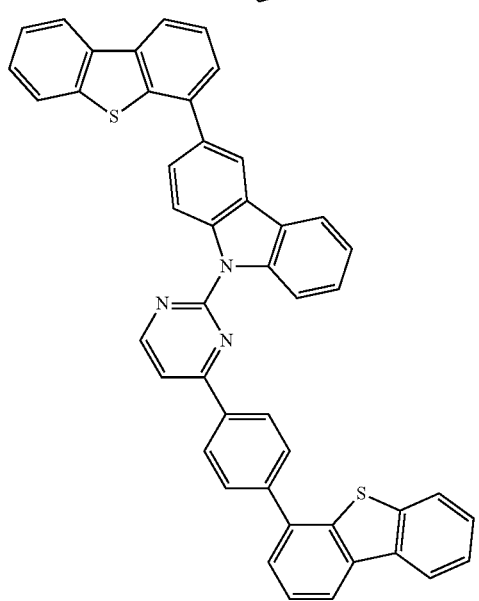
122
-continued
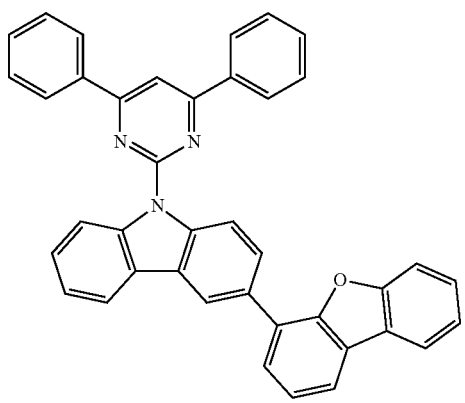
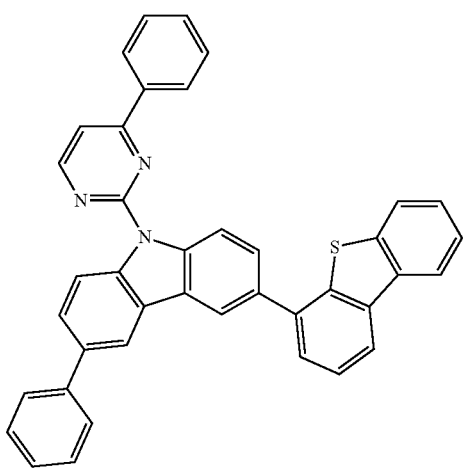
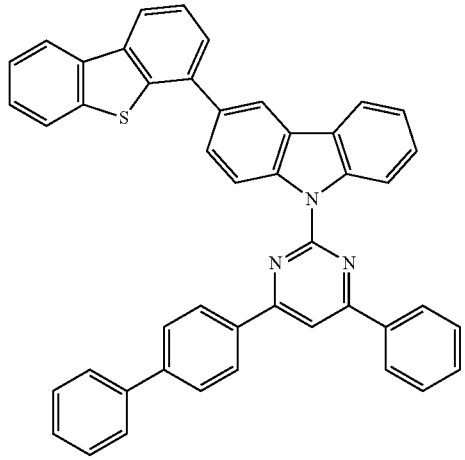

123
-continued
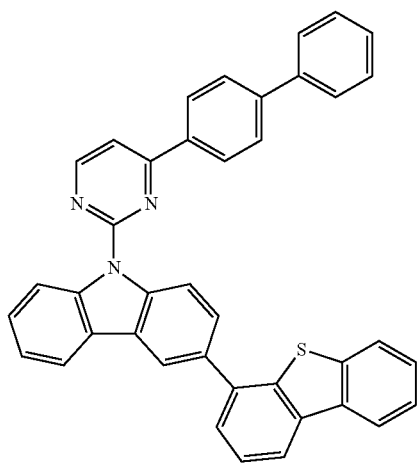
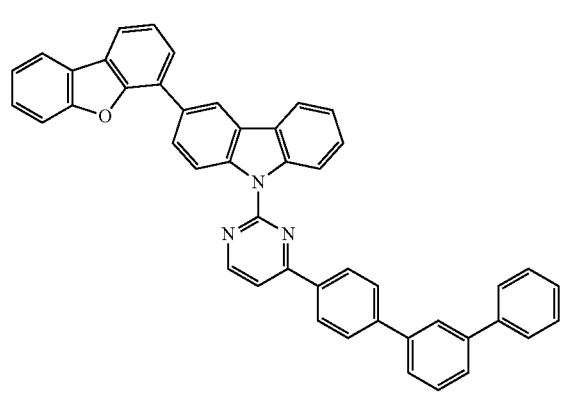
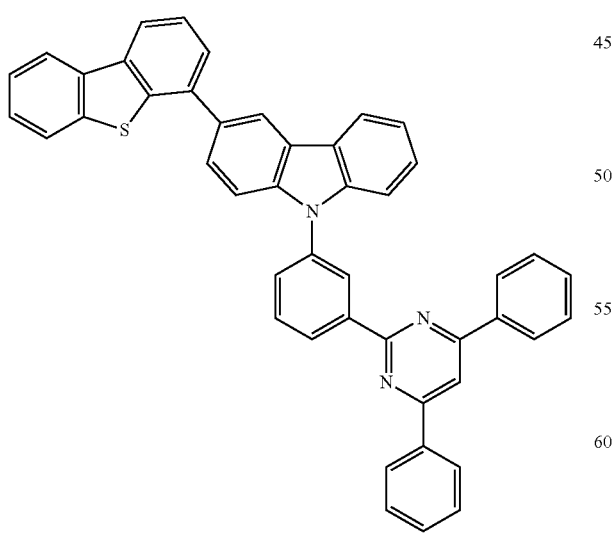
124
-continued
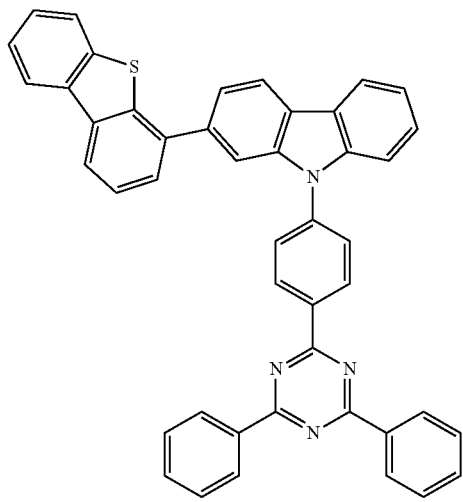
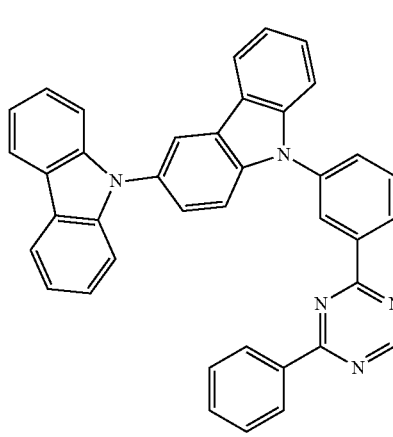
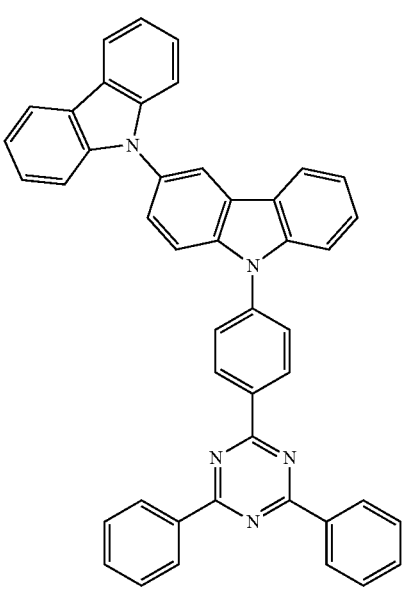

125
-continued
126
-continued
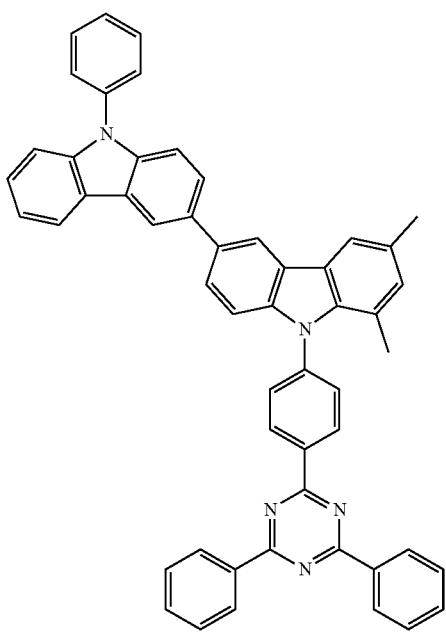
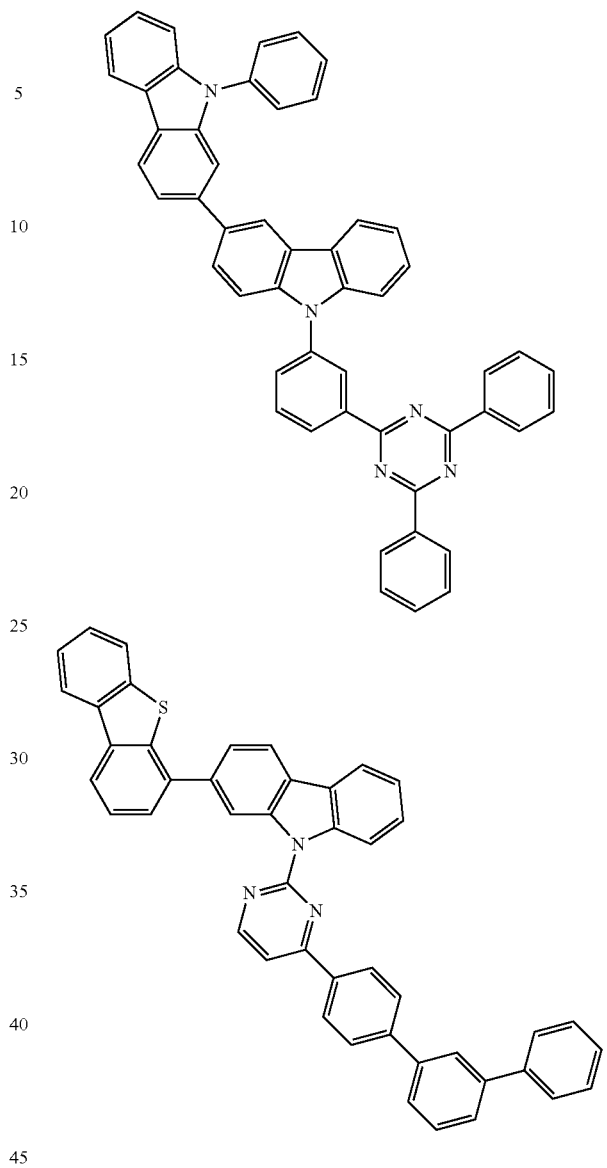
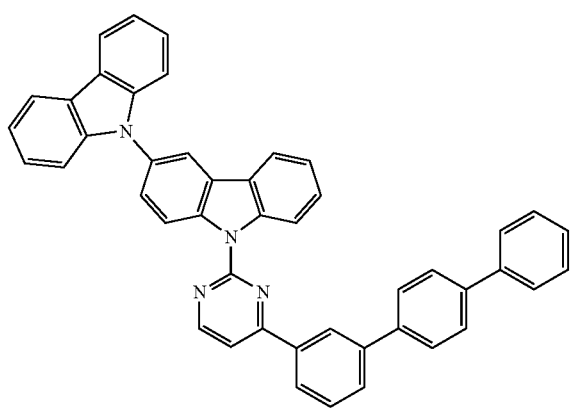
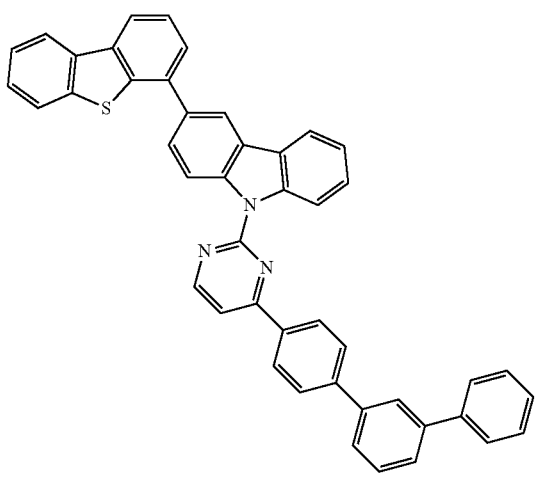

127
-continued
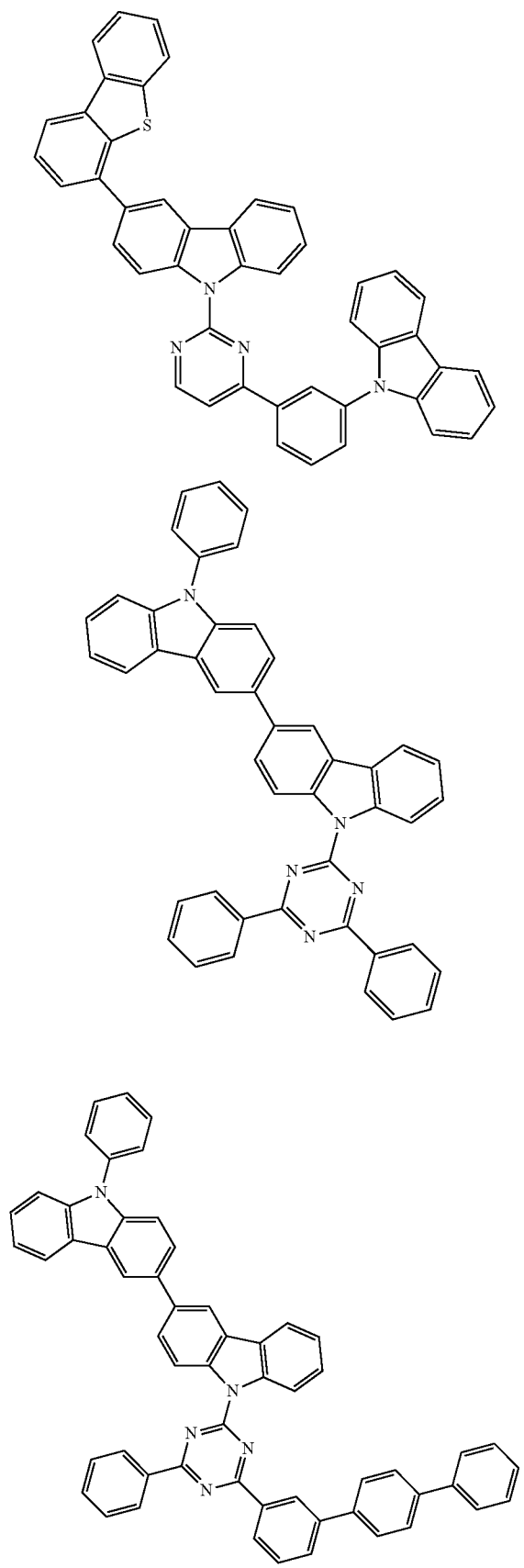
128
-continued
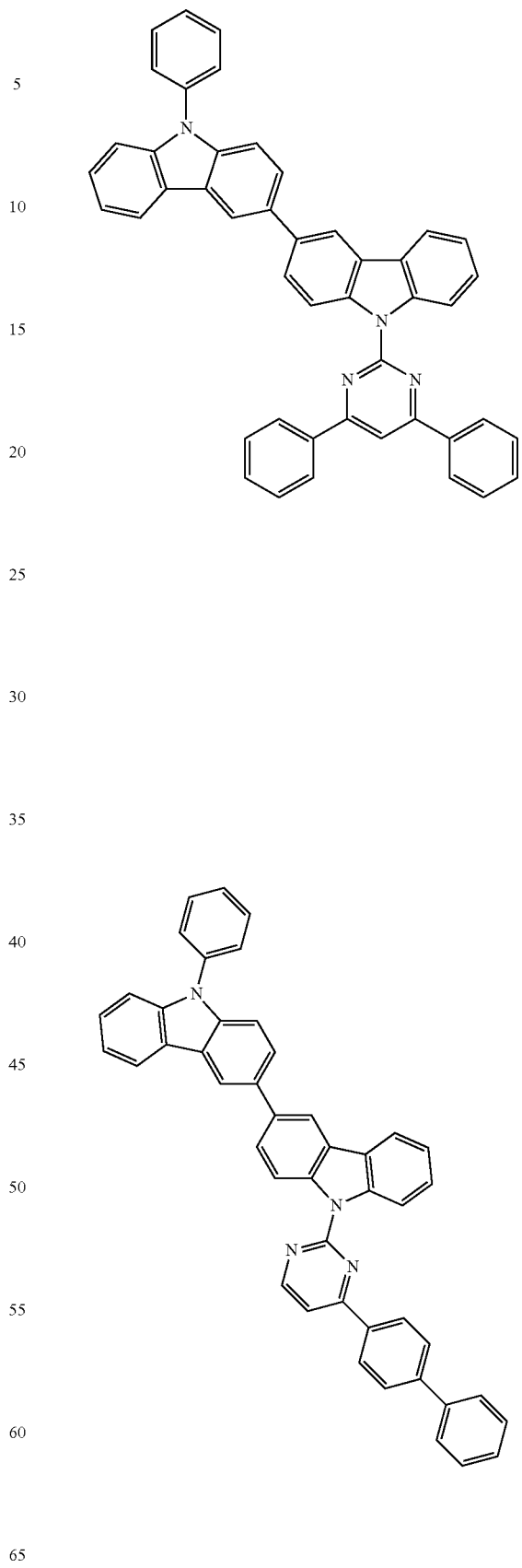

129
-continued
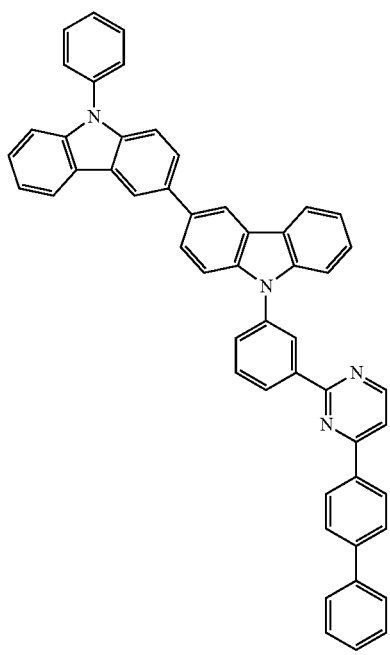
130
-continued
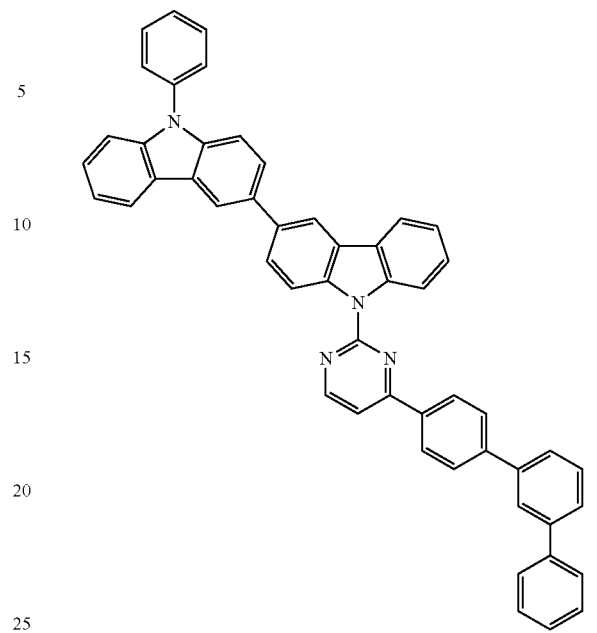
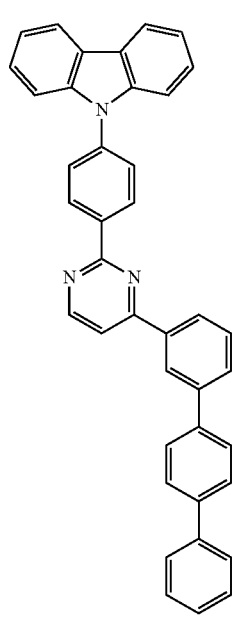
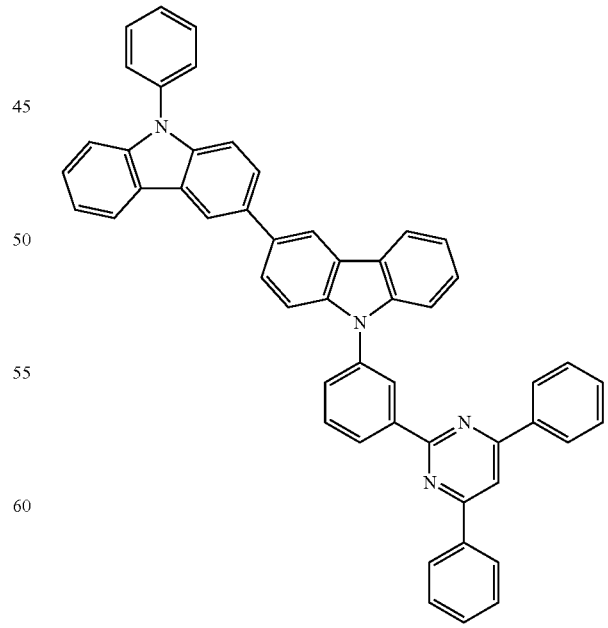

131
-continued
132
-continued
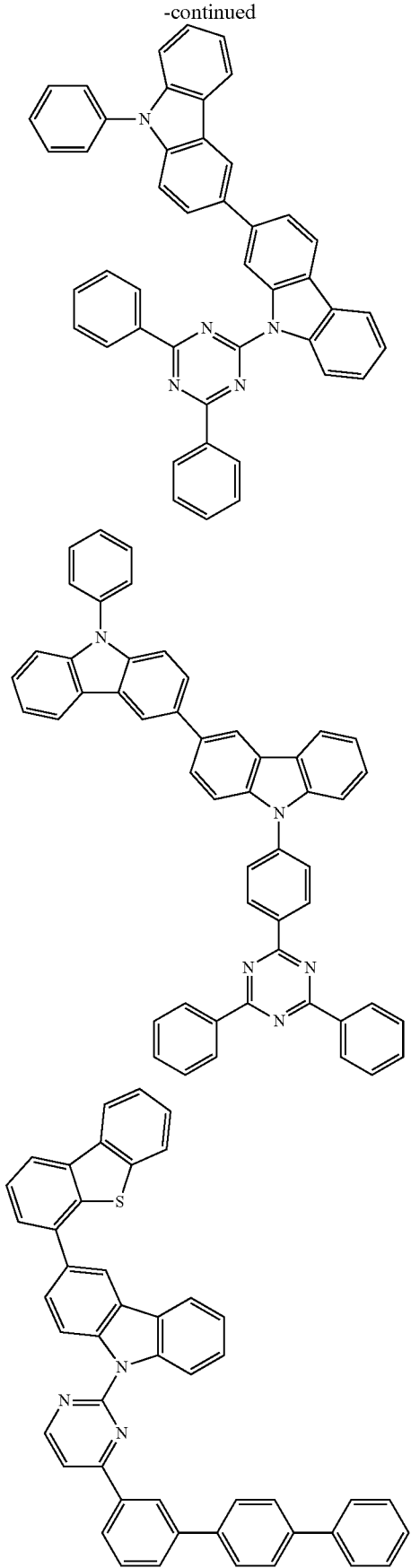
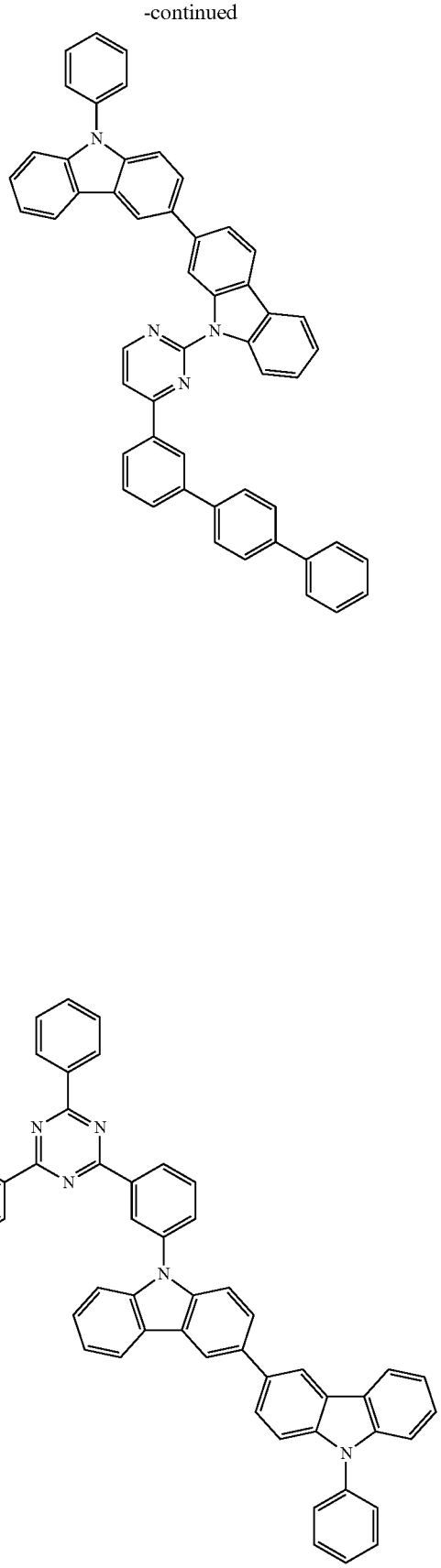

133
-continued
134
-continued
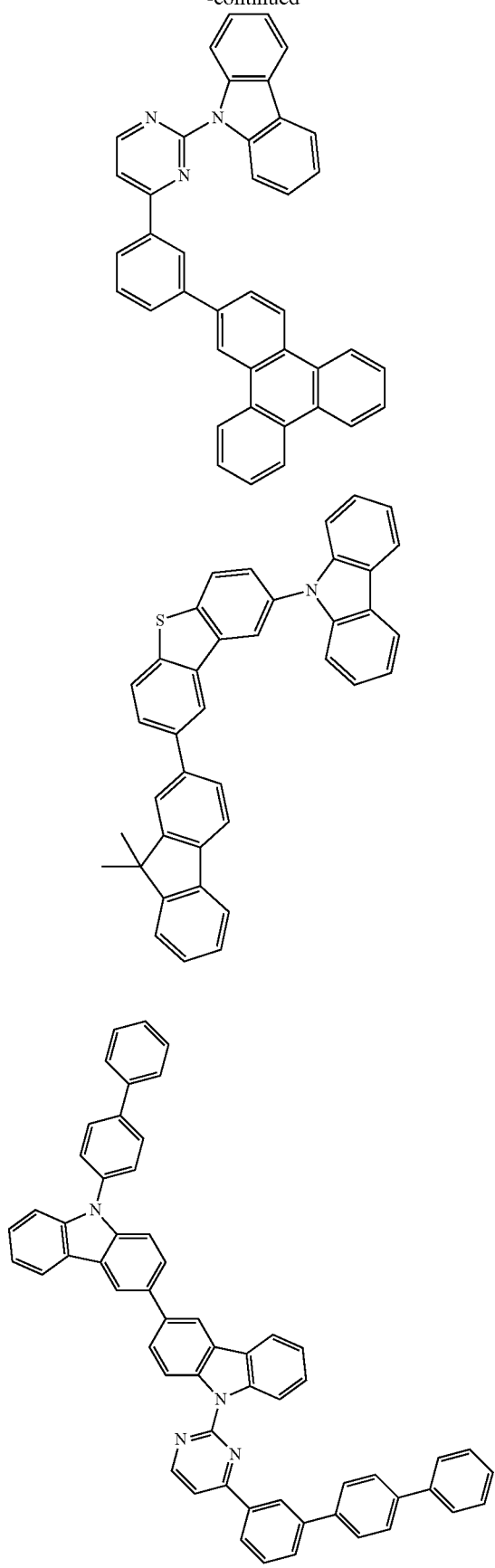
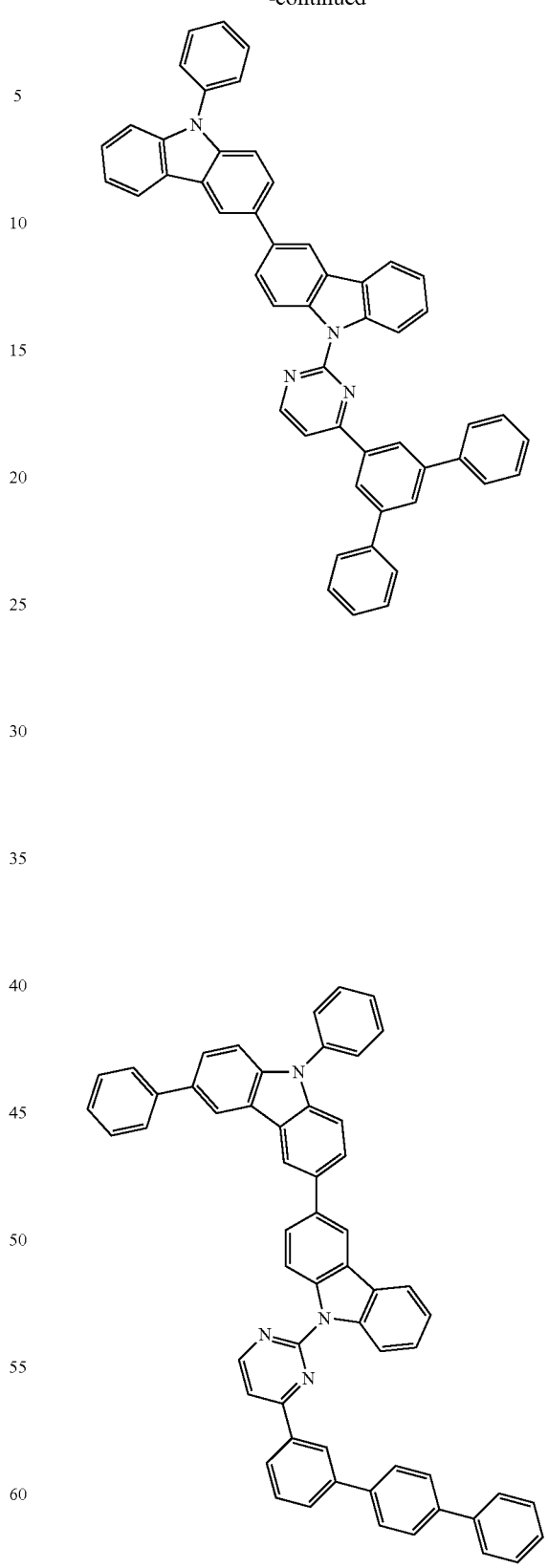

135
-continued
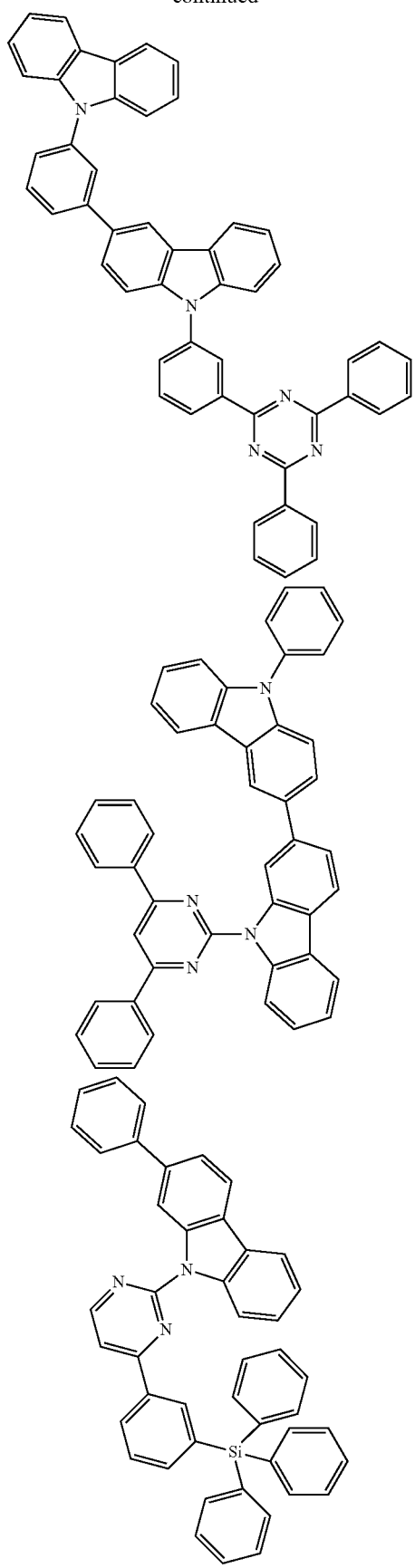
136
-continued
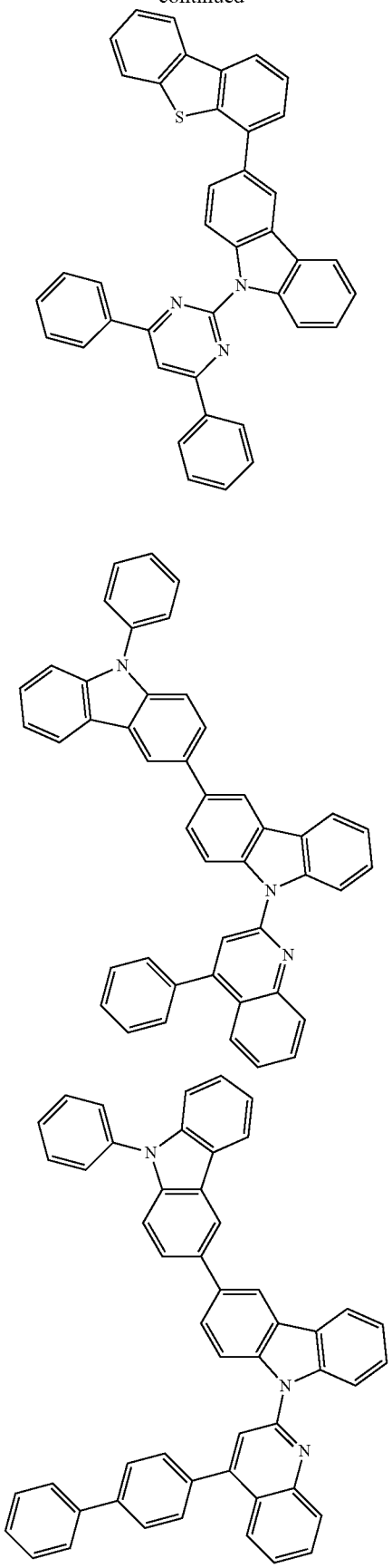

137
-continued
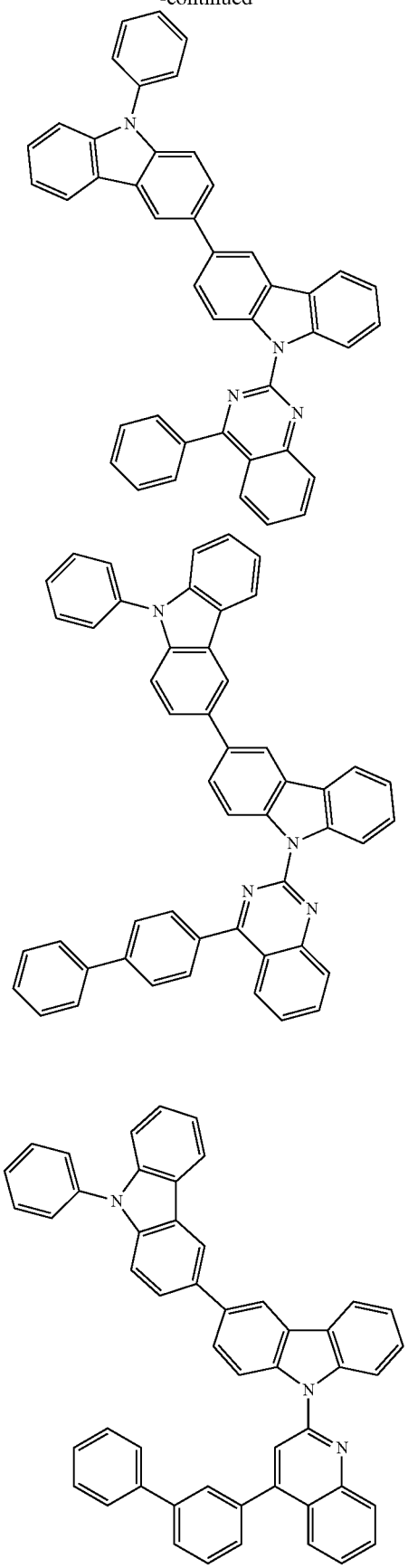
138
-continued
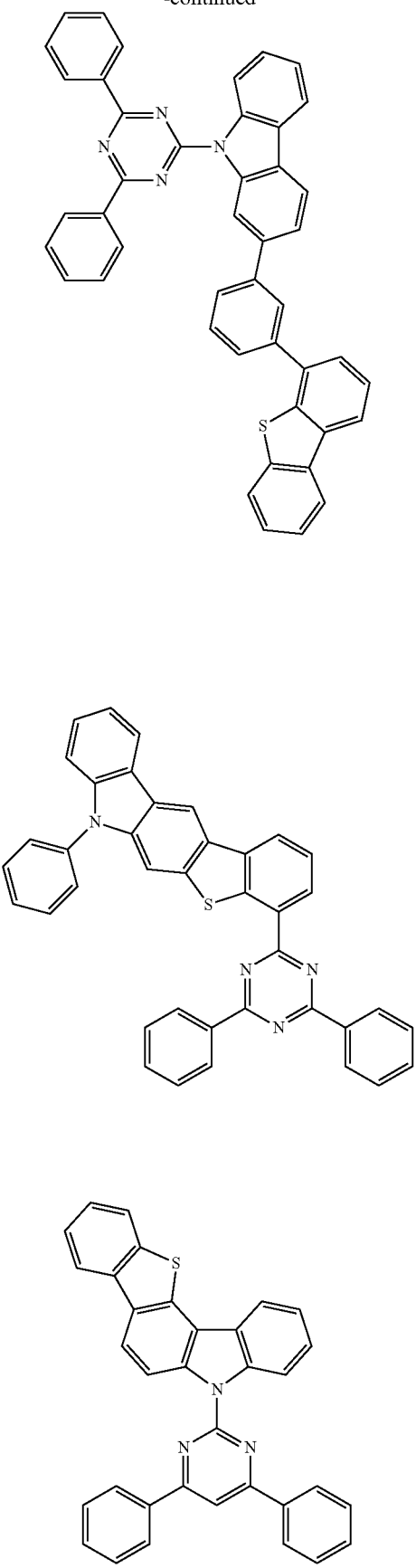

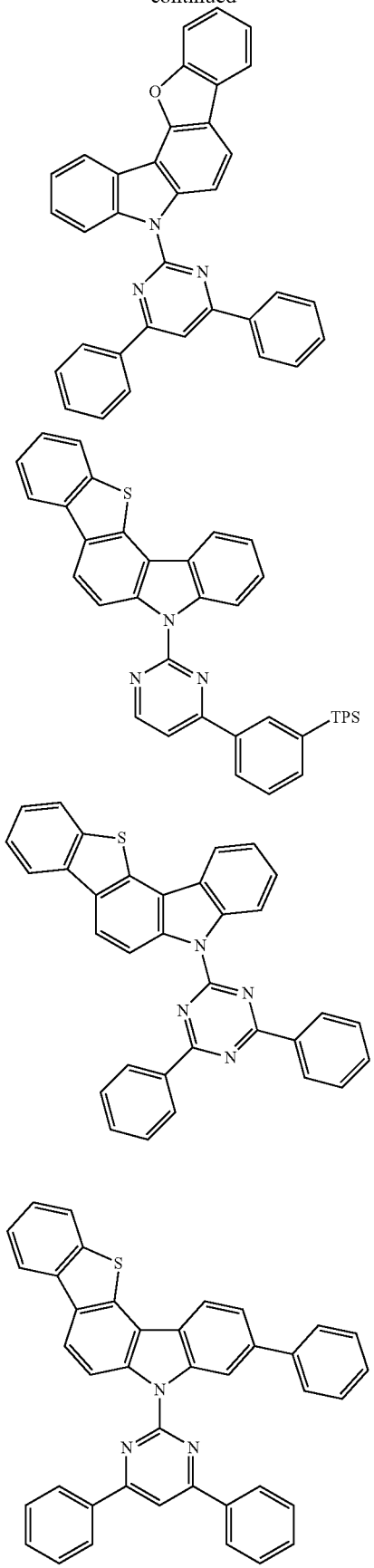
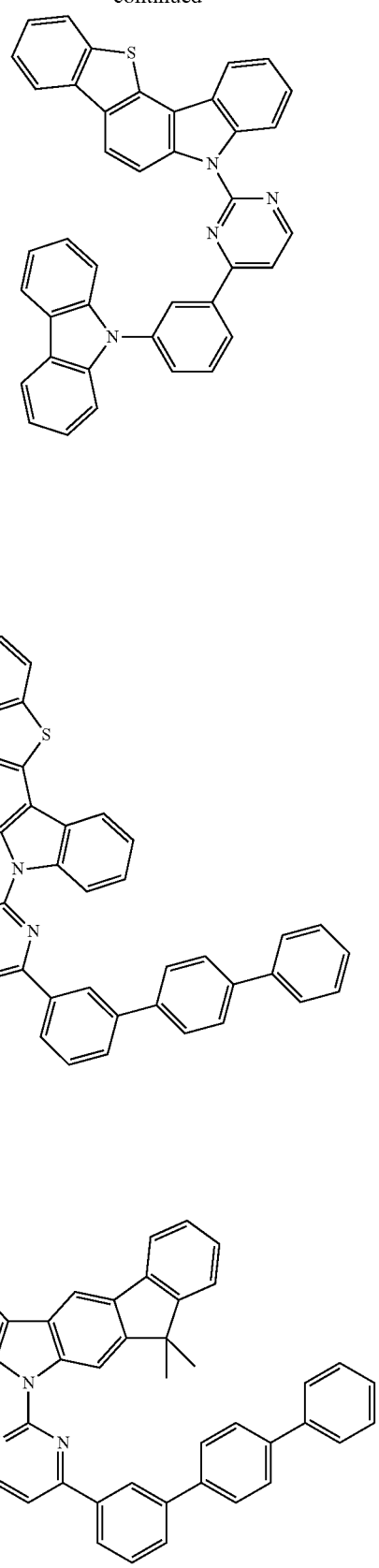

141
-continued
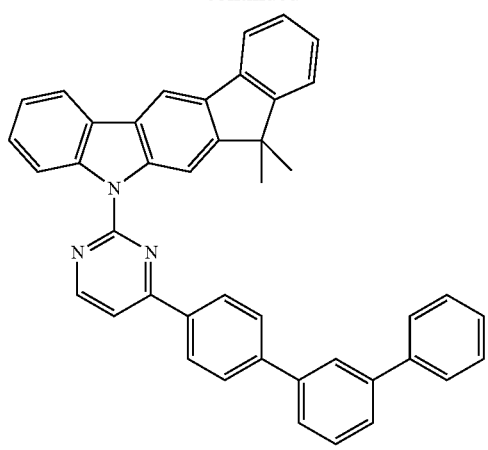
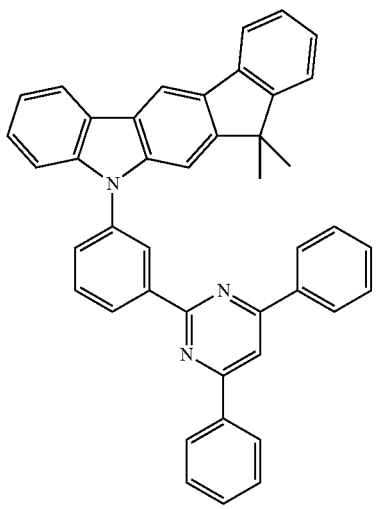
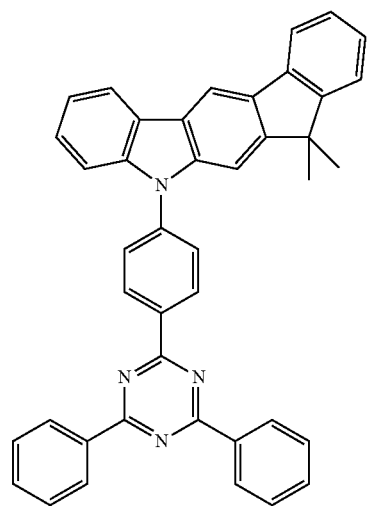
142
-continued
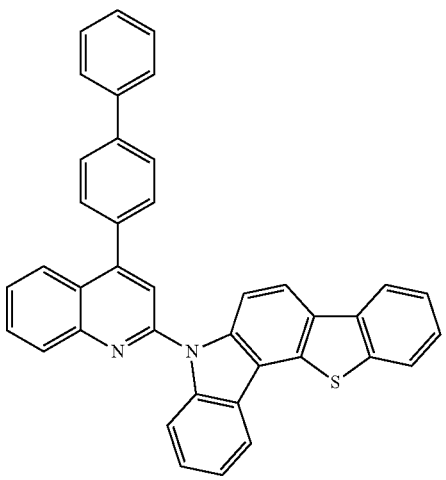
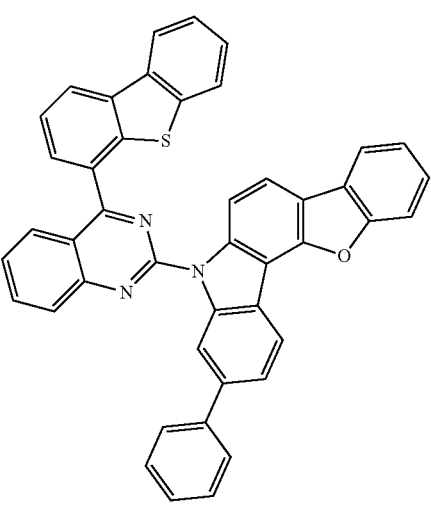
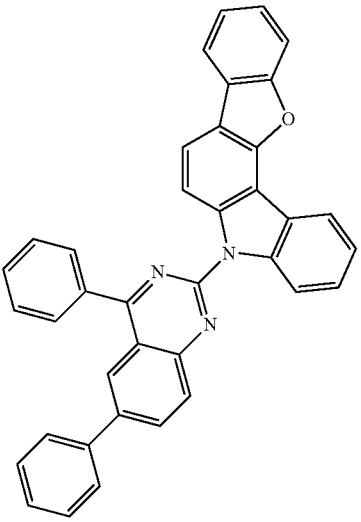

143
-continued
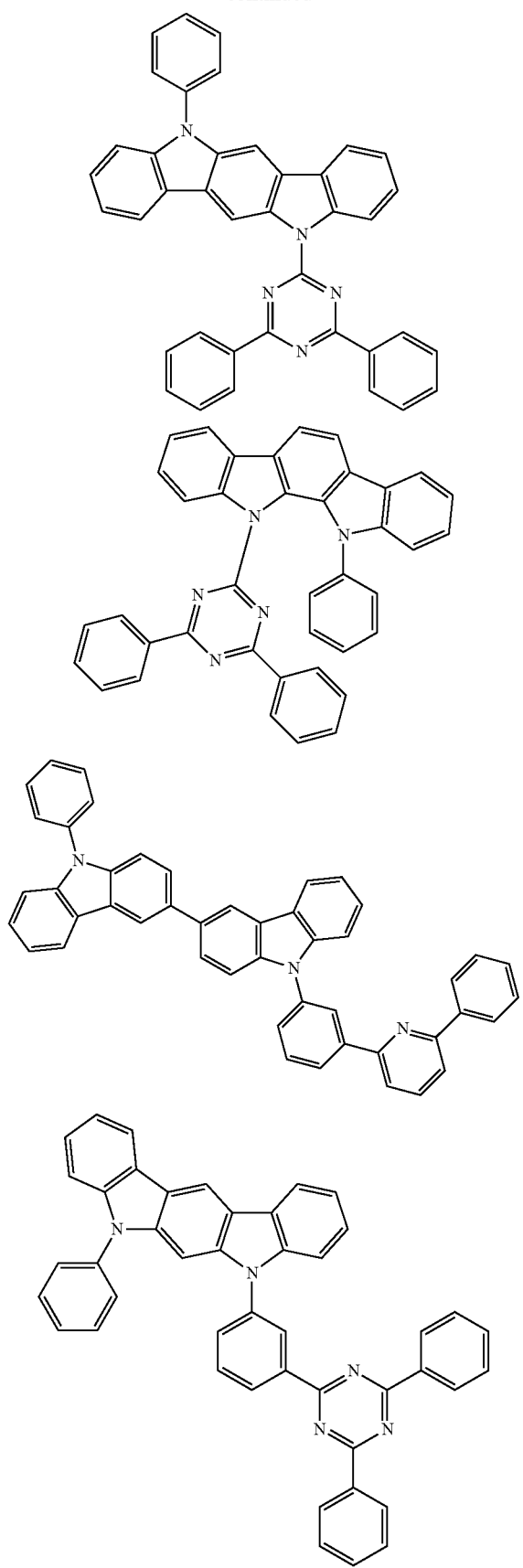
144
-continued
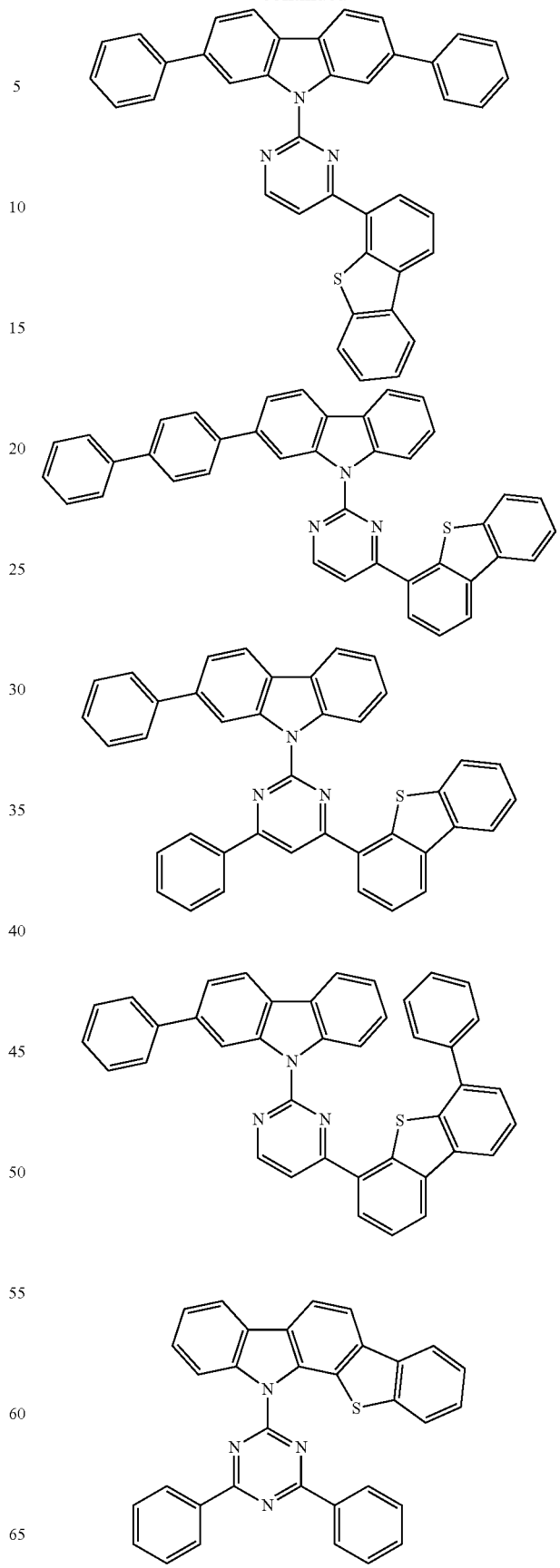

-continued

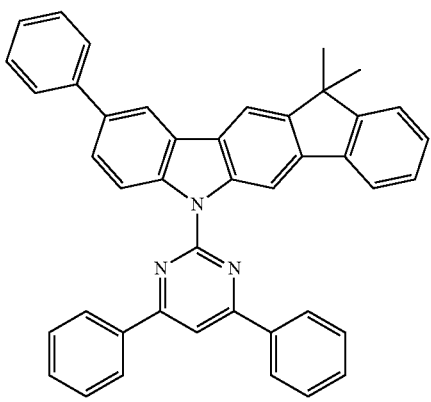

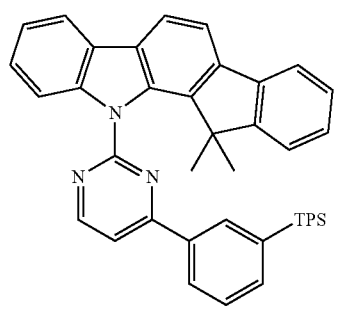

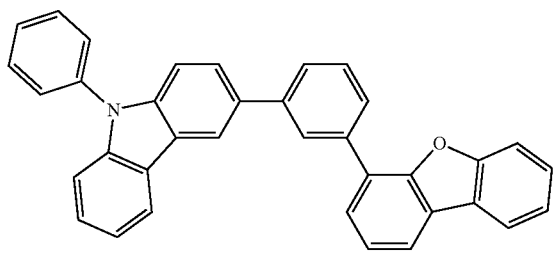

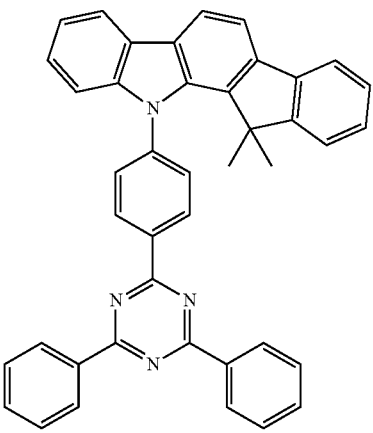

-continued

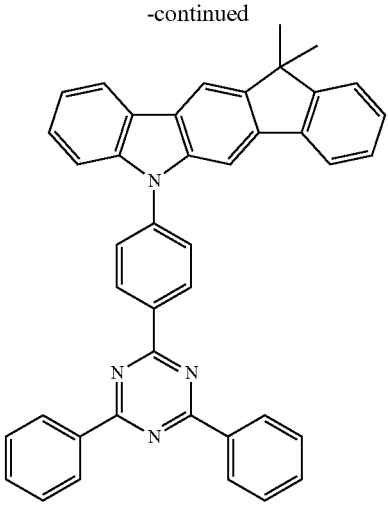

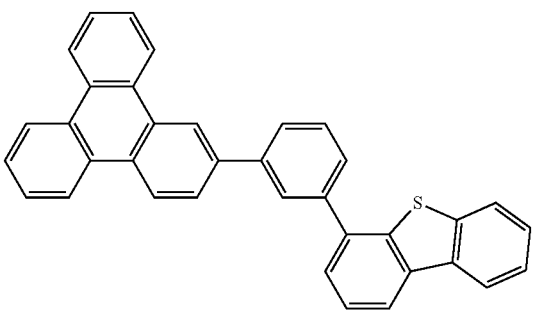

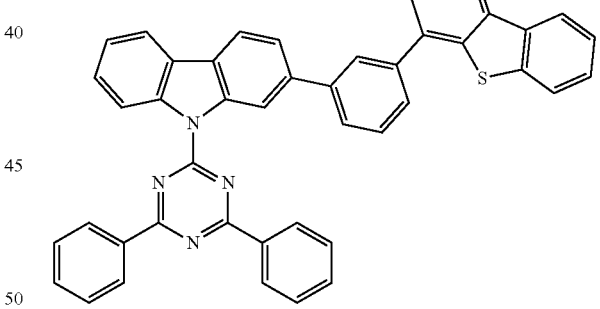

(wherein, TPS represents triphenylsilyl.)

The dopant is preferably at least one phosphorescent dopant. The phosphorescent dopant material for the organic electroluminescent device of the present disclosure is not specifically limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds.

A compound represented by any of the following formulae 12 to 14 may be used for the dopant to be comprised in the organic electroluminescent device of the present disclosure.

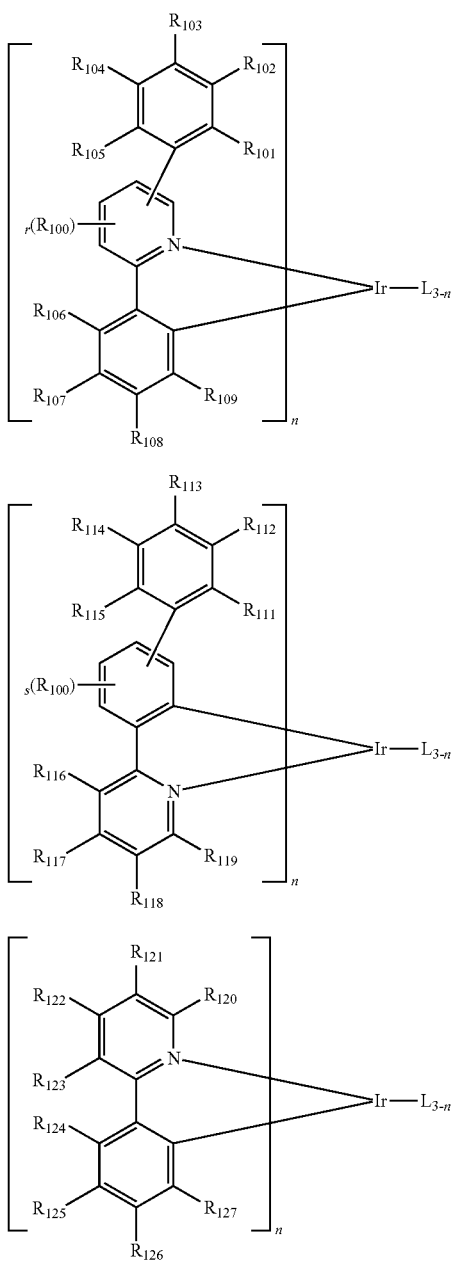

(12)

(13)

(14)

wherein L is selected from the following structures:

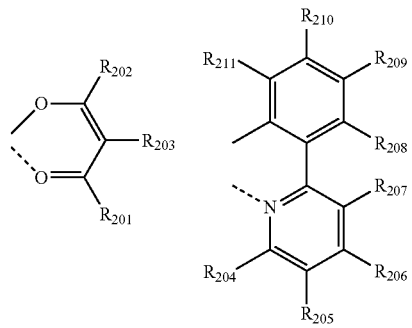

$R_{100}$ represents hydrogen, a substituted or unsubstituted (C1-C30)alkyl, or a substituted or unsubstituted (C3-C30) cycloalkyl; $R_{101}$ to $R_{109}$ and $R_{111}$ to $R_{123}$, each independently, represent hydrogen, deuterium, a halogen, a (C1-C30)alkyl unsubstituted or substituted with a halogen, a substituted or unsubstituted (C3-C30)cycloalkyl, a cyano, or a substituted or unsubstituted (C1-C30)alkoxy; $R_{106}$ to $R_{109}$ may be linked to an adjacent substituent(s) to form a substituted or unsubstituted fused ring, for example, a substituted or unsubstituted fluorene, a substituted or unsubstituted dibenzothiophene, or a substituted or unsubstituted dibenzofuran; $R_{120}$ to $R_{123}$ may be linked to an adjacent substituent(s) to form a substituted or unsubstituted fused ring, for example, a substituted or unsubstituted quinoline; $R_{124}$ to $R_{127}$, each independently, represent hydrogen, deuterium, a halogen, a substituted or unsubstituted (C1-C30) alkyl, or a substituted or unsubstituted (C1-C30)aryl; where any of $R_{124}$ to $R_{127}$ is aryl, it may be linked to an adjacent substituent(s) to form a substituted or unsubstituted fused ring, for example, a substituted or unsubstituted fluorene, a substituted or unsubstituted dibenzofuran, or a substituted or unsubstituted dibenzothiophene; $R_{201}$ to $R_{211}$, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; $R_{208}$ to $R_{211}$ may be linked to an adjacent substituent(s) to form a substituted or unsubstituted fused ring, for example, a substituted or unsubstituted fluorene, a substituted or unsubstituted dibenzothiophene, or a substituted or unsubstituted dibenzofuran; r and s, each independently, represent an integer of 1 to 3; when r or s is an integer of 2 or more, each of $R_{100}$ may be the same or different; and n represents an integer of 1 to 3.

Specifically, the dopant material includes the following:

D-1

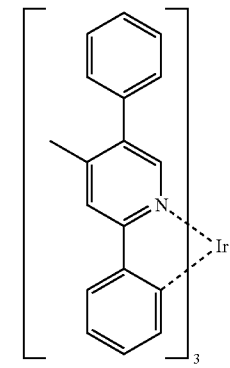

D-2

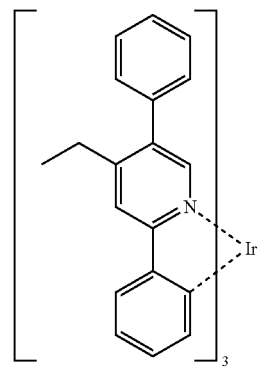

-continued
D-3
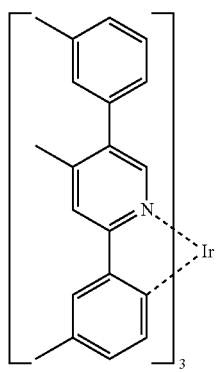
D-4
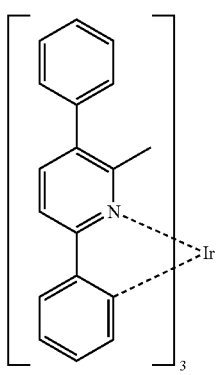
D-5
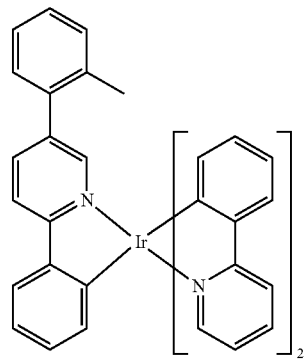
D-6
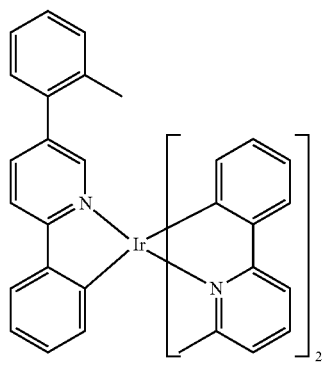
D-7
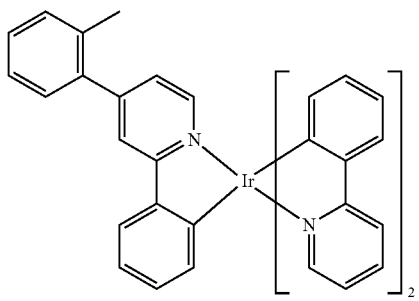
D-8
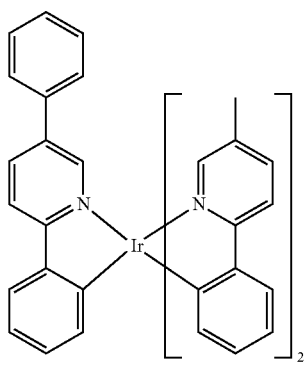
D-9
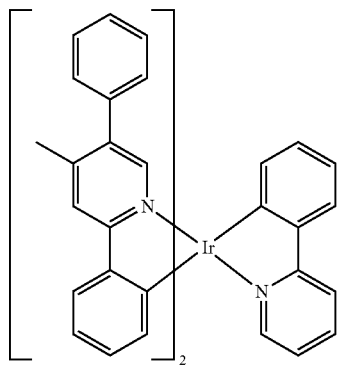
D-10
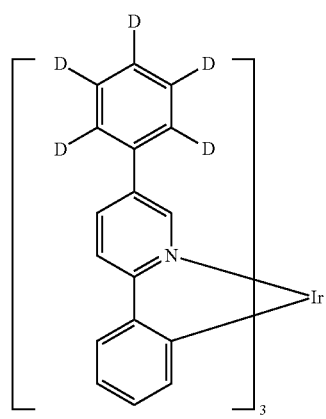

-continued
D-11 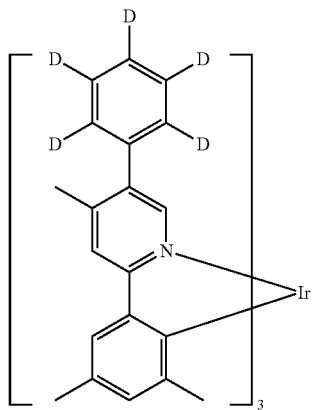
D-12 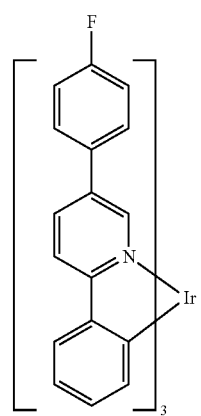
D-13 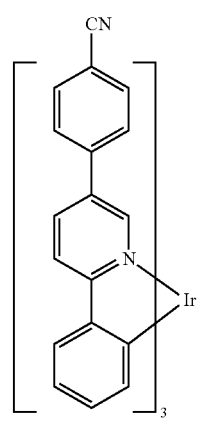
-continued
D-14 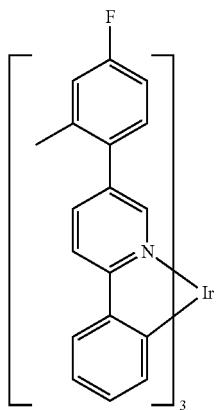
D-15 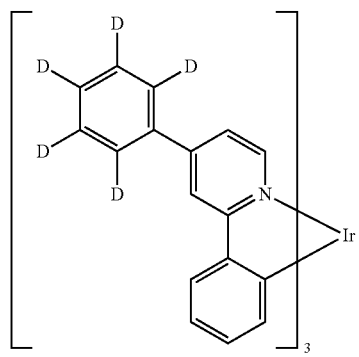
D-16 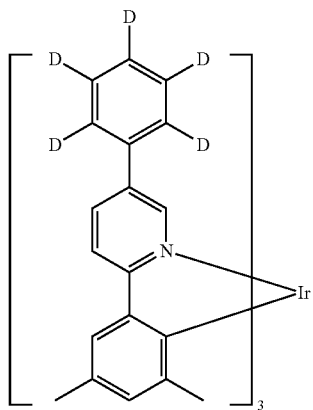
D-17 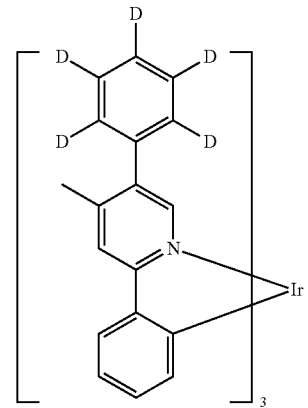

D-18
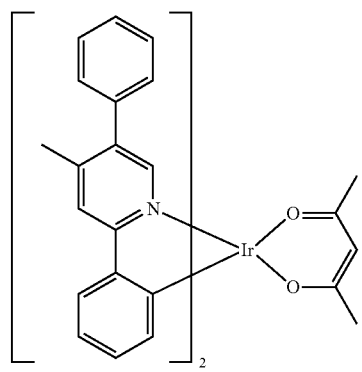
D-19
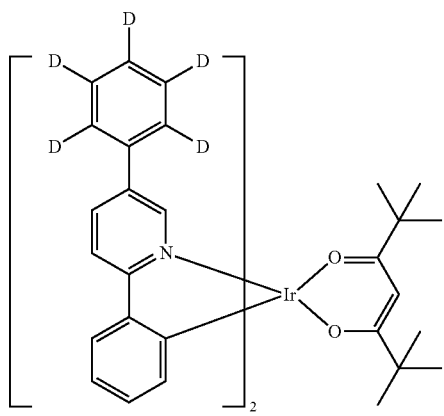
D-20
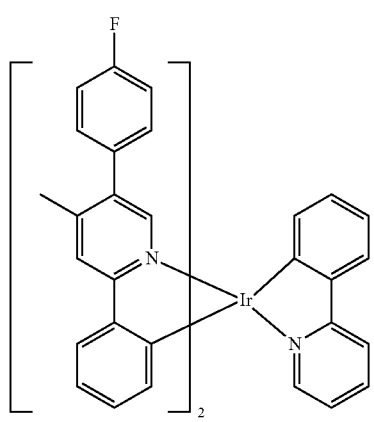
D-21
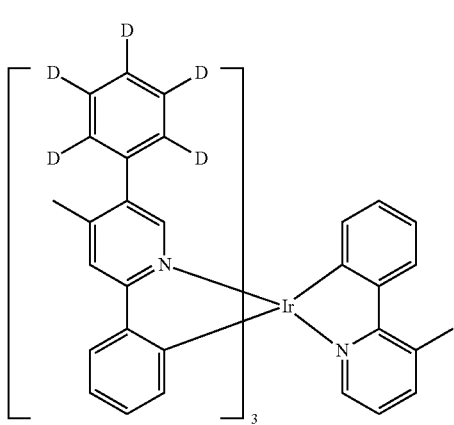
D-22
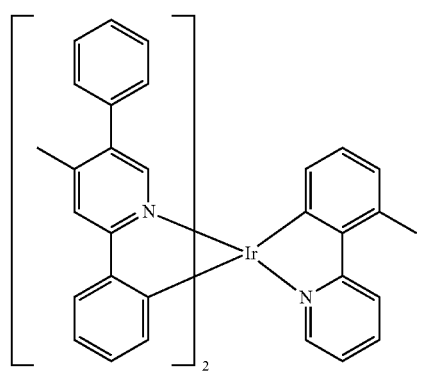
D-23
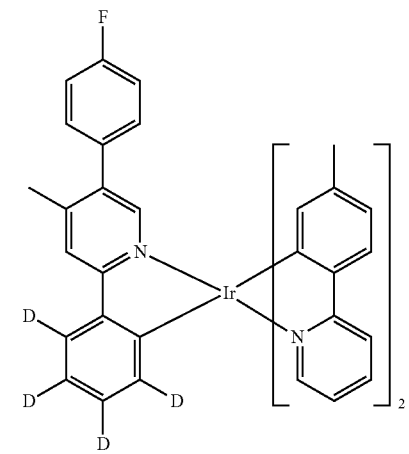
D-24
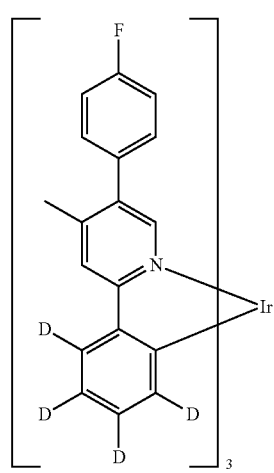

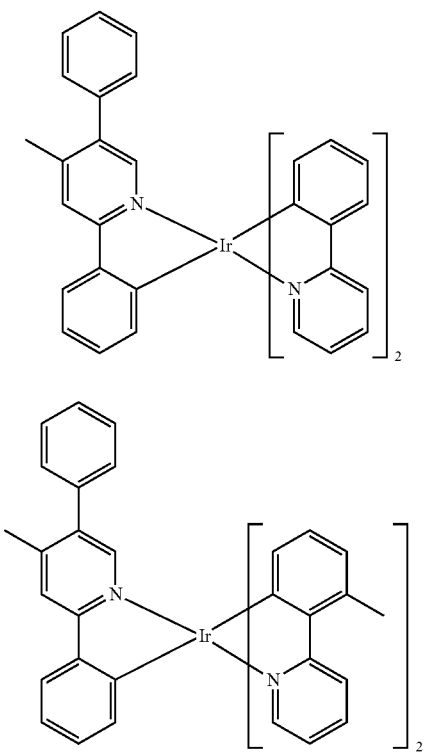
D-25
D-26
D-27
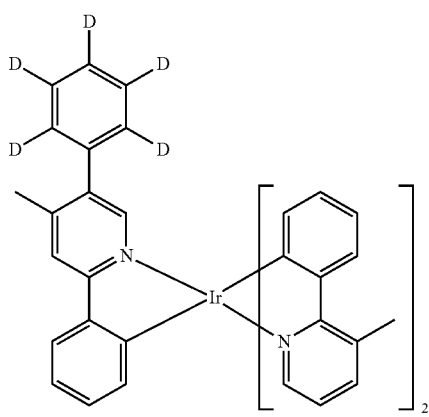
D-28
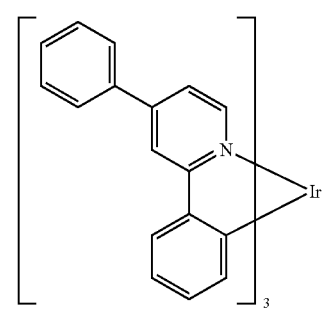
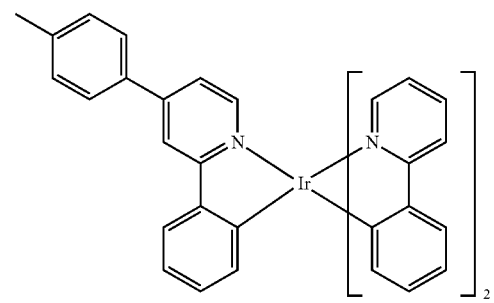
D-29
D-30
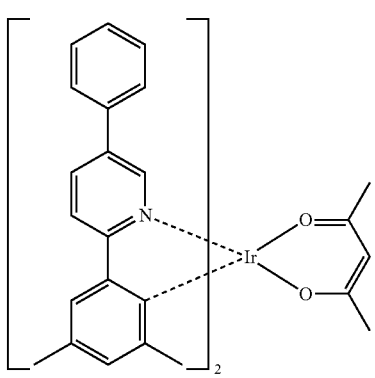
D-31
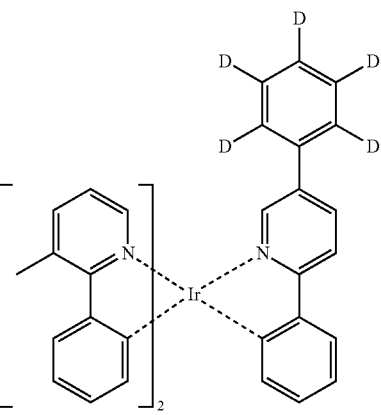
D-32
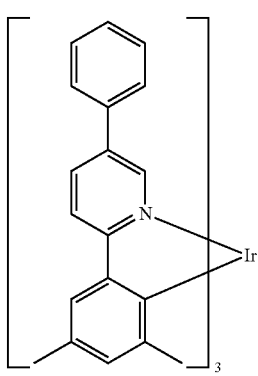

D-33 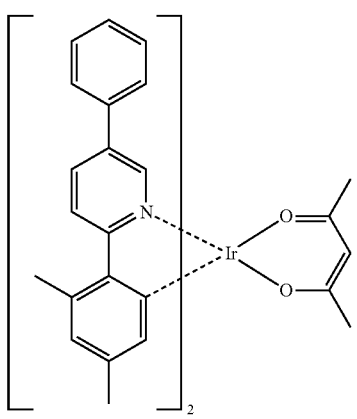
D-34 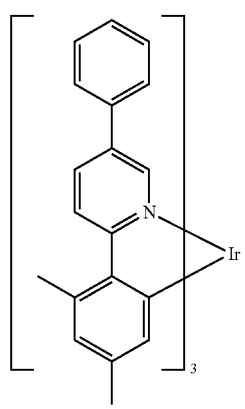
D-35 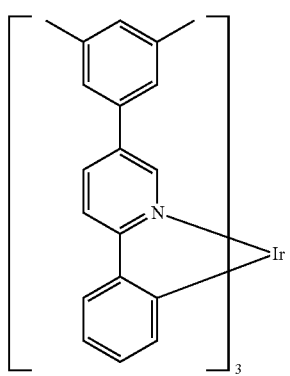
D-36 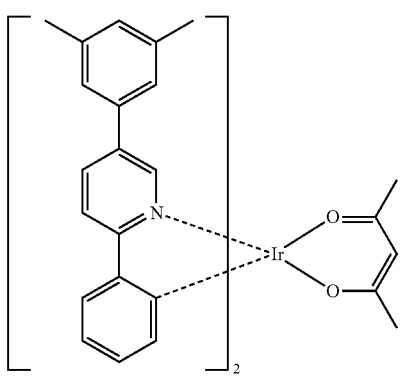
D-37 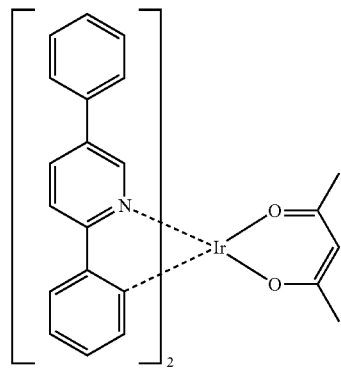
D-38 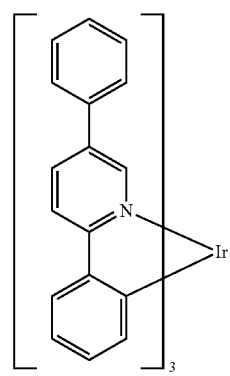
D-39 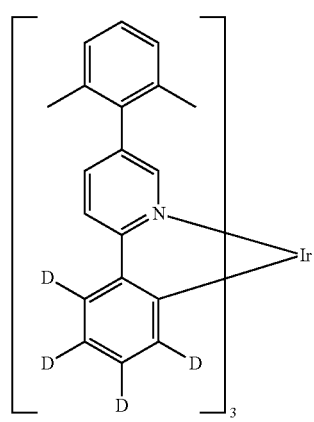
D-40 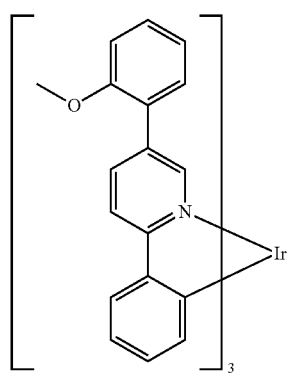

-continued
D-41
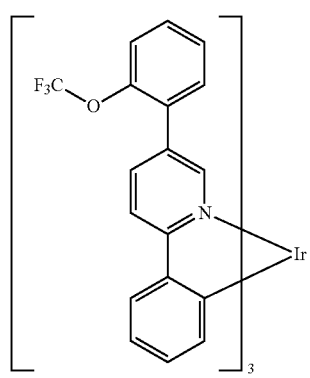
D-42
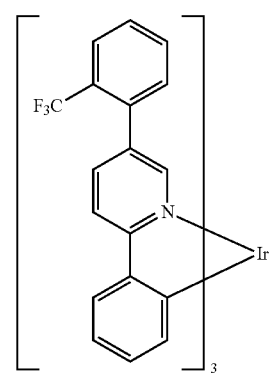
D-43
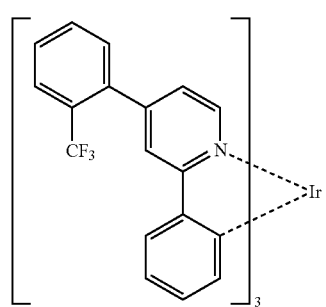
D-44
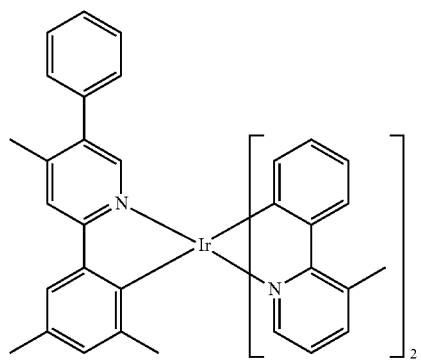
-continued
D-45
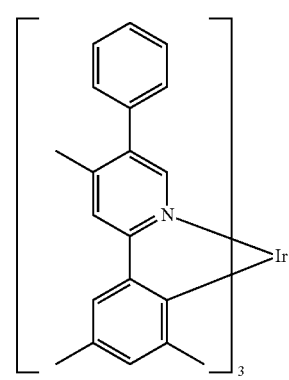
D-46
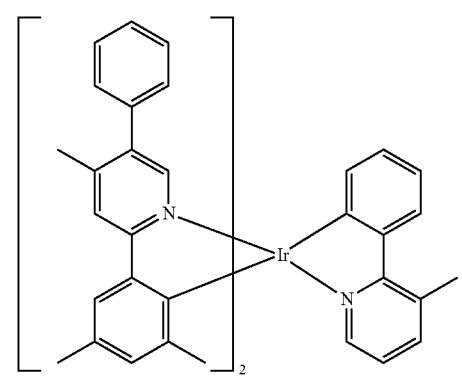
D-47
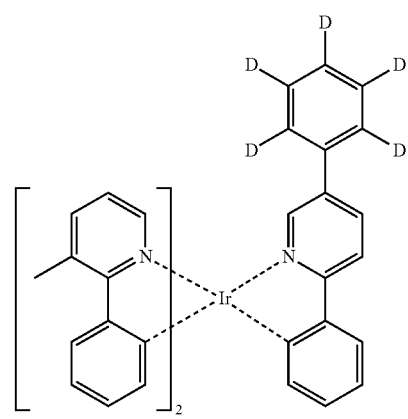
D-48
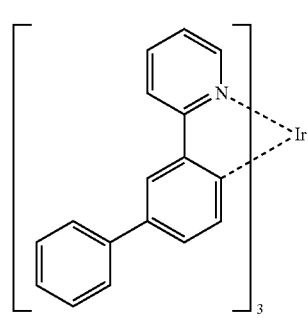

-continued
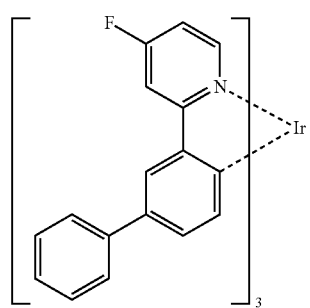
D-49
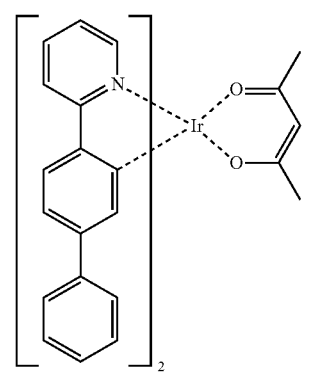
D-50
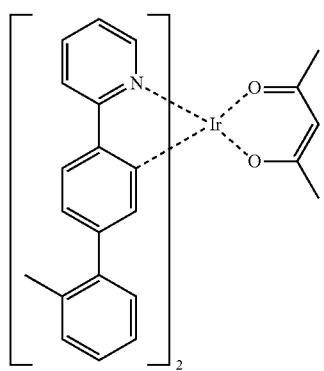
D-51
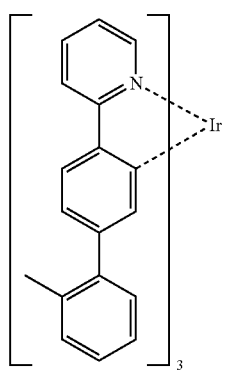
D-52
-continued
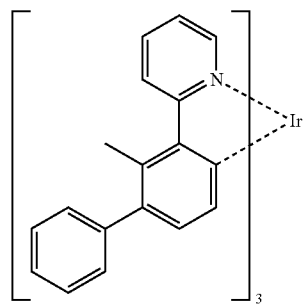
D-53
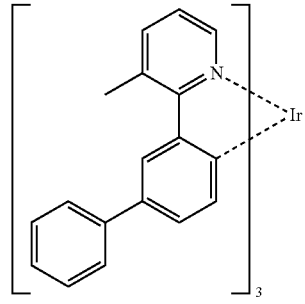
D-54
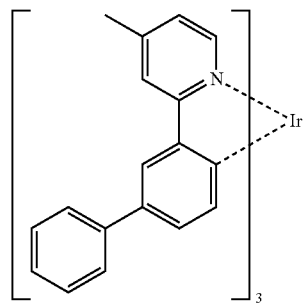
D-55
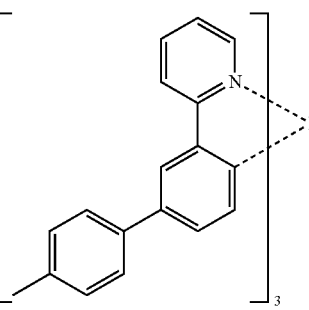
D-56
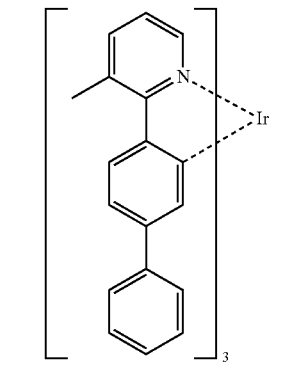
D-57

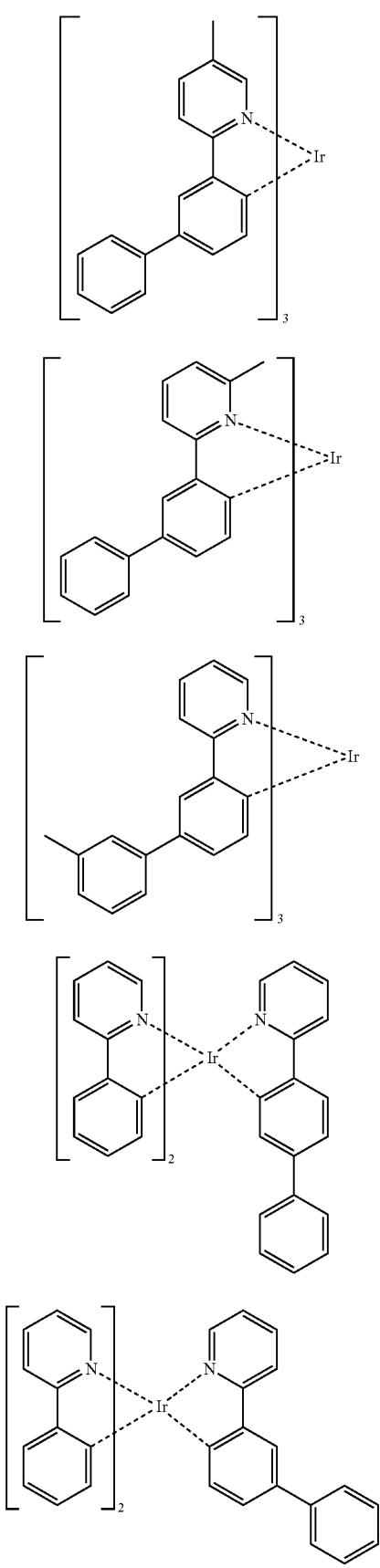
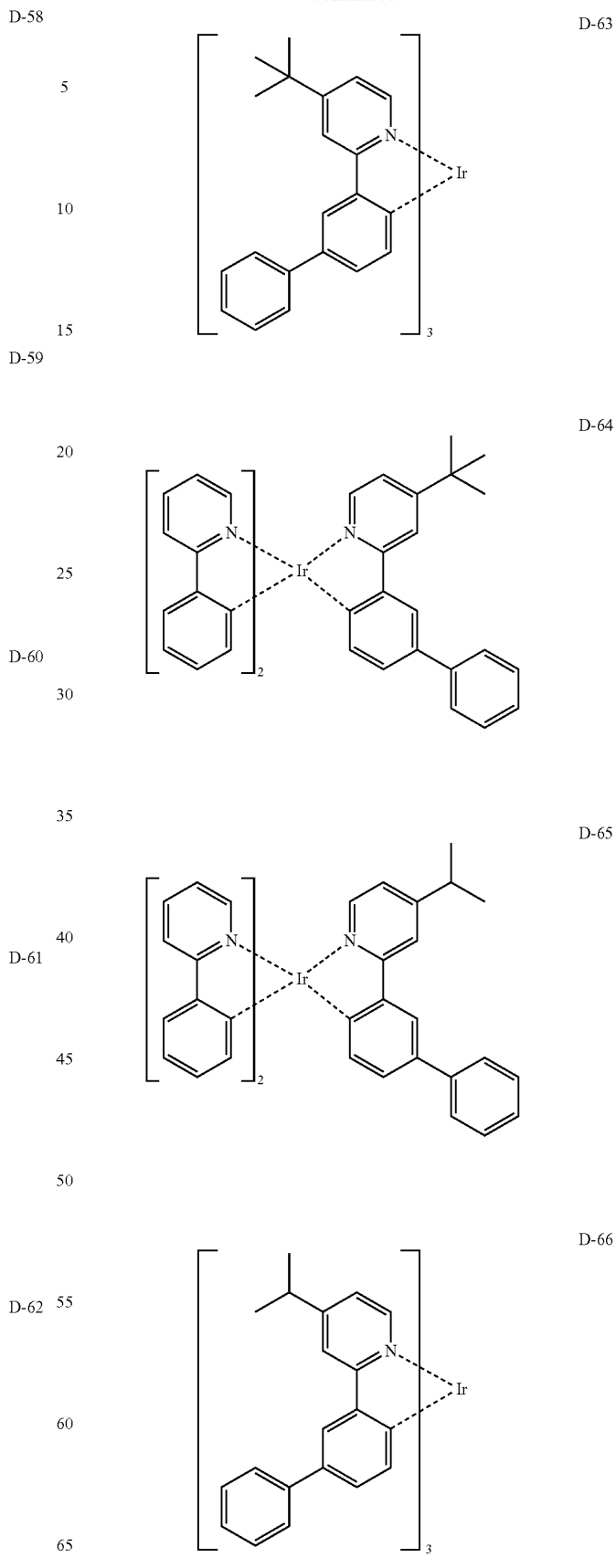

D-67
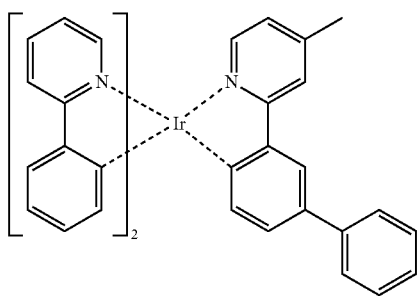
D-68
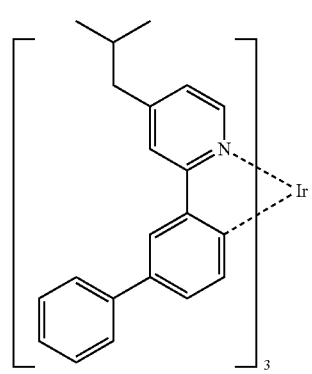
D-69
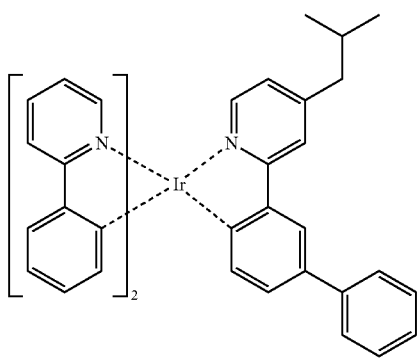
D-70
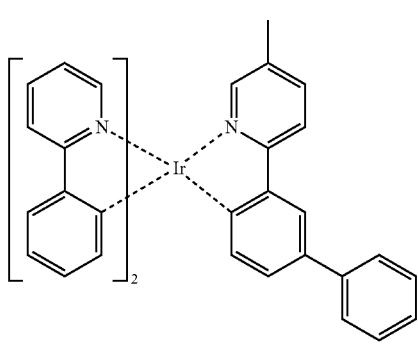
D-71
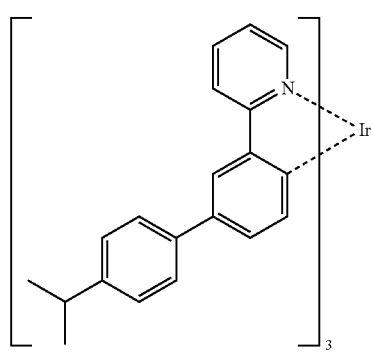
D-72
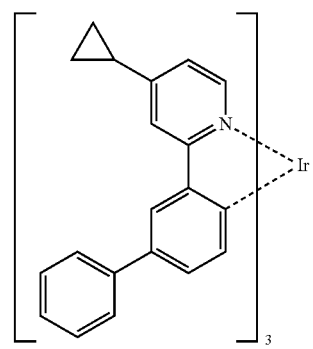
D-73
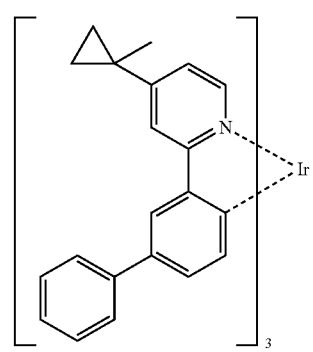
D-74
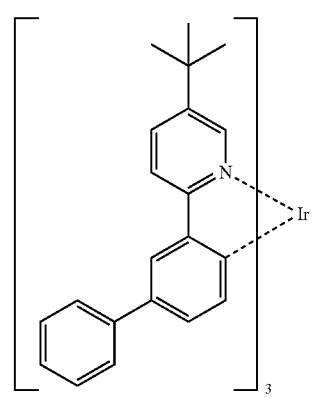

-continued
D-75
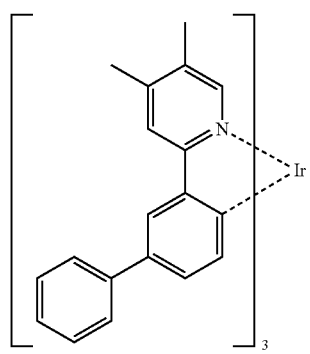
D-76
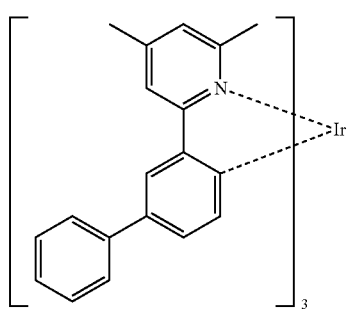
D-77
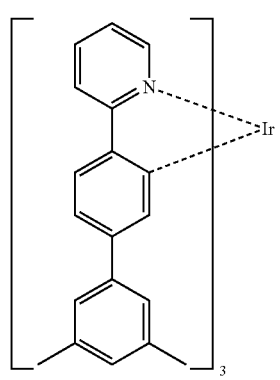
D-78
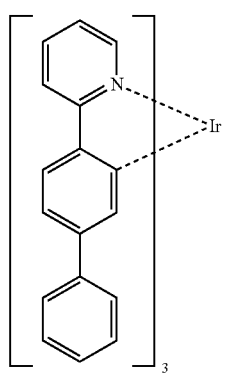
-continued
D-79
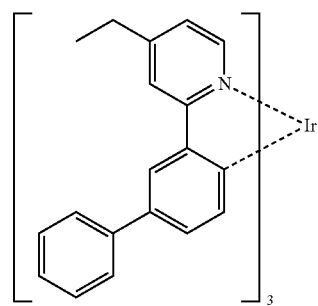
D-80
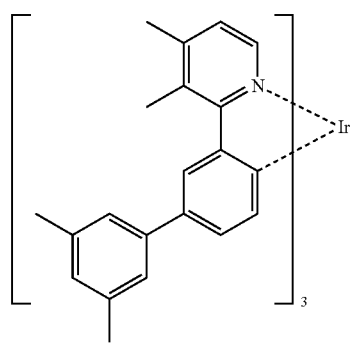
D-81
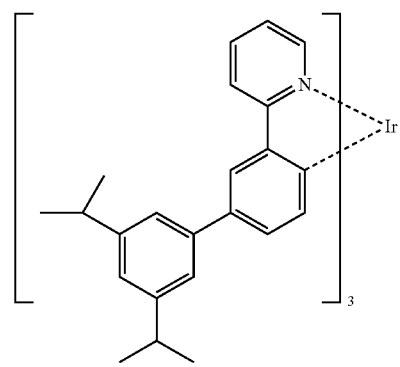
D-82
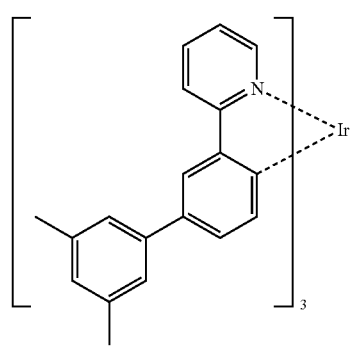

D-83
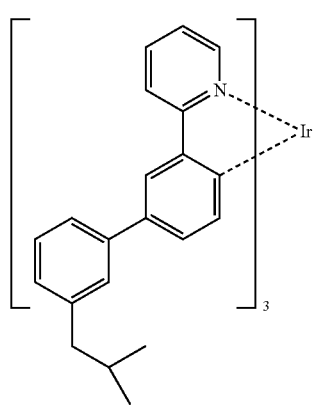
D-84
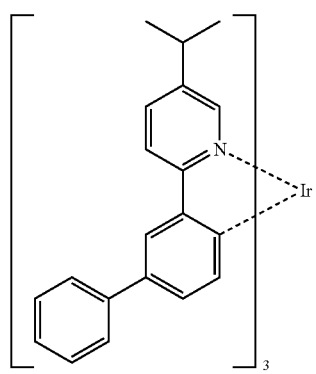
D-85
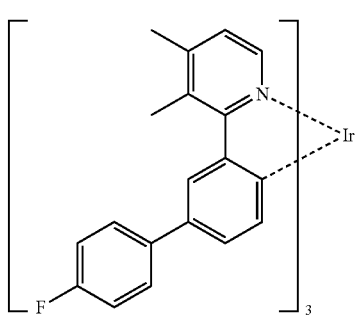
D-86
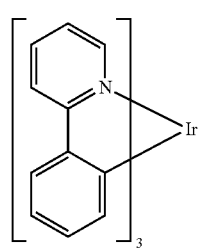
D-87
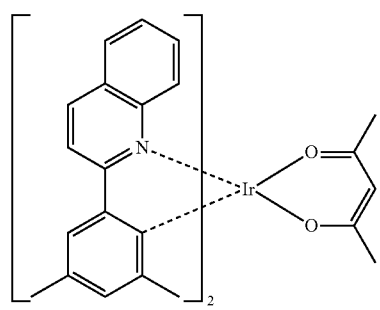
D-88
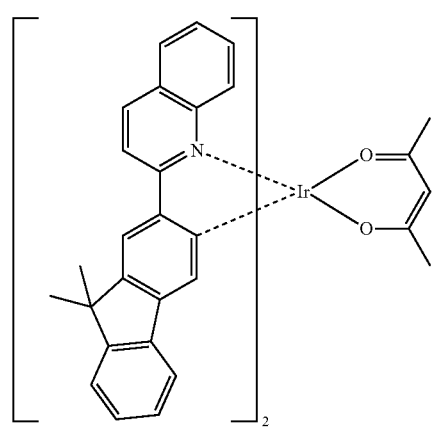
D-89
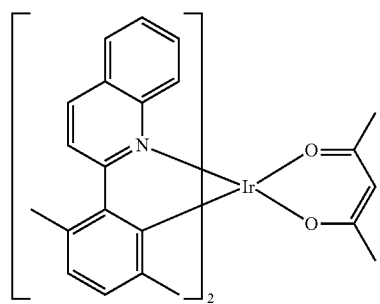
D-90
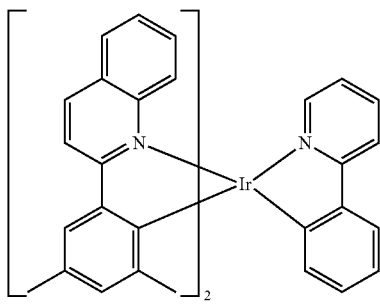

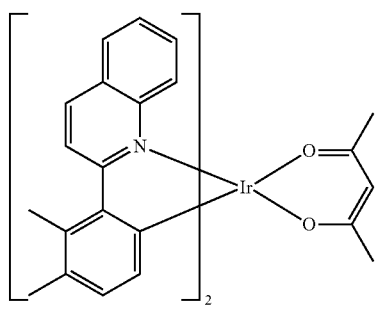
D-91
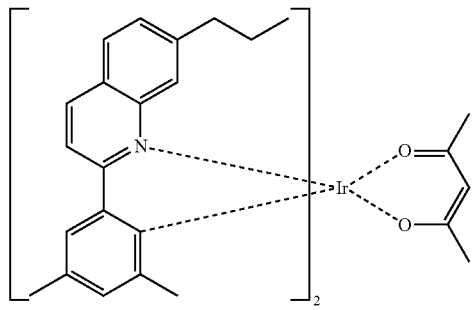
D-95
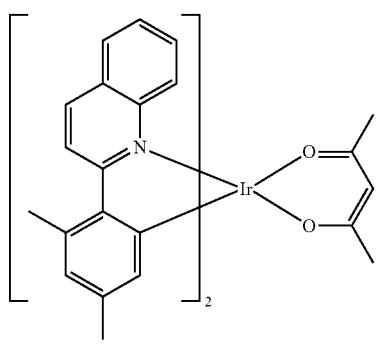
D-92
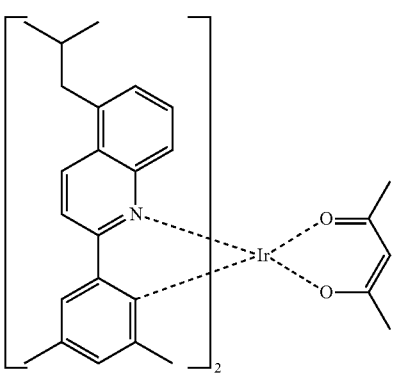
D-96
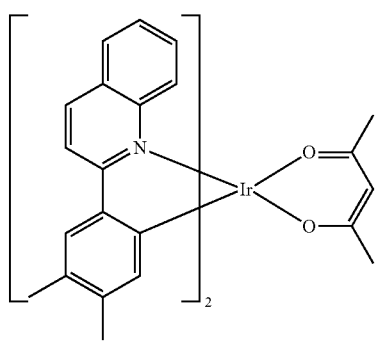
D-93
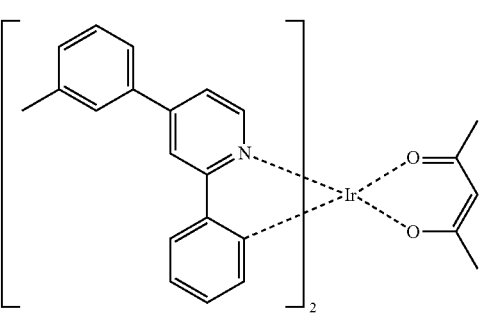
D-97
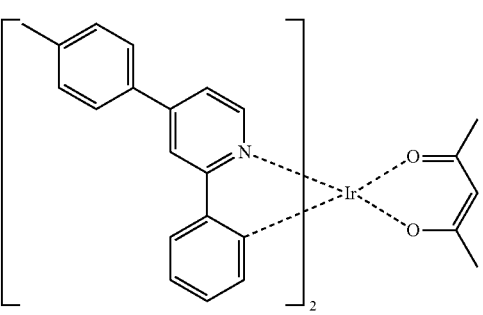
D-98
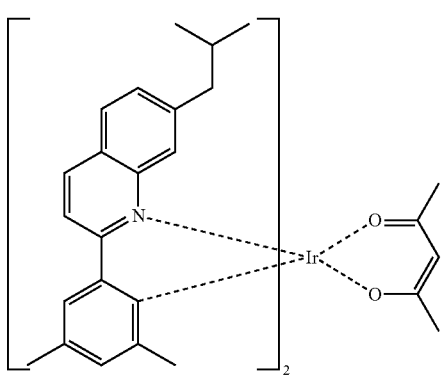
D-94
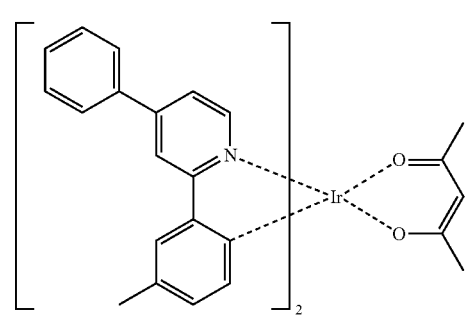
D-99

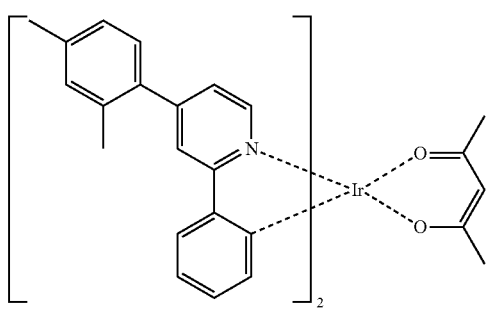
D-100
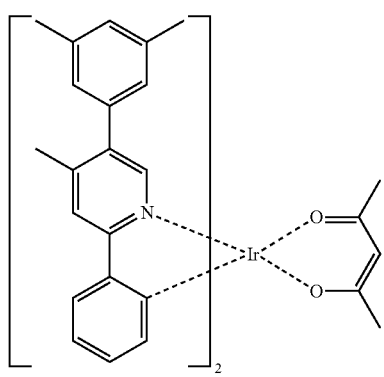
D-101
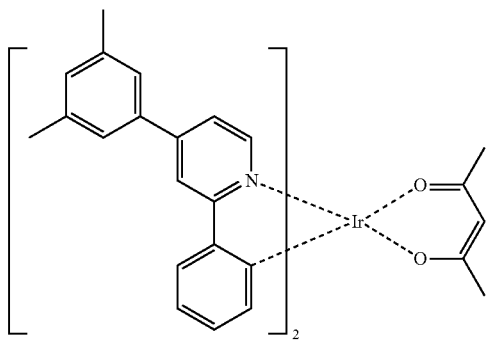
D-102
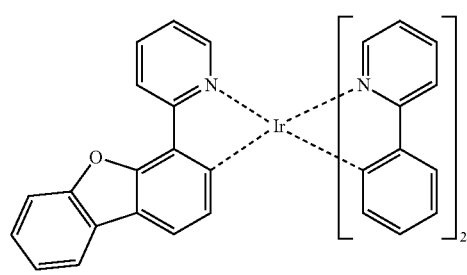
D-103
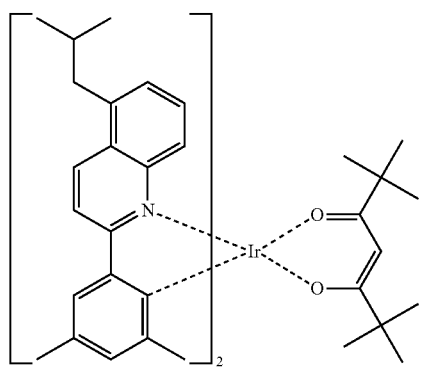
D-104
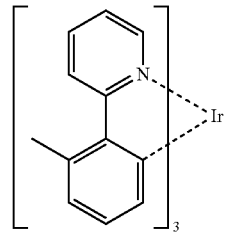
D-105
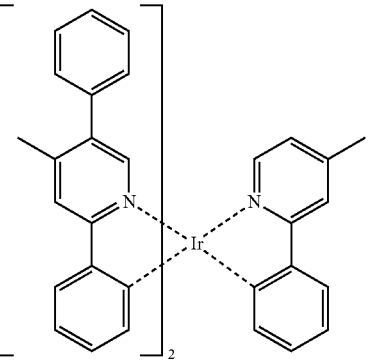
D-106
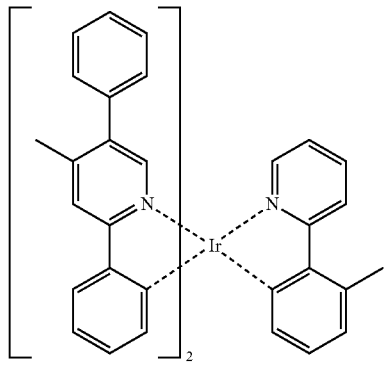
D-107
D-108

D-109
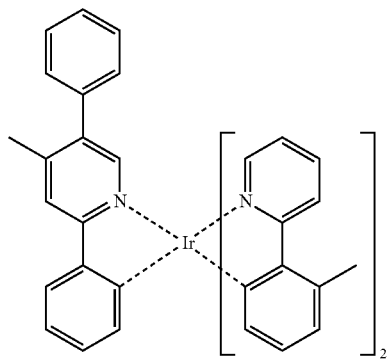
D-110
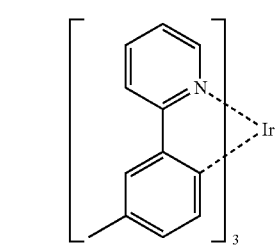
D-111
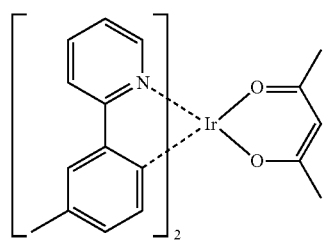
D-112
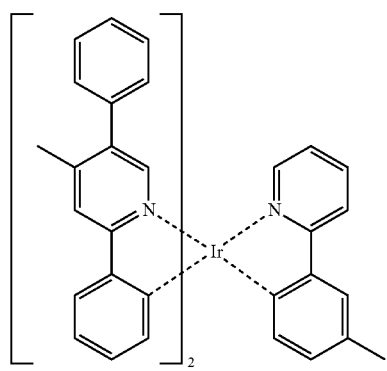
D-113
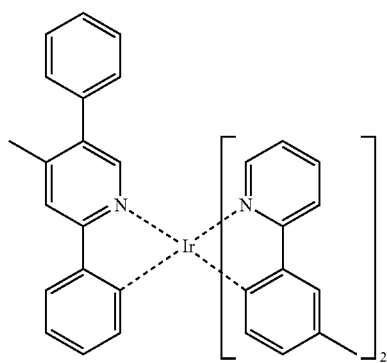
D-114
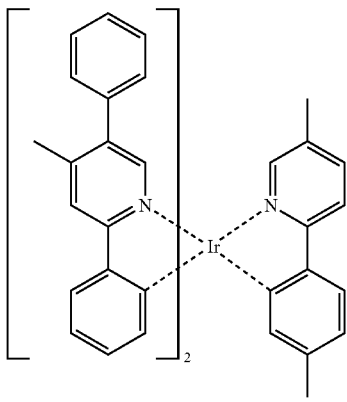
D-115
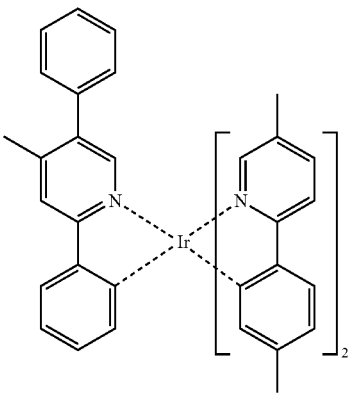
D-116
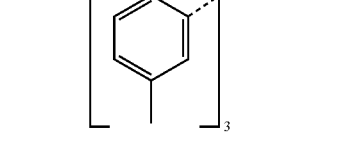
D-117
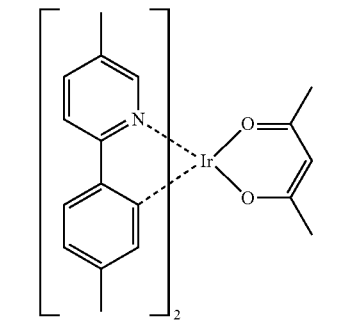

D-118 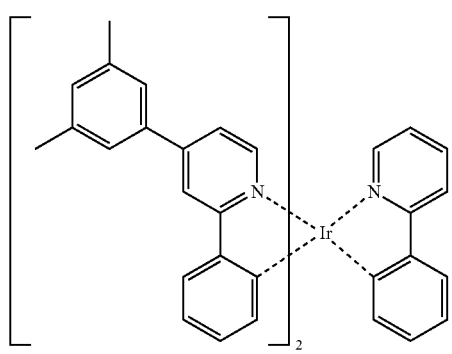
D-119 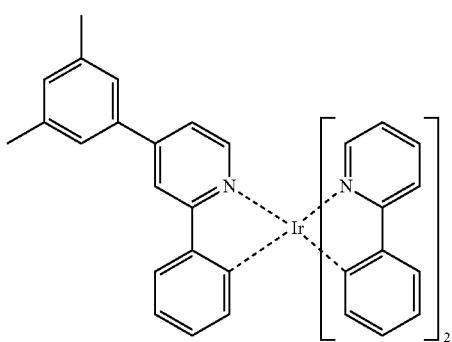
D-120 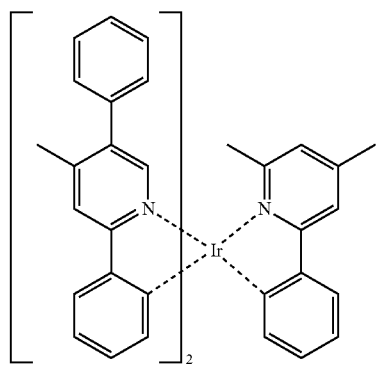
D-121 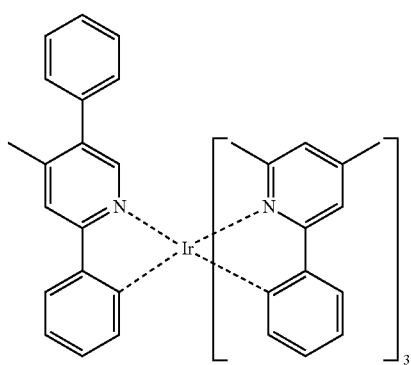
D-122 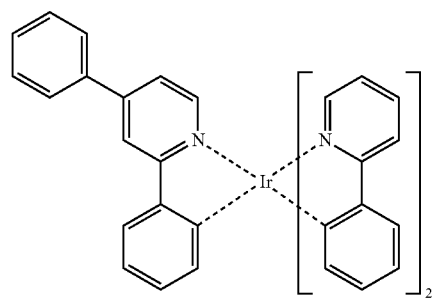
D-123 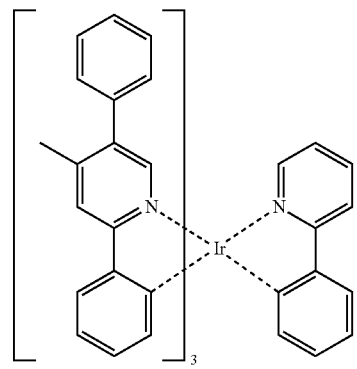
D-124 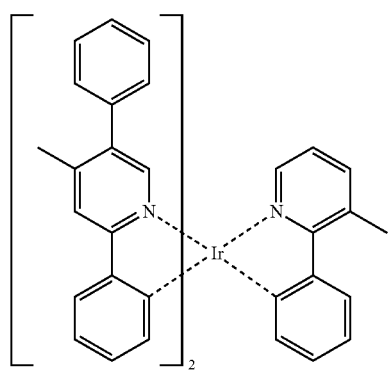
D-125 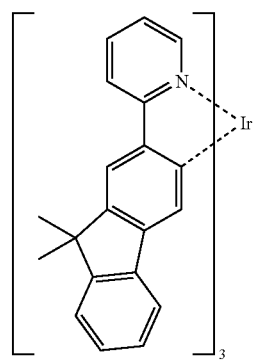

-continued
D-126
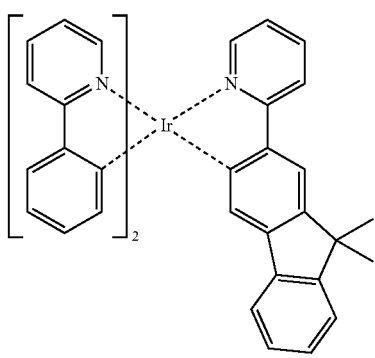
D-127
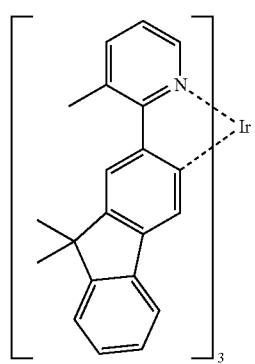
D-129
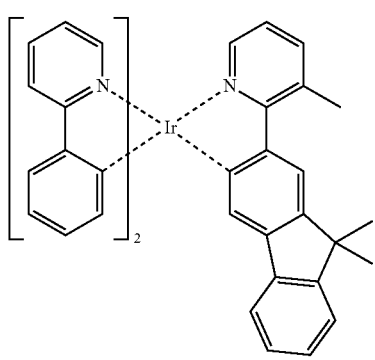
D-130
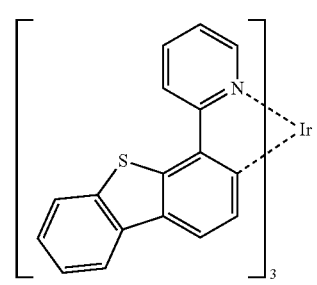
-continued
D-131
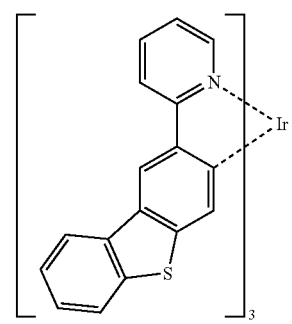
D-132
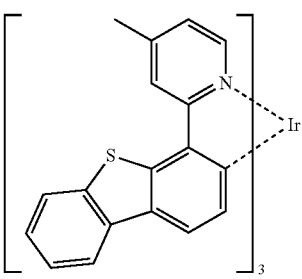
D-133
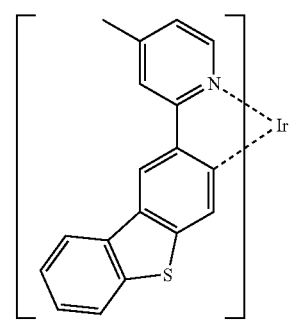
D-134
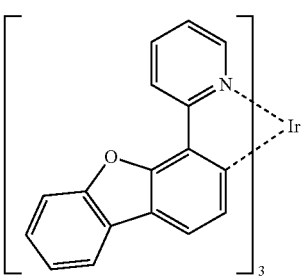
D-135
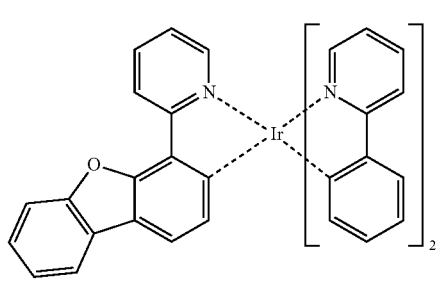

D-136
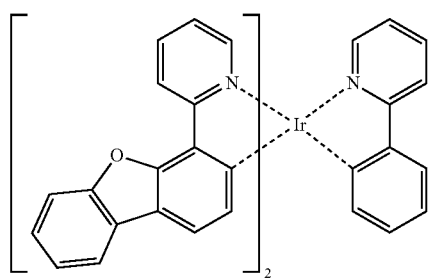
D-137
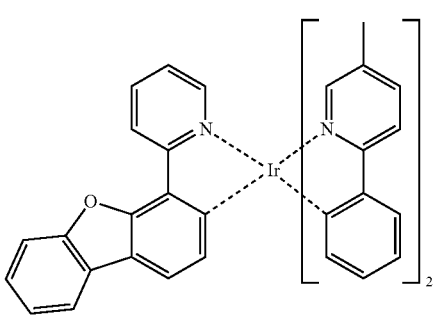
D-138
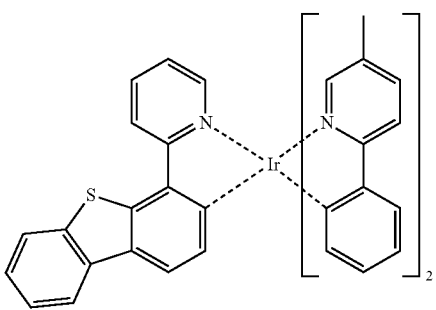
D-139
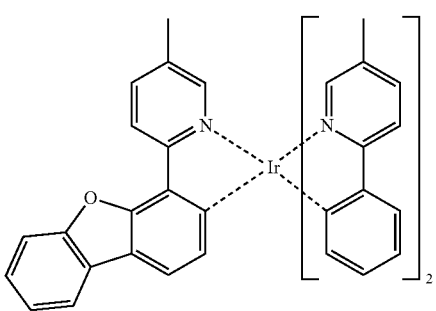
D-140
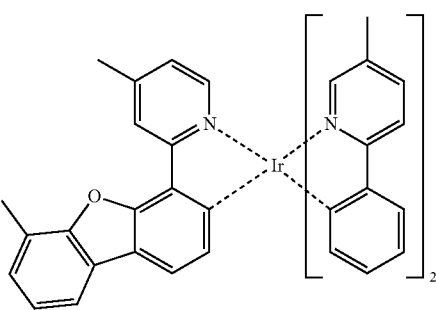
D-141
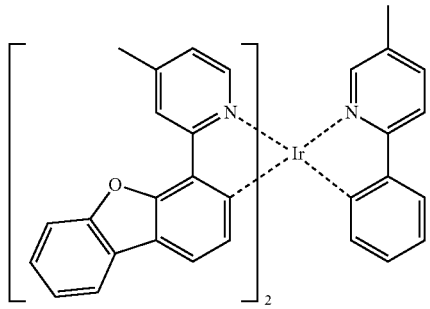
D-142
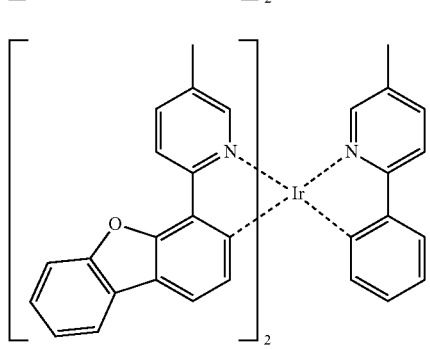
D-143
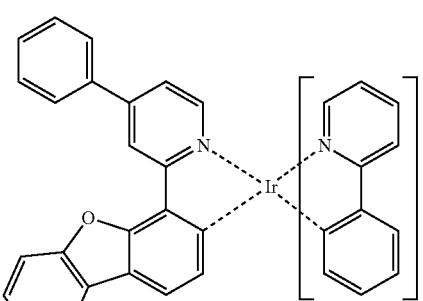
D-144
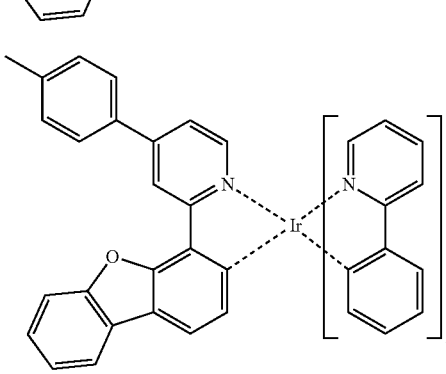
D-145
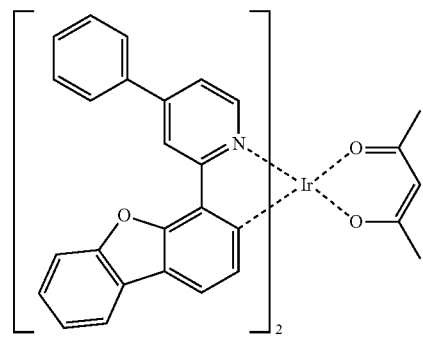

D-146
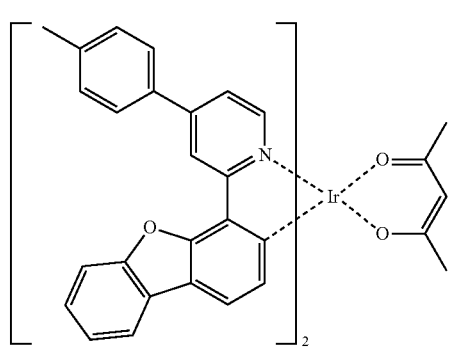
D-147
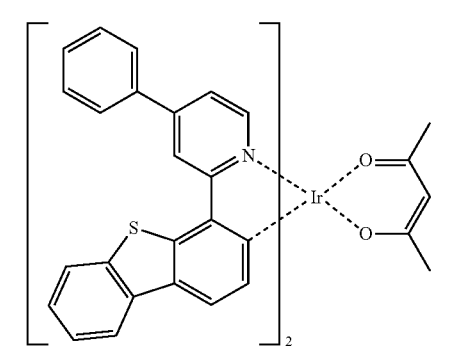
D-148
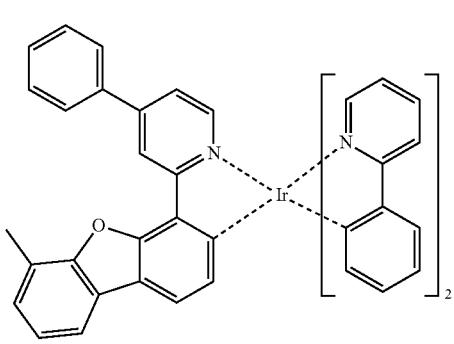
D-149
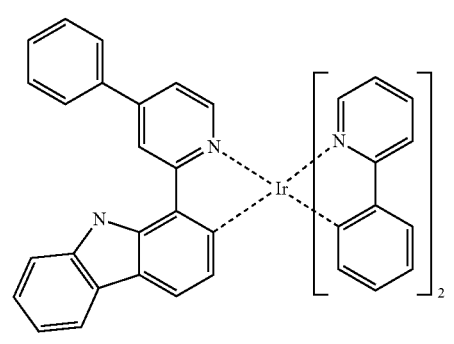
D-150
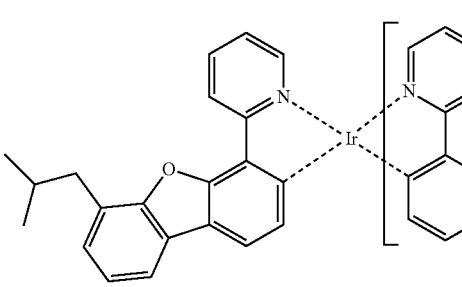
D-151
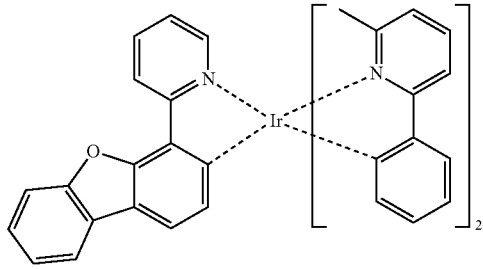
D-152
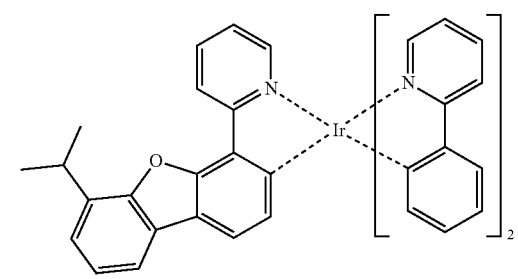
D-153
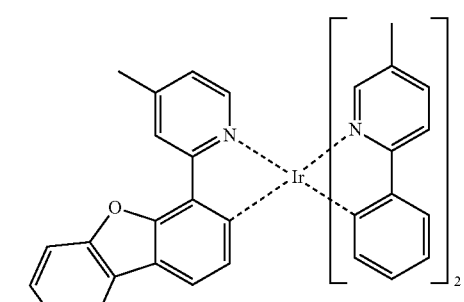
D-154
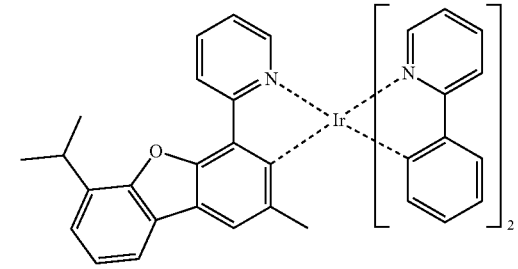
D-155
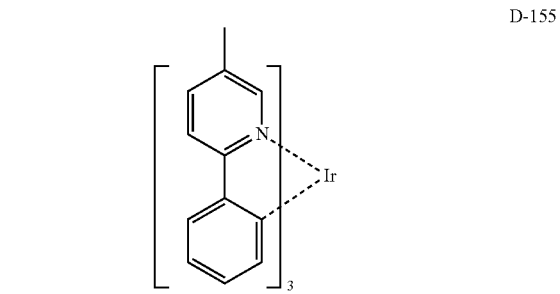

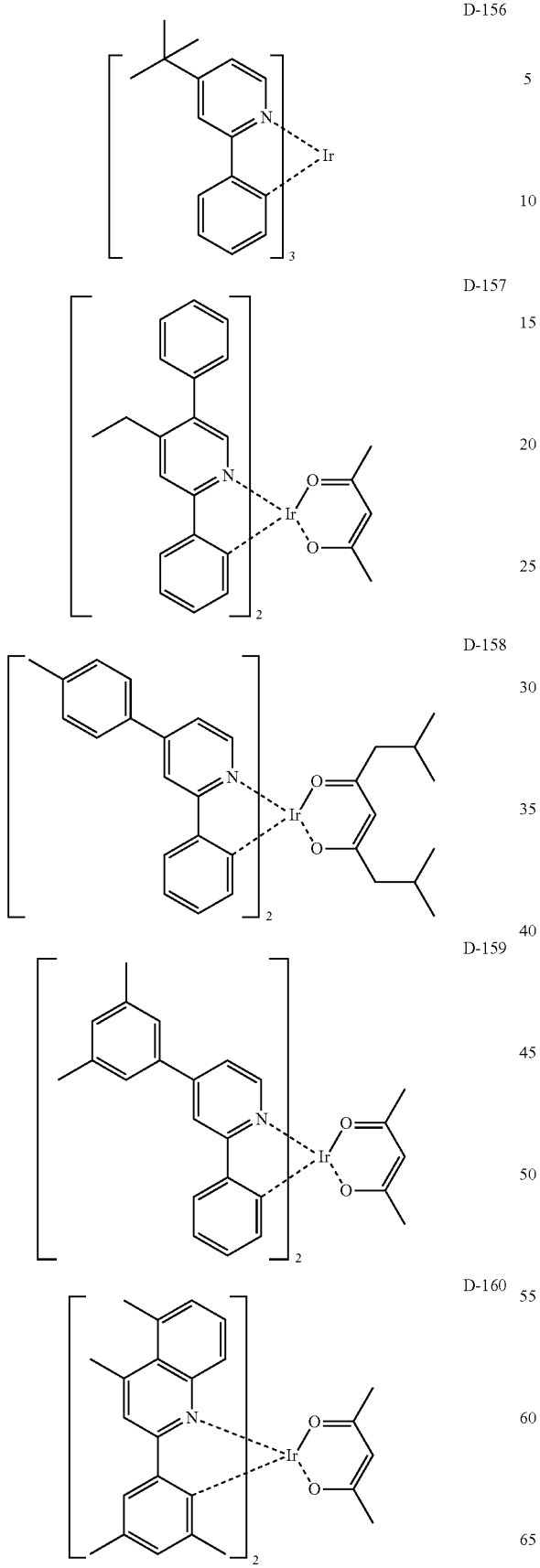

D-165
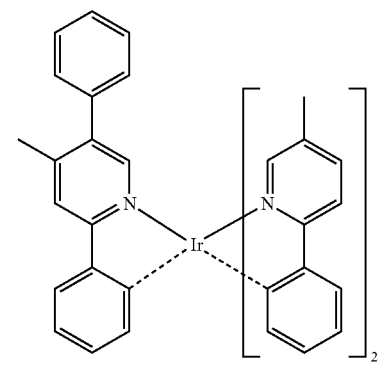
D-166
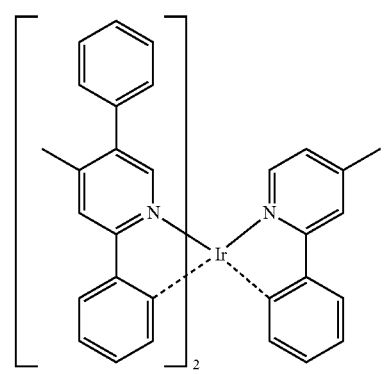
D-167
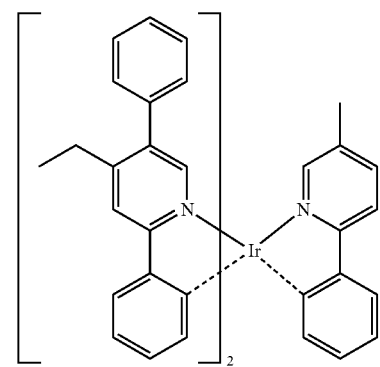
D-168
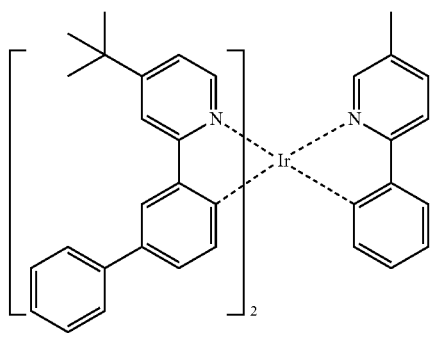
D-169
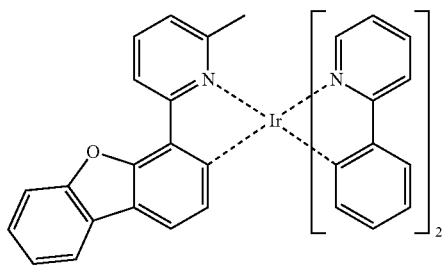
D-170
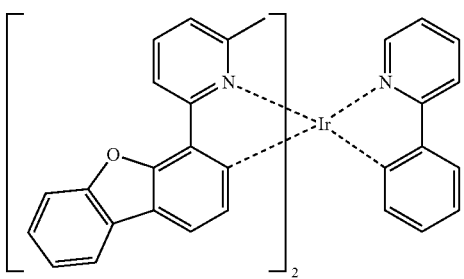
D-171
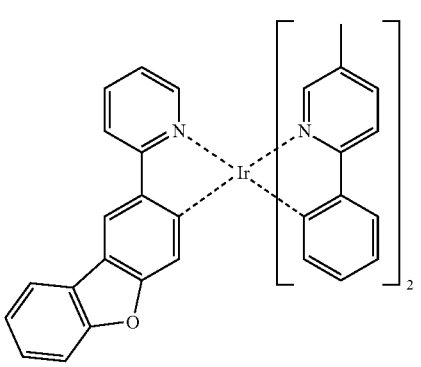
D-172
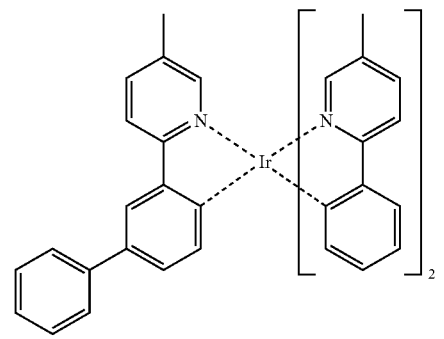
D-173
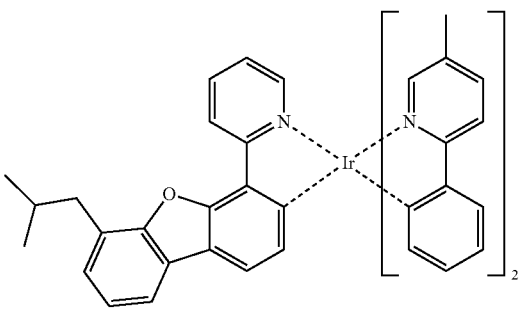

D-174
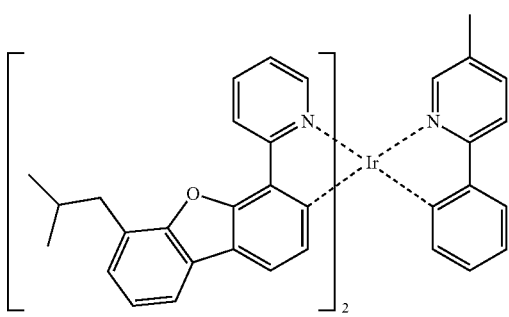
D-175
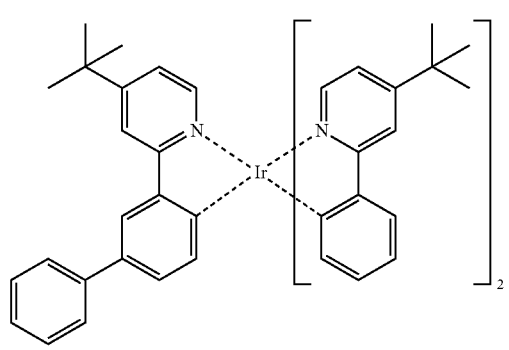
D-176
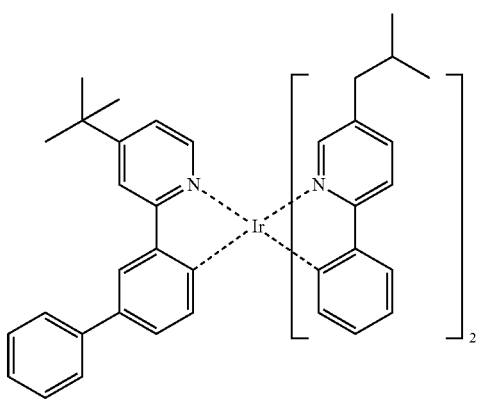
D-177
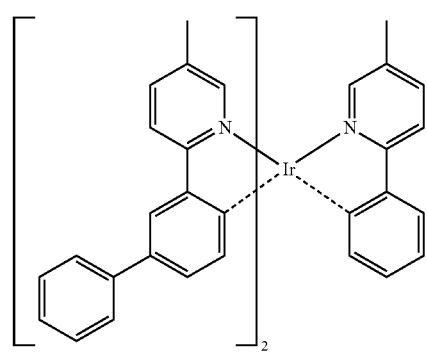
D-178
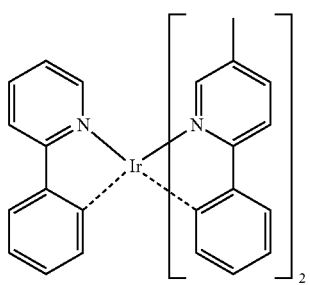
D-179
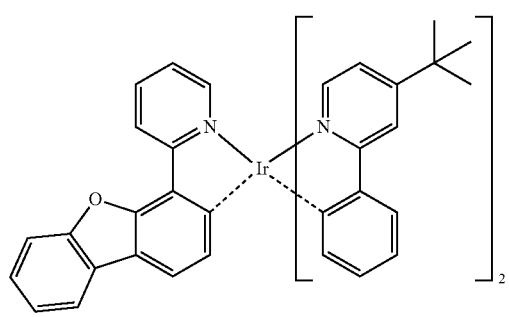
D-180
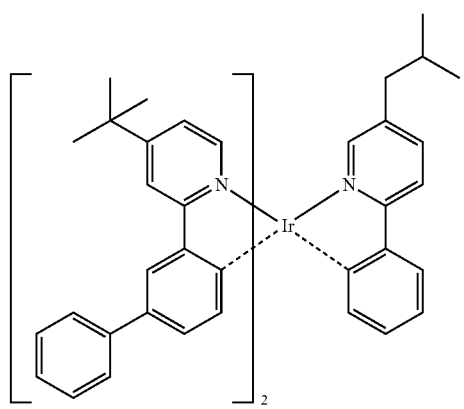
D-181
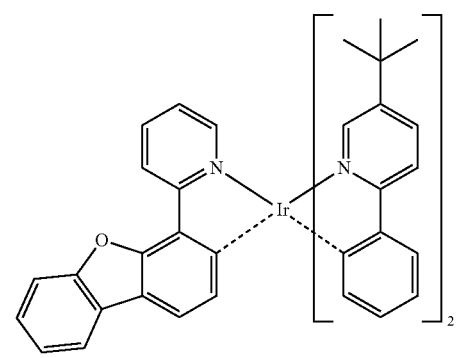

-continued
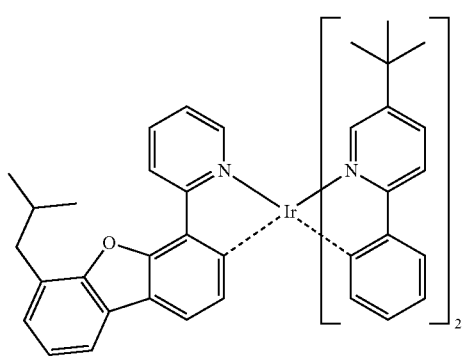
D-182
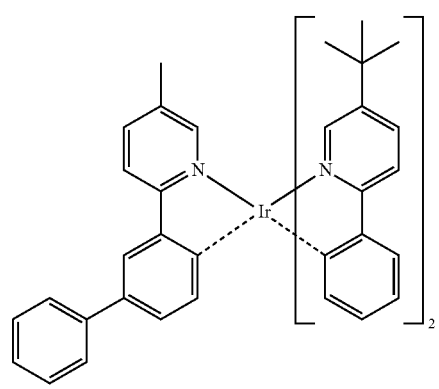
D-183
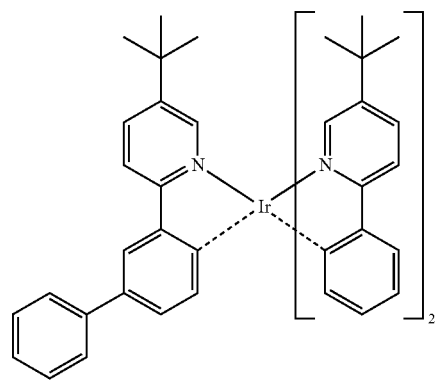
D-184
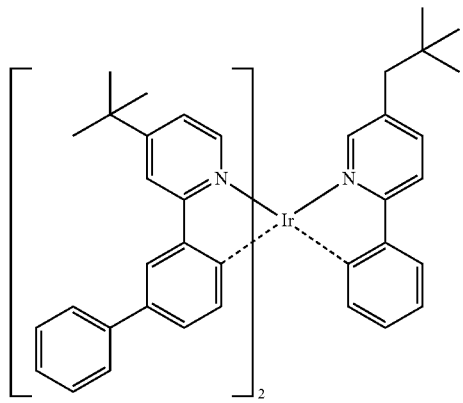
D-185
-continued
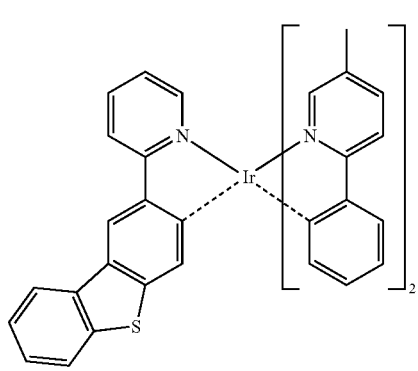
D-186
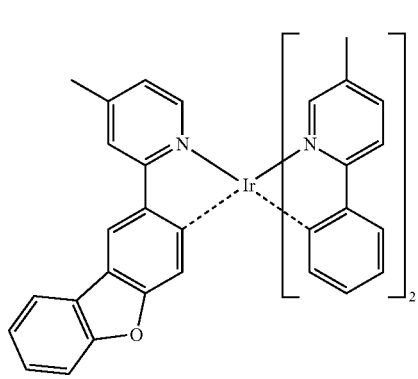
D-187
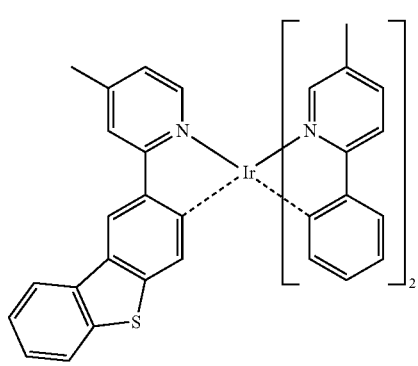
D-188
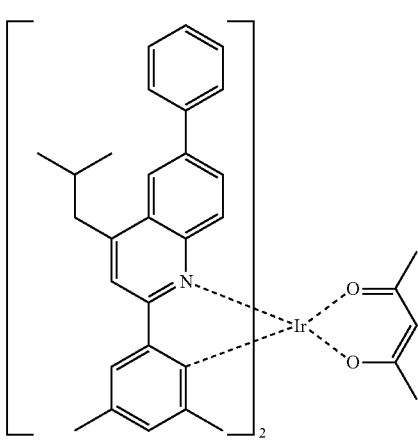
D-189

D-190 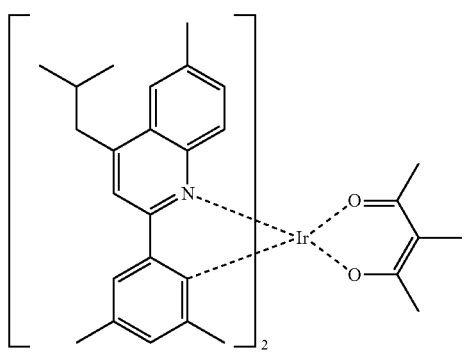
D-194 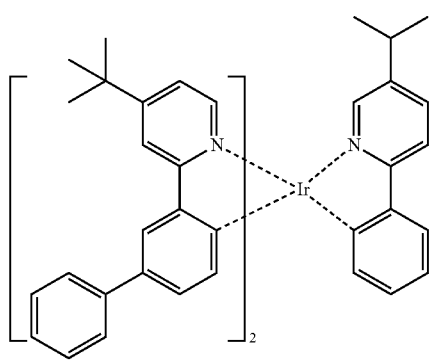
D-191 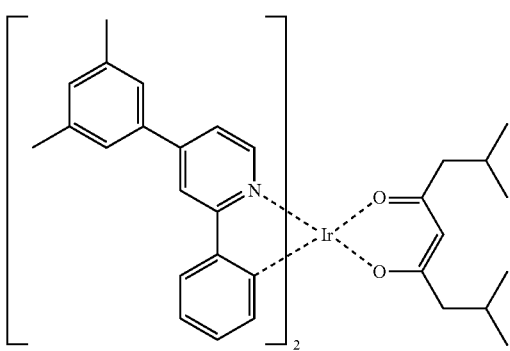
D-195 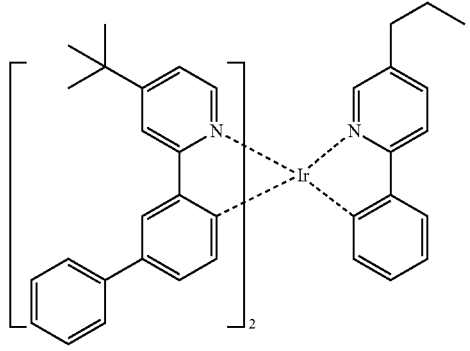
D-192 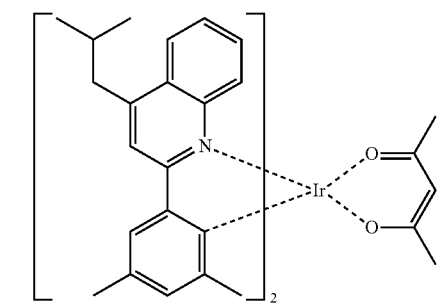
D-196 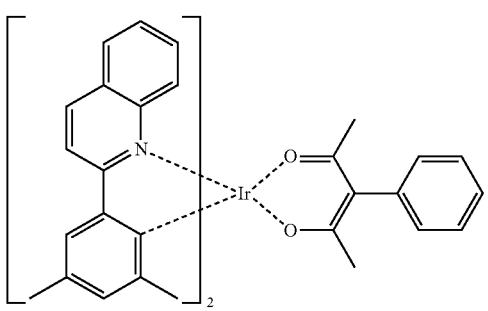
D-193 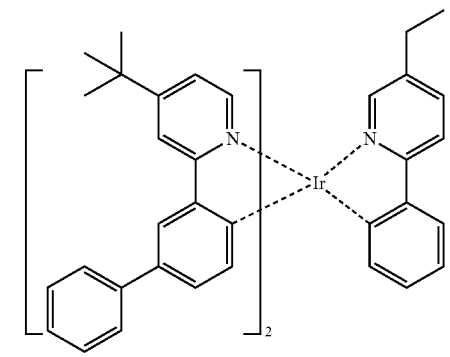
D-197 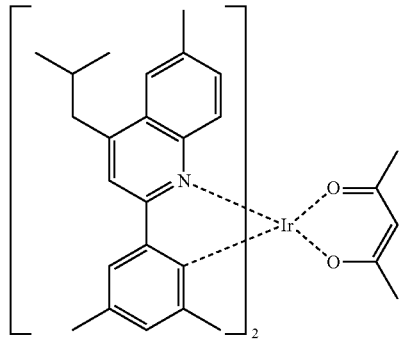

-continued
D-198
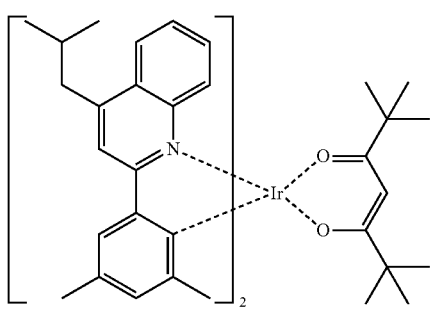
D-199
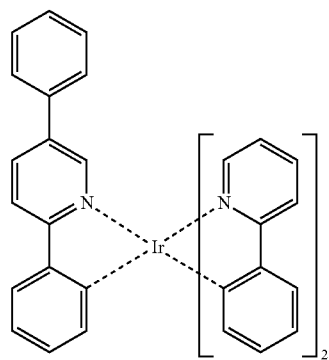
D-200
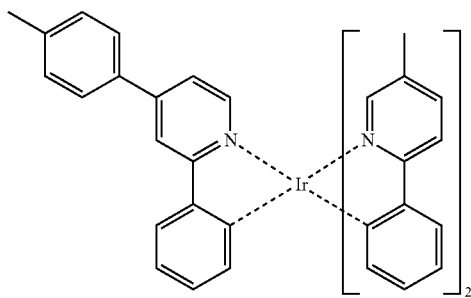
D-201
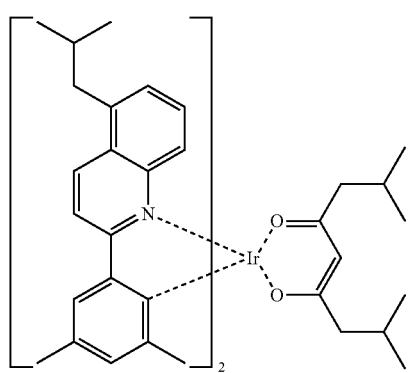
D-202
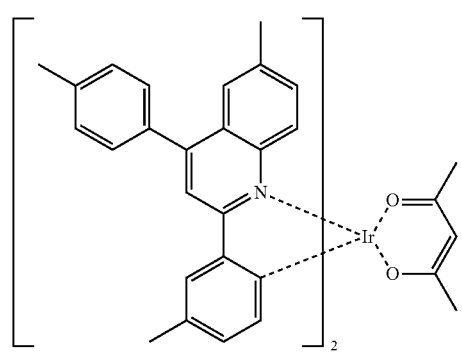
D-203
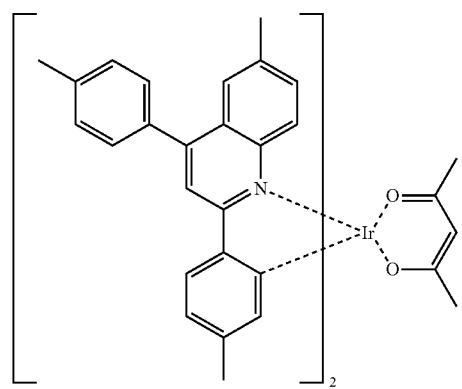
D-204
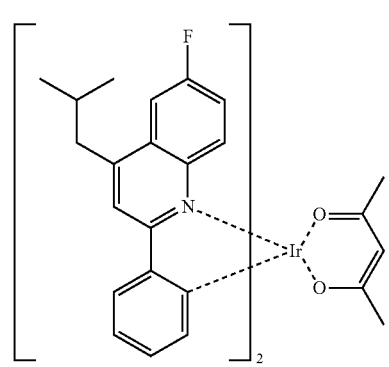
D-205
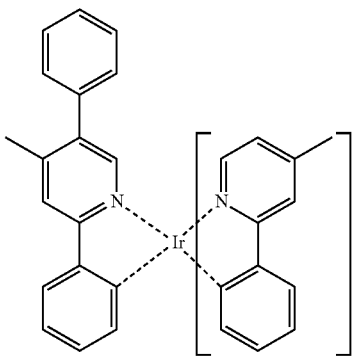

-continued
D-206
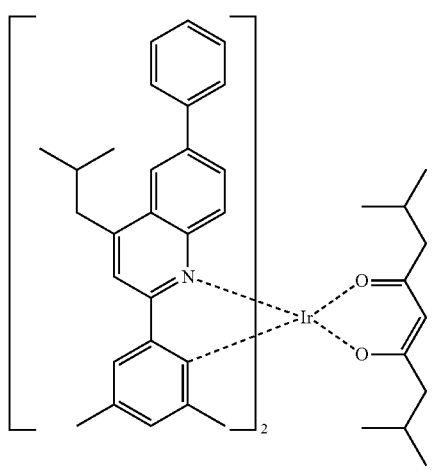
D-207
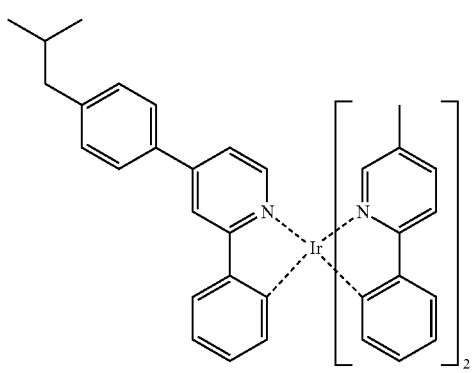
D-208
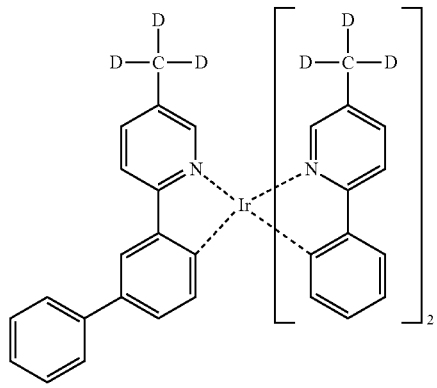
-continued
D-209
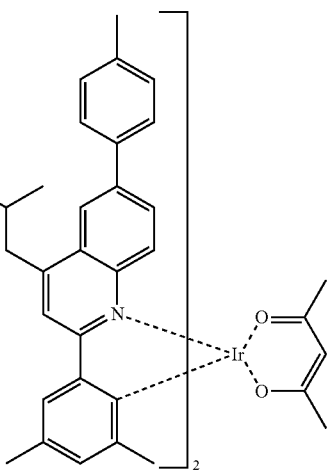
D-210
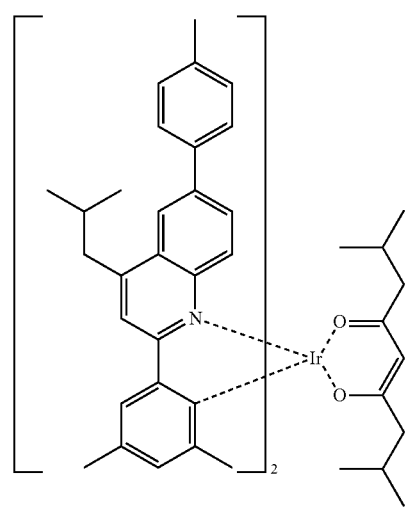
D-211
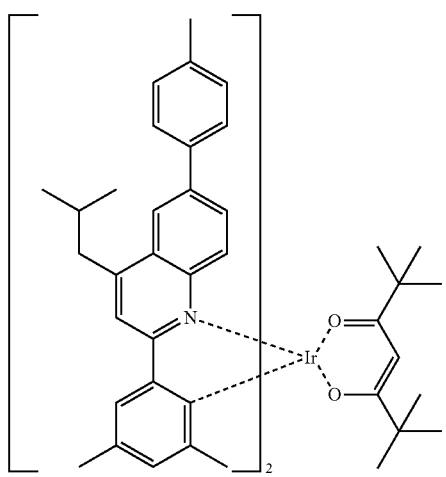

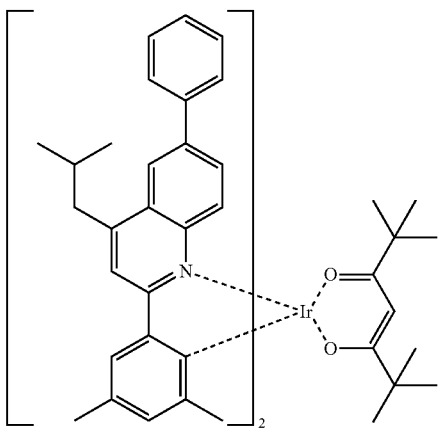

D-212

According to an additional aspect of the present disclosure, a material for preparing an organic electroluminescent device is provided. The material comprises a compound of the present disclosure. In addition to a compound of the present disclosure, the material may further comprise a conventional material which has been comprised in a material for preparing an organic electroluminescent device. The material may be preferably a host material for preparing an organic electroluminescent device, more preferably a phosphorescent host material for preparing an organic electroluminescent device, and even more preferably a red-emitting phosphorescent host material for preparing an organic electroluminescent device. When the compound of the present disclosure is comprised as a host material, the material may further comprise a second host material. The weight ratio between the first host material and the second host material is in the range of 1:99 to 99:1. The second host material includes a compound selected from the group consisting of compounds represented by the aforementioned formulae 7 to 11. The material may be a composition or mixture.

The organic electroluminescent device of the present disclosure may comprise a first electrode, a second electrode, and at least one organic layer disposed between the first and second electrodes, and the organic layer may comprise the material for the organic electroluminescent device of the present disclosure.

The organic layer of the organic electroluminescent device of the present disclosure may further comprise, in addition to the compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the 4$^{th}$ period, transition metals of the 5$^{th}$ period, lanthanides and organic metals of the d-transition elements of the Periodic Table, or at least one complex compound comprising the metal. The organic layer may further comprise one or more additional light-emitting layer and a charge generating layer.

In addition, the organic electroluminescent device of the present disclosure may emit white light by further comprising at least one light-emitting layer, which comprises a blue electroluminescent compound, a red electroluminescent compound or a green electroluminescent compound known in the field, besides the compound of the present disclosure. If necessary, it may further comprise an orange light-emitting layer or a yellow light-emitting layer.

In the organic electroluminescent device of the present disclosure, preferably, at least one layer (hereinafter, "a surface layer") may be placed on an inner surface (s) of one or both electrode (s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma, and ion plating methods, or wet film-forming methods such as ink jet printing, nozzle printing, slot coating, spin coating, dip coating, and flow coating methods can be used.

When using a wet film-forming method, a thin film can be formed by dissolving or diffusing materials forming each layer in any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the compound of the present disclosure, the preparation method of the compound, and the properties of the device will be explained in detail with reference to the following examples.

Example 1: Preparation of Compound A-14

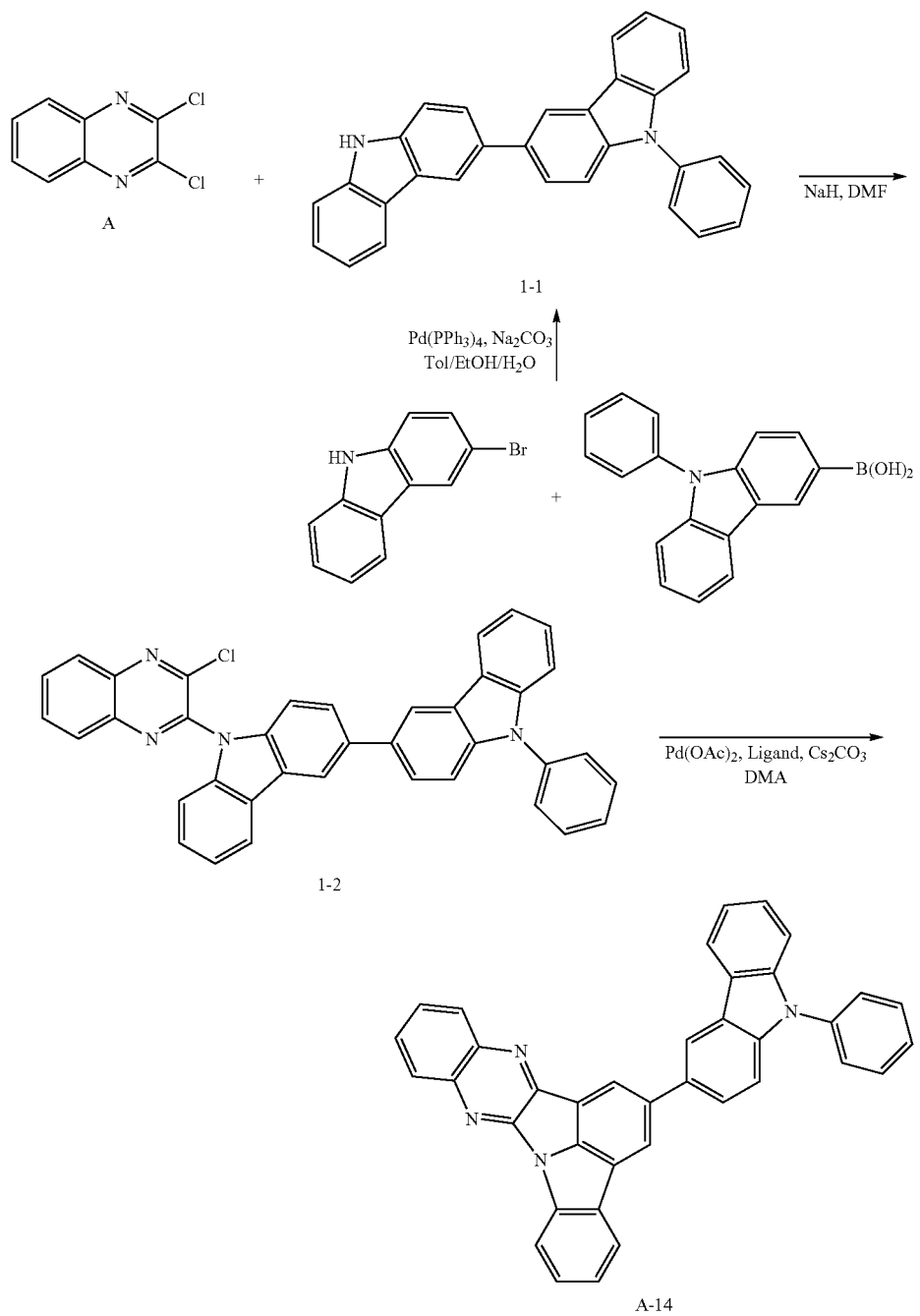

1) Preparation of Compound 1-1

After dissolving 3-bromo-9H-carbazole (60 g, 243.80 mmol), (9-phenyl-9H-carbazol-3-yl)boronic acid (84 g, 292.56 mmol), and tetrakis(triphenylphosphine)palladium (Pd(PPh$_3$)$_4$) (14 g, 12.19 mmol) in 2M Na$_2$CO$_3$ (500 mL), toluene (1000 mL), and ethanol (500 mL) of a flask, the mixture was under reflux at 120° C. for 5 hours. After completion of the reaction, the mixture was extracted with ethyl acetate. The remaining moisture was removed from the obtained organic layer with magnesium sulfate. The product was then dried, and purified by column chromatography to obtain compound 1-1 (73 g, yield: 73%).

2) Preparation of Compound 1-2

After dissolving compound A (2,3-dichloroquinoxaline) (20 g, 100.48 mmol) and compound 1-1 (34 g, 83.73 mmol) in dimethylformamide (DMF)(500 mL), NaH (5 g, 125.59 mmol, 60% in a mineral oil) was added thereto. After the mixture was stirred at room temperature for 1 hour, methanol and distilled water were added thereto. The obtained solid substance was filtered under reduced pressure, and then purified by column chromatography to obtain compound 1-2 (26 g, yield: 54%).

3) Preparation of Compound A-14

After mixing compound 1-2 (2 g, 3.5 mmol), palladium (II) acetate (Pd(OAc)$_2$) (0.1 g, 0.35 mmol), ligand (tricyclohexylphosphoniumtetrafluoroborate) (128 mg, 0.35 mmol), Cs$_2$CO$_3$ (3.4 g, 10.5 mmol), and dimethylacetamide (DMA) (20 mL), the mixture was stirred under reflux for 1 hour. After cooling to room temperature, distilled water was added to the mixture. The mixture was then extracted with methylene chloride (MC), dried with magnesium sulfate, and distilled under reduced pressure. The product was purified by column chromatography to obtain compound A-14 (0.9 g, yield: 50%).

|  | Molecular Weight (MW) | UV | PL | Melting Point (M.P) |
|---|---|---|---|---|
| A-14 | 534.60 | 386 nm | 511 nm | 309.9° C. |

Example 2: Preparation of Compound A-39

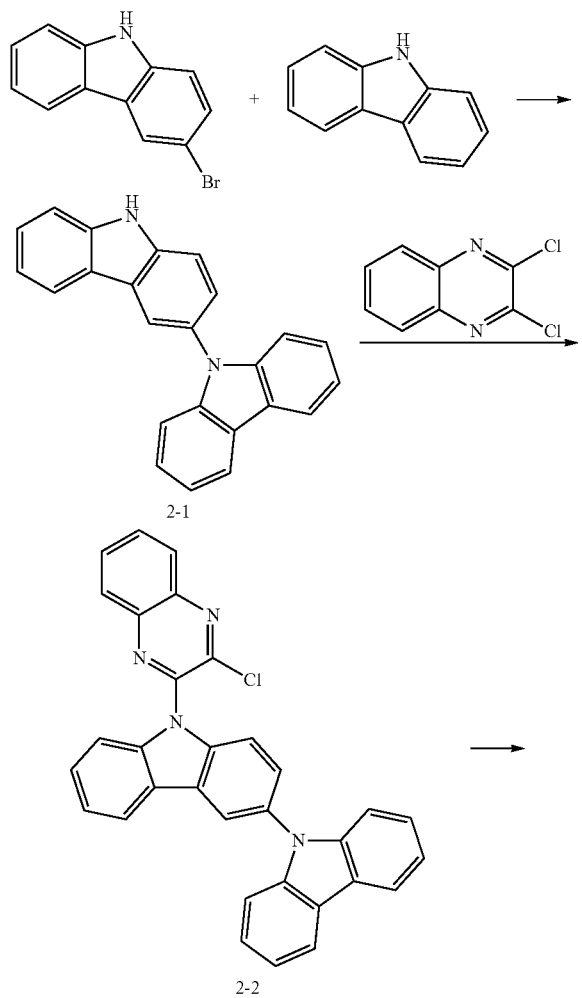

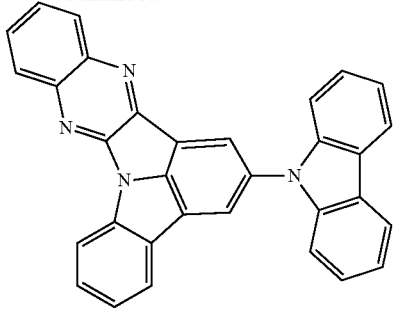

A-39

1) Preparation of Compound 2-1

After introducing 9H-carbazole (20 g, 119.6 mmol), 3-bromo-9H-carbazole (35.3 g, 143.5 mmol), copper(I) iodide (59.8 g, 59.8 mmol), cesium carbonate (97.4 g, 229 mmol), ethylene diamine (7.18 g, 119.6 mmol), and toluene (600 mL) into a flask, the mixture was stirred under reflux for 12 hours. After cooling to room temperature, the mixture was extracted with ethyl acetate, washed with purified water, dried with anhydrous MgSO$_4$, and distilled under reduced pressure. The residues were purified by column chromatography to obtain compound 2-1 (31.6 g, yield: 79.6%).

2) Preparation of Compound 2-2

After introducing compound 2-1 (15.1 g, 45.4 mmol), sodium hydride (60%) (2.2 g, 54.5 mmol), 1,2-dichloroquinoxaline (10.8 g, 54.5 mmol), and DMF (200 mL) into a flask, the mixture was stirred at room temperature for 1 hour. Methanol and purified water were added to the mixture to obtain a solid substance. The solid substance was filtered, and dried under reduced pressure to obtain compound 2-2 (21 g, 94%).

3) Preparation of Compound A-39

After introducing compound 2-2 (20 g, 40.4 mmol), palladiumacetate (907 mg, 4.04 mmol), tricyclohexylphosphoniumtetrafluoroborate (1.5 g, 4.04 mmol), cesium carbonate (39.5 g, 121.2 mmol), and dimethylacetamide (DMA) (200 mL) into a flask, the mixture was heated under reflux for 2 hours. After cooling to room temperature, methanol and purified water were added to the mixture to obtain a solid substance. The solid substance was filtered, dried under reduced pressure, and purified by column chromatography to obtain compound A-39 (6 g, yield 32.4%).

|  | MW | UV | PL | M.P |
|---|---|---|---|---|
| A-39 | 458 | 440 nm | 499 nm | 308° C. |

Example 3: Preparation of Compounds A-40 and A-119

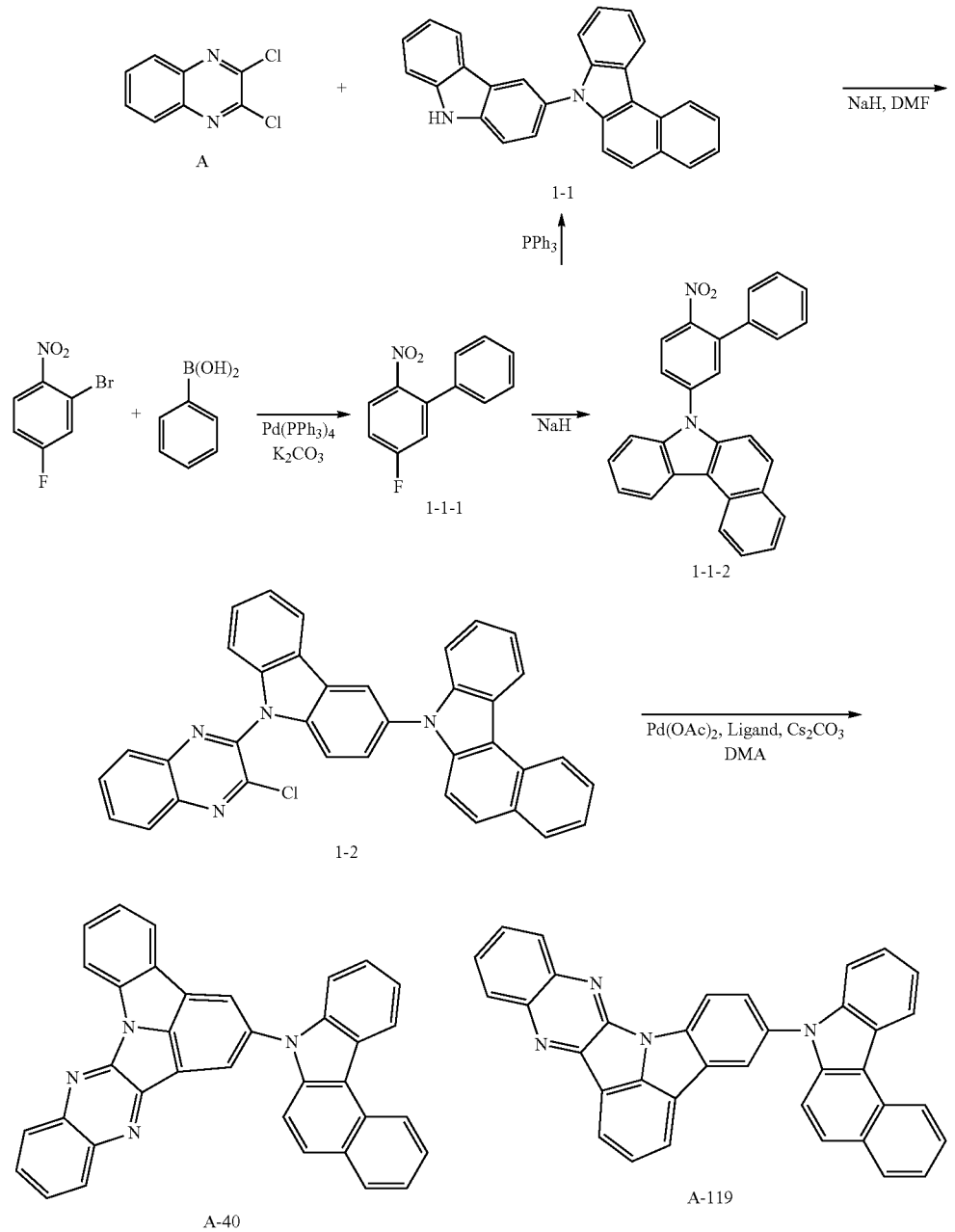

1) Preparation of Compound 1-1-1

After introducing 2-bromo-4-fluoro-1-nitrobenzene (50 g, 227.3 mmol), phenylboronic acid (30.5 g, 250.0 mmol), Pd(PPh$_3$)$_4$ (13.1 g, 11.37 mmol), 2M K$_2$CO$_3$ (200 mL), toluene (600 mL), and ethanol (200 mL) into a flask, the mixture was under reflux at 120° C. for 5 hours. After completion of the reaction, the mixture was extracted with ethyl acetate. The remaining moisture was removed from the obtained organic layer with magnesium sulfate. The product was dried, and purified by column chromatography to obtain compound 1-1-1 (46.4 g, yield: 94%).

2) Preparation of Compound 1-1-2

After dissolving compound 1-1-1 (5-fluoro-2-nitro-1,1'-biphenyl) (20 g, 92.1 mmol) and 7H-benzo[c]carbazole (20 g, 92.0 mmol) in DMF (500 mL), NaH (4.42 g, 110.5 mmol, 60% in a mineral oil) was added thereto. The mixture was stirred at 150° C. for 1 hour, and methanol and distilled water were then added thereto. The obtained solid substance was filtered under reduced pressure, and purified by column chromatography to obtain compound 1-1-2 (32.5 g, yield: 85%).

3) Preparation of Compound 1-1

After introducing compound 1-1-2 (7-(6-nitro-[1,1'-biphenyl]-3-yl)-7H-benzo[c]carbazole) (20 g, 48.26 mmol), triphenylphosphine (31.6 g, 120.6 mmol), and 1,2-dichlorobenzene (DCB) (250 mL) into a flask, the mixture was stirred at 200° C. for 5 hours, and distilled to remove DCB. The residue was purified by column chromatography to obtain compound 1-1 (9.0 g, yield: 48.8%).

4) Preparation of Compound 1-2

After dissolving compound 1-1 (7-(9H-carbazol-3-yl)-7H-benzo[c]carbazole) (9.0 g, 23.53 mmol) and compound A (2,3-dichloroquinoxaline) (5.15 g, 25.88 mmol) in DMF (100 mL), NaH (1.2 g, 28.24 mmol, 60% in a mineral oil) was added thereto. The mixture was stirred at 150° C. for 1 hour, and methanol and distilled water were added thereto. The obtained solid substance was filtered under reduced pressure, and purified by column chromatography to obtain compound 1-2 (12.0 g, yield: 93.5%).

5) Preparation of Compound A-40

After introducing compound 1-2 (12 g, 22.02 mmol), Pd(OAc)$_2$ (742 mg, 3.3 mmol), ligand (tricyclohexylphosphoniumtetrafluoroborate) (1.22 mg, 3.3 mmol), Cs$_2$CO$_3$ (21.5 g, 66.06 mmol), and o-xylene (100 mL) into a flask, the mixture was stirred under reflux for 1 hour, and cooled to room temperature, and distilled water was then added thereto. The mixture was then extracted with ethyl acetate (EA), dried with magnesium sulfate, distilled under reduced pressure, and purified by column chromatography to obtain compound A-40 (4.3 g, yield: 38.4%).

|  | MW | UV | PL | M.P |
| --- | --- | --- | --- | --- |
| A-40 | 508.57 | 418 nm | 495 nm | 255° C. |

5) Preparation of Compound A-119

After introducing compound 1-2 (12 g, 22.02 mmol), Pd(OAc)$_2$ (742 mg, 3.3 mmol), ligand (tricyclohexylphosphoniumtetrafluoroborate) (1.22 mg, 3.3 mmol), Cs$_2$CO$_3$ (21.5 g, 66.06 mmol), and o-xylene (100 mL) into a flask, the mixture was stirred under reflux for 1 hour, and cooled to room temperature, and distilled water was then added thereto. The mixture was then extracted with EA, dried with magnesium sulfate, distilled under reduced pressure, and purified by column chromatography to obtain compound A-119 (1.9 g, yield: 17.0%).

|  | MW | UV | PL | M.P |
| --- | --- | --- | --- | --- |
| A-119 | 508.57 | 402 nm | 483 nm | 297.4° C. |

Example 4: Preparation of Compound A-1

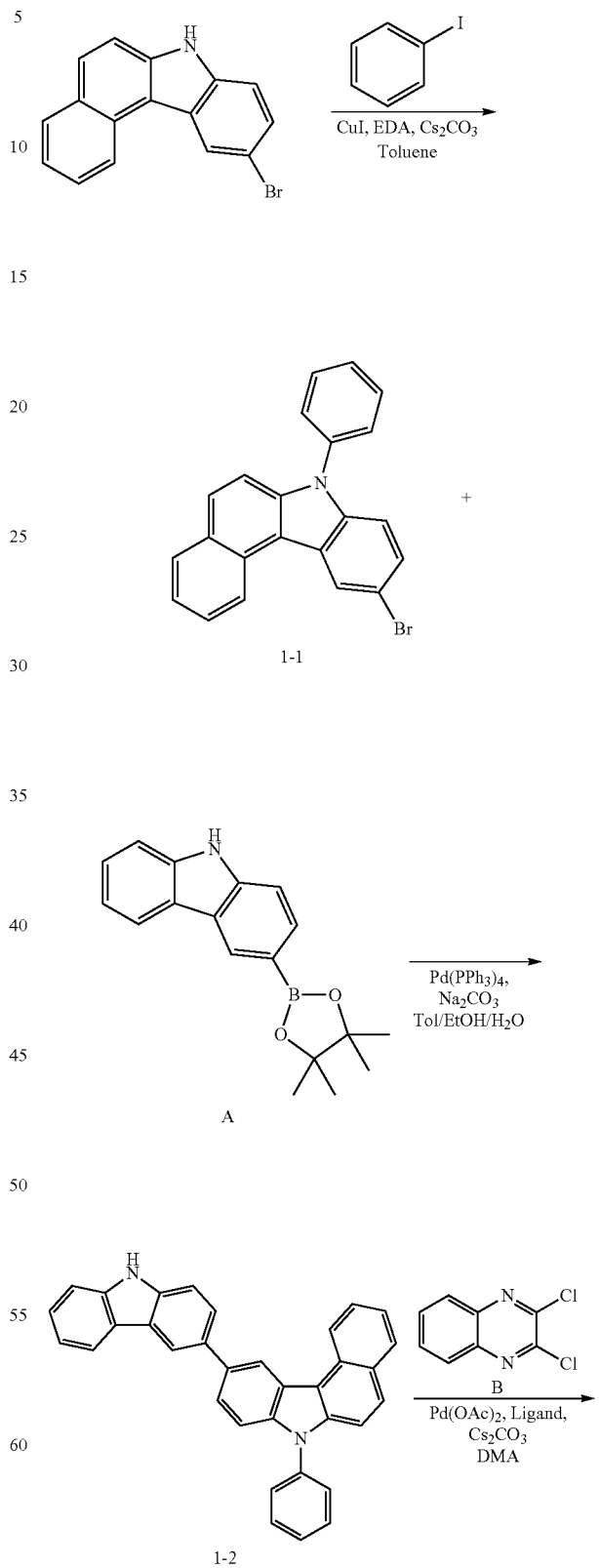

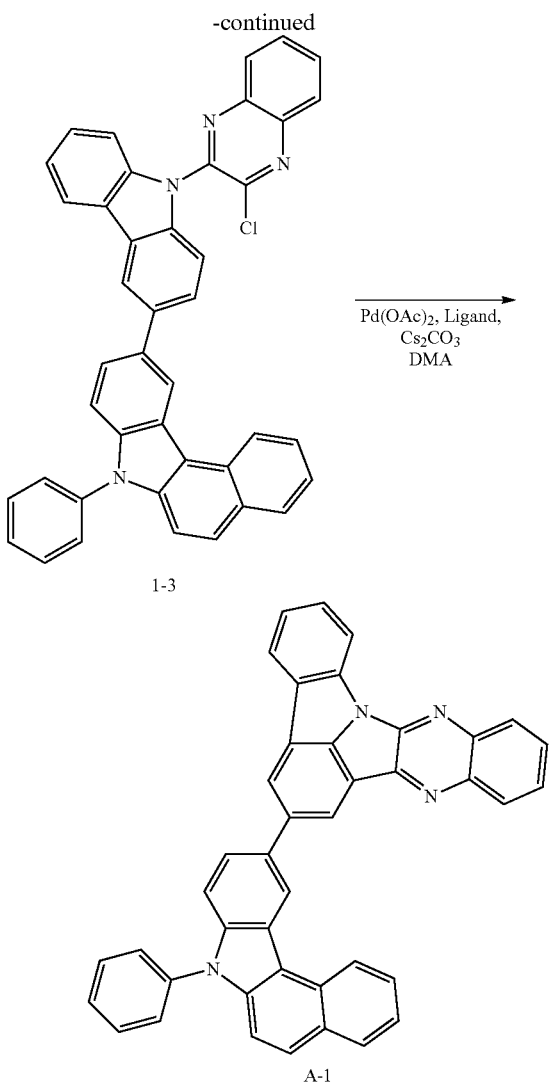

1-3

A-1

1) Preparation of Compound 1-1

After dissolving 10-bromo-7H-benzo[c]carbazole (26 g, 87.79 mmol), iodobenzene (12 mL, 105.35 mmol), CuI (8.4 g, 43.89 mmol), ethylene diamine (EDA) (3 mL, 43.89 mmol), and Cs$_2$CO$_3$ (85 g, 263.37 mmol) in toluene (500 mL) of a flask, the mixture was under reflux at 120° C. for 5 hours. After completion of the reaction, the mixture was extracted with ethyl acetate. The remaining moisture was removed from the obtained organic layer with magnesium sulfate. The product was dried, and purified by column chromatography to obtain compound 1-1 (18 g, yield: 70%).

2) Preparation of Compound 1-2

After dissolving compound 1-1 (18 g, 60.68 mmol), compound A (19 g, 66.75 mmol), and Pd(PPh$_3$)$_4$ (3.3 g, 3.03 mmol) in 2M Na$_2$CO$_3$ (300 mL), toluene (600 mL), and ethanol (300 mL), the mixture was under reflux at 120° C. for 5 hours. After completion of the reaction, the mixture was extracted with ethyl acetate. The remaining moisture was removed from the obtained organic layer with magnesium sulfate. The product was dried, and purified by column chromatography to obtain compound 1-2 (17 g, yield: 63%).

3) Preparation of Compound 1-3

After dissolving compound B (2,3-dichloroquinoxaline) (19 g, 94.12 mmol), and compound 1-2 (36 g, 78.51 mmol) in DMF (500 mL), NaH (4.7 g, 117.76 mmol, 60% in a mineral oil) was added thereto. The mixture was stirred at room temperature for 1 hour, and methanol and distilled water were added thereto. The obtained solid substance was filtered under reduced pressure, and purified by column chromatography to obtain compound 1-3 (44.6 g, yield: 92%).

4) Preparation of Compound A-1

After introducing compound 1-3 (44.6 g, 71.08 mmol), Pd(OAc)$_2$ (1.6 g, 7.18 mmol), ligand (tricyclohexylphosphoniumtetrafluoroborate) (2.6 g, 7.18 mmol), Cs$_2$CO$_3$ (70 g, 215.4 mmol), and xylene (360 mL) into a flask, the mixture was stirred under reflux for 1 hour. The mixture was cooled to room temperature, and distilled water was then added thereto. The mixture was then extracted with MC, dried with magnesium sulfate, distilled under reduced pressure, and purified by column chromatography to obtain compound A-1 (14.6 g, yield: 36%).

|     | MW     | UV     | PL     | M.P       |
| --- | ------ | ------ | ------ | --------- |
| A-1 | 584.67 | 358 nm | 503 nm | 217.5° C. |

Example 5: Preparation of Compound A-16

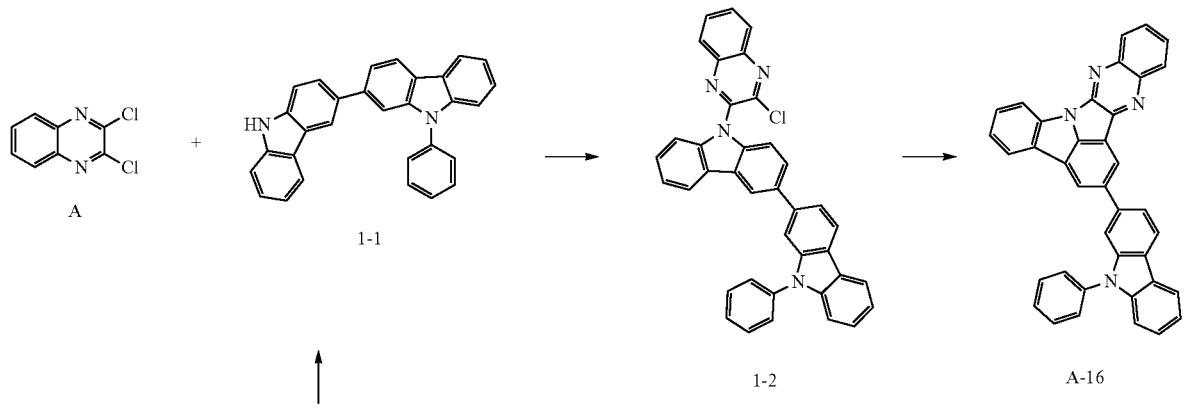

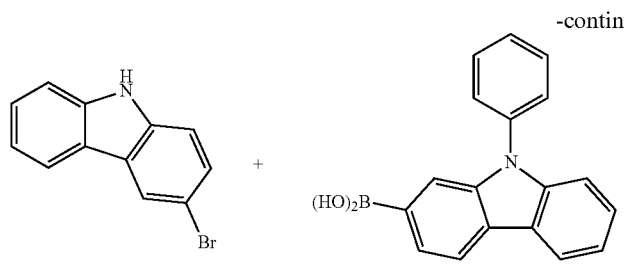

1) Preparation of Compound 1-1

After dissolving 3-bromo-9H-carbazole (14 g, 56.99 mmol), (9-phenyl-9H-carbazol-2-yl)boronic acid (18 g, 62.69 mmol), and Pd(PPh$_3$)$_4$ (3.2 g, 2.85 mmol) in 2M Na$_2$CO$_3$ (150 mL), toluene (300 mL), and ethanol (150 mL) of a flask, the mixture was under reflux at 120° C. for 5 hours. After completion of the reaction, the mixture was extracted with ethyl acetate. The remaining moisture was removed from the obtained organic layer with magnesium sulfate. The product was dried, and purified by column chromatography to obtain compound 1-1 (21.3 g, yield: 93%).

2) Preparation of Compound 1-2

After dissolving compound A (2,3-dichloroquinoxaline) (12 g, 62.57 mmol) and compound 1-1 (21.3 g, 52.14 mmol) in DMF (300 mL), NaH (1.8 g, 78.21 mmol, 60% in a mineral oil) was added thereto. The mixture was stirred at room temperature for 1 hour, and methanol and distilled water were added thereto. The obtained solid substance was filtered under reduced pressure, and purified by column chromatography to obtain compound 1-2 (21 g, yield: 72%).

3) Preparation of Compound A-16

After introducing compound 1-2 (21 g, 36.77 mmol), Pd(OAc)$_2$ (0.8 g, 3.677 mmol), ligand (tricyclohexylphosphoniumtetrafluoroborate) (1.4 g, 3.677 mmol), Cs$_2$CO$_3$ (36 g, 110.3 mmol), and xylene (200 mL) into a flask, the mixture was stirred under reflux for 1 hour, cooled to room temperature, and distilled water was then added thereto. The mixture was extracted with MC, dried with magnesium sulfate, distilled under reduced pressure, and purified by column chromatography to obtain compound A-16 (4.2 g, yield: 22%).

|      | MW     | UV     | PL     | M.P      |
|------|--------|--------|--------|----------|
| A-16 | 534.61 | 344 nm | 489 nm | 268.6° C.|

Example 6: Preparation of Compound A-280

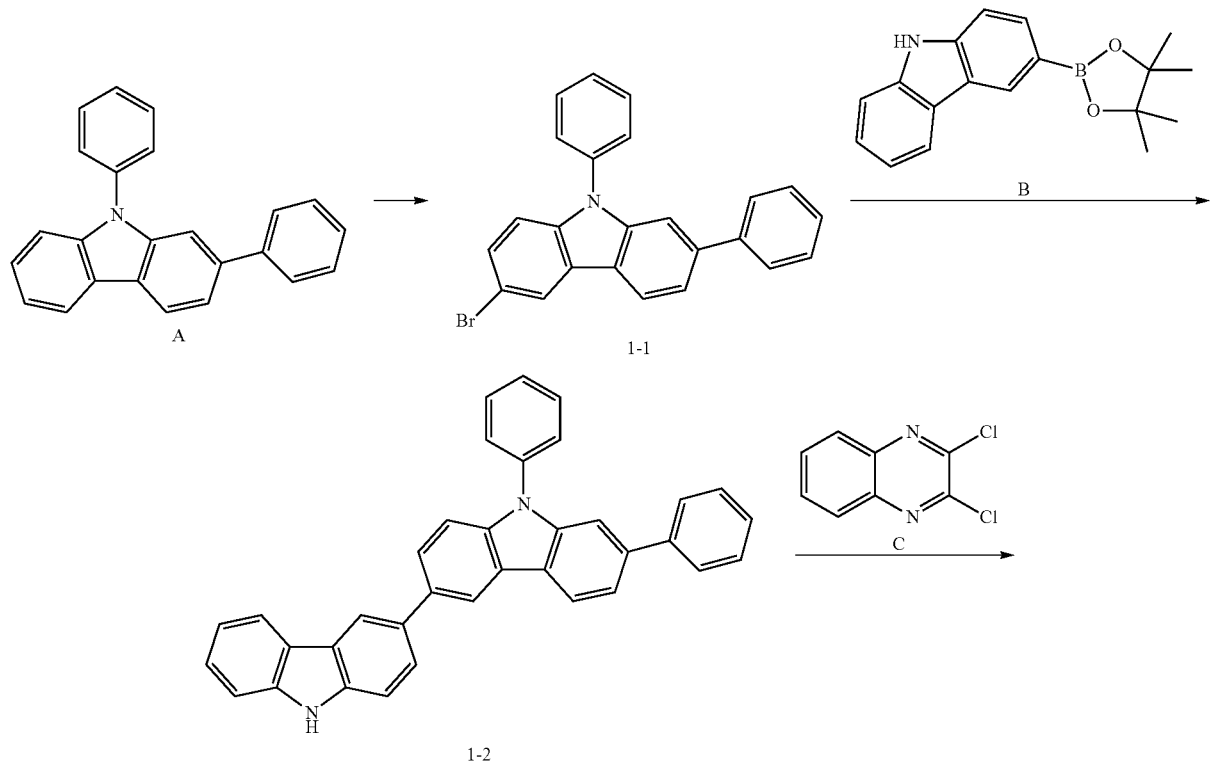

-continued

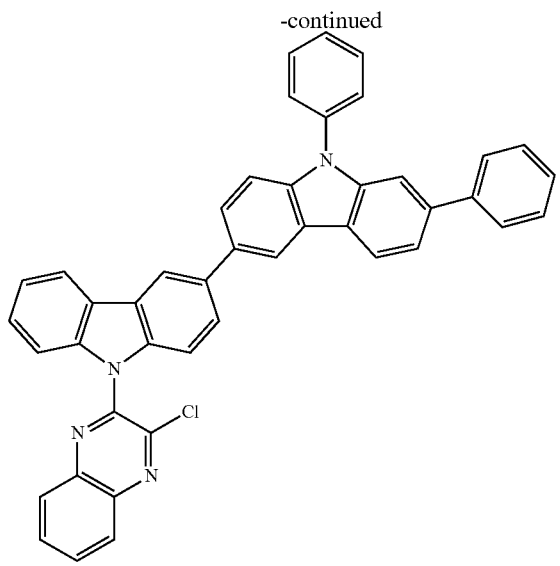

1-3

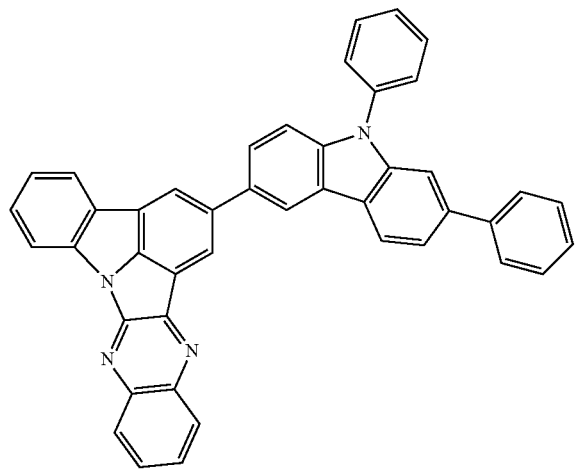

A-280

1) Preparation of Compound 1-1

After dissolving compound A (25.7 g, 80.46 mmol) in dimethylformamide of a reaction vessel, N-bromosuccinamide (14.3 g, 80.46 mmol) dissolved in dimethylformamide was added thereto. The reaction mixture was stirred for 4 hours, washed with distilled water, and extracted with ethyl acetate. The obtained organic layer was dried with magnesium sulfate, and the solvent was removed therefrom by a rotary evaporator. The product was purified by column chromatography to obtain compound 1-1 (12.6 g, yield: 39%).

2) Preparation of Compound 1-2

After introducing compound 1-1 (12.6 g, 31.63 mmol), compound B (11.1 g, 37.96 mmol), tetrakis(triphenylphosphine)palladium (1.1 g, 0.95 mmol), potassium carbonate (11 g, 79.08 mmol), toluene (160 mL), and ethanol (40 mL) into a reaction vessel, distilled water (40 mL) was added thereto. The mixture was stirred at 120° C. for 4 hours. After completion of the reaction, the mixture was washed with distilled water, and extracted with ethyl acetate. The obtained organic layer was dried with magnesium sulfate, and the solvent was removed therefrom by a rotary evaporator. The product was purified by column chromatography to obtain compound 1-2 (11 g, yield: 72%).

3) Preparation of Compound 1-4

After dissolving compound 1-2 (11 g, 22.70 mmol) in DMF (110 mL) of a reaction vessel, sodium hydride (1.4 g, 34.05 mmol) was slowly added dropwise to the mixture at 0° C. The mixture was stirred for 30 minutes, and 2,3-dichloroquinoxaline (5.4 g, 27.24 mmol) was then added dropwise thereto. The mixture was stirred at room temperature for 3 hours, and methanol and distilled water were added thereto. The obtained solid substance was filtered under reduced pressure, and purified by column chromatography to obtain compound 1-3 (8.3 g, yield: 56%).

4) Preparation of Compound A-280

After adding xylene (64 mL) to compound 1-3 (8.3 g, 12.83 mmol), palladium acetate (0.4 g, 1.92 mmol), PCy$_3$HBF$_4$ (0.7 g, 1.92 mmol), and cesium carbonate (12.5 g, 38.49 mmol) in a reaction vessel, the mixture was under reflux at 180° C. for 5 hours. After completion of the reaction, the mixture was washed with distilled water, and extracted with ethyl acetate. The obtained organic layer was dried with magnesium sulfate, and the solvent was removed therefrom by a rotary evaporator. The product was purified by column chromatography to obtain compound A-280 (1.8 g, yield: 23%).

|       | MW     | UV     | PL     | M.P    |
|-------|--------|--------|--------|--------|
| A-280 | 610.70 | 374 nm | 491 nm | 322° C. |

Example 7: Preparation of Compound A-278

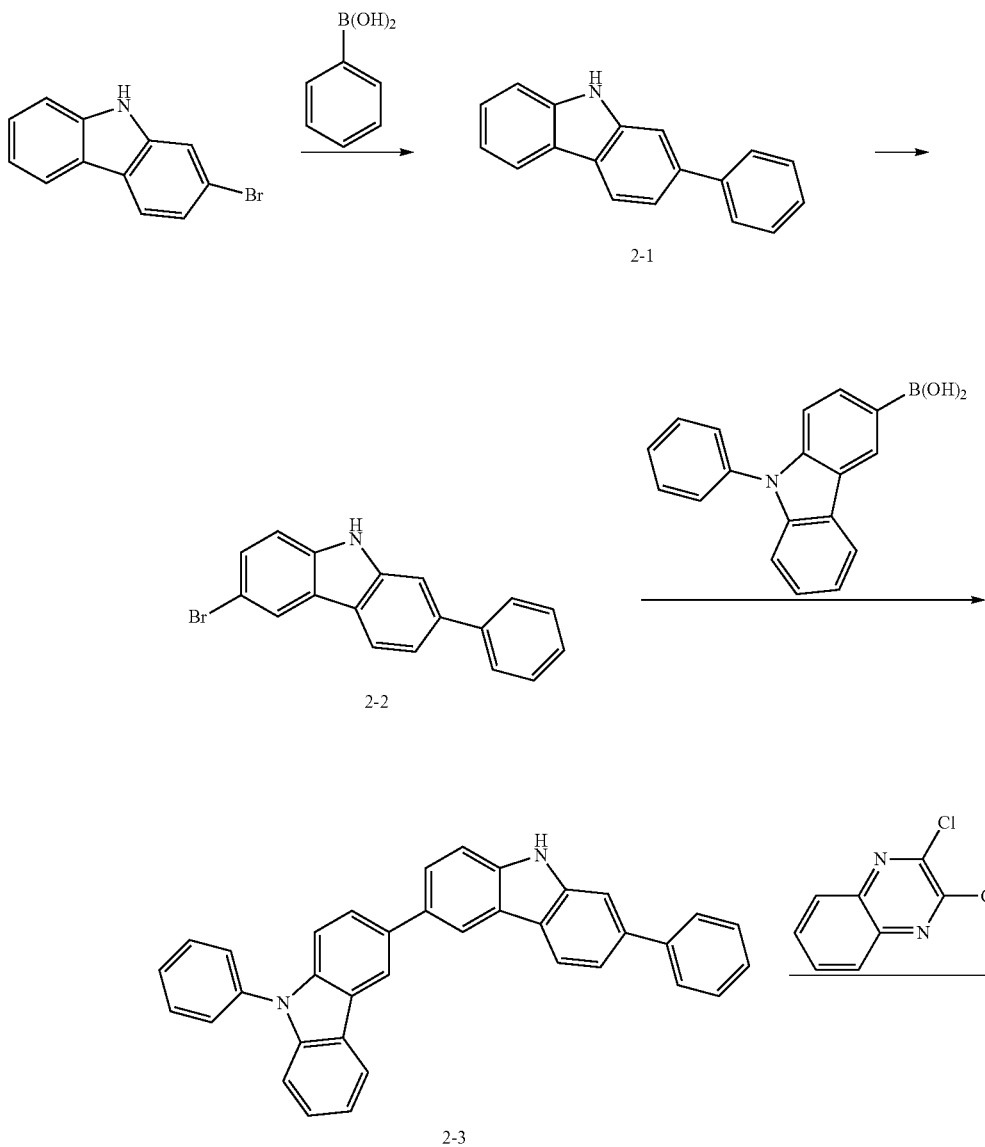

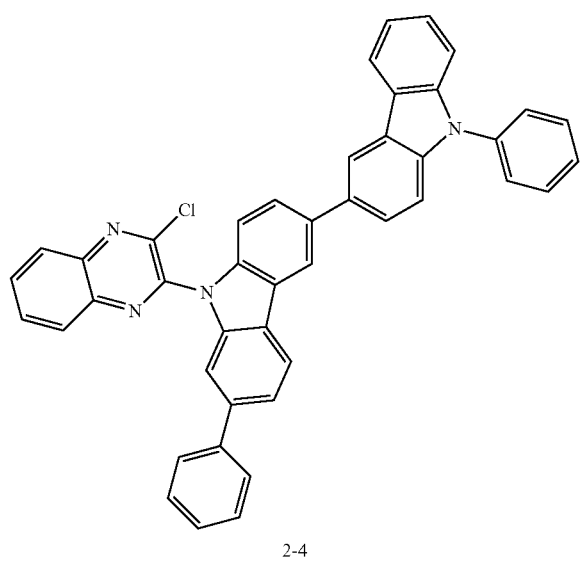

2-4

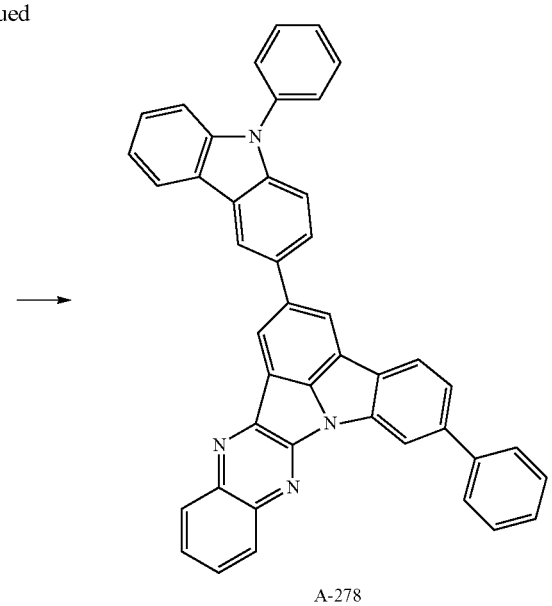

A-278

1) Preparation of Compound 2-1

After dissolving 2-bromo-9H-carbazole (50 g, 203.1 mmol), phenylboronic acid (30 g, 243.8 mmol), and Pd(PPh$_3$)$_4$ (12 g, 10.15 mmol) in 2M Na$_2$CO$_3$ (500 mL), toluene (1000 mL), and ethanol (500 mL) of a flask, the mixture was under reflux at 120° C. for 5 hours. After completion of the reaction, the mixture was extracted with ethyl acetate. The remaining moisture was removed from the obtained organic layer with magnesium sulfate. The product was dried, and purified by column chromatography to obtain compound 2-1 (48.3 g, yield: 97%).

2) Preparation of Compound 2-2

After dissolving compound 2-1 (20 g, 82.20 mmol) in DMF (830 mL), the mixture was kept at 0° C., and N-bromosuccinimide (NBS) (14 g, 82.20 mmol) dissolved in DMF (100 mL) was added thereto. The mixture was under reflux at room temperature for 4 hours. After completion of the reaction, the mixture was extracted with ethyl acetate. The remaining moisture was removed from the obtained organic layer with magnesium sulfate. The product was dried, and purified by column chromatography to obtain compound 2-2 (20 g, yield: 77%).

3) Preparation of Compound 2-3

After dissolving compound 2-3 (20 g, 62.07 mmol), (9-phenyl-9H-carbazol-3-yl)boronic acid (19 g, 68.28 mmol), and Pd(PPh$_3$)$_4$ (3.6 g, 3.103 mmol) in 2M Na$_2$CO$_3$ (160 mL), toluene (320 mL), and ethanol (160 mL), the mixture was under reflux at 120° C. for 5 hours. After completion of the reaction, the mixture was extracted with ethyl acetate. The remaining moisture was removed from the obtained organic layer with magnesium sulfate. The product was dried, and purified by column chromatography to obtain compound 2-4 (18.5 g, yield: 60%).

4) Preparation of Compound 2-4

After dissolving compound A (2,3-dichloroquinoxaline) (10 g, 45.81 mmol) and compound 2-3 (18.5 g, 38.18 mmol) in DMF (200 mL), NaH (2.3 g, 57.27 mmol, 60% in a mineral oil) was added thereto. The mixture was stirred at room temperature for 1 hour, and methanol and distilled water were added thereto. The obtained solid substance was filtered under reduced pressure, and purified by column chromatography to obtain compound 2-4 (15.8 g, yield: 66%).

5) Preparation of Compound A-278

After introducing compound 2-4 (15.8 g, 24.41 mmol), Pd(OAc)$_2$ (0.5 g, 2.441 mmol), ligand (tricyclohexylphosphoniumtetrafluoroborate) (0.9 g, 2.441 mmol), Cs$_2$CO$_3$ (23.8 g, 73.23 mmol), and xylene (125 mL) into a flask, the mixture was stirred under reflux for 1 hour, cooled to room temperature, and distilled water was then added thereto. The mixture was extracted with MC, dried with magnesium sulfate, distilled under reduced pressure, and purified by column chromatography to obtain compound A-278 (1.6 g, yield: 11%).

| | MW | UV | PL | M.P |
|---|---|---|---|---|
| A-278 | 610.70 | 356 nm | 502 nm | 369.9° C. |

Example 8: Preparation of Compound A-78

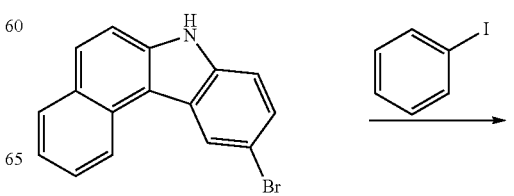

-continued

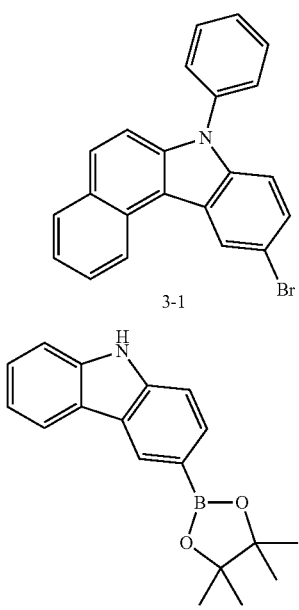

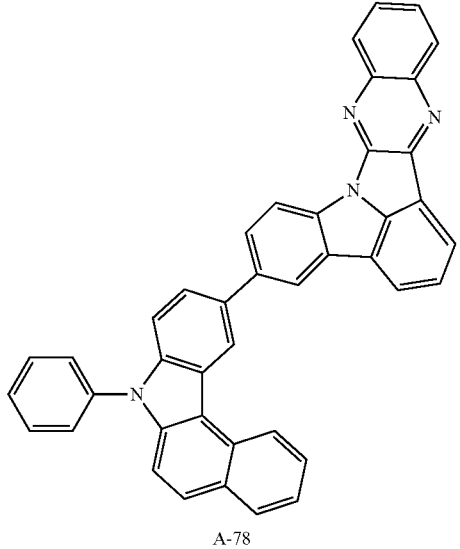
A-78

1) Preparation of Compound 3-1

After dissolving 10-bromo-7H-benzo[c]carbazole (26 g, 87.79 mmol), iodobenzene (12 mL, 105.35 mmol), CuI (8.4 g, 43.89 mmol), EDA (3 mL, 43.89 mmol), and $Cs_2CO_3$ (85 g, 263.37 mmol) in toluene (500 mL) of a flask, the mixture was under reflux at 120° C. for 5 hours. After completion of the reaction, the mixture was extracted with ethyl acetate. The remaining moisture was removed from the obtained organic layer with magnesium sulfate. The product was dried, and purified by column chromatography to obtain compound 3-1 (18 g, yield: 70%).

2) Preparation of Compound 3-2

After dissolving compound 3-1 (18 g, 60.68 mmol), compound A (19 g, 66.75 mmol), and $Pd(PPh_3)_4$ (3.3 g, 3.03 mmol) in 2M $Na_2CO_3$ (300 mL), toluene (600 mL), and ethanol (300 mL), the mixture was under reflux at 120° C. for 5 hours. After completion of the reaction, the mixture was extracted with ethyl acetate. The remaining moisture was removed from the obtained organic layer with magnesium sulfate. The product was dried, and purified by column chromatography to obtain compound 3-2 (17 g, yield: 63%).

3) Preparation of Compound 3-3

After dissolving compound B (2,3-dichloroquinoxaline) (19 g, 94.12 mmol) and compound 3-2 (36 g, 78.51 mmol) in DMF (500 mL), NaH (4.7 g, 117.76 mmol, 60% in a mineral oil) was added thereto. The mixture was stirred at room temperature for 1 hour, and methanol and distilled water were added thereto. The obtained solid substance was filtered under reduced pressure, and purified by column chromatography to obtain compound 3-3 (44.6 g, yield: 92%).

4) Preparation of Compound A-78

After introducing compound 3-3 (44.6 g, 71.08 mmol), $Pd(OAc)_2$ (1.6 g, 7.18 mmol), ligand (tricyclohexylphosphoniumtetrafluoroborate) (2.6 g, 7.18 mmol), $Cs_2CO_3$ (70 g, 215.4 mmol), and xylene (360 mL) into a flask, the mixture was stirred under reflux for 1 hour. The mixture was cooled to room temperature, and distilled water was added thereto. The mixture was extracted with MC, dried with magnesium sulfate, distilled under reduced pressure, and purified by column chromatography to obtain compound A-78 (2.5 g, yield: 6%).

|      | MW     | UV     | PL     | M.P      |
|------|--------|--------|--------|----------|
| A-78 | 584.67 | 374 nm | 487 nm | 337.4° C.|

Example 9: Preparation of Compound A-159

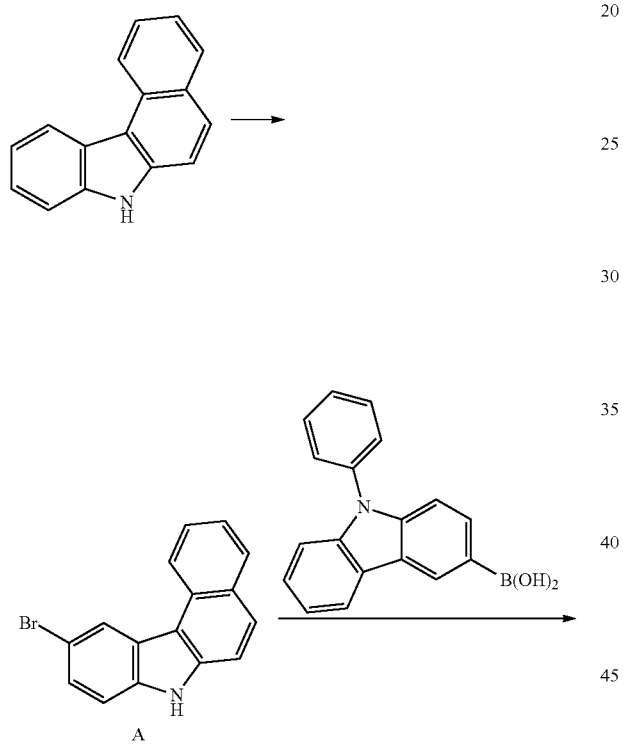

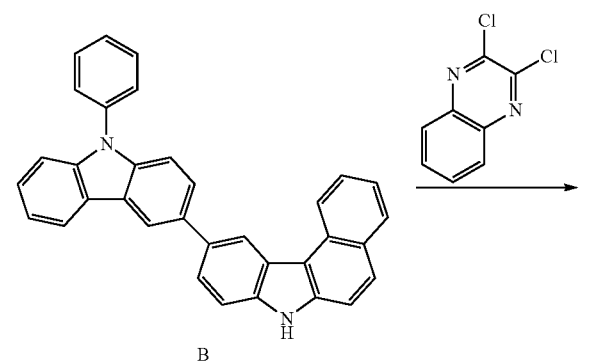

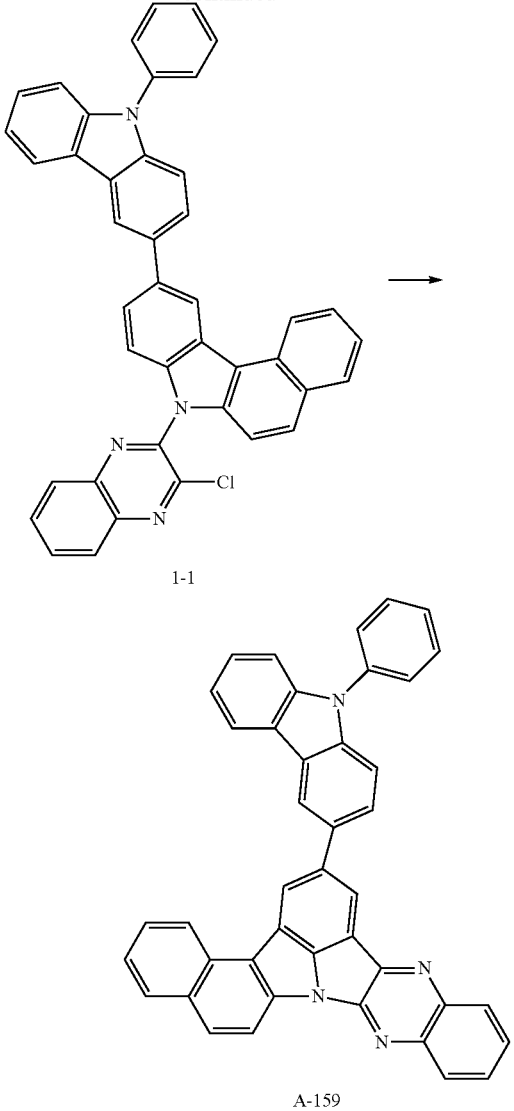

1) Preparation of Compound A

After introducing 7H-benzo[c]carbazole (50 g, 230 mmol) and DMF (200 mL) into a flask, the mixture was stirred, and N-bromosuccinimide (42 g, 230 mmol) dissolved in DMF (50 mL) was added thereto. The resultant mixture was stirred at room temperature for 12 hours, and extracted with distilled water and MC. The obtained organic layer was dried with magnesium sulfate, and distilled under reduced pressure. The residue was purified by column chromatography to obtain compound A (10-bromo-7H-benzo[c]carbazole) (16 g, yield: 23.5%).

2) Preparation of Compound B

After introducing compound A (10-bromo-7H-benzo[c]carbazole) (16 g, 54 mmol), (9-phenyl-9H-carbazol-3-yl) boronic acid (17 g, 59.4 mmol), Pd(PPh$_3$)$_4$ (3.1 g, 2.7 mmol), K$_2$CO$_3$ (25.7 g, 108 mmol), distilled water (50 mL), toluene (250 mL), and ethanol (EtOH) (50 mL) in a flask, the mixture was stirred under reflux for 12 hours. After cooling to room temperature, the mixture was extracted with EA and distilled water, dried with magnesium sulfate, distilled under reduced pressure, and purified by column chromatography to obtain compound B (10-(9-phenyl-9H-carbazol-3-yl)-7H-benzo[c]carbazole) (22 g, yield: 88.7%).

3) Preparation of Compound 1-1

After introducing compound B (10-(9-phenyl-9H-carbazol-3-yl)-7H-benzo[c]carbazole) (22 g, 48 mmol), sodium hydride (60%) (2.3 g, 57.6 mmol), 2,3-dichloroquinoxaline (10.5 g, 52.8 mmol), and DMF (250 mL) into a flask, the mixture was stirred at room temperature for 1 hour. Methanol and purified water were added thereto. The obtained solid substance was filtered, and dried under reduced pressure to obtain compound 1-1 (22.4 g, yield: 75.1%).

4) Preparation of Compound A-159

After introducing compound 1-1 (22.4 g, 36 mmol), Pd(OAc)$_2$ (1.22 g, 5.4 mmol), tricyclohexylphosphonium tetrafluoroborate (2 g, 5.4 mmol), Cs$_2$CO$_3$ (35.3 g, 108 mmol), and o-xylene (200 mL) into a flask, the mixture was stirred under reflux for 3 hours, cooled to room temperature, extracted with EA and distilled water, dried with magnesium sulfate, and distilled under reduced pressure. The product was purified by column chromatography to obtain compound A-159 (5.8 g, yield: 28%).

|  | MW | UV | PL | M.P |
|---|---|---|---|---|
| A-159 | 584.67 | 434 nm | 499 nm | 340° C. |

Example 10: Preparation of Compound A-289

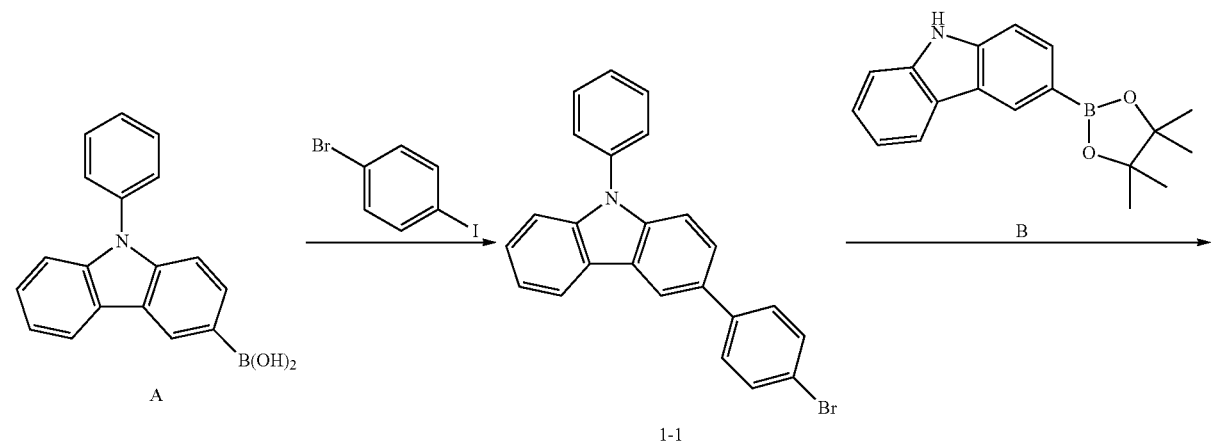

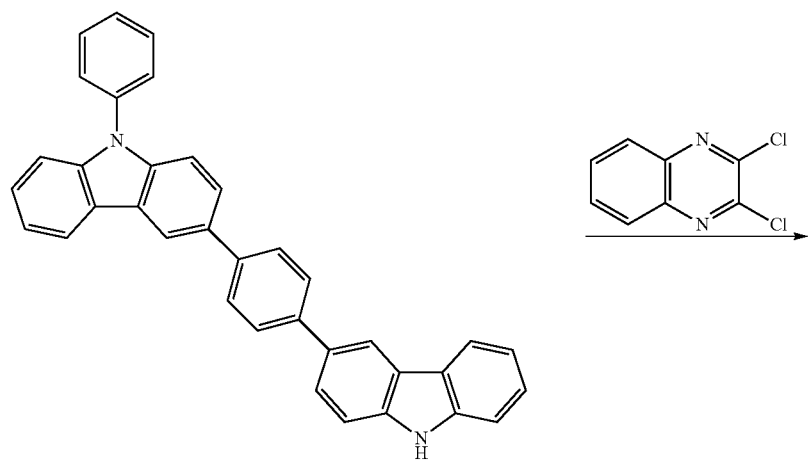

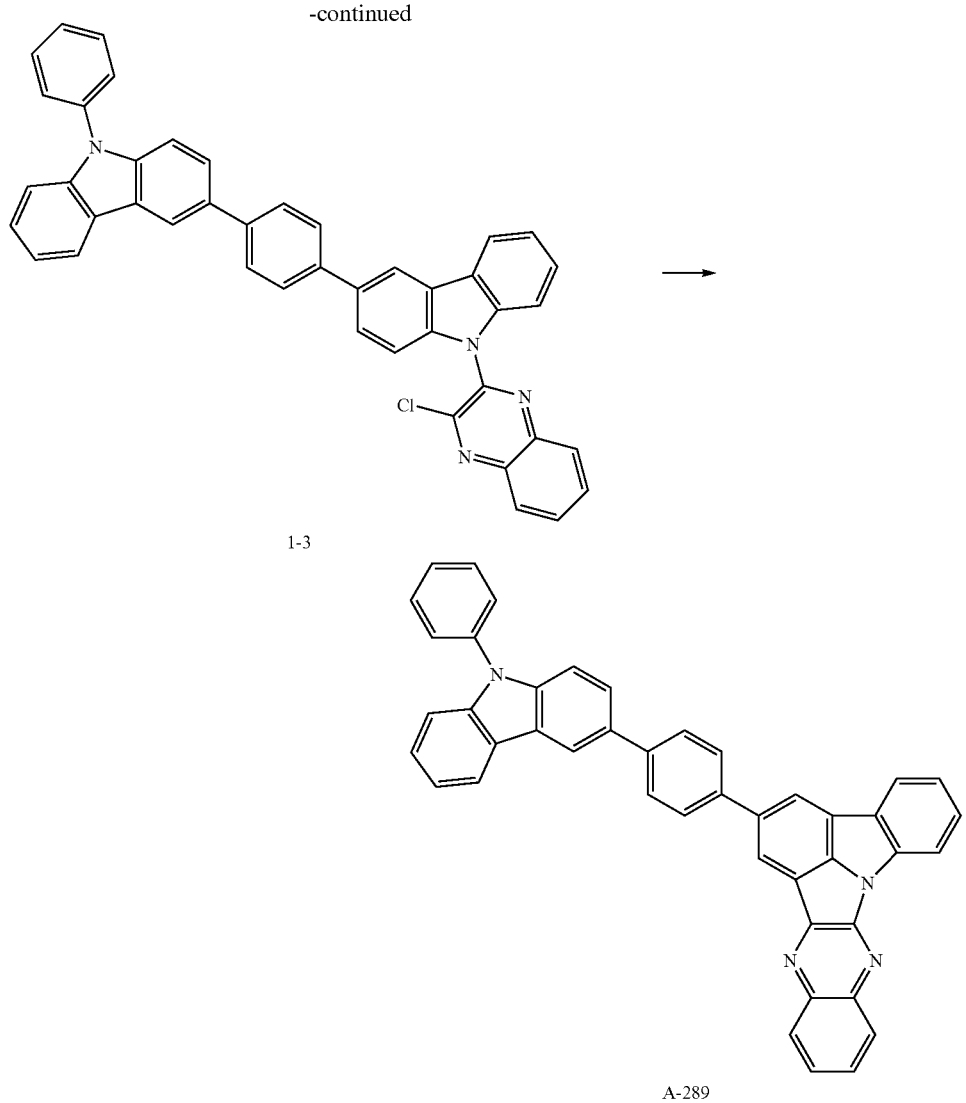

1-3

A-289

1) Preparation of Compound 1-1

After introducing compound A (15 g, 52.2 mmol), 4-bromo-1-iodobenzene (17.8 g, 62.7 mmol), tetrakis(triphenylphosphine)palladium (1.8 g, 1.6 mmol), sodium carbonate (14 g, 130.5 mmol), toluene (260 mL), and ethanol (60 mL) into a reaction vessel, distilled water (60 mL) was added thereto. The mixture was stirred at 120° C. for 4 hours. After completion of the reaction, the mixture was washed with distilled water, and extracted with ethyl acetate. The obtained organic layer was dried with magnesium sulfate, and the solvent was removed therefrom by a rotary evaporator. The product was purified by column chromatography to obtain compound 1-1 (11.3 g, yield: 53%).

2) Preparation of Compound 1-2

After introducing compound 1-1 (11.3 g, 28.42 mmol), compound B (10.0 g, 34.11 mmol), tetrakis(triphenylphosphine)palladium (0.6 g, 0.55 mmol), potassium carbonate (6.3 g, 45.90 mmol), toluene (100 mL), and ethanol (25 mL) into a reaction vessel, distilled water (25 mL) was added thereto. The mixture was stirred at 120° C. for 4 hours. After completion of the reaction, the mixture was washed with distilled water, and extracted with ethyl acetate. The obtained organic layer was dried with magnesium sulfate, and the solvent was removed therefrom by a rotary evaporator. The product was purified by column chromatography to obtain compound 1-2 (8 g, yield: 58%).

3) Preparation of Compound 1-3

After dissolving compound 1-2 (5.3 g, 10.94 mmol) in DMF (55 mL) of a reaction vessel, sodium hydride (0.7 g, 16.41 mmol) was slowly added dropwise to the mixture at 0° C. The mixture was stirred for 30 minutes, and 2,3-dichloroquinoxaline (2.6 g, 13.12 mmol) was then added dropwise to the mixture. The mixture was stirred at room temperature for 3 hours, and methanol and distilled water were added thereto. The obtained solid substance was filtered under reduced pressure, and purified by column chromatography to obtain compound 1-3 (5.5 g, yield: 79%).

4) Preparation of Compound A-289

After adding xylene (43 mL) to compound 1-3 (5.5 g, 8.50 mmol), palladium acetate (0.3 g, 1.28 mmol), tricyclohexylphosphinetetrafluoroborate (PCy$_3$HBF$_4$) (0.5 g, 1.28 mmol), and cesium carbonate (8.3 g, 25.50 mmol), the mixture was under reflux at 180° C. for 5 hours. After completion of the reaction, the mixture was washed with distilled water, and extracted with ethyl acetate. The obtained organic layer was dried with magnesium sulfate, and the solvent was removed therefrom by a rotary evaporator. The product was purified by column chromatography to obtain compound A-289 (1 g, yield: 20%).

|  | MW | UV | PL | M.P |
|---|---|---|---|---|
| A-289 | 610.70 | 360 nm | 491 nm | 337° C. |

Example 11: Preparation of Compound A-91

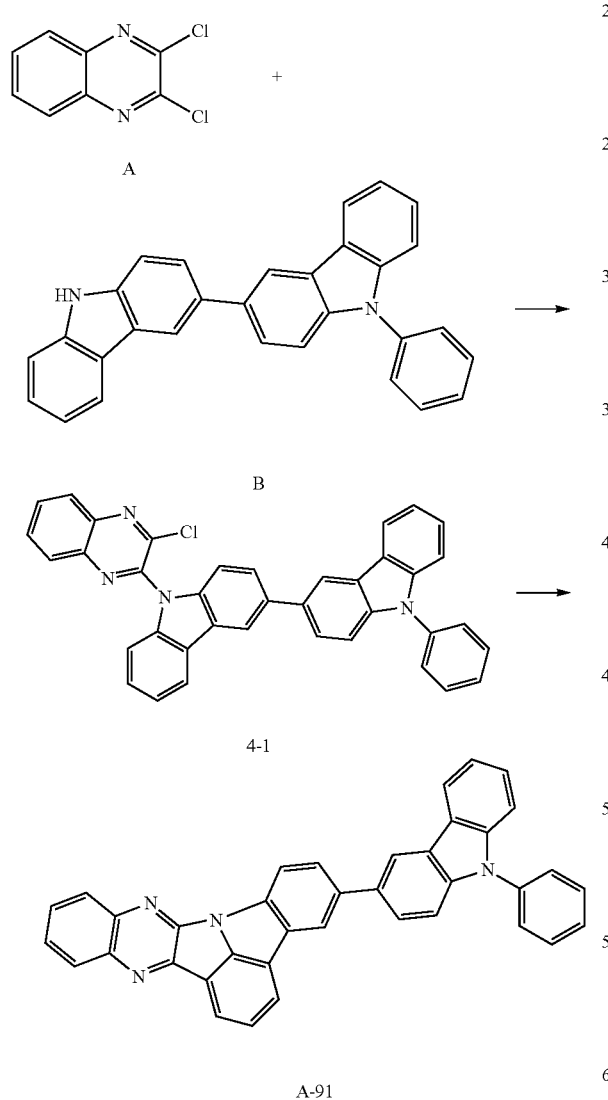

1) Preparation of Compound 4-1

After dissolving compound A (2,3-dichloroquinoxaline) (20 g, 100.48 mmol) and compound B (34 g, 83.73 mmol) in DMF (500 mL), NaH (5 g, 125.59 mmol, 60% in a mineral oil) was added thereto. The mixture was stirred at room temperature for 1 hour, and methanol and distilled water were added thereto. The obtained solid substance was filtered under reduced pressure, and purified by column chromatography to obtain compound 4-1 (45 g, yield: 95%).

2) Preparation of Compound A-91

After introducing compound 4-1 (25 g, 43.77 mmol), Pd(OAc)$_2$ (1 g, 4.377 mmol), ligand (tricyclohexylphosphoniumtetrafluoroborate) (1.6 g, 4.377 mmol), Cs$_2$CO$_3$ (42 g, 131.3 mmol), and xylene (220 mL) into a flask, the mixture was stirred under reflux for 1 hour, cooled to room temperature, and distilled water was then added thereto. The mixture was extracted with MC, dried with magnesium sulfate, distilled under reduced pressure, and purified by column chromatography to obtain compound A-91 (2.4 g, yield: 10%).

|  | MW | UV | PL | M.P. |
|---|---|---|---|---|
| A-91 | 534.61 | 344 nm | 497 nm | 321° C. |

Example 12: Preparation of Compound A-287

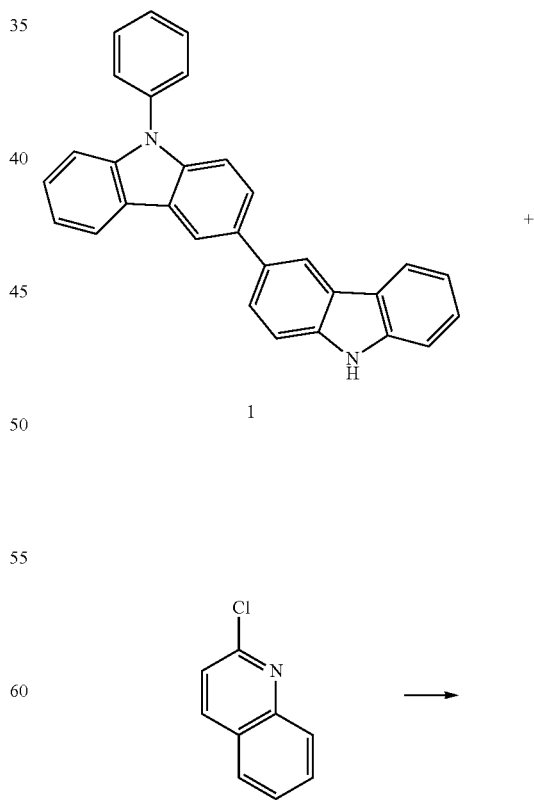

-continued

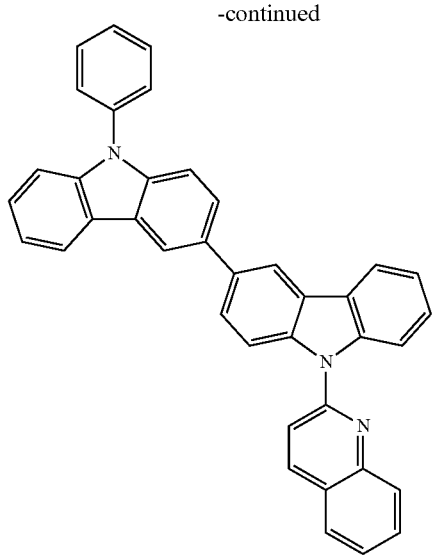

A-287

1) Preparation of Compound 3

After dissolving compound 1 (9-phenyl-9H,9'H-3,3'-bicarbazole) (15 g, 36.72 mmol), compound 2 (2-chloroquinoline) (6.6 g, 40.39 mmol), CuI (13.9 g, 73.44 mmol), trans-1,2-diaminocyclohexane (2.7 mL, 22.03 mmol), and Cs₂CO₃ (35.8 g, 110.16 mmol) in o-DCB (250 mL) of a flask, the mixture was under reflux at 200° C. for 8 hours. After completion of the reaction, the mixture was filtered with MC under reduced pressure, and purified by column chromatography. Methanol was added to the purified product. The obtained solid substance was filtered under reduced pressure to obtain compound 3 (12.5 g, yield: 64%).

2) Preparation of Compound A-287

After adding compound 3 (9-phenyl-9'-(quinoline-2-yl)-9H,9'H-3,3'-bicarbazole) (10.5 g, 19.6 mmol), Pd(OAc)₂ (0.44 g, 1.96 mmol), K₂CO₃ (0.54 g, 3.92 mmol) to pivalic acid (40 mL), the mixture was under reflux at 170° C. for 24 hours. After completion of the reaction, the mixture was neutralized with NaHCO₃, extracted with MC, dried with MgSO₄, and purified by column chromatography. Methanol was added to the purified product, and the obtained solid substance was filtered under reduced pressure to obtain compound A-287 (0.6 g, yield: 6%).

|       | MW     | UV     | PL     | M.P     |
|-------|--------|--------|--------|---------|
| A-287 | 533.62 | 332 nm | 487 nm | 215° C. |

Example 13: Preparation of Compound A-92

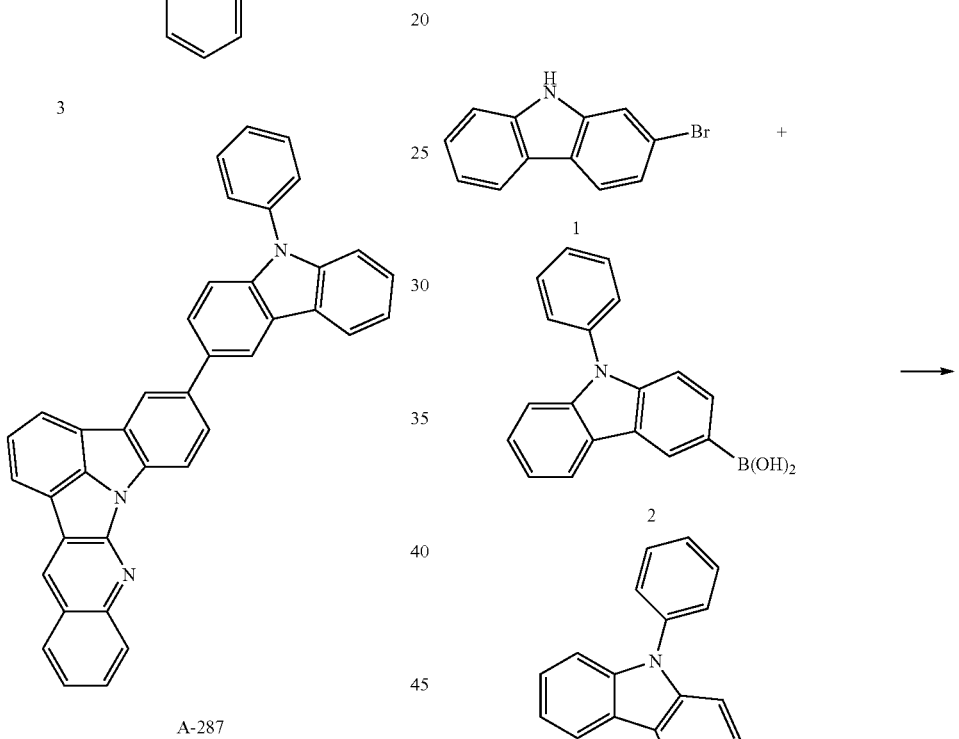

-continued

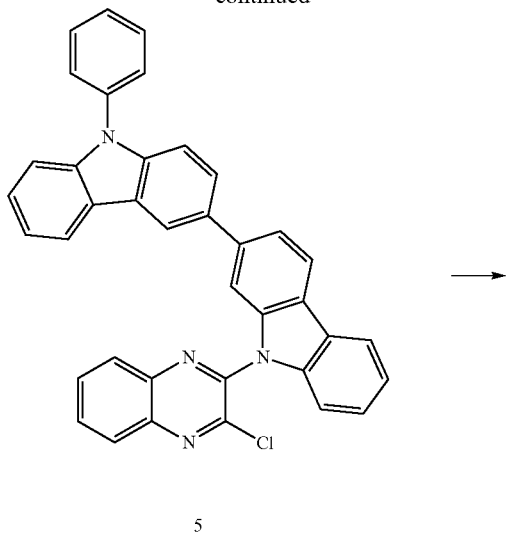

5

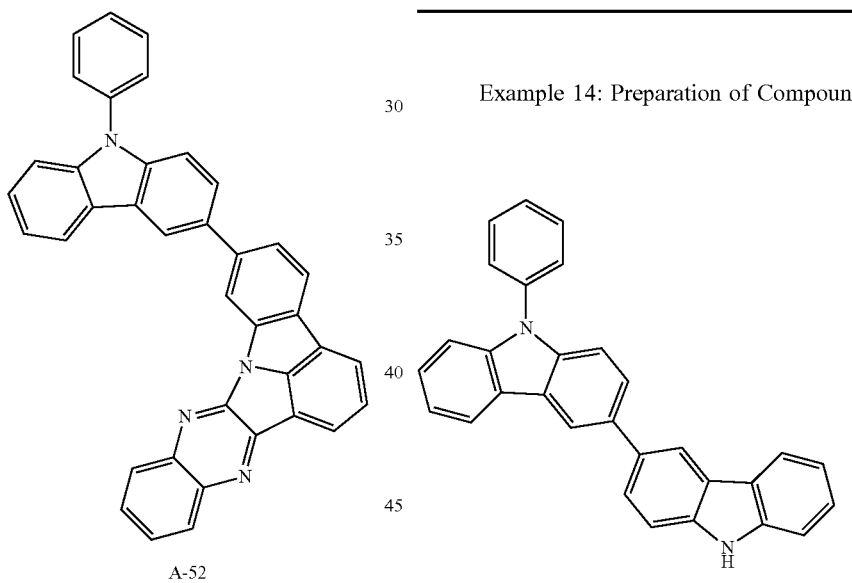

A-52

1) Preparation of Compound 3

After dissolving compound 1 (2-bromo-9H-carbazole) (20 g, 69.70 mmol), compound 2 ((9-phenyl-9H-carbazol-3-yl)boronic acid) (17.2 g, 69.70 mmol), Pd(PPh$_3$)$_4$ (2.4 g, 2.10 mmol), and Na$_2$CO$_3$ (18.5 g, 174.30 mmol) in toluene, ethanol, and H$_2$O, the mixture was under reflux at 120° C. for 1 day. After completion of the reaction, the mixture was extracted with ethyl acetate. The obtained organic layer was dried, and purified by column chromatography to obtain compound 3 (12.8 g, yield: 45%).

2) Preparation of Compound 5

After dissolving compound 3 (9'-phenyl-9H,9'H-2,3'-bicarbazole) (11.8 g, 28.90 mmol) and compound 4 (7.5 g, 37.60 mmol) in DMF (200 mL), NaH (1.8 g, 43.4 mmol, 60% in a mineral oil) was added thereto. The mixture was stirred at room temperature for 2.5 hours, and methanol was added thereto. The obtained solid substance was filtered under reduced pressure, and purified by column chromatography to obtain compound 5 (9.7 g, yield: 59%).

3) Preparation of Compound A-92

After introducing compound 5 (8.4 g, 14.70 mmol), Pd(OAc)$_2$ (330 mg, 1.47 mmol), ligand (tricyclohexylphosphoniumtetrafluoroborate) (541 mg, 0.35 mmol), Cs$_2$CO$_3$ (14.4 g, 44.10 mmol), and xylene (74 mL) into a flask, the mixture was stirred under reflux for 1.5 hours, cooled to room temperature, and distilled water was then added thereto. After completion of the reaction, the mixture was extracted with ethyl acetate. The obtained organic layer was dried, and purified by column chromatography to obtain compound A-92 (6.5 g, yield: 60.2%).

|  | MW | UV | PL | M.P |
|---|---|---|---|---|
| A-92 | 534.61 | 390 nm | 467 nm | 309.9° C. |

Example 14: Preparation of Compound A-286

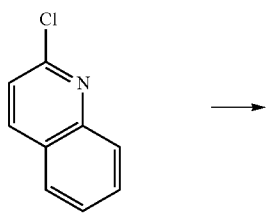

-continued

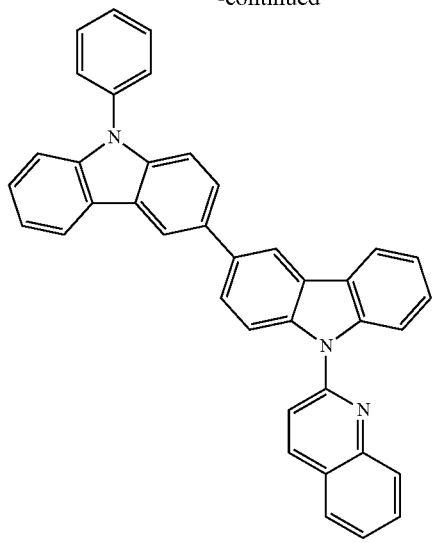

3

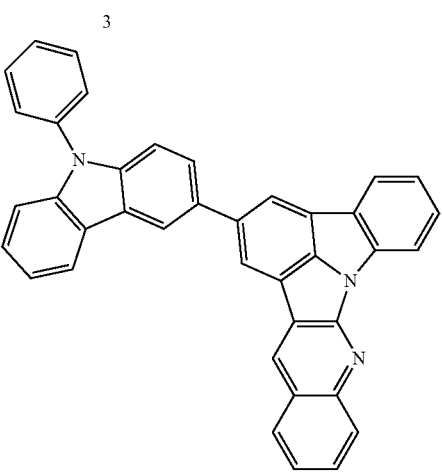

A-286

1) Preparation of Compound 3

After dissolving compound 1 (9-phenyl-9H,9'H-3,3'-bicarbazole) (15 g, 36.72 mmol), compound 2 (2-chloroquinoline) (6.6 g, 40.39 mmol), CuI (13.9 g, 73.44 mmol), trans-1,2-diaminocyclohexane (2.7 mL, 22.03 mmol), and $Cs_2CO_3$ (35.8 g, 110.16 mmol) in o-DCB (250 mL) of a flask, the mixture was under reflux at 200° C. for 8 hours. After completion of the reaction, the mixture was filtered under reduced pressure, and purified by column chromatography. Methanol was added to the purified product. The obtained solid substance was filtered under reduced pressure to obtain compound 3 (12.5 g, yield: 64%).

2) Preparation of Compound A-286

After adding compound 3 (9-phenyl-9'-(quinoline-2-yl)-9H,9'H-3,3'-bicarbazole) (10.5 g, 19.6 mmol), Pd(OAc)$_2$ (0.44 g, 1.96 mmol), and $K_2CO_3$ (0.54 g, 3.92 mmol) to pivalic acid (40 mL), the mixture was under reflux at 170° C. for 24 hours. After completion of the reaction, the mixture was neutralized with $NaHCO_3$, extracted with MC, and then dried with $MgSO_4$. The product was purified by column chromatography. Methanol was added to the purified product, and the obtained solid substance was filtered under reduced pressure to obtain compound A-286 (1.2 g, yield: 12%).

|       | MW     | UV     | PL     | M.P    |
|-------|--------|--------|--------|--------|
| A-286 | 533.62 | 342 nm | 477 nm | 229° C. |

[Device Example 1] OLED Using the Compound of the Present Disclosure

OLED was produced using the organic electroluminescent compound of the present disclosure as follows. A transparent electrode indium tin oxide (ITO) thin film (10 Ω/sq) on a glass substrate for an organic light-emitting diode (OLED) (Geomatec) was subjected to an ultrasonic washing with trichloroethylene, acetone, ethanol, and distilled water, sequentially, and then was stored in isopropanol. The ITO substrate was then mounted on a substrate holder of a vacuum vapor depositing apparatus. HI-1 was introduced into a cell of the vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. HI-2 was introduced into another cell of the vacuum vapor depositing apparatus, and was evaporated by applying an electric current to the cell, thereby forming a second hole injection layer having a thickness of 5 nm on the first hole injection layer. HT-1 was introduced into a cell of the vacuum vapor depositing apparatus, and was evaporated by applying an electric current to the cell, thereby forming a first hole transport layer having a thickness of 10 nm on the second hole injection layer. HT-2 was introduced into another cell of the vacuum vapor depositing apparatus, and was evaporated by applying an electric current to the cell, thereby forming a second hole transport layer having a thickness of 60 nm on the first hole transport layer. Thereafter, compound A-14 was introduced into one cell of the vacuum vapor depositing apparatus as a host, and compound D-96 was introduced into another cell as a dopant. The two materials were evaporated at different rates, so that the dopant was deposited in a doping amount of 3 wt % based on the total amount of the host and dopant to form a light-emitting layer having a thickness of 40 nm on the second hole transport layer. ET-1 and EI-1 were introduced into two cells of the vacuum vapor depositing apparatus, respectively, and evaporated at 1:1 rate to form an electron transport layer having a thickness of 30 nm on the light-emitting layer. After depositing EI-1 as an electron injection layer having a thickness of 2 nm, an Al cathode having a thickness of 80 nm was then deposited by another vacuum vapor deposition apparatus on the electron injection layer to produce OLED. The produced OLED showed a red emission having a luminance of 1,000 cd/m$^2$, and a current efficiency of 26.4 cd/A at a driving voltage of 3.4V. Time taken to be reduced from 100% to 90% of the luminance at 5,000 nit was 390 hours or more.

HI-1
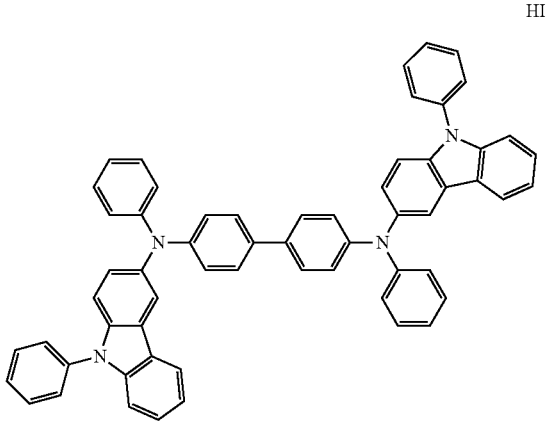

HI-2
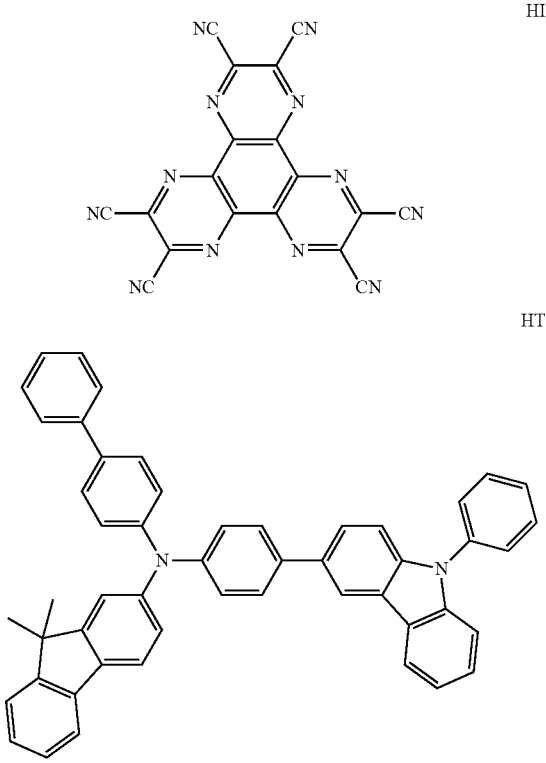

HT-1
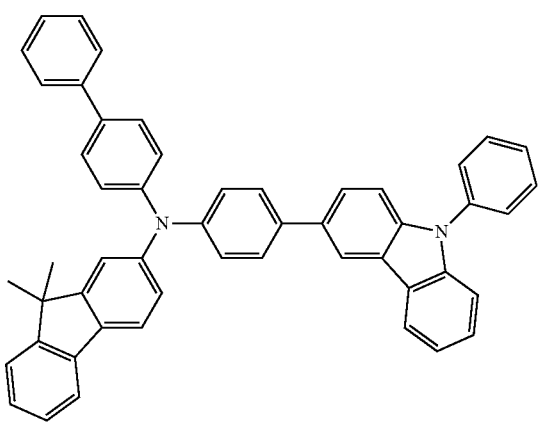

HT-2
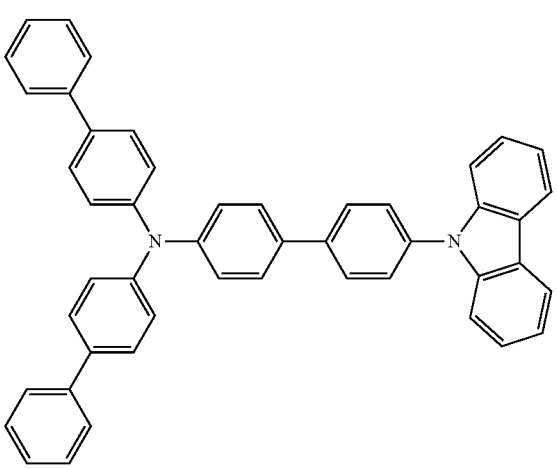

HT-3
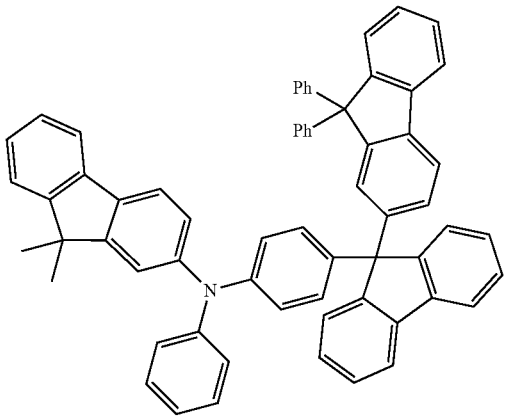

ET-1
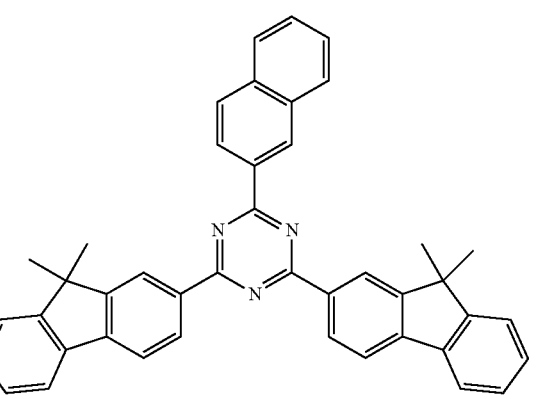

EI-1
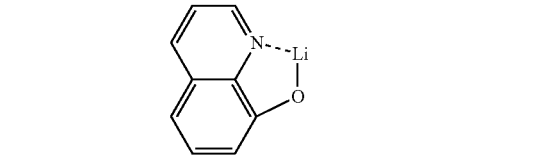

[Device Example 2] OLED Using the Compound of the Present Disclosure

OLED was produced in the same manner as in Device Example 1, except that compound A-40 was used as a host of a light-emitting material. The produced OLED showed a red emission having a luminance of 1,000 cd/m$^2$, and a current efficiency of 27 cd/A at a driving voltage of 4.1 V. Time taken to be reduced from 100% to 90% of the luminance at 5,000 nit was 60 hours or more.

[Device Example 3] OLED Using the Compound of the Present Disclosure

OLED was produced in the same manner as in Device Example 1, except that compound A-39 was used as a host of a light-emitting material. The produced OLED showed a red emission having a luminance of 1,000 cd/m$^2$, and a current efficiency of 27.6 cd/A at a driving voltage of 4.4 V. Time taken to be reduced from 100% to 90% of the luminance at 5,000 nit was 110 hours or more.

[Device Example 4] OLED Using the Compound of the Present Disclosure

OLED was produced in the same manner as in Device Example 1, except that compound A-1 was used as a host of a light-emitting material. The produced OLED showed a red emission having a luminance of 1,000 cd/m$^2$, and a current efficiency of 26.2 cd/A at a driving voltage of 3.8 V. Time taken to be reduced from 100% to 90% of the luminance at 5,000 nit was 100 hours or more.

[Device Example 5] OLED Using the Compound of the Present Disclosure

OLED was produced in the same manner as in Device Example 1, except that compound A-119 was used as a host of a light-emitting material. The produced OLED showed a red emission having a luminance of 1,000 cd/m$^2$, and a current efficiency of 26.5 cd/A at a driving voltage of 4.9 V. Time taken to be reduced from 100% to 90% of the luminance at 5,000 nit was 50 hours or more.

[Device Example 6] OLED Using the Compound of the Present Disclosure

OLED was produced in the same manner as in Device Example 1, except that compound A-16 was used as a host of a light-emitting material. The produced OLED showed a red emission having a luminance of 1,000 cd/m$^2$, and a current efficiency of 19.5 cd/A at a driving voltage of 3.4 V. Time taken to be reduced from 100% to 90% of the luminance at 5,000 nit was 70 hours or more.

[Device Example 7] OLED Using the Compound of the Present Disclosure

OLED was produced in the same manner as in Device Example 1, except that compound A-286 was used as a host of a light-emitting material. The produced OLED showed a red emission having a luminance of 1,000 cd/m$^2$, and a current efficiency of 28.4 cd/A at a driving voltage of 3.9 V. Time taken to be reduced from 100% to 90% of the luminance at 5,000 nit was 10 hours or more.

[Device Example 8] OLED Using the Compound of the Present Disclosure

OLED was produced in the same manner as in Device Example 1, except that compound A-278 was used as a host of a light-emitting material. The produced OLED showed a red emission having a luminance of 1,000 cd/m$^2$, and a current efficiency of 24.7 cd/A at a driving voltage of 3.4 V. Time taken to be reduced from 100% to 90% of the luminance at 5,000 nit was 140 hours or more.

[Device Example 9] OLED Using the Compound of the Present Disclosure

OLED was produced in the same manner as in Device Example 1, except that compound A-78 was used as a host of a light-emitting material. The produced OLED showed a red emission having a luminance of 1,000 cd/m$^2$, and a current efficiency of 26.6 cd/A at a driving voltage of 3.7 V. Time taken to be reduced from 100% to 90% of the luminance at 5,000 nit was 110 hours or more.

[Device Example 10] OLED Using the Compound of the Present Disclosure

OLED was produced in the same manner as in Device Example 1, except that compound A-159 was used as a host of a light-emitting material. The produced OLED showed a red emission having a luminance of 1,000 cd/m$^2$, and a current efficiency of 23.8 cd/A at a driving voltage of 3.5 V. Time taken to be reduced from 100% to 90% of the luminance at 5,000 nit was 180 hours or more.

[Device Example 11] OLED Using the Compound of the Present Disclosure

OLED was produced in the same manner as in Device Example 1, except that compound A-289 was used as a host of a light-emitting material. The produced OLED showed a red emission having a luminance of 1,000 cd/m$^2$, and a current efficiency of 26.0 cd/A at a driving voltage of 3.6 V. Time taken to be reduced from 100% to 90% of the luminance at 5,000 nit was 200 hours or more.

[Device Example 12] OLED Using the Compound of the Present Disclosure

OLED was produced in the same manner as in Device Example 1, except that compound A-91 was used as a host of a light-emitting material. The produced OLED showed a red emission having a luminance of 1,000 cd/m$^2$, and a current efficiency of 27.3 cd/A at a driving voltage of 3.4 V. Time taken to be reduced from 100% to 90% of the luminance at 5,000 nit was 380 hours or more.

[Device Example 13] OLED Using the Compound of the Present Disclosure

OLED was produced in the same manner as in Device Example 1, except that compound A-287 was used as a host of a light-emitting material. The produced OLED showed a red emission having a luminance of 1,000 cd/m$^2$, and a current efficiency of 26.0 cd/A at a driving voltage of 4.5 V. Time taken to be reduced from 100% to 90% of the luminance at 5,000 nit was 10 hours or more.

[Device Example 14] OLED Using the Compound of the Present Disclosure

OLED was produced in the same manner as in Device Example 1, except that HT-3 was used to form a second hole transport layer, and compound A-92 was used as a host of a light-emitting material. The produced OLED showed a red emission having a luminance of 1,000 cd/m$^2$, and a current efficiency of 27.5 cd/A at a driving voltage of 3.4 V. Time taken to be reduced from 100% to 90% of the luminance at 5,000 nit was 90 hours or more.

[Comparative Example 1] OLED Using a Conventional Organic Electroluminescent Compound OLED was produced in the same manner as in Device Example 1, except that 4,4'-di(9H-carbazol-9-yl)-1,1'-biphenyl was used as a host of a light-emitting material. The produced OLED showed red emission having a luminance of 1,000 cd/m$^2$, and a current efficiency of 17 cd/A at a driving voltage of 10.3 V. Time taken to be reduced from 100% to 90% of the luminance at 5,000 nit was less than 1 hour.

The organic electroluminescent compound of the present disclosure has not been disclosed in prior art documents, and cannot be synthesized by any processes disclosed in prior art documents concerning a compound of a crosslinked triarylamine structure. The organic electroluminescent compound of the present disclosure can provide an organic electroluminescent device showing a lowered driving voltage, long lifespan, and excellence in luminous efficiency such as current efficiency and power efficiency. In particular, while a conventional compound such as indolo[3,2,1-jk] carbazole does not have an appropriate HOMO level, LUMO level, and triplet to be used as a phosphorescent host, and specifically a red-emitting phosphorescent host, the compound of the present disclosure has a suitable HOMO level, LUMO level, and triplet as a red-emitting phosphorescent host. Accordingly, as confirmed in the Device Examples above, the compound of the present disclosure can be used as a red-emitting phosphorescent host providing a lowered driving voltage, good luminous efficiency, and high color purity.

The invention claimed is:

1. An organic electroluminescent compound represented by the following formula 1:

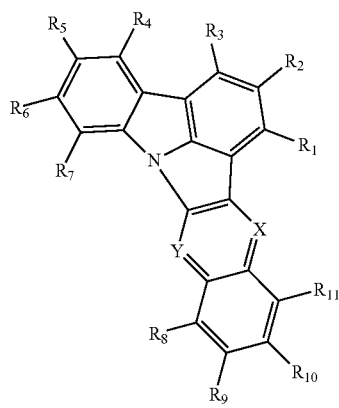

(1)

wherein
X and Y, each independently, represent —CR$_{12}$— or —N—, with the proviso that X and Y are not be simultaneously —CR$_{12}$—, and
R$_1$ to R$_{12}$, each independently, represent hydrogen, deuterium, a halogen, a cyano, a substituted or unsubstituted (C1-C30)alkyl, a substituted or unsubstituted (C6-C30)aryl, a substituted or unsubstituted 3- to 30-memberedheteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or may be linked to an adjacent substituent(s) to form a substituted or unsubstituted benzene ring or a substituted or unsubstituted naphthalene ring, wherein the heteroaryl of the substituted or unsubstituted 3- to 30-memberedheteroaryl contains one or more hetero atoms selected from the group consisting of N, O and S.

2. The organic electroluminescent compound according to claim 1, wherein the substituents of the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted benzene ring or naphthalene ring in R$_1$ to R$_{12}$, each independently, are at least one selected from the group consisting of deuterium, a halogen, a cyano, a carboxy, a nitro, a hydroxy, a (C1-C30) alkyl, a halo(C1-C30)alkyl, a (C1-C30)alkoxy, a (C1-C30) alkylthio, a (C3-C30)cycloalkyl, a 3- to 7-membered heterocycloalkyl, a (C6-C30)aryloxy, a (C6-C30)arylthio, a 3- to 30-membered heteroaryl unsubstituted or substituted with a (C6-C30)aryl or a di(C6-C30)arylamino, a (C6-C30)aryl unsubstituted or substituted with a 3- to 30-membered heteroaryl or a di(C6-C30)arylamino, atri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30) arylamino, a (C1-C30)alkyl(C6-C30)arylamino, a (C1-C30) alkylcarbonyl, a (C1-C30)alkoxycarbonyl, a (C6-C30)arylcarbonyl, a di(C6-C30)arylboronyl, a di(C1-C30) alkylboronyl, a (C1-C30)alkyl(C6-C30)arylboronyl, a (C6-C30)aryl(C1-C30)alkyl, and a (C1-C30)alkyl(C6-C30)aryl.

3. The organic electroluminescent compound according to claim 1, wherein the compound of formula 1 is represented by any one of the following formulae 2 to 4:

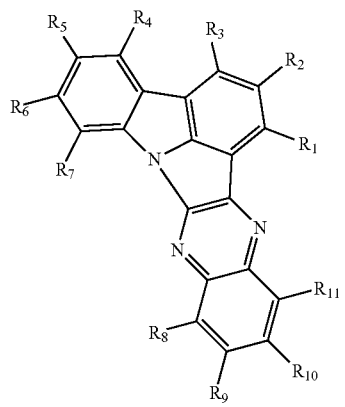

(2)

(3)

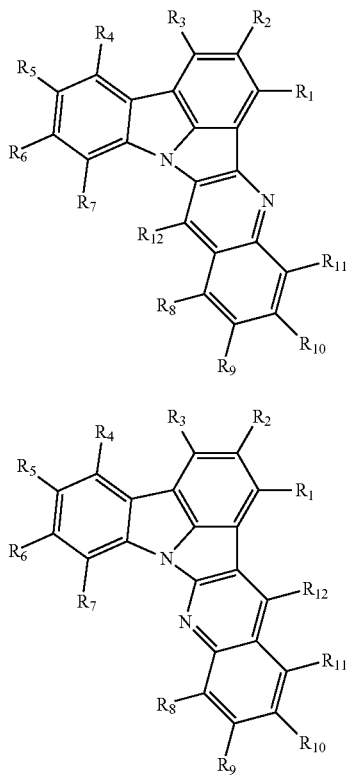

(4)

wherein R₁ to R₁₂ are as defined in claim 1.

4. The organic electroluminescent compound according to claim 1, wherein R₁ to R₁₂, each independently, represent hydrogen, a substituted or unsubstituted (C1-C20)alkyl, a substituted or unsubstituted (C6-C20)aryl, a substituted or unsubstituted 5- to 30-membered heteroaryl, or a substituted or unsubstituted di(C6-C20)arylamino, or may be linked to an adjacent substituent(s) to form a substituted or unsubstituted benzenering or a substituted or unsubstituted naphthalene ring.

5. The organic electroluminescent compound according to claim 4, wherein R₁ to R₁₂, each independently, represent hydrogen, a substituted or unsubstituted (C1-C20)alkyl, or any one of the following formulae 5-1 to 5-9, or may be linked to an adjacent substituent(s) to form a substituted or unsubstituted benzene ring or a substituted or unsubstituted naphthalene ring:

(5-1)

(5-2)

(5-3)

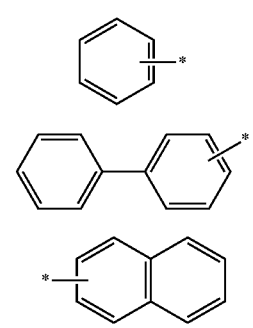

(5-4)

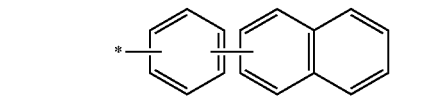

(5-5)

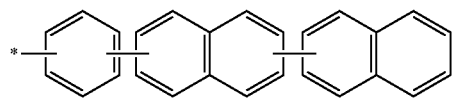

(5-6)

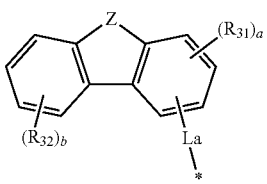

(5-7)

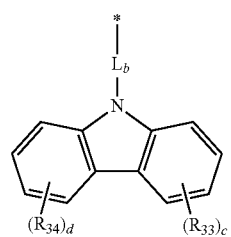

(5-8)

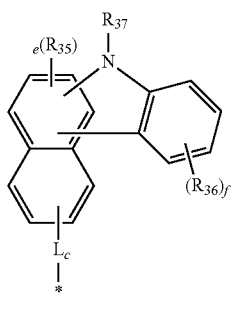

(5-9)

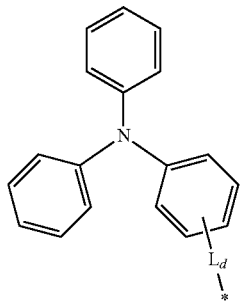

wherein
L_a, L_b, L_c, and L_d, each independently, represent a single bond, a substituted or unsubstituted (C6-C30)arylene, or a substituted or unsubstituted 3- to 30-membered heteroarylene;
Z represents —S—, —O—, —NR₁₃—, or —CR₁₄R₁₅—;
R₁₃ to R₁₅, each independently, represent hydrogen, a substituted or unsubstituted (C1-C30)alkyl, a substituted or unsubstituted (C6-C30)aryl, a substituted or unsubstituted 3- to 30-membered heteroaryl, a substituted or unsubstituted (C3-C30)cycloalkyl, or a substituted or unsubstituted 3- to 7-membered heterocycloalkyl;
R₃₁ to R₃₇, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted 3- to 7-membered heterocycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a mono- or di-(C1-C30)alkylamino, a mono- or di-(C6-C30)arylamino, or a (C1-C30)alkyl(C6-C30)arylamino; or may be linked to an adjacent substituent(s) to form a substituted or unsubstituted, 3- to 30-membered, mono- or polycyclic, alicyclic or aromatic ring, whose carbon atom(s) may be replaced with at least one hetero atom selected from the group consisting of nitrogen, oxygen and sulfur;

a represents an integer of 1 to 3; b to d and f, each independently, represent an integer of 1 to 4; e represents an integer of 1 to 5; where a, b, c, d, e, or f is an integer of 2 or more, each of $R_{31}$, $R_{32}$, $R_{33}$, $R_{34}$, $R_{35}$, or $R_{36}$ may be the same or different; and

* represents a bonding site;

wherein the heteroaryl(ene) and heterocycloalkyl, each independently, contain at least one hetero atom(s) selected from the group consisting of N, O and S.

6. The organic electroluminescent compound according to claim 5, wherein at least one of $R_1$ to $R_7$ represents any one of formulae 5-6 to 5-8, and Z of formula 5-6 represents —$NR_{13}$—.

7. The organic electroluminescent compound according to claim 1, wherein the compound is selected from the group consisting of:

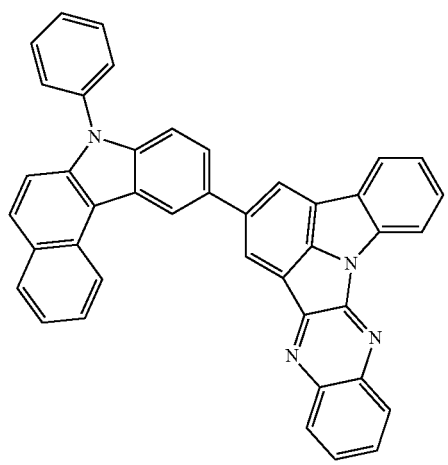

A-1

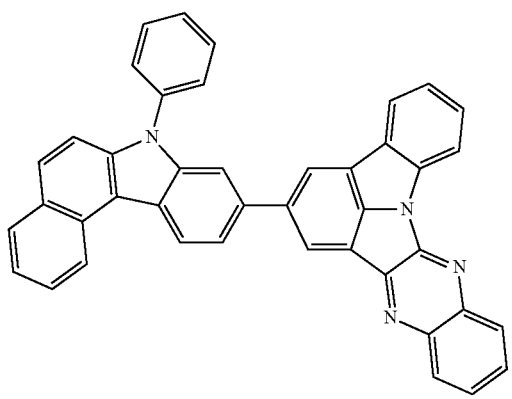

A-2

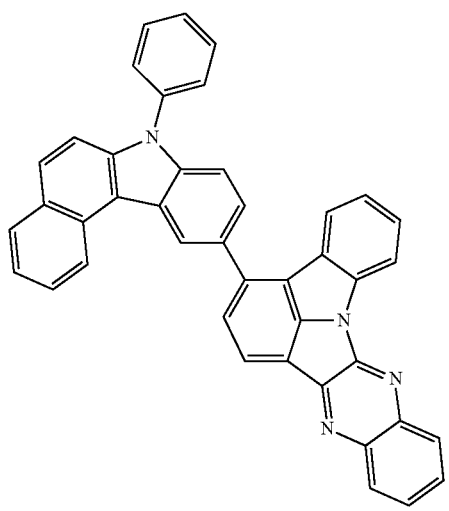

A-3

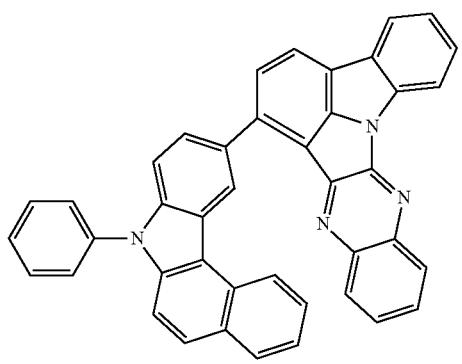

A-4

-continued
A-5
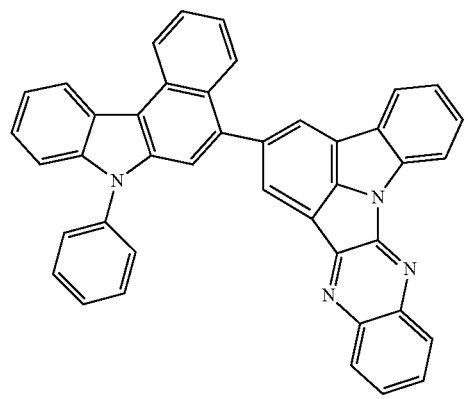
A-6
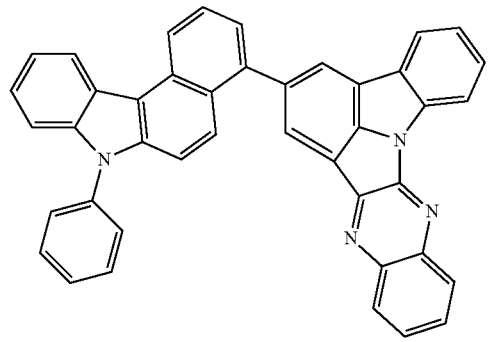
A-7
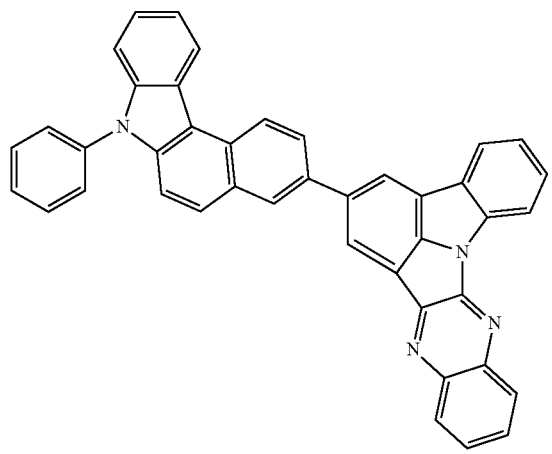
A-8
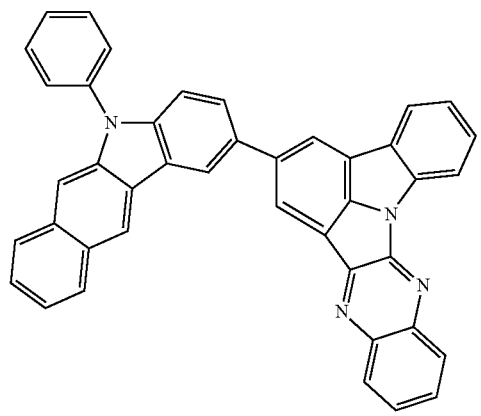
A-9
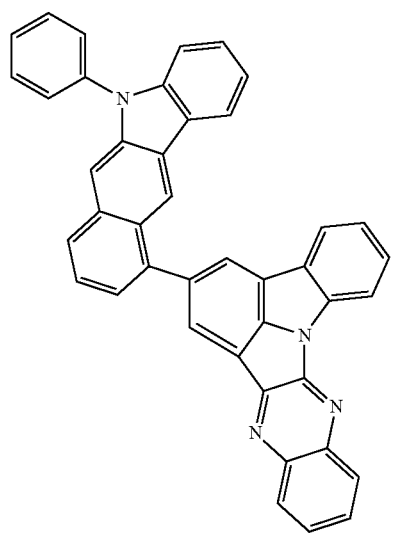
A-10
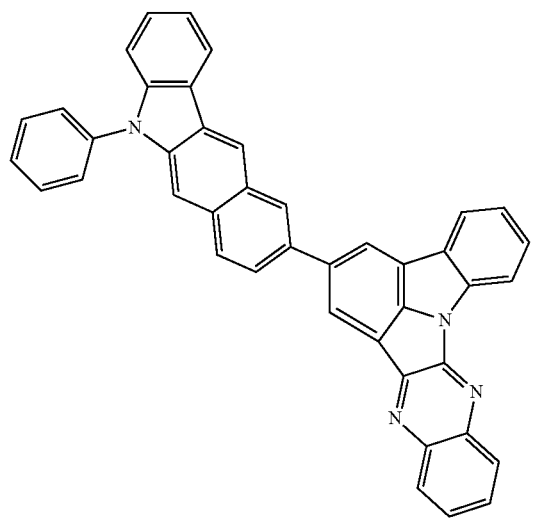

-continued
A-11
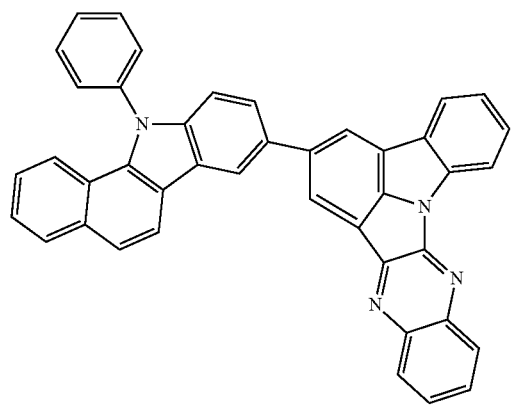
A-12
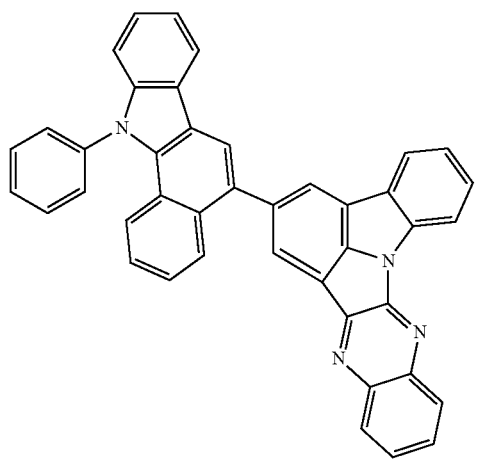
A-13
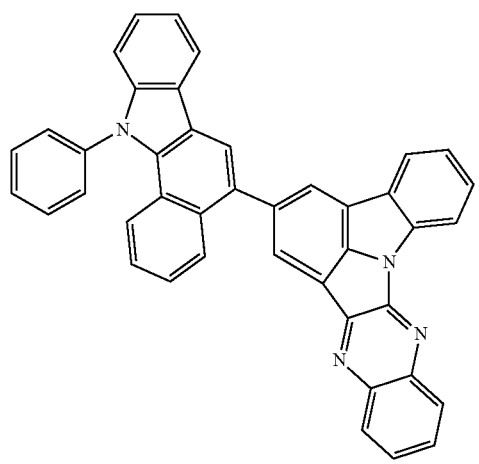
A-14
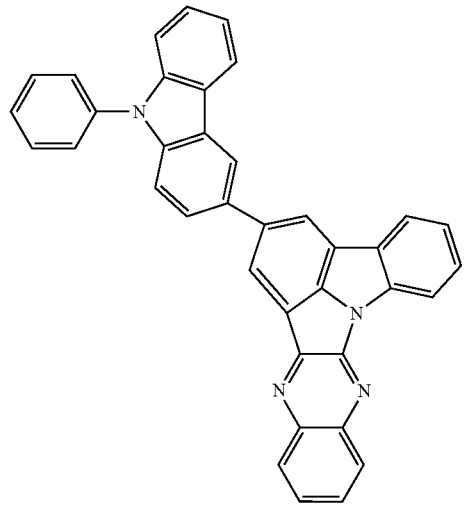
A-15
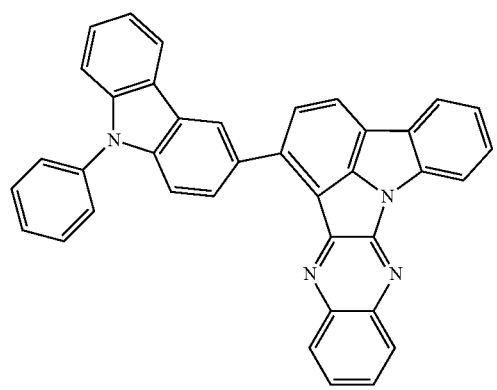
A-16
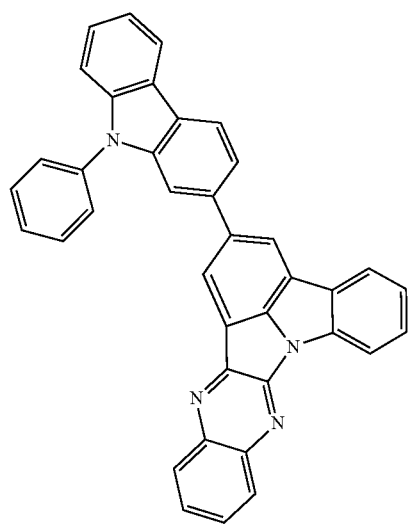

-continued
A-17
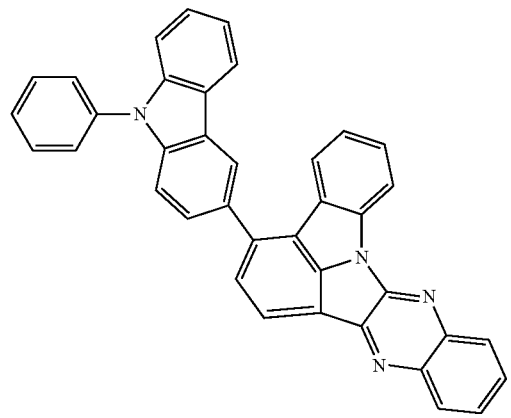
A-18
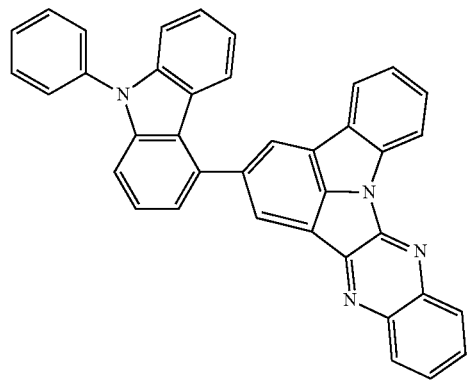
A-19
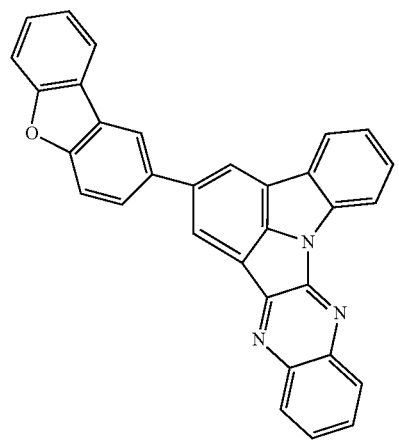
A-20
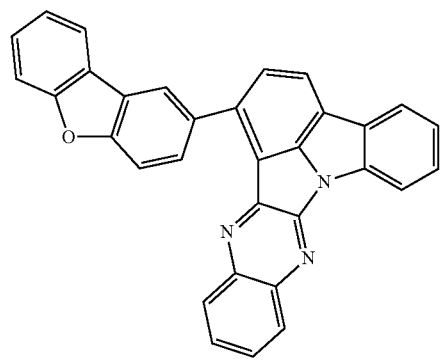
A-21
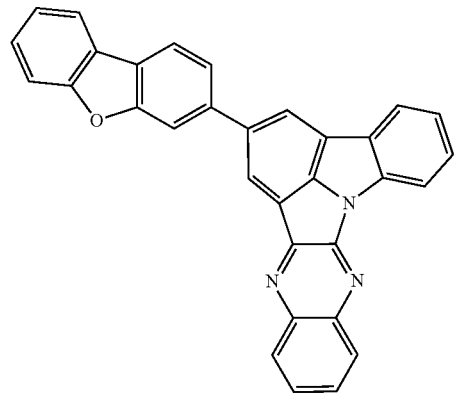
A-22
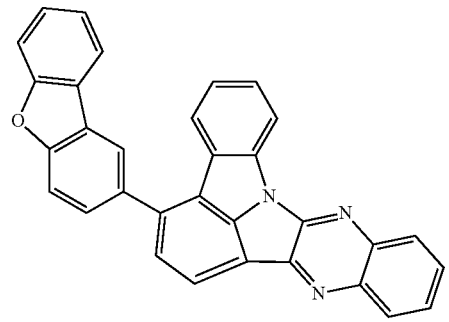

-continued
A-23
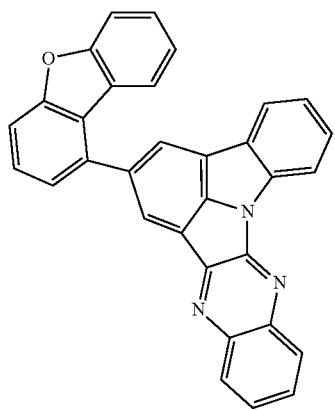
A-24
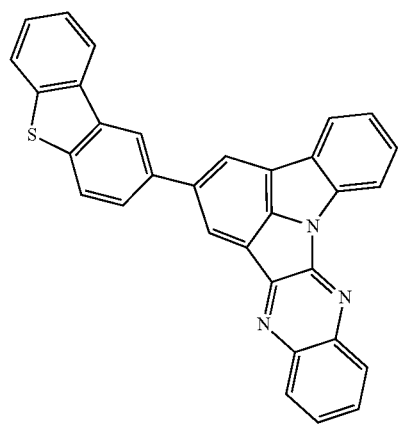
A-25
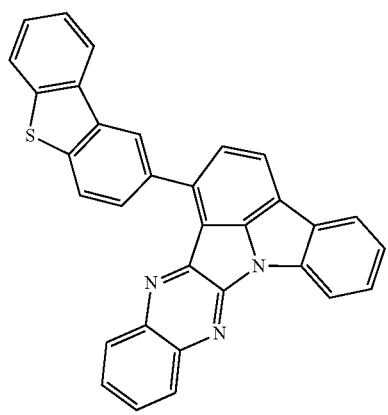
A-26
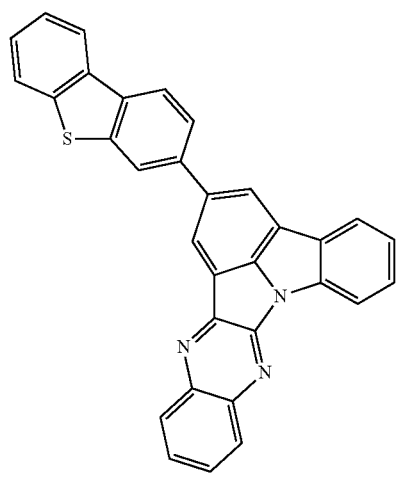
A-27
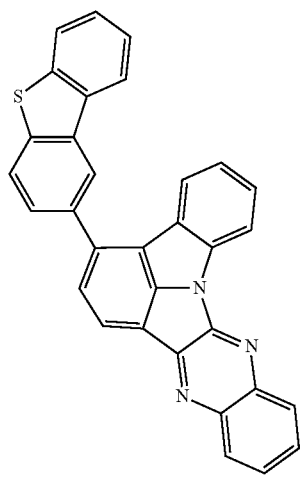
A-28
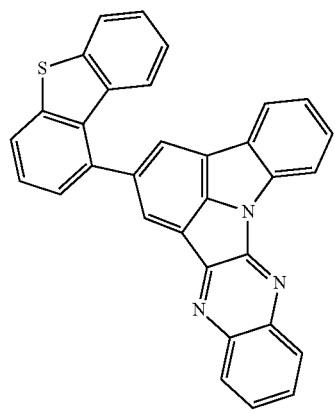

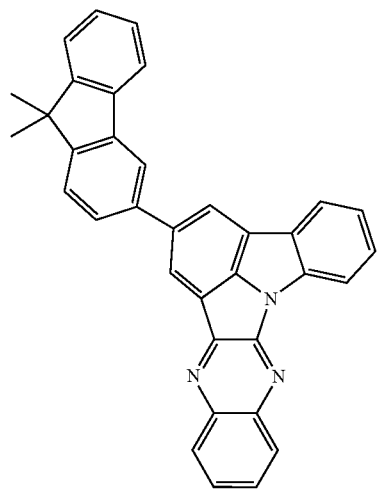
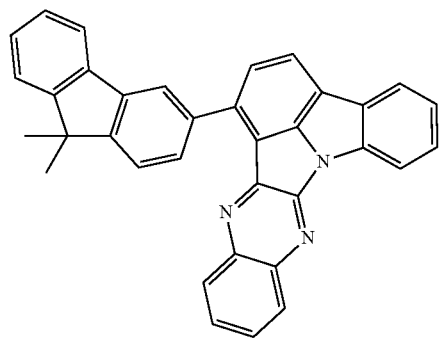
A-29
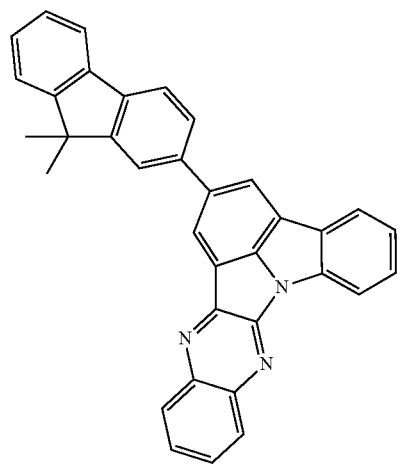
A-31
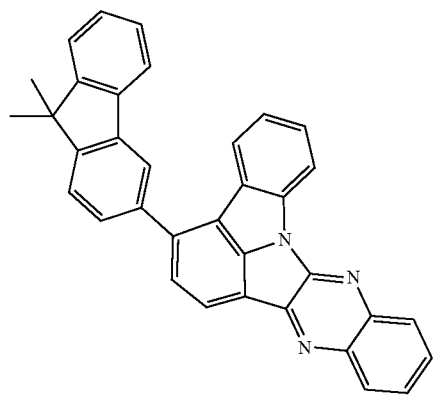
A-32
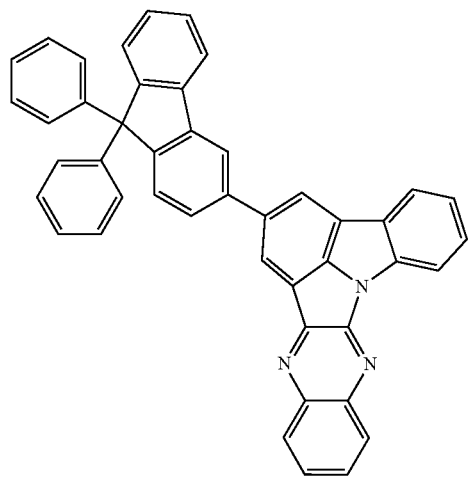
A-33
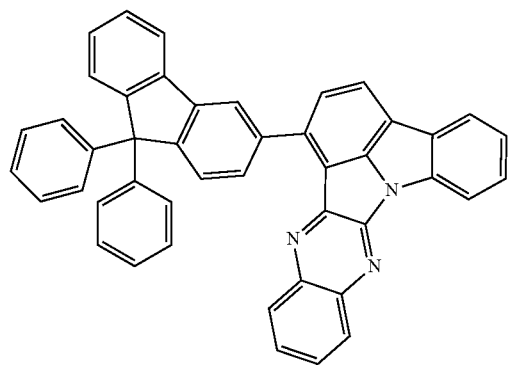
A-34

-continued
A-35
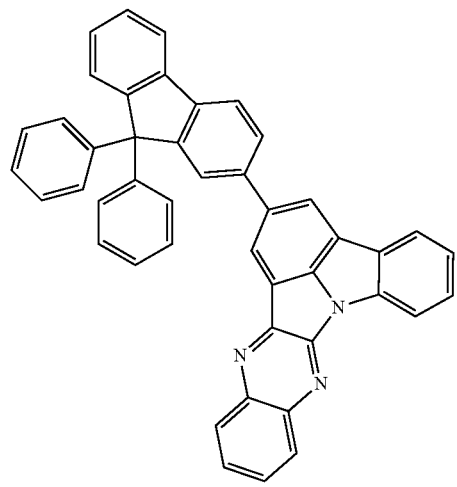
A-36
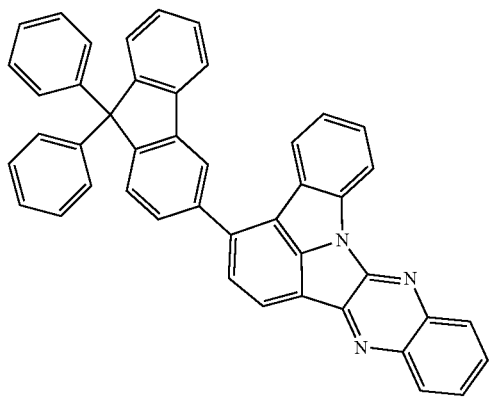
A-37
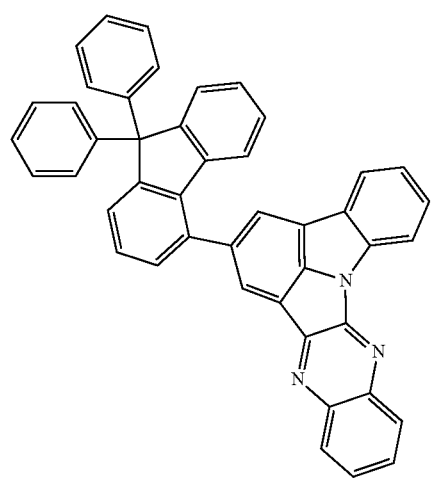
A-38
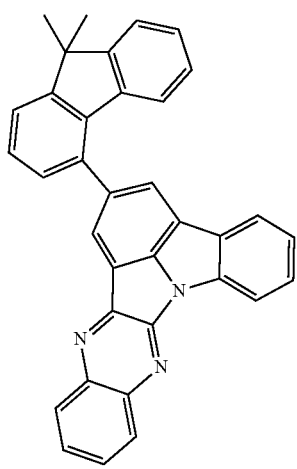
A-39
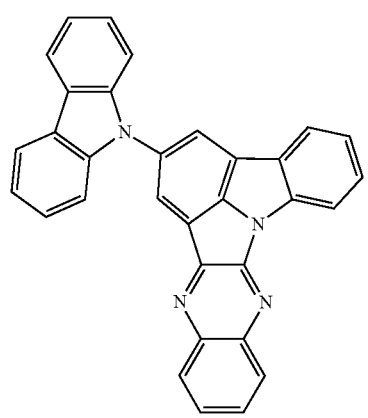
A-40
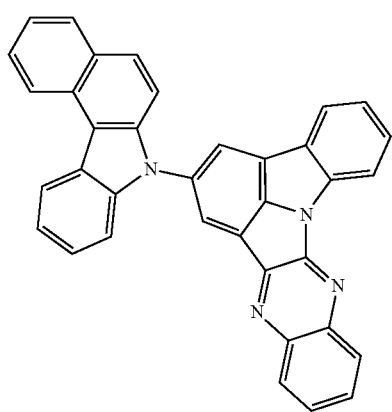

-continued
A-41
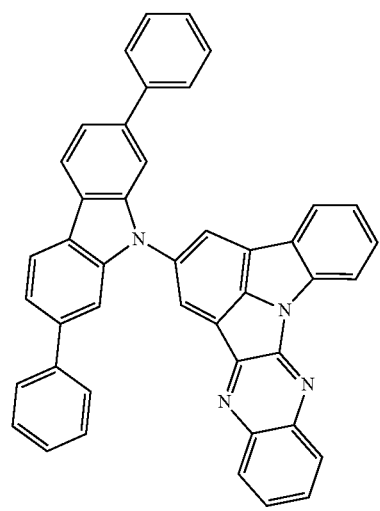
A-42
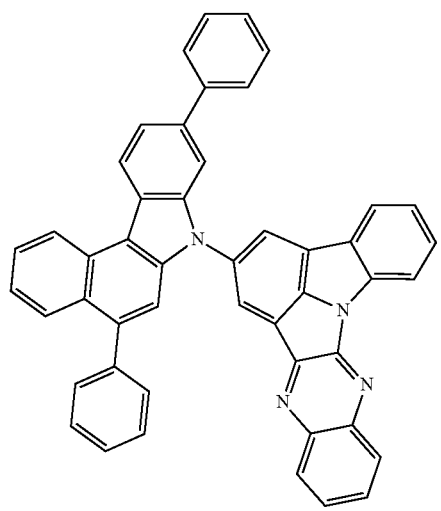
A-43
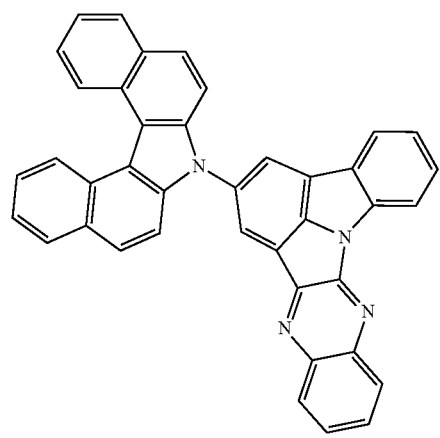
A-44
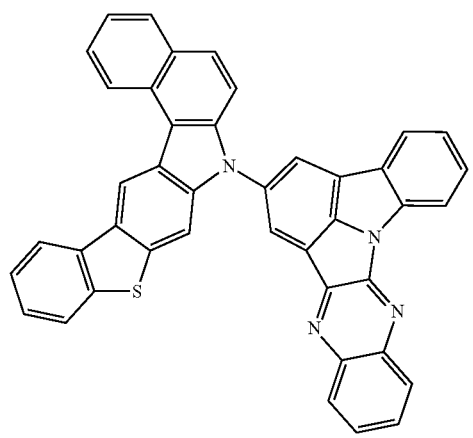
A-45
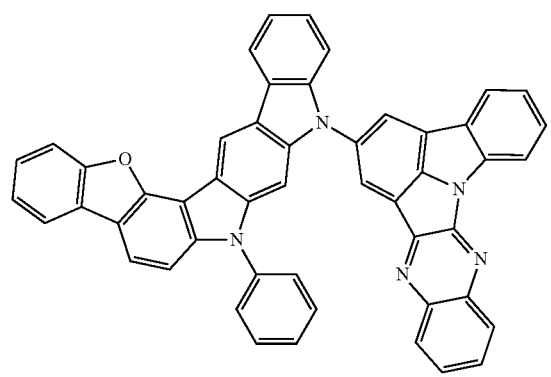
A-46
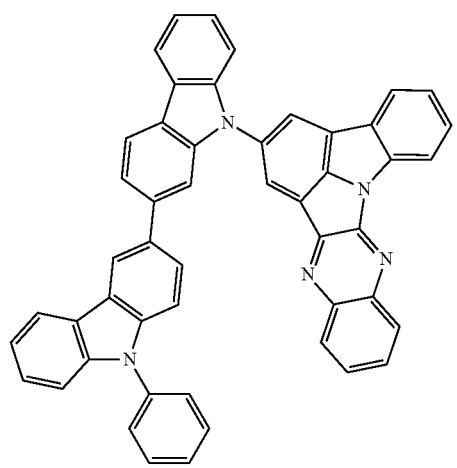

-continued
A-47
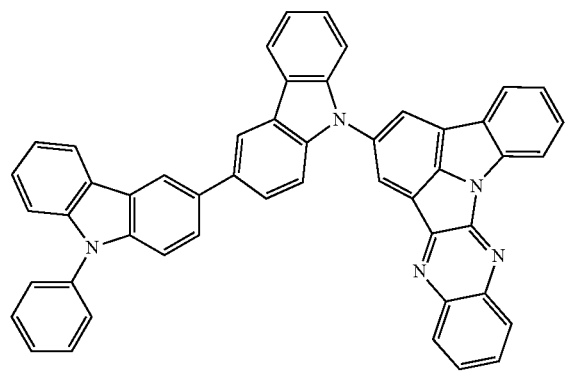
A-48
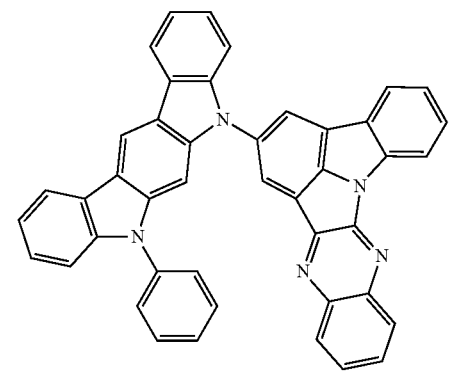
A-49
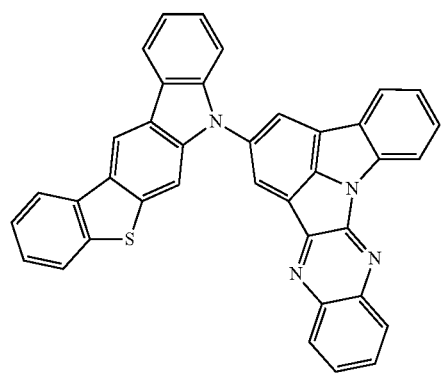
A-50
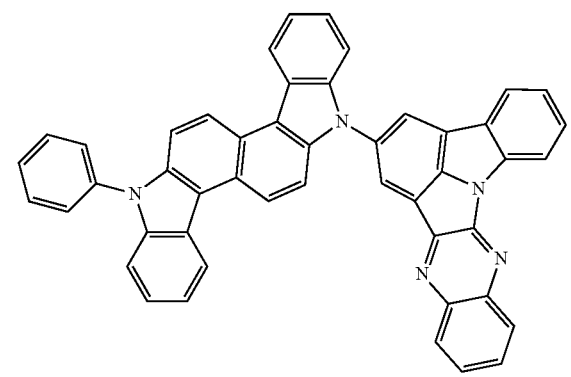
A-51
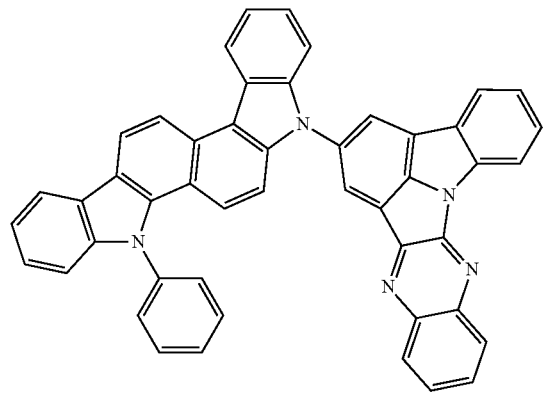
A-52
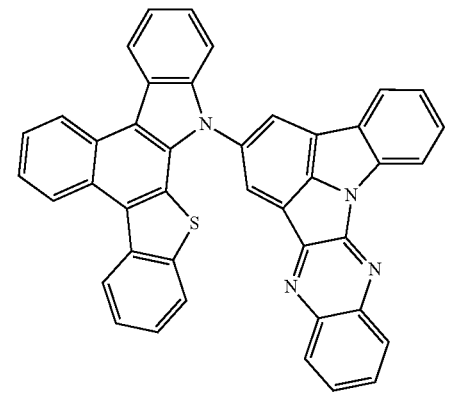
A-53
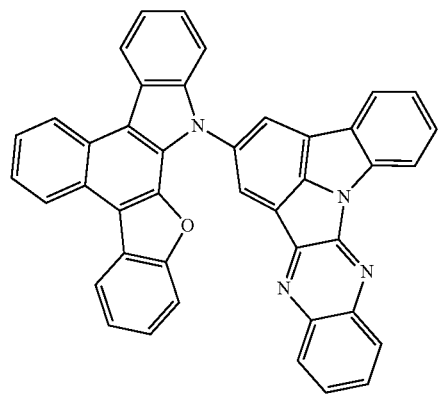
A-54
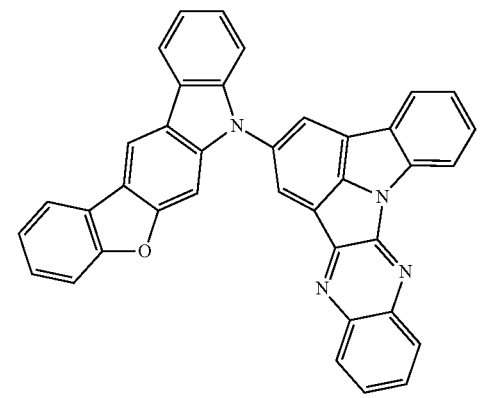

-continued
A-55
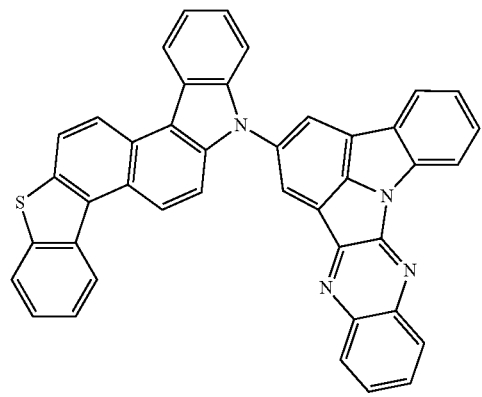
A-56
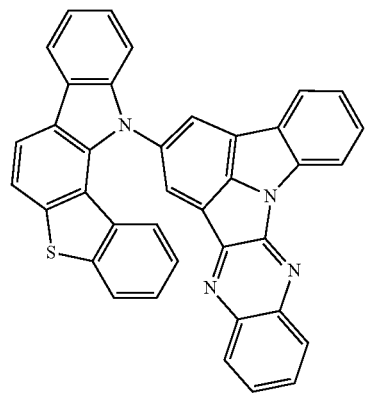
A-57
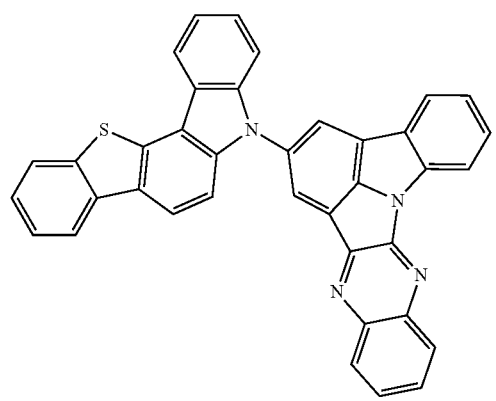
A-58
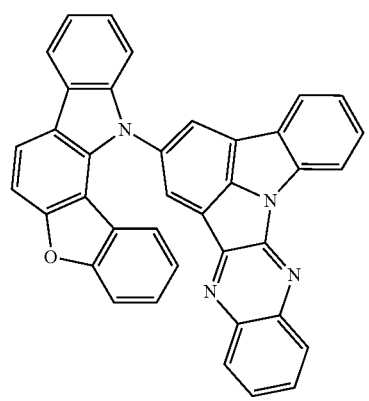
A-59
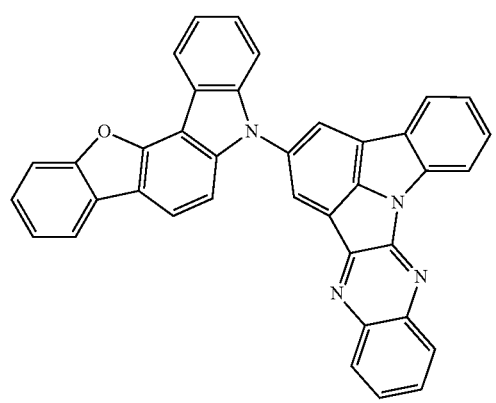
A-60
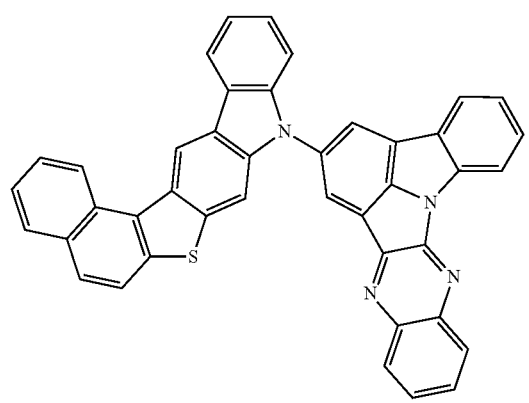

-continued
A-61
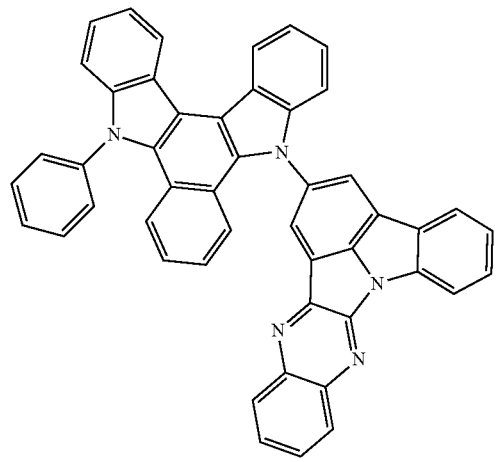
A-62
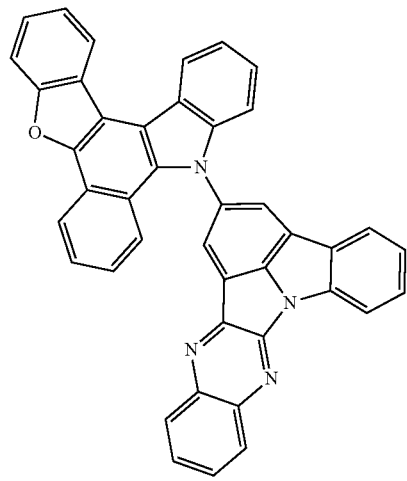
A-63
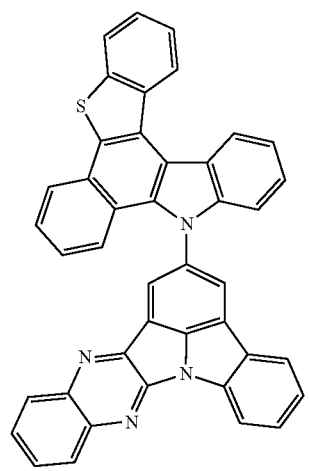
A-64
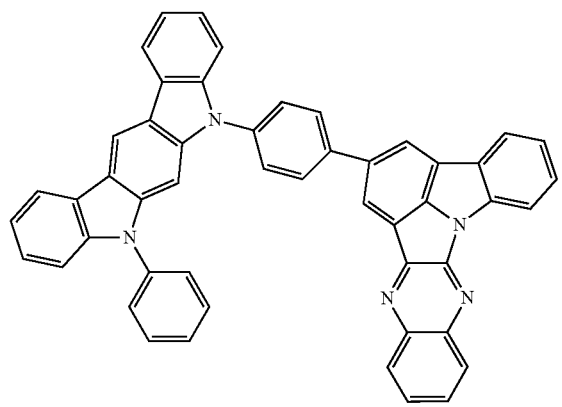
A-65
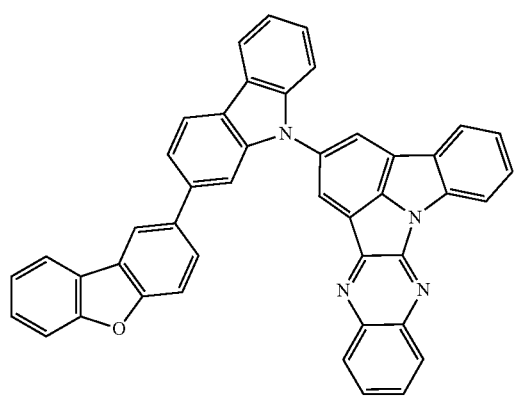
A-66
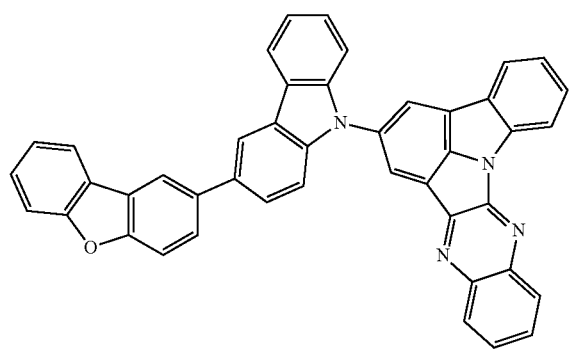

-continued
A-67
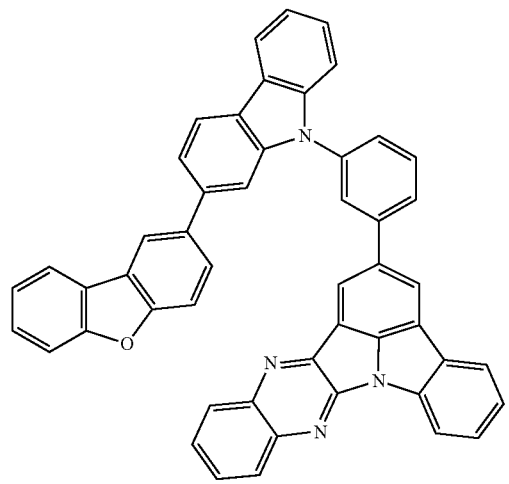
A-68
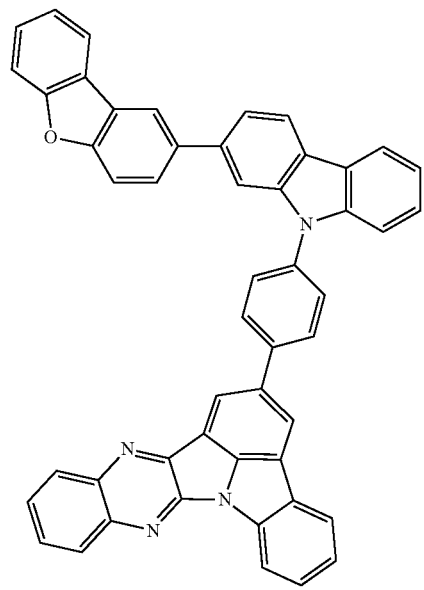
A-69
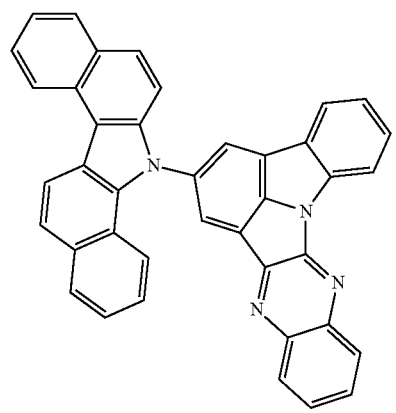
A-70
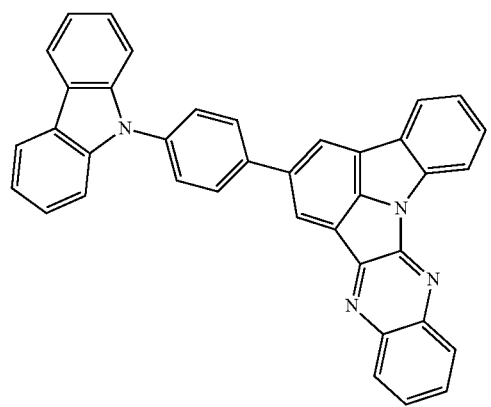
A-71
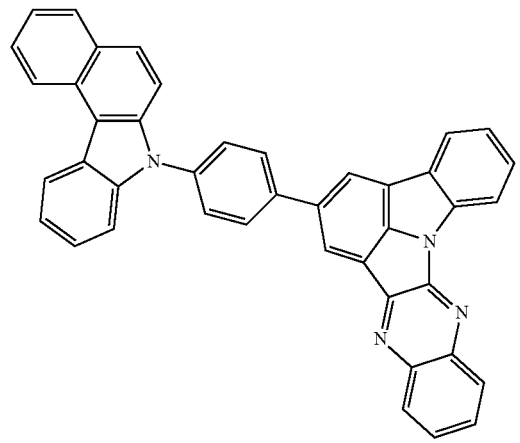
A-72
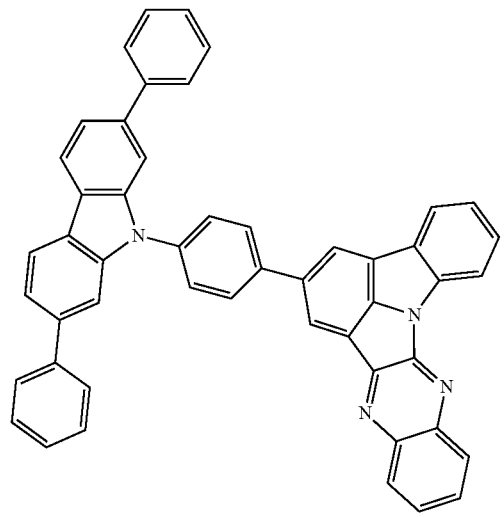

-continued
A-73
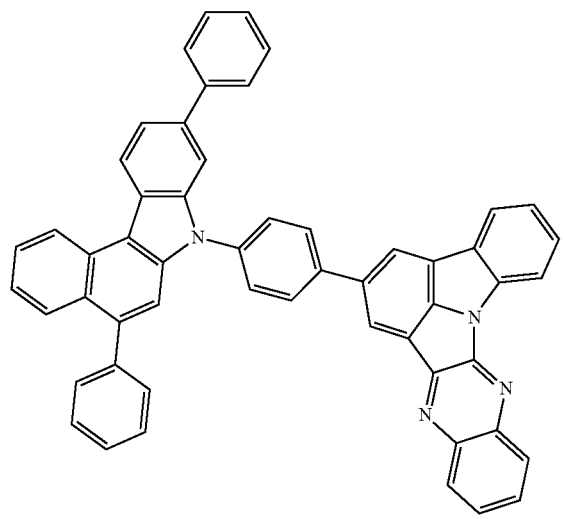
A-74
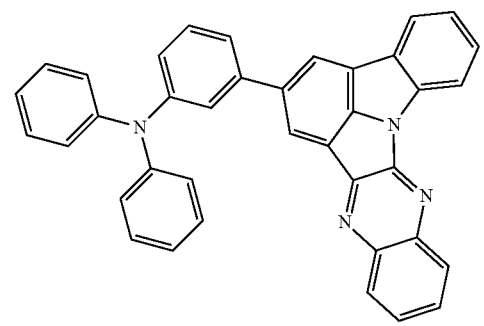
A-75
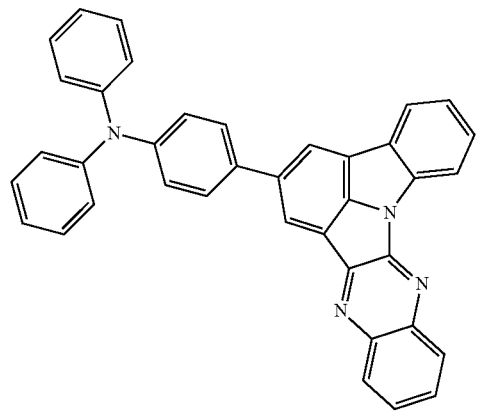
A-76
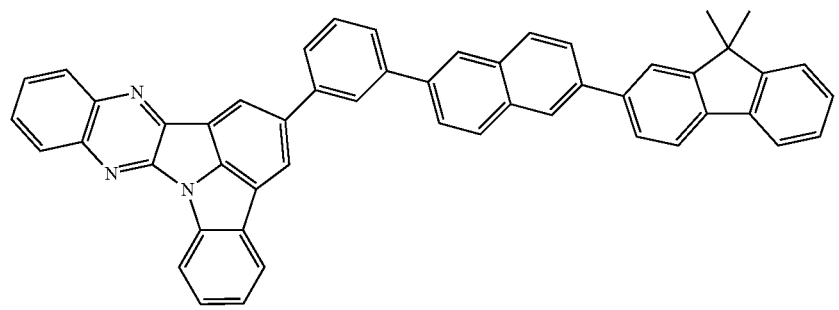
A-77
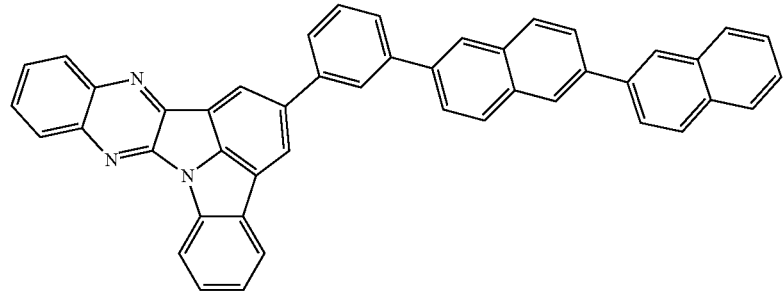

-continued
A-78
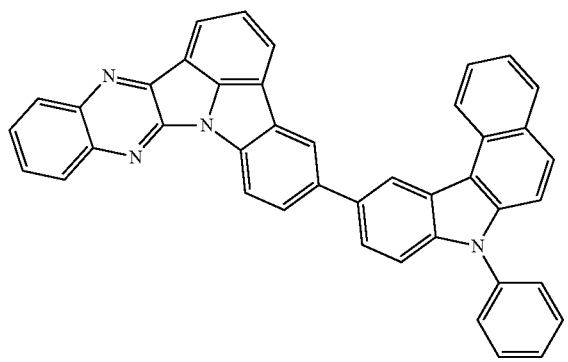
A-79
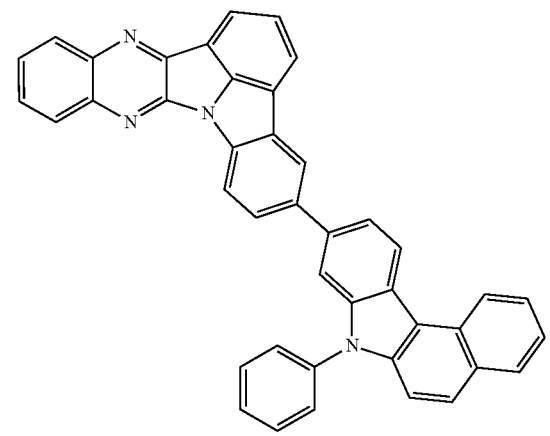
A-80
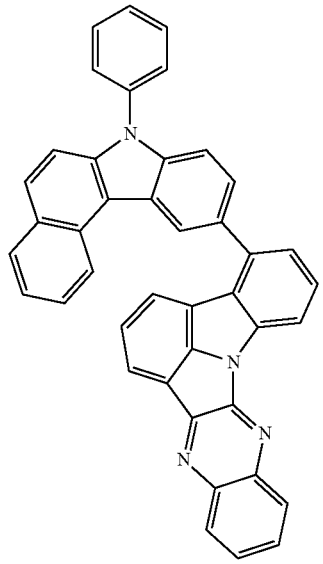
A-81
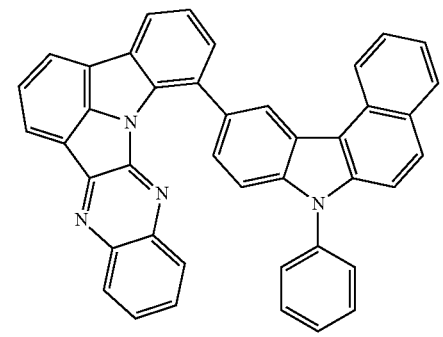
A-82
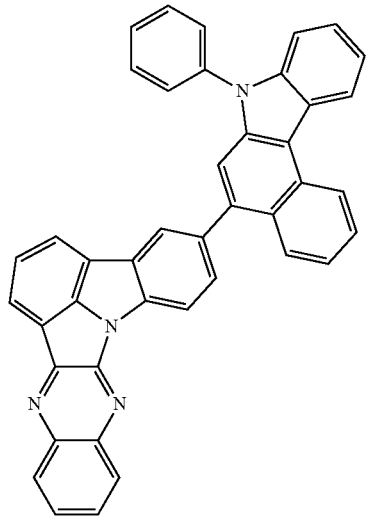
A-83
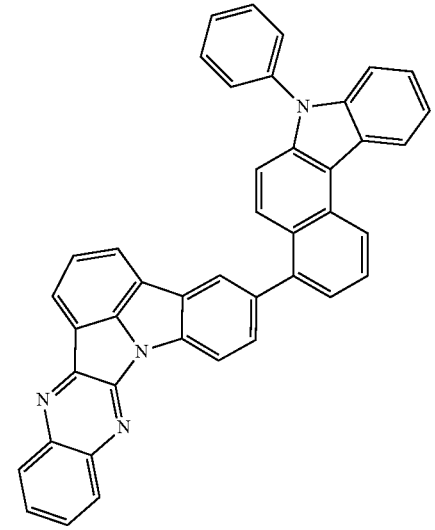

-continued
A-84
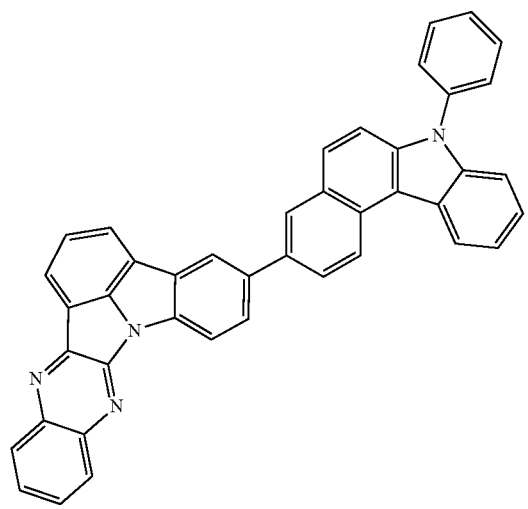
A-85
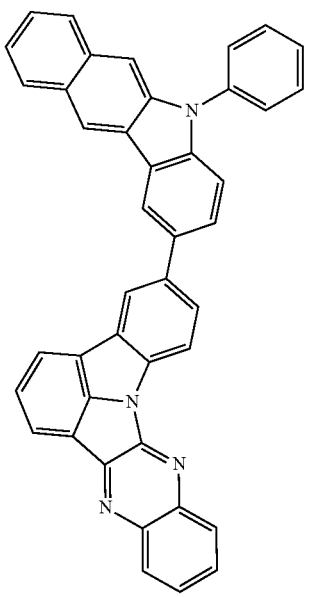
A-86
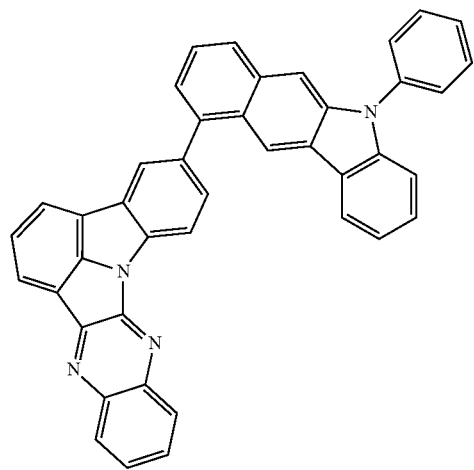
A-87
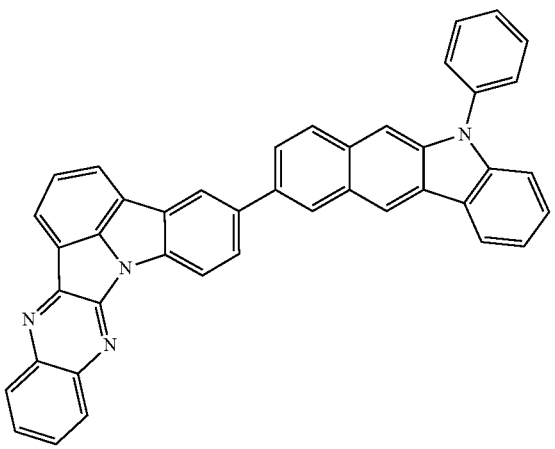

-continued
A-88
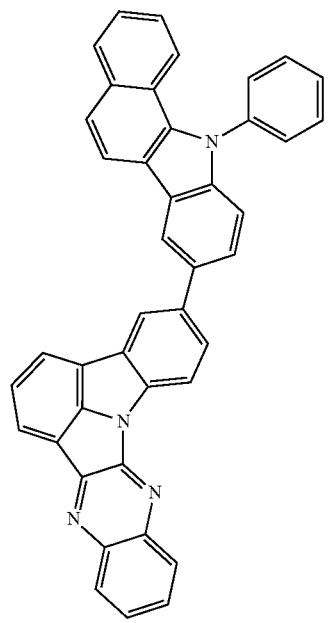
A-89
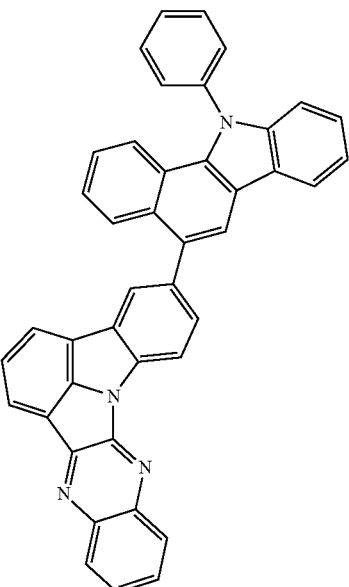
A-90
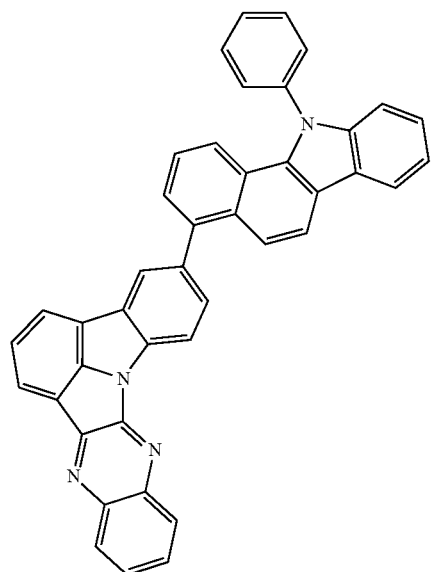
A-91
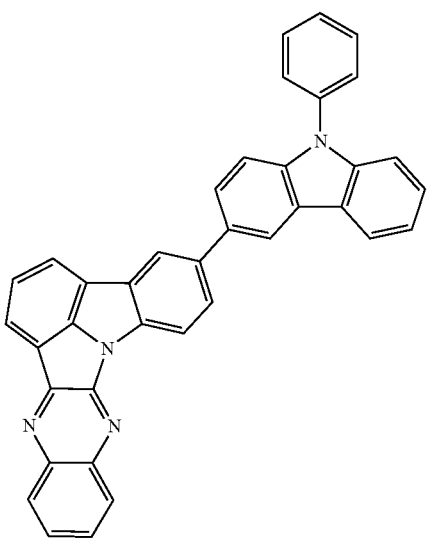

-continued
A-92
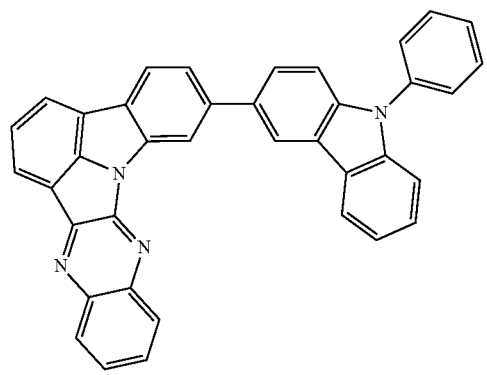
A-93
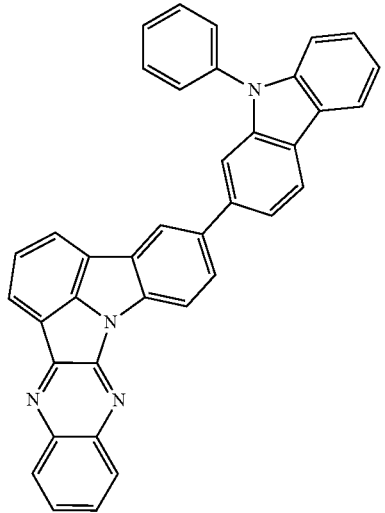
A-94
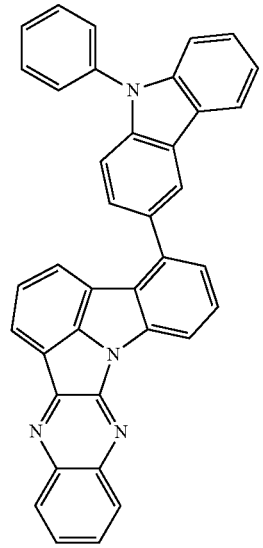
A-95
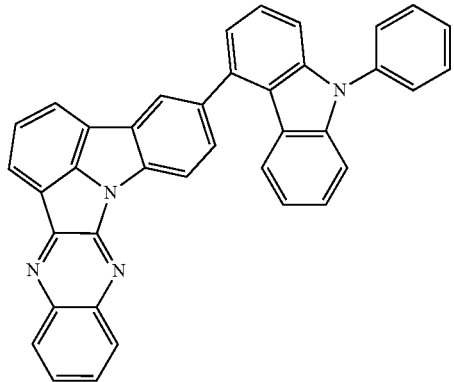

-continued
A-96
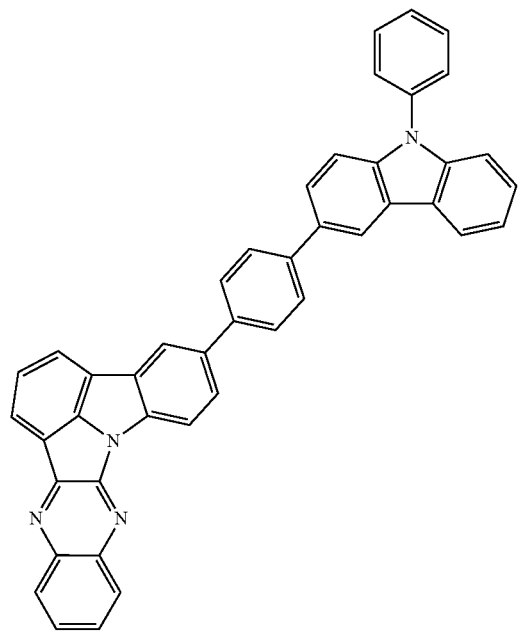
A-97
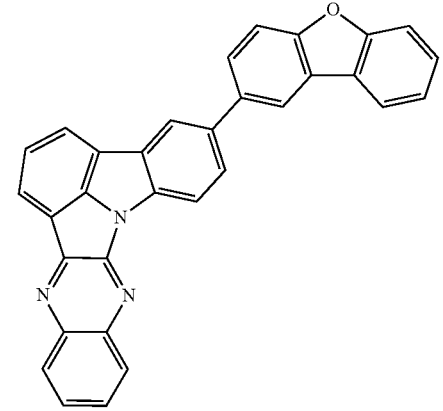
A-98
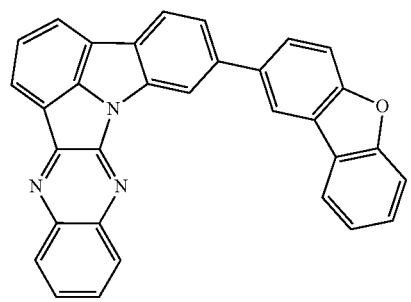
A-99
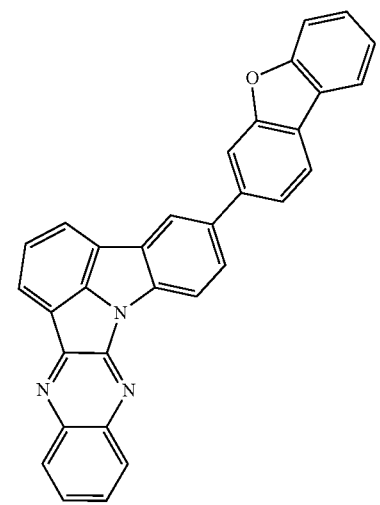
A-100
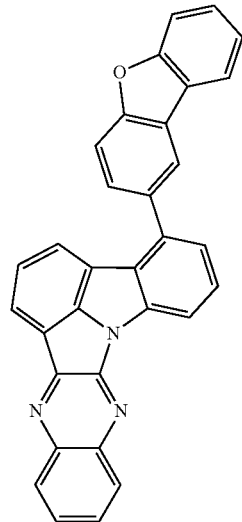
A-101
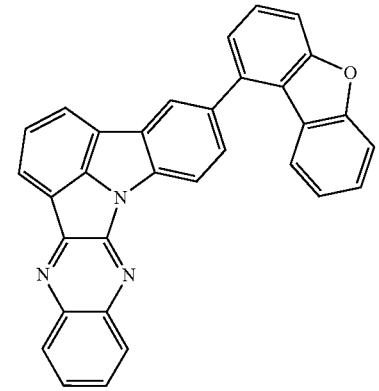

-continued
A-102
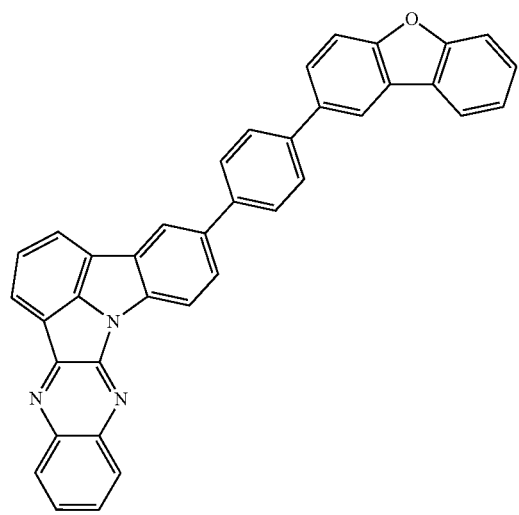
A-103
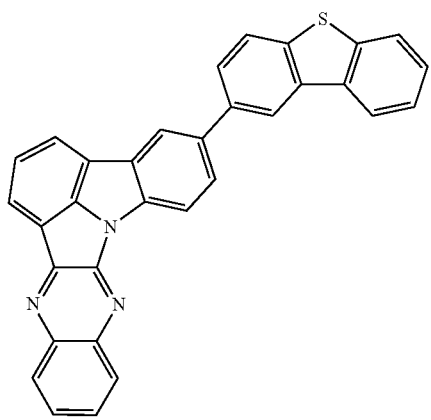
A-104
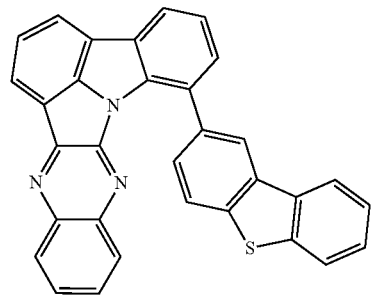
A-105
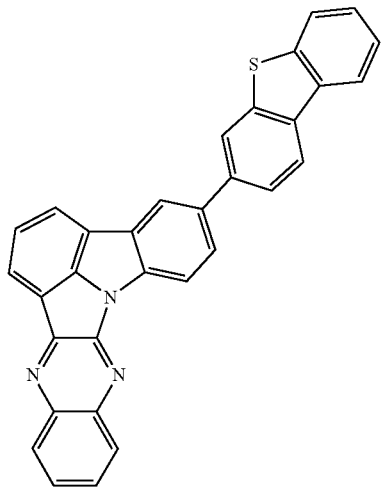
A-106
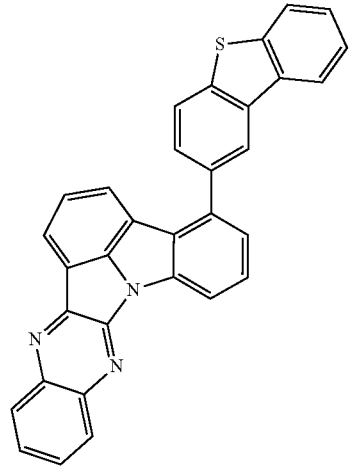
A-107
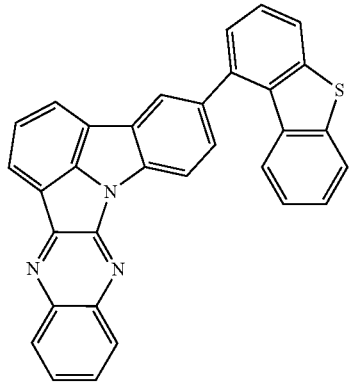

-continued
A-108
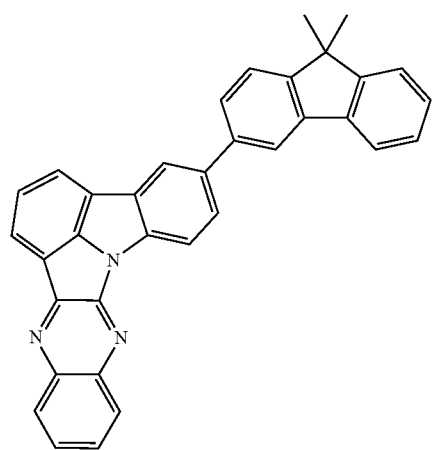
A-109
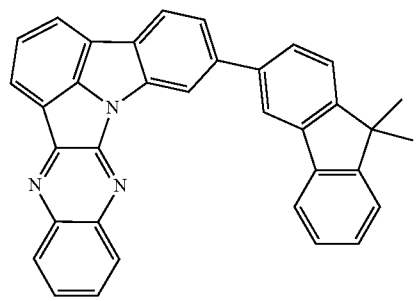
A-110
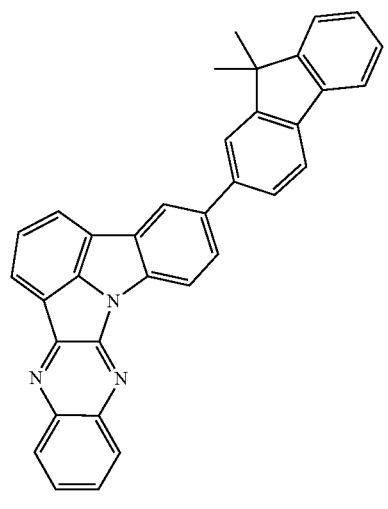
A-111
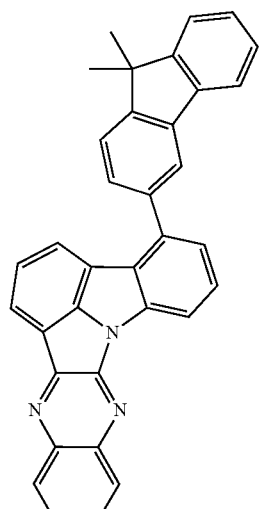
A-112
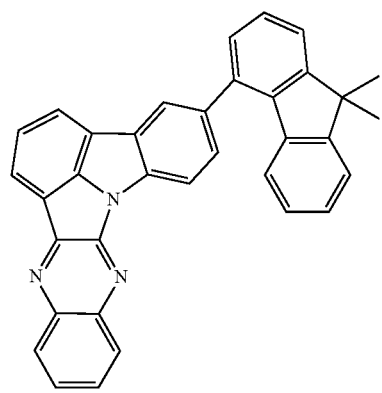
A-113
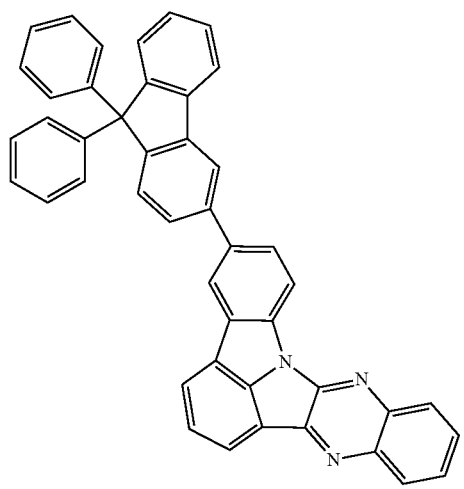

-continued
A-114
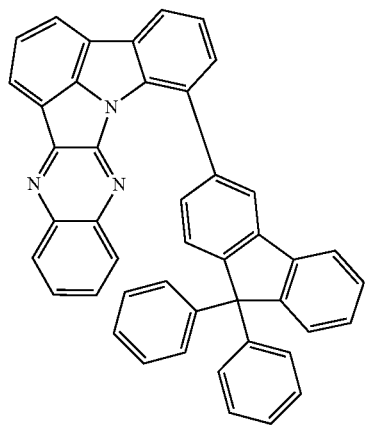
A-115
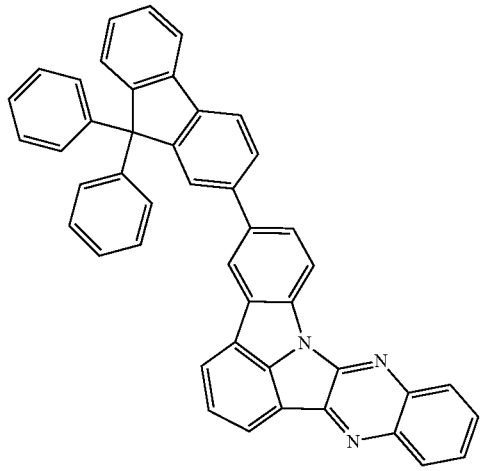
A-116
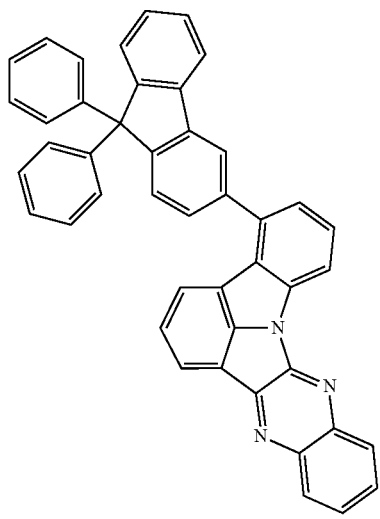
A-117
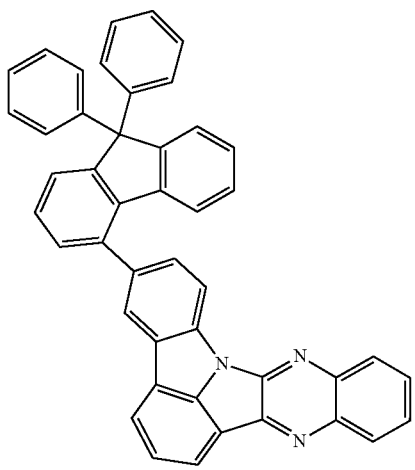
A-118
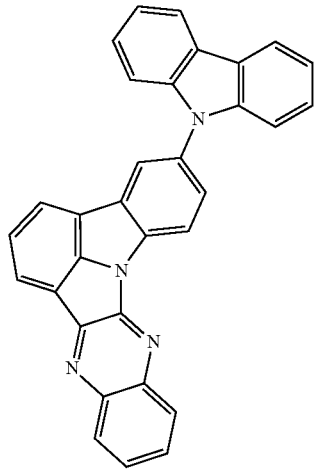
A-119
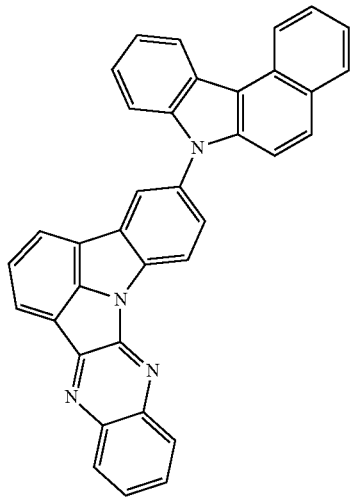

-continued
A-120
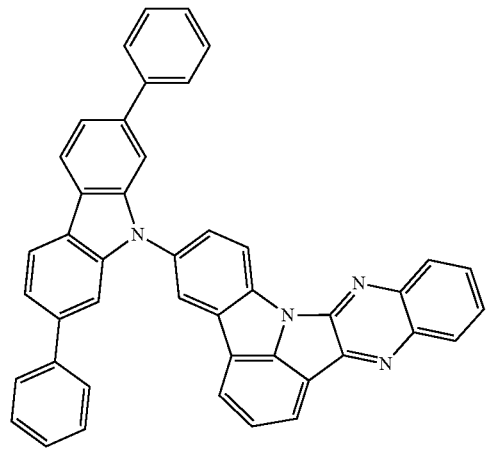
A-121
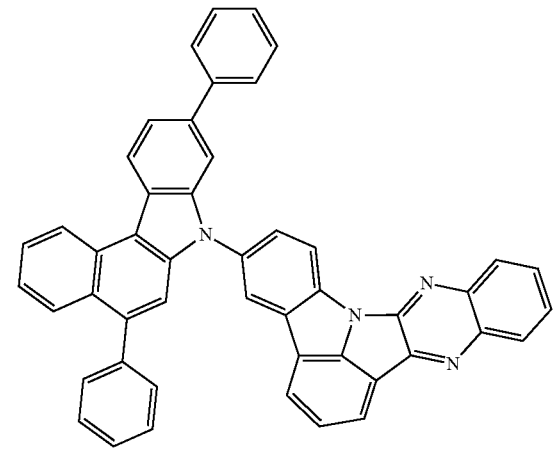
A-122
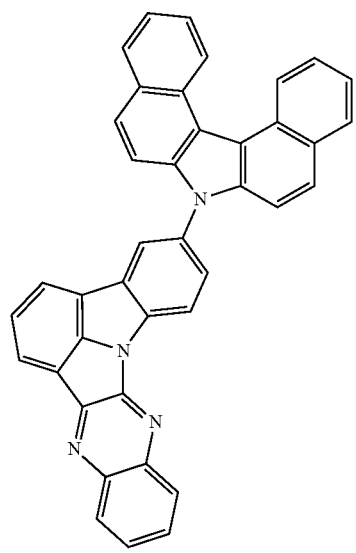
A-123
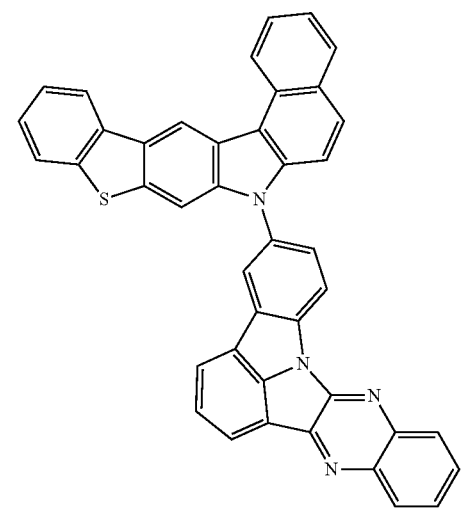
A-124
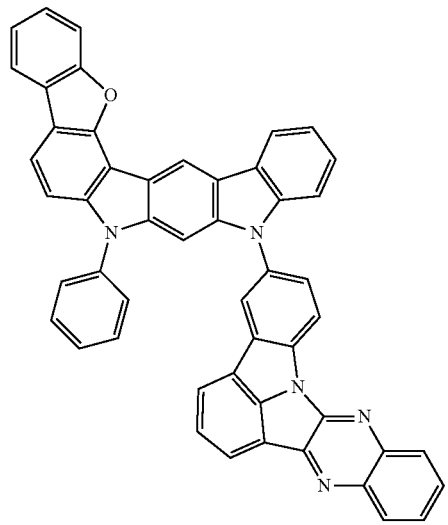
A-125
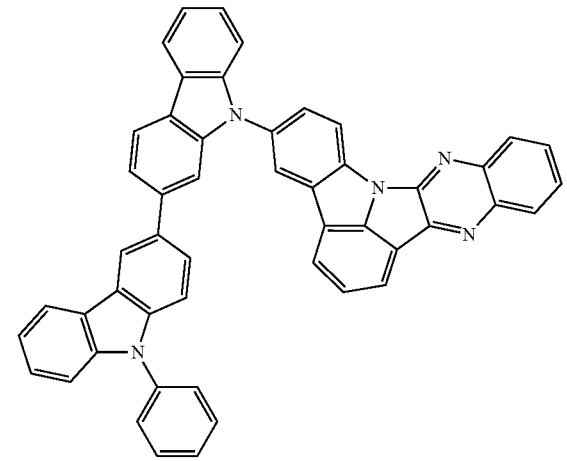

-continued
A-126
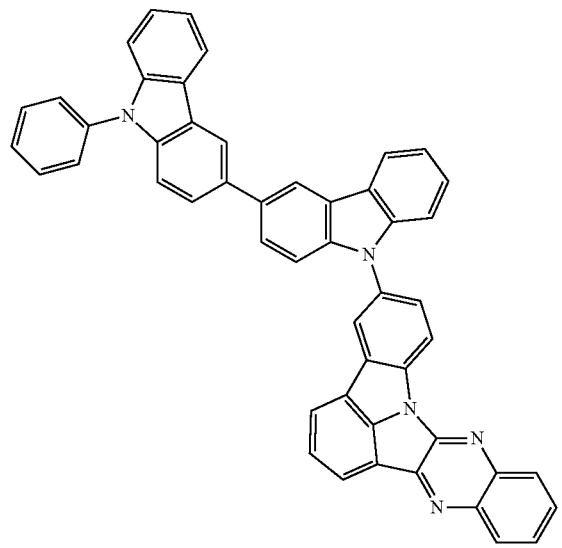
A-127
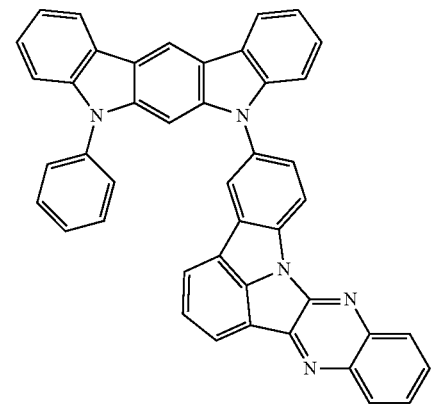
A-128
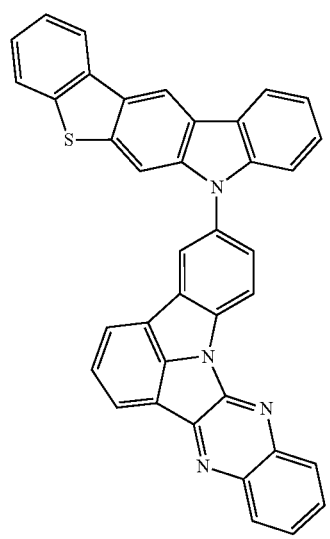
A-129
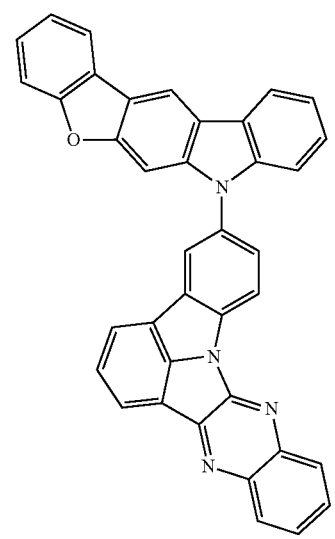
A-130
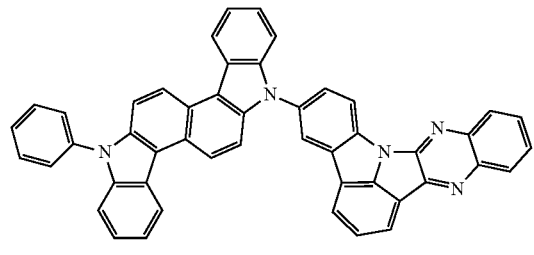
A-131
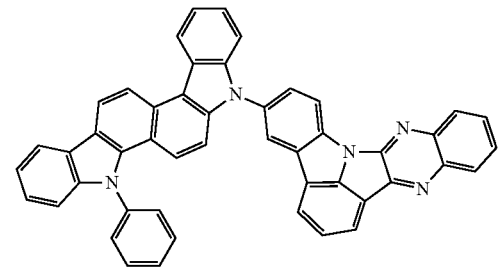

-continued
A-132
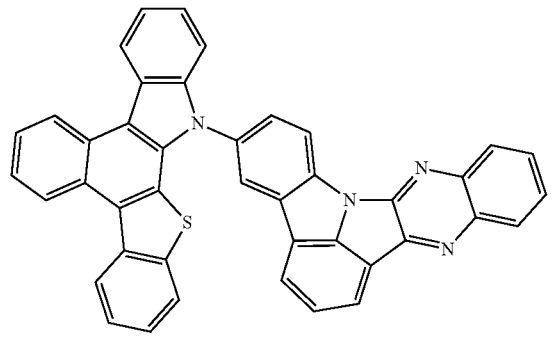
A-133
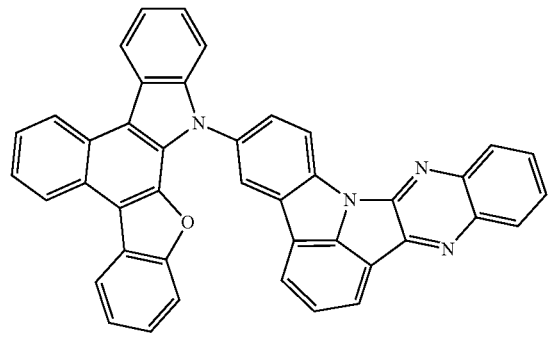
A-134
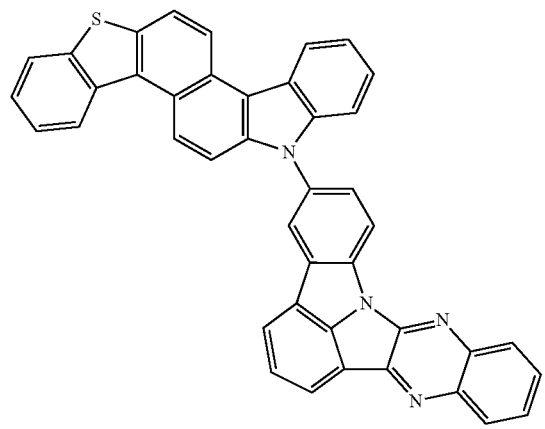
A-135
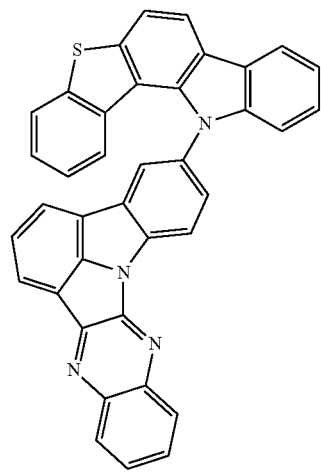
A-136
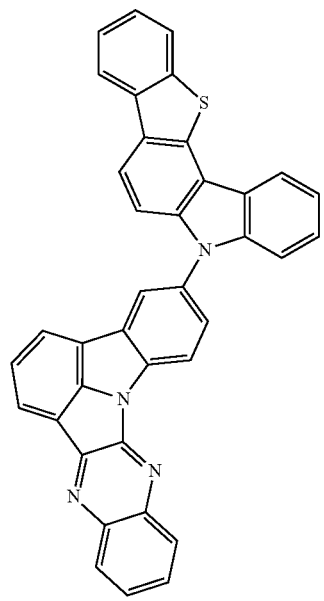
A-137
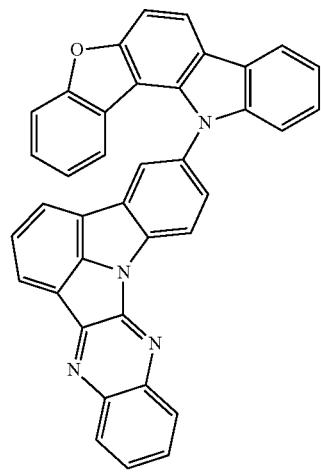

-continued
A-138
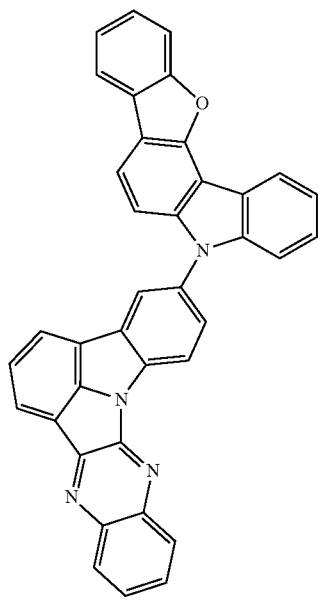
A-139
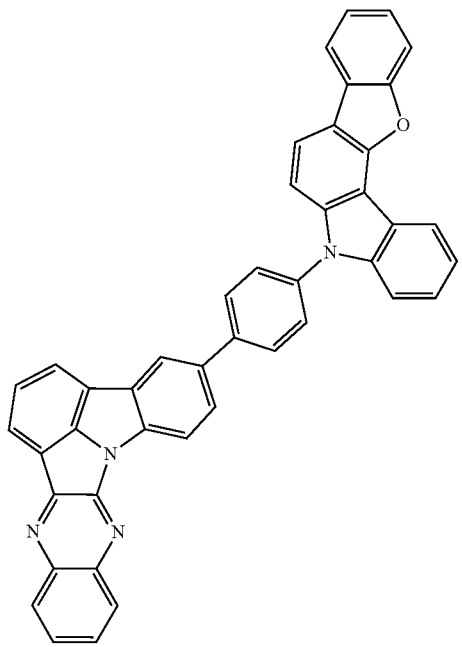
A-140
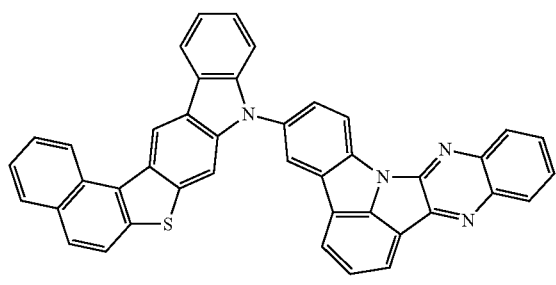
A-141
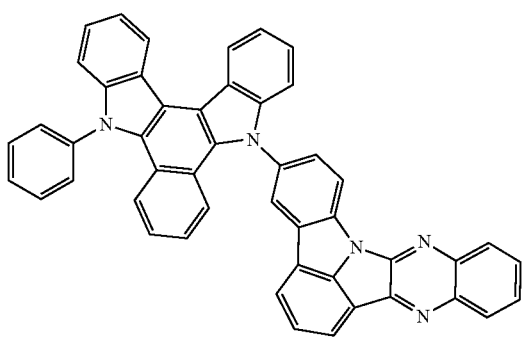
A-142
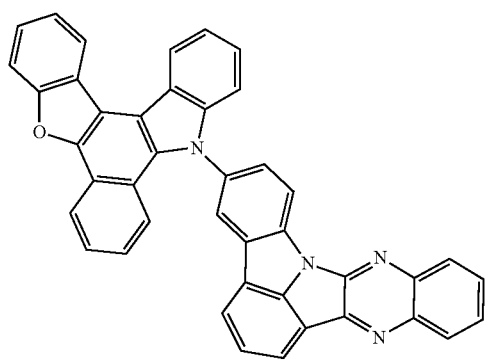
A-143
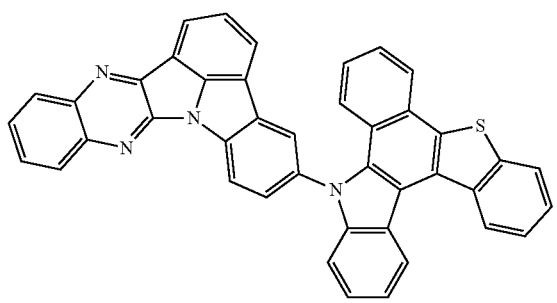

-continued
A-144
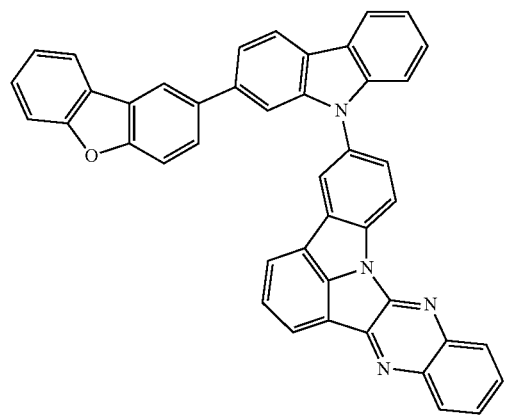
A-145
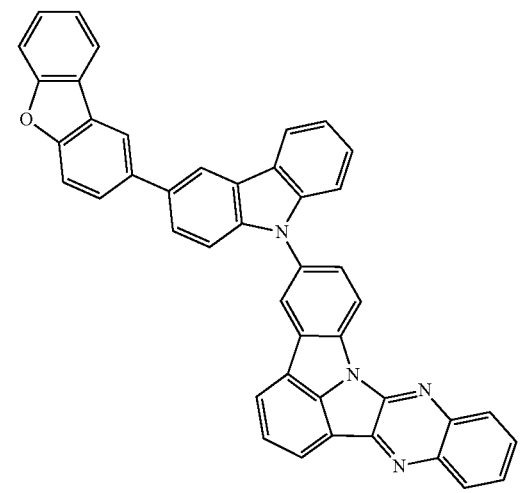
A-146
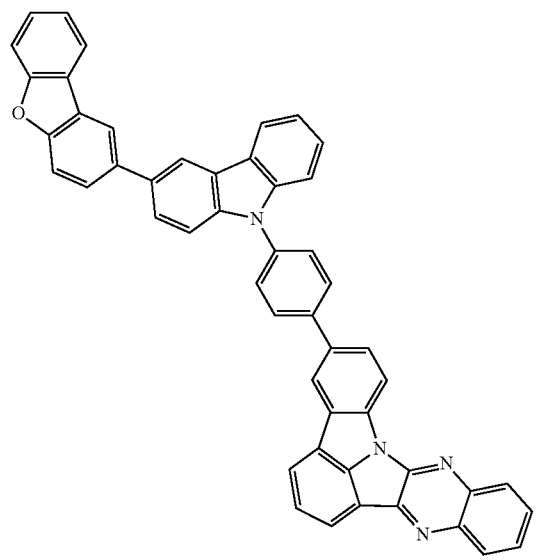
A-147
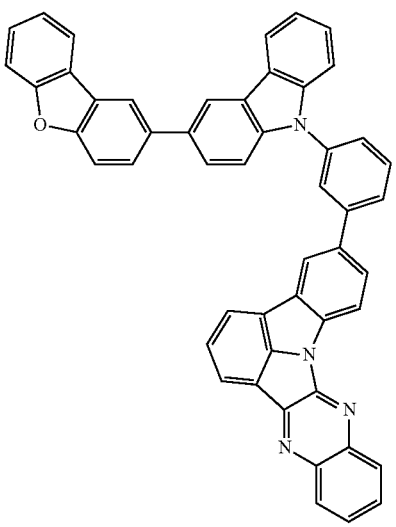

-continued
A-148
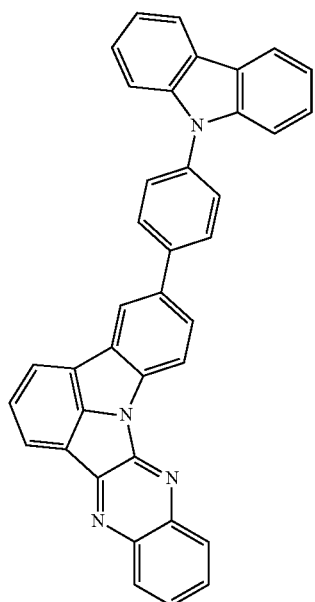
A-149
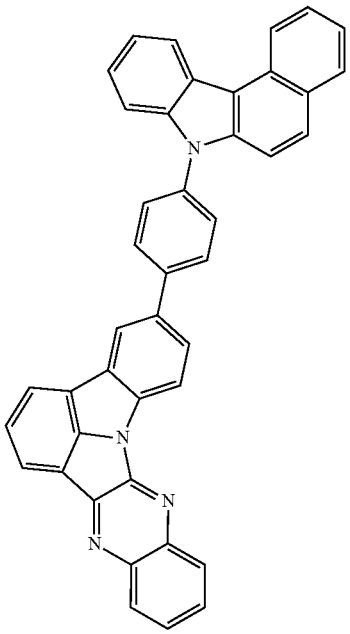
A-150
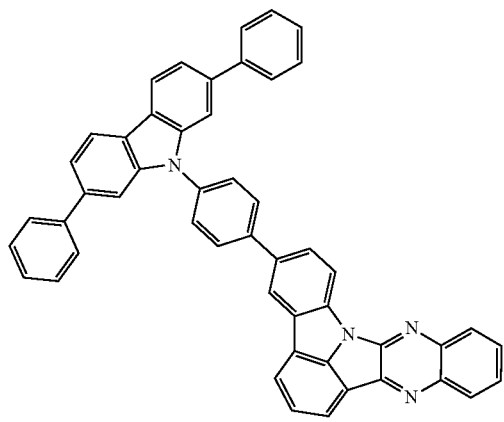
A-151
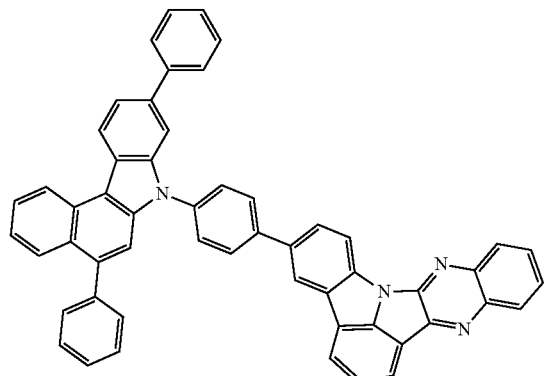
A-152
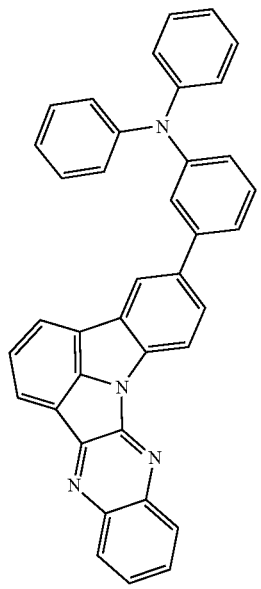
A-153
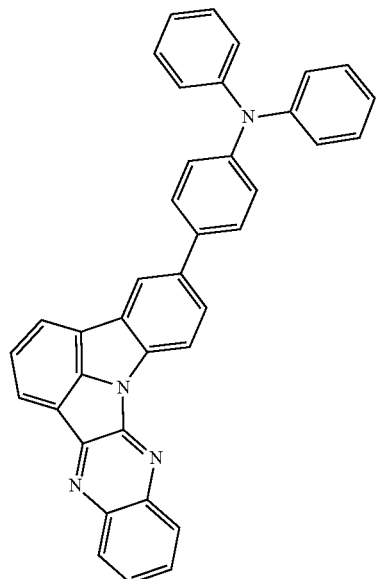

-continued
A-154
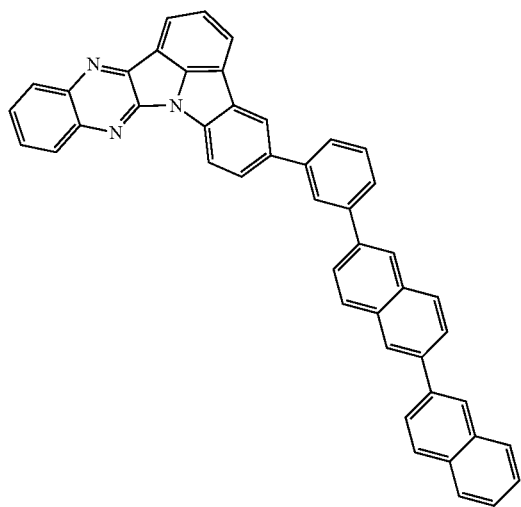
A-155
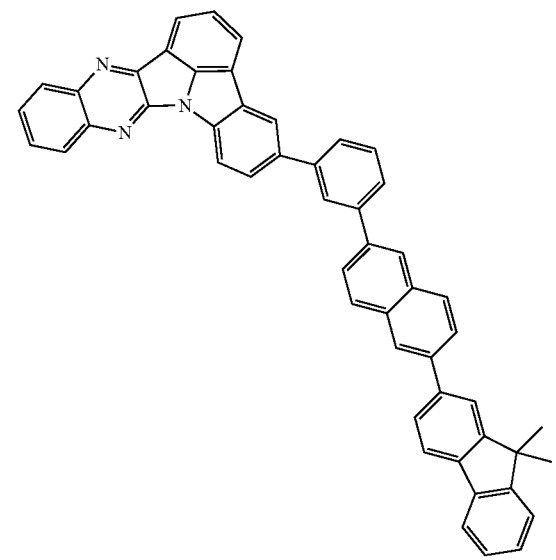
A-156
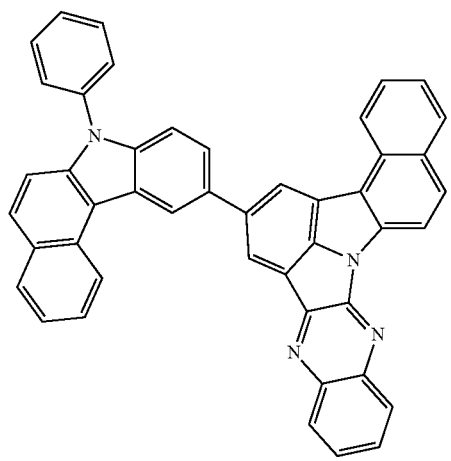
A-157
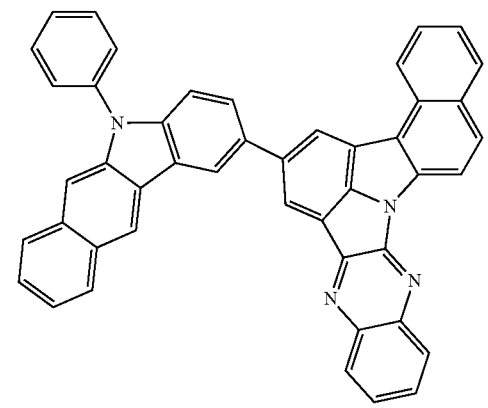
A-158
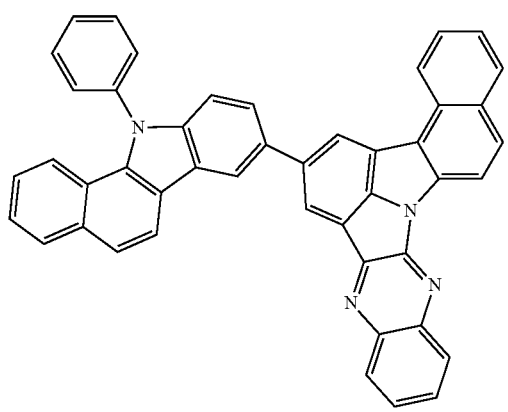
A-159
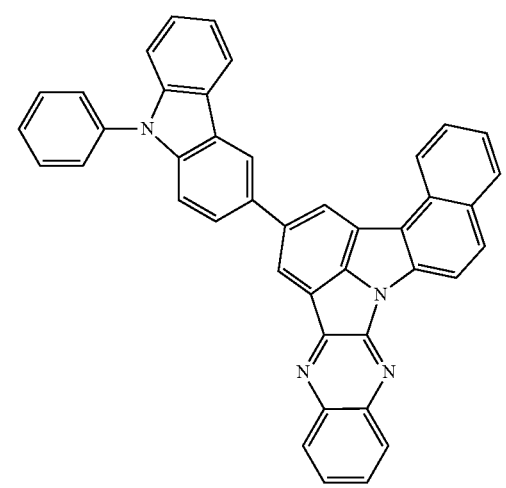

-continued
A-160
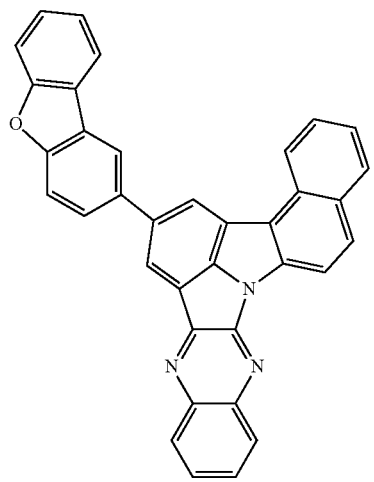
A-161
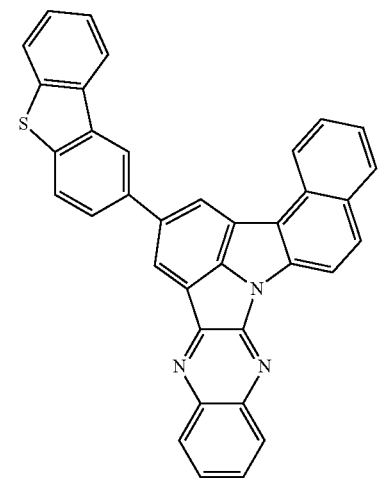
A-162
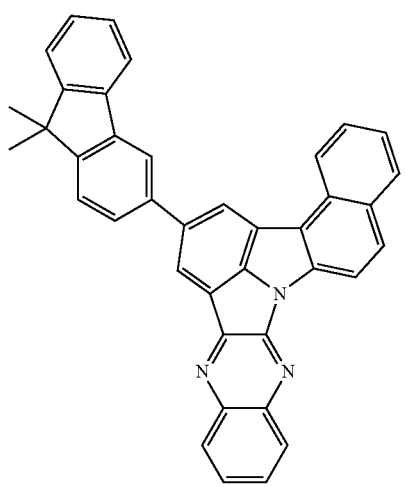
A-163
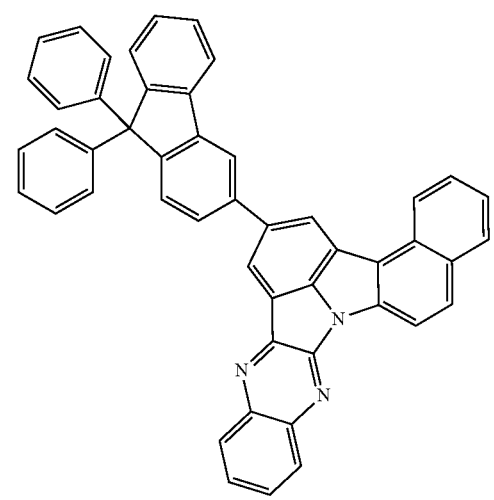
A-164
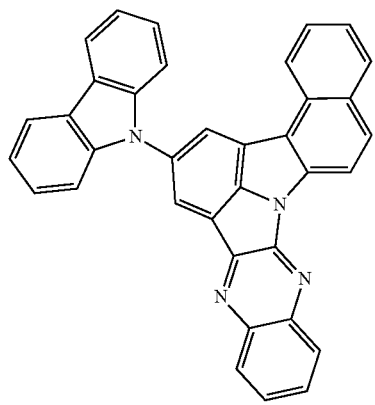
A-165
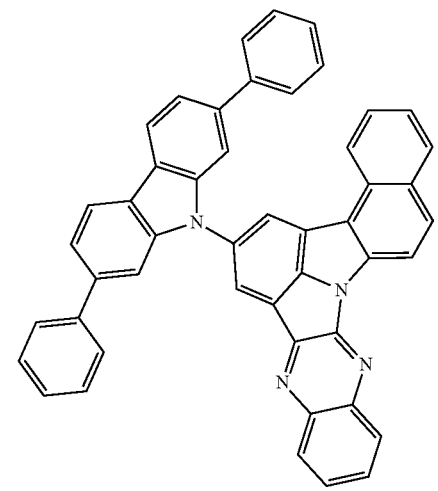

-continued
A-166
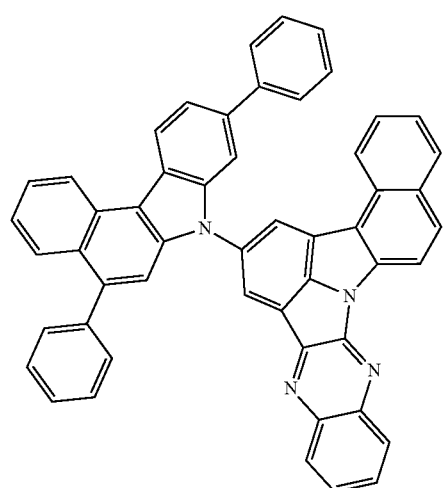
A-167
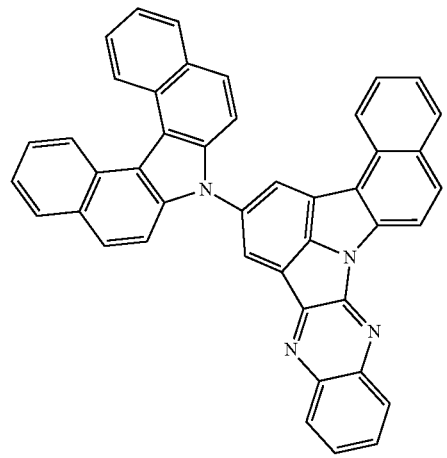
A-168
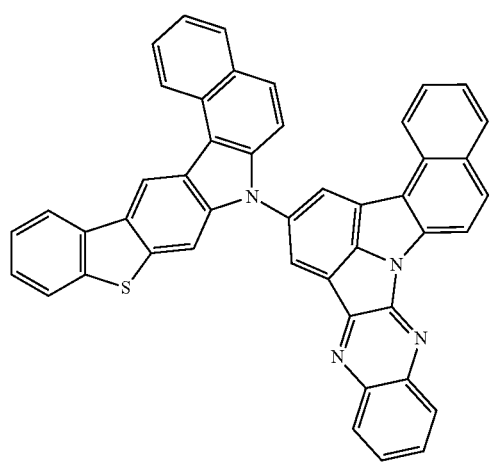
A-169
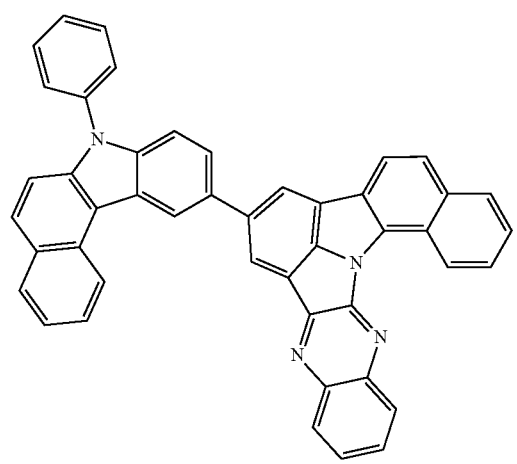
A-170
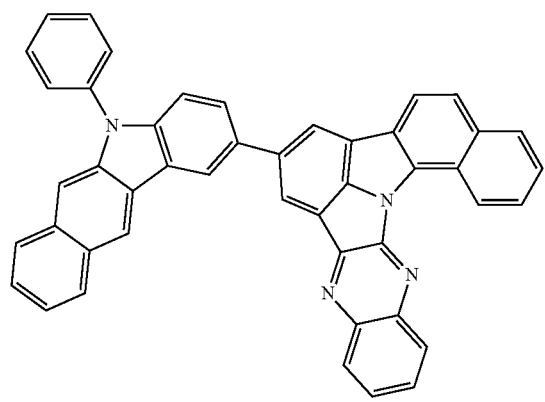
A-171
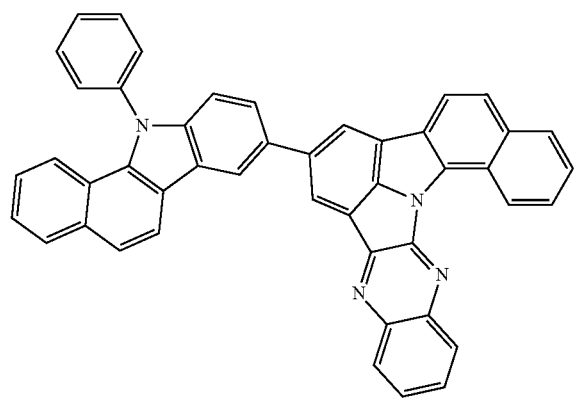

-continued
A-172
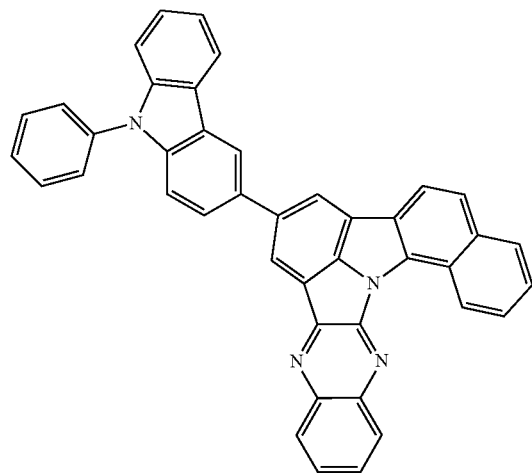
A-173
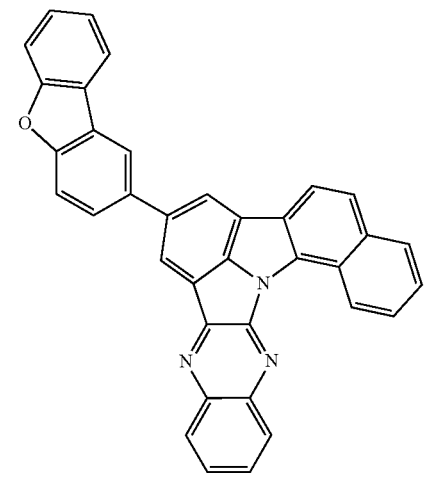
A-174
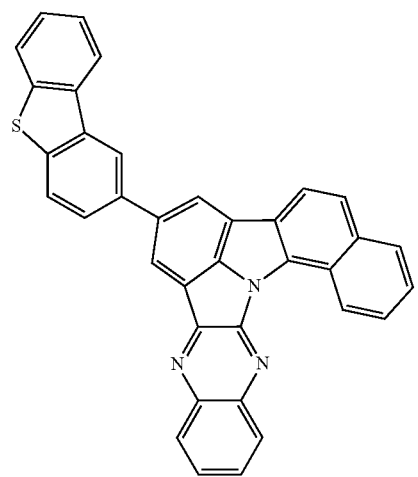
A-175
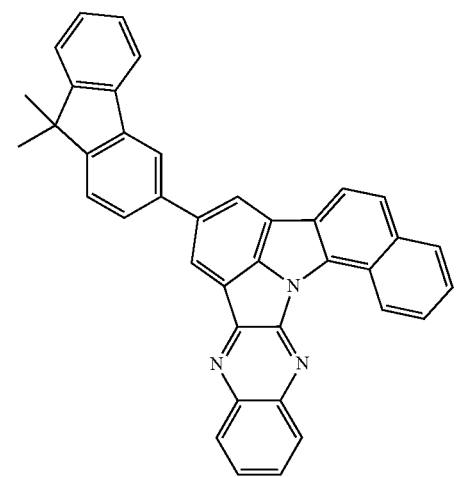
A-176
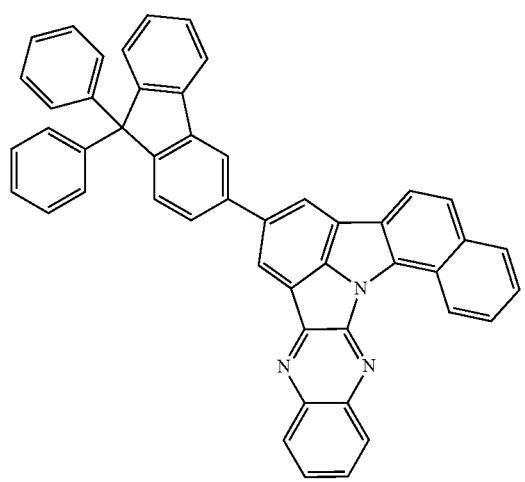
A-177
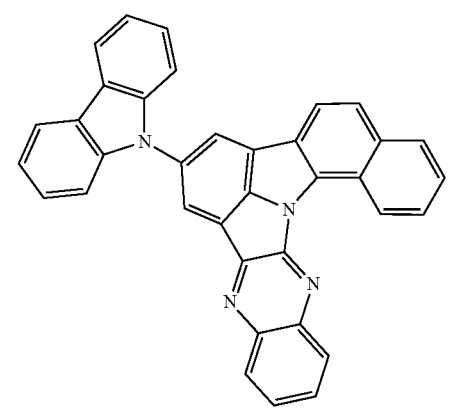

-continued
A-178
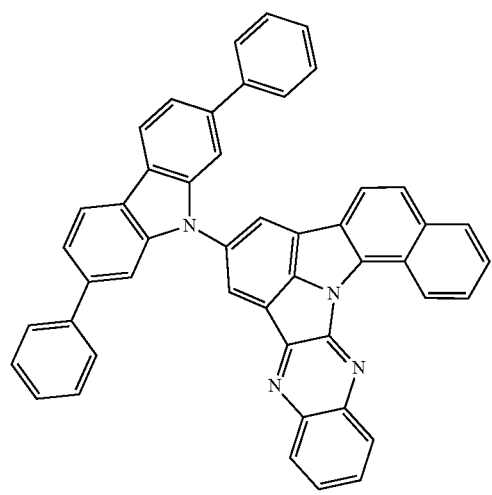
A-179
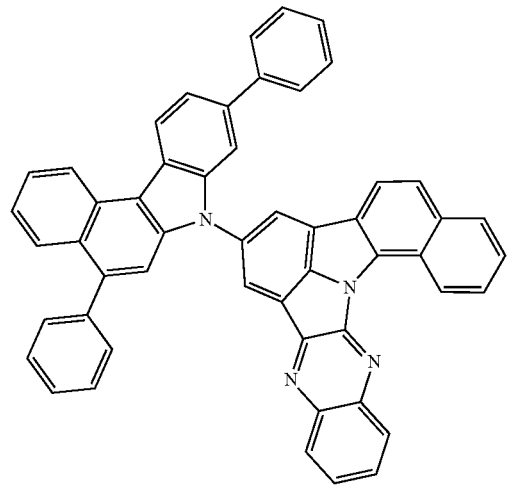
A-180
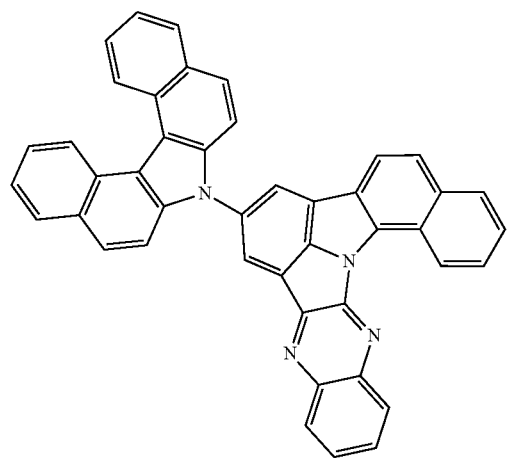
A-181
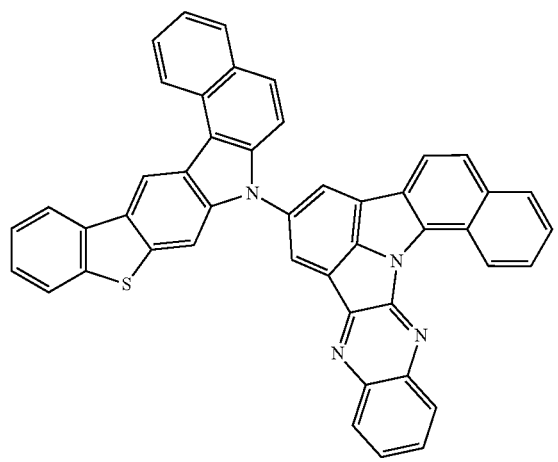
A-182
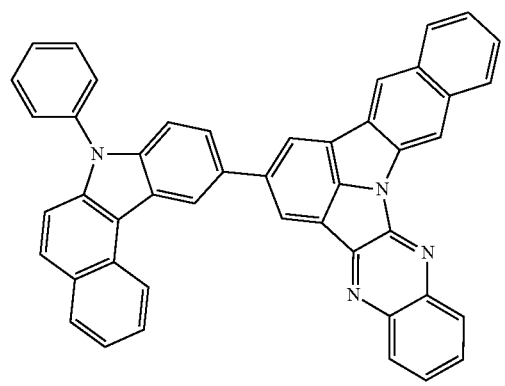
A-183
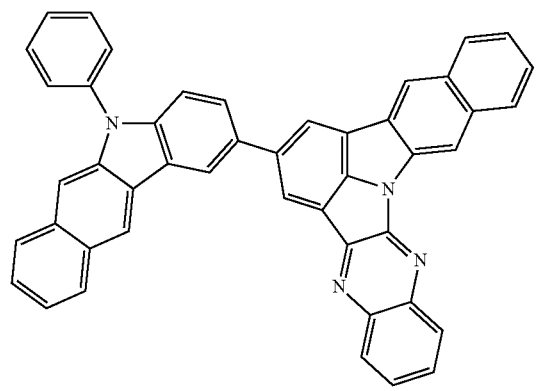

-continued
A-184
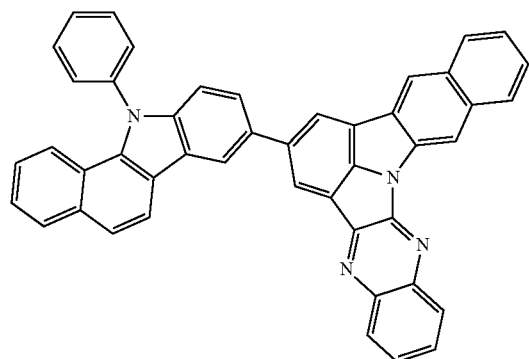
A-185
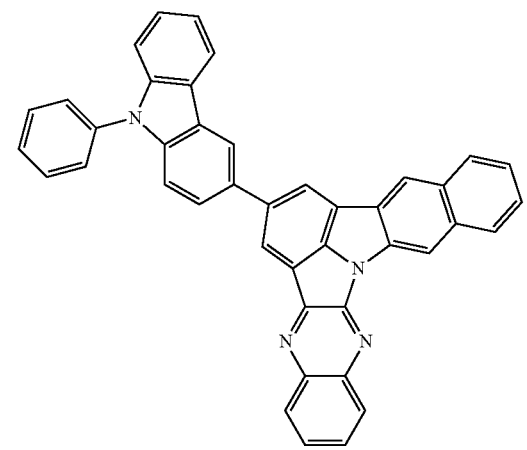
A-186
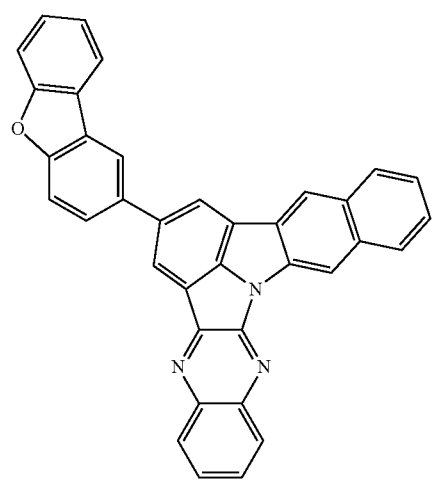
A-187
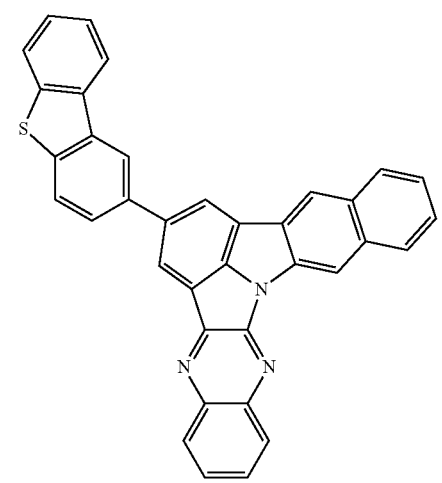
A-188
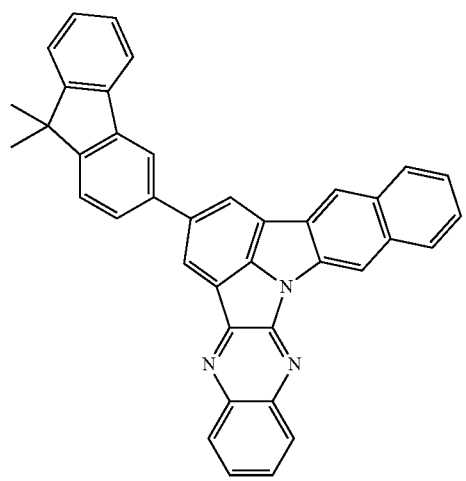
A-189
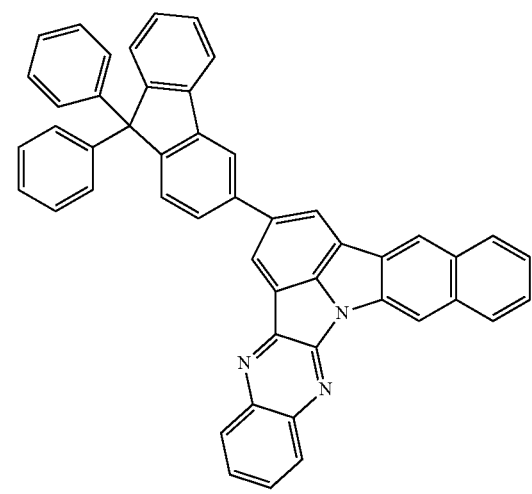

-continued
A-190
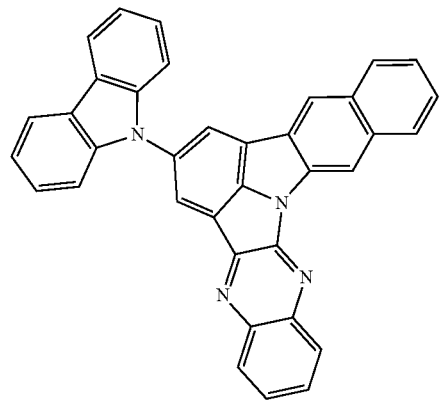
A-191
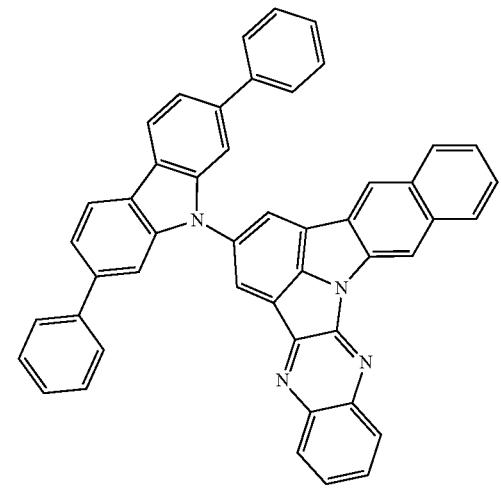
A-192
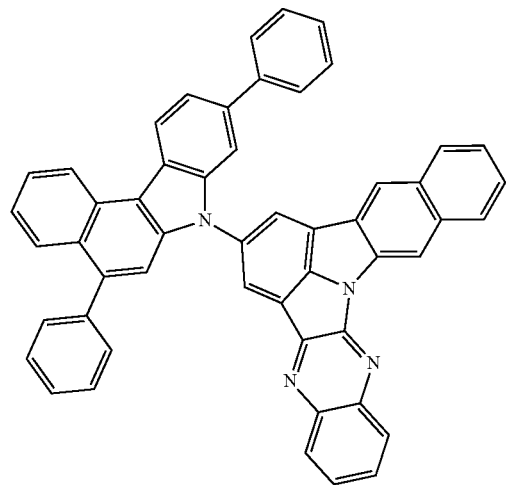
A-193
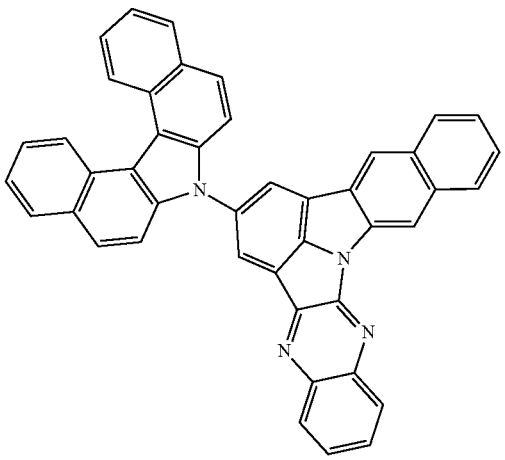
A-194
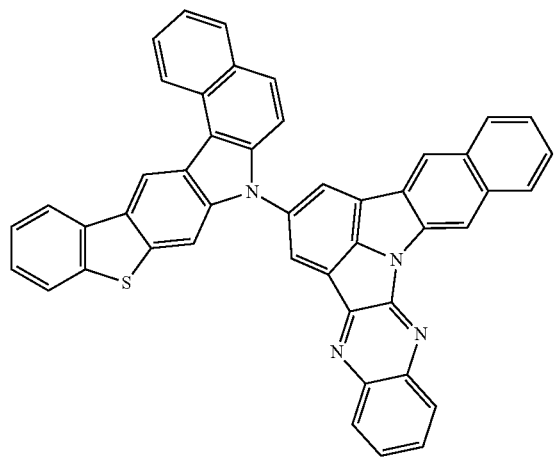
A-195
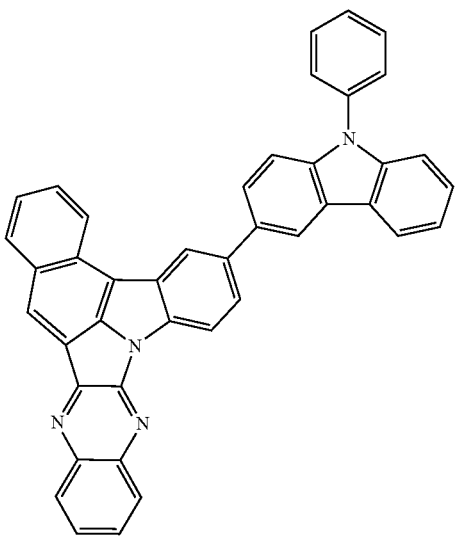

-continued
A-196
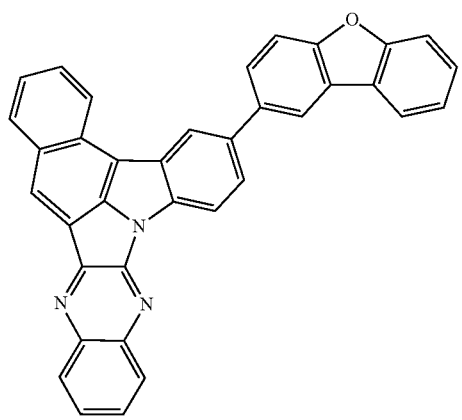
A-197
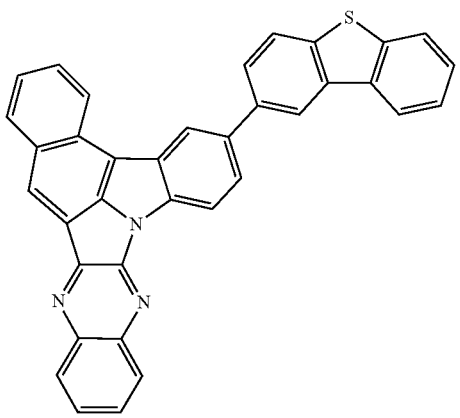
A-198
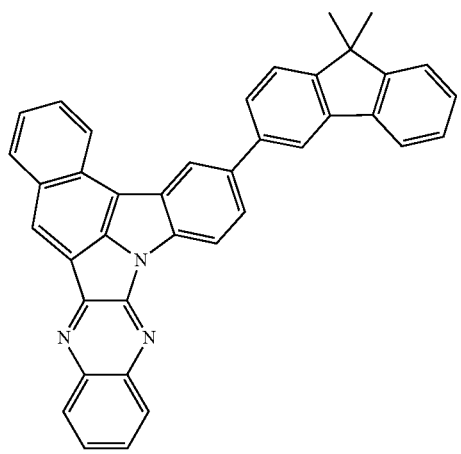
A-199
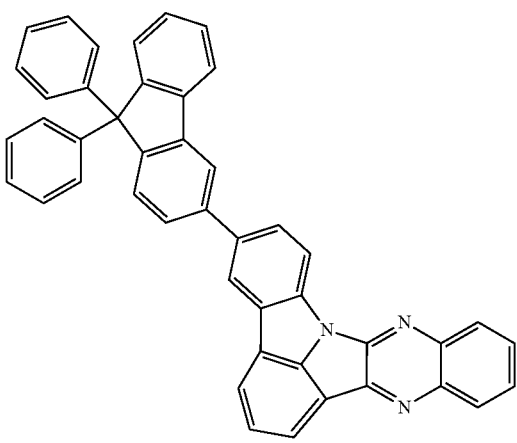
A-200
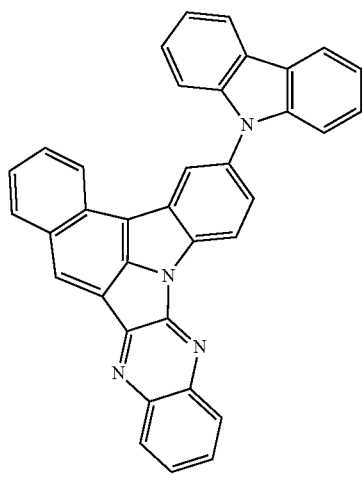
A-201
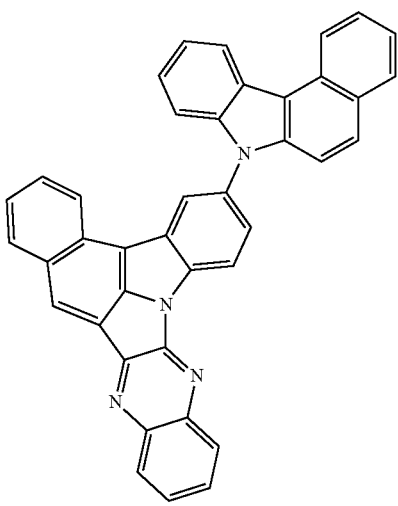

-continued
A-202
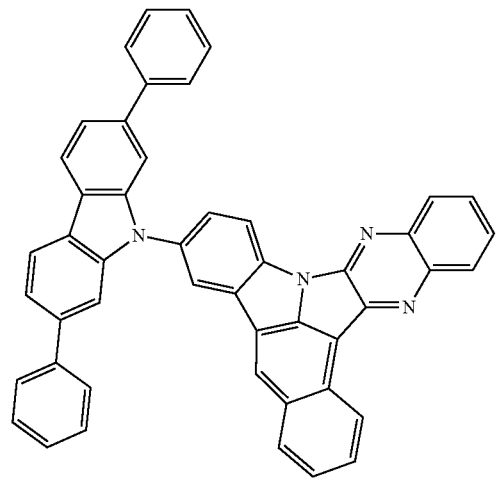
A-203
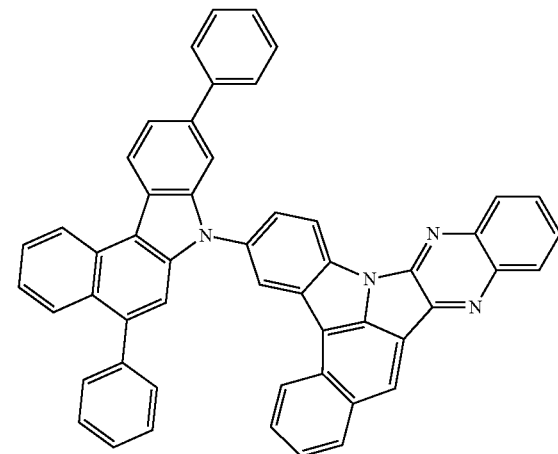
A-204
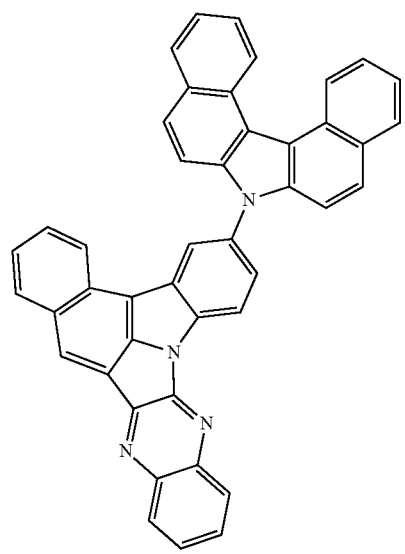
A-205
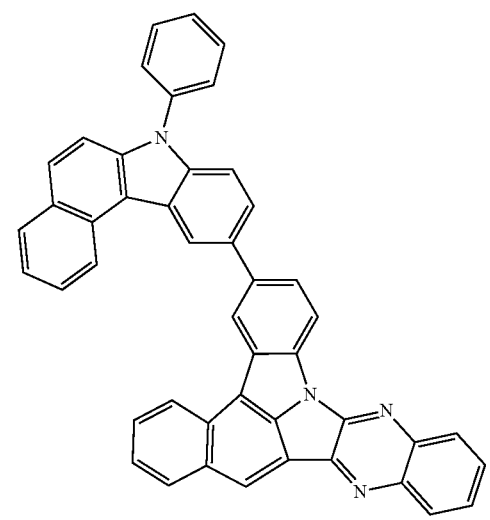
A-206
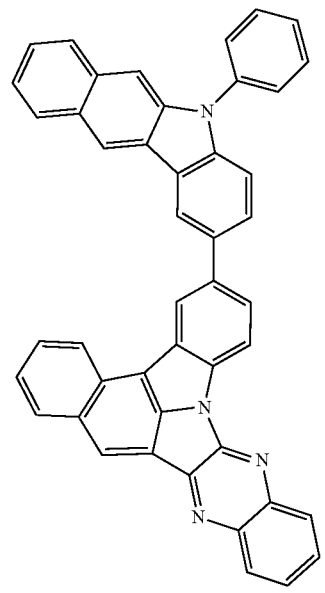
A-207
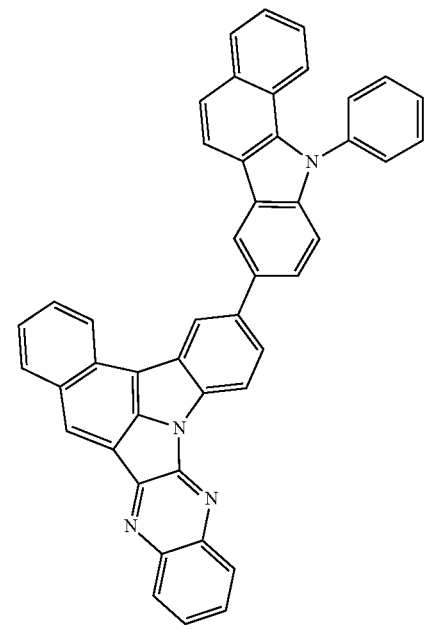

-continued
A-208
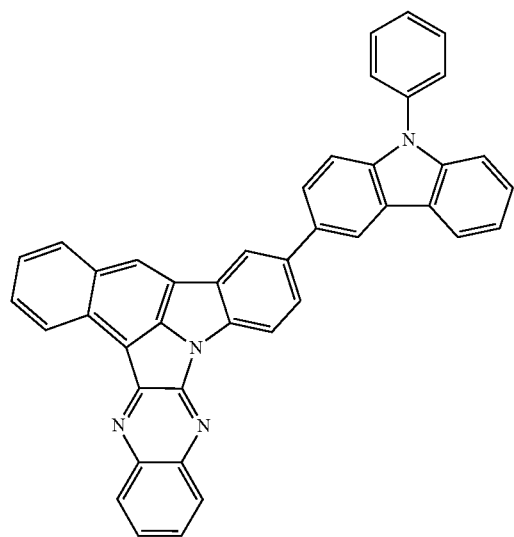
A-209
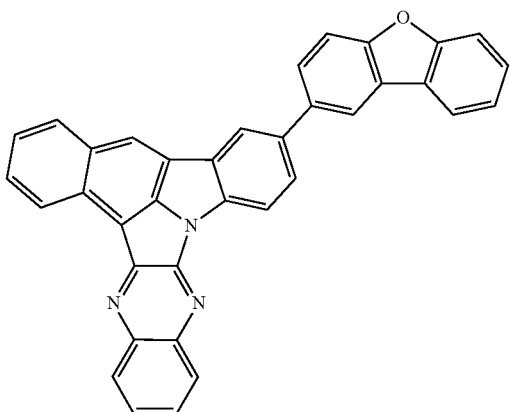
A-210
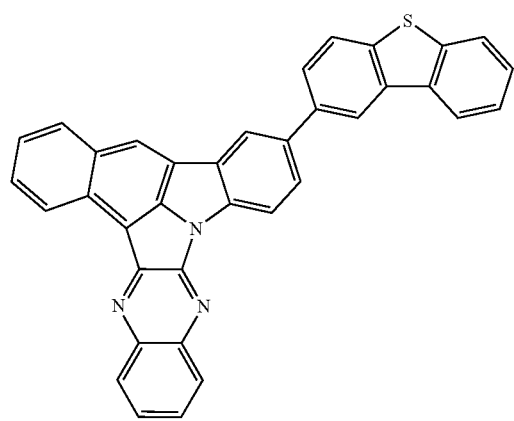
A-211
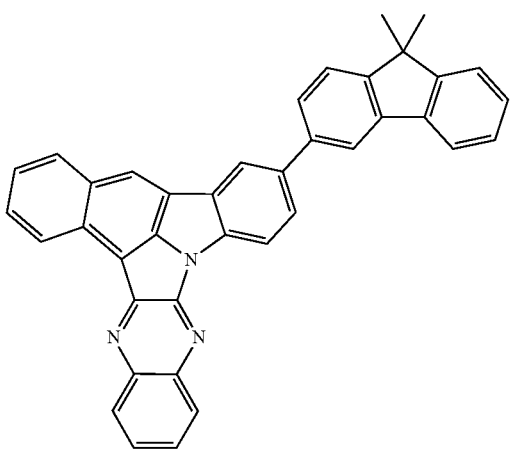
A-212
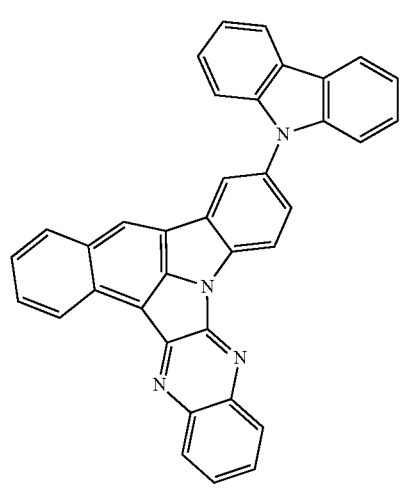
A-213
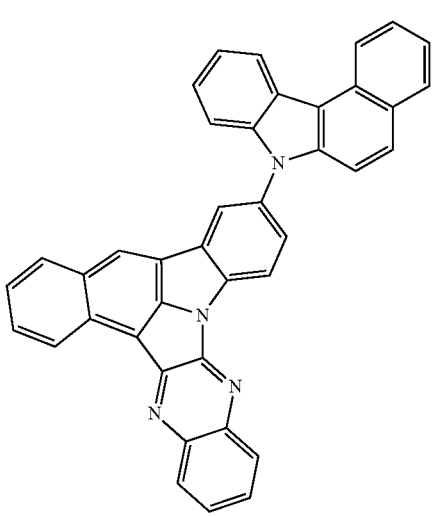

-continued
A-214
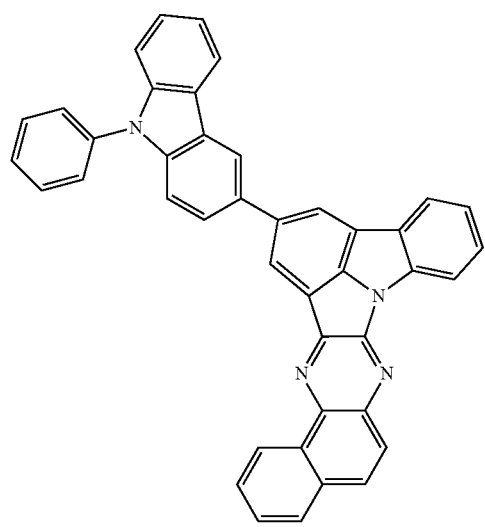
A-215
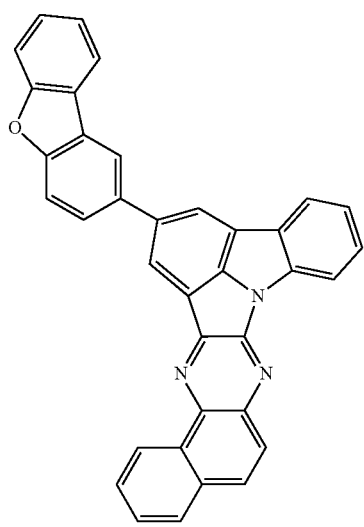
A-216
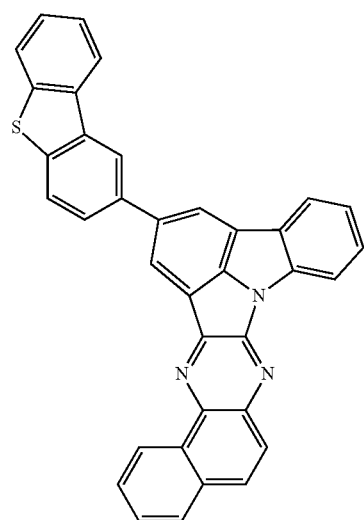
A-217
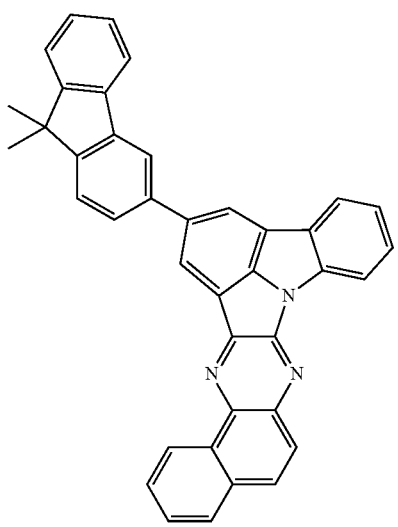
A-218
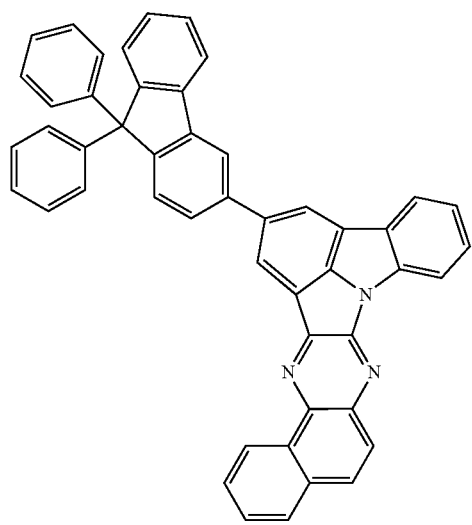
A-219
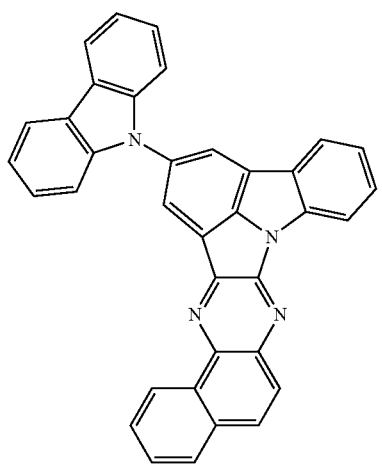

-continued
A-220
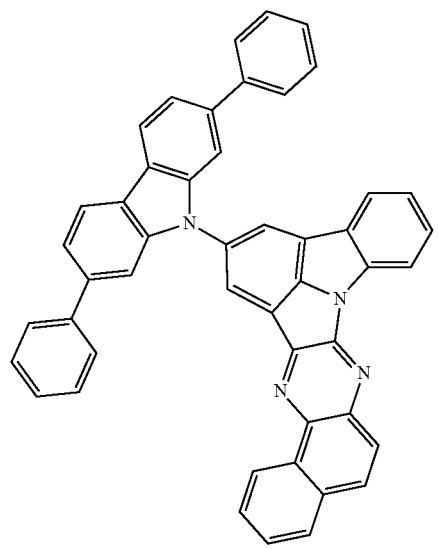
A-221
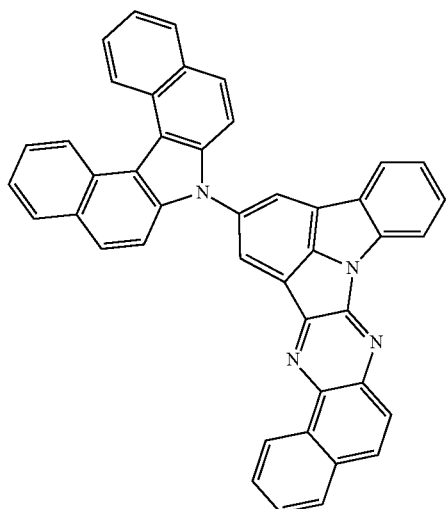
A-223
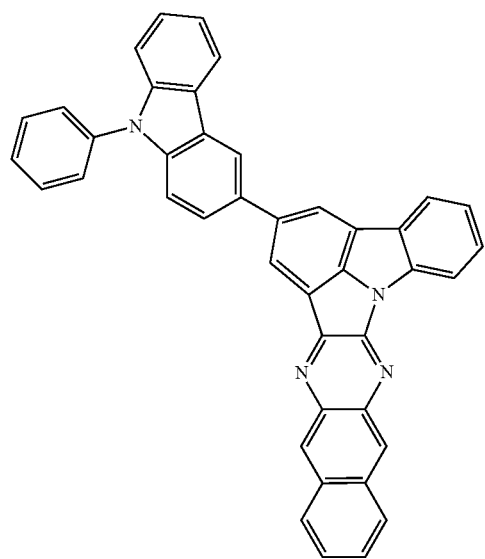
A-224
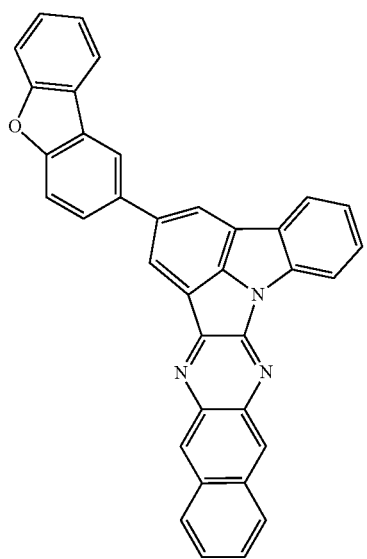
A-225
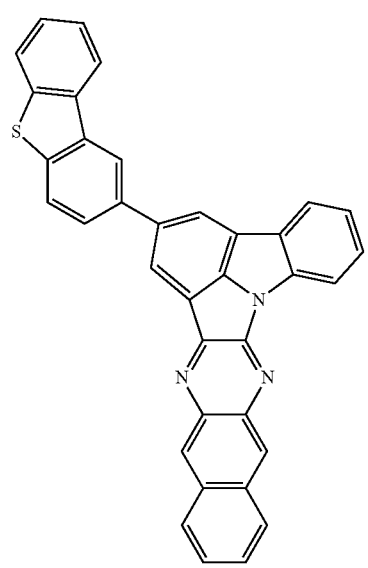
A-226
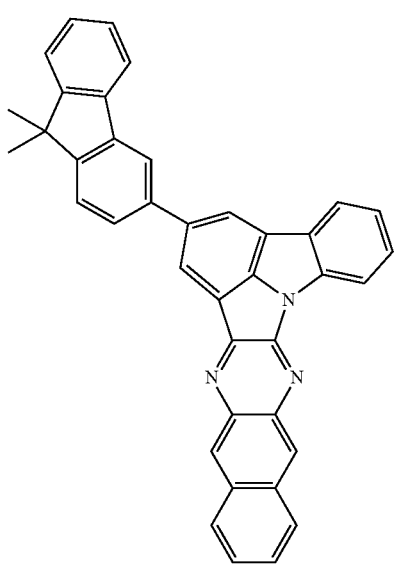

-continued
A-227
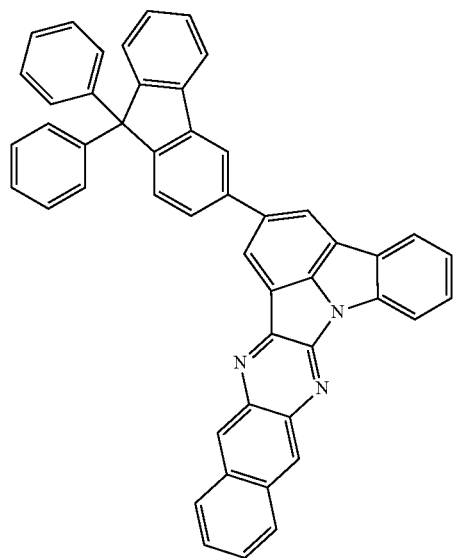
A-228
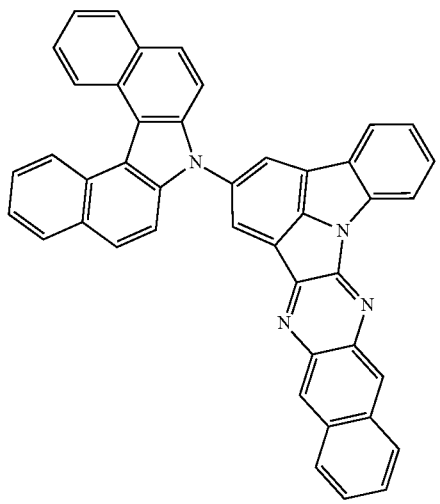
A-229
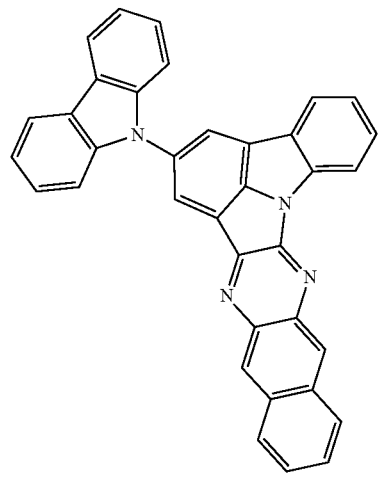
A-230
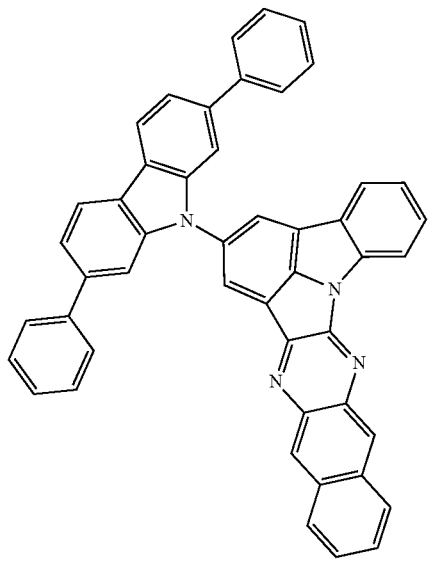
A-231
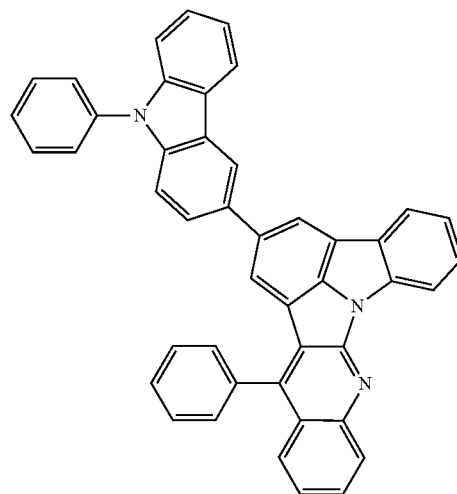
A-232
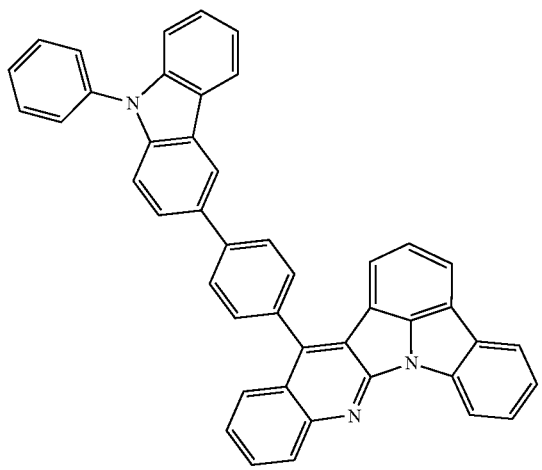

-continued
A-233
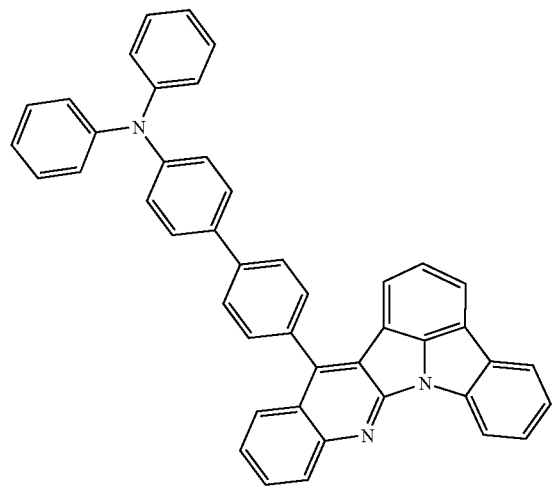
A-234
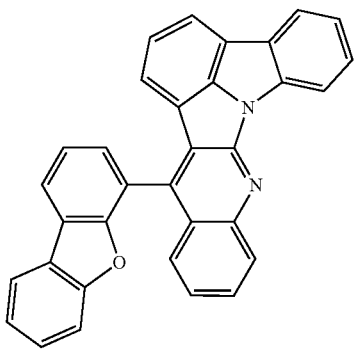
A-235
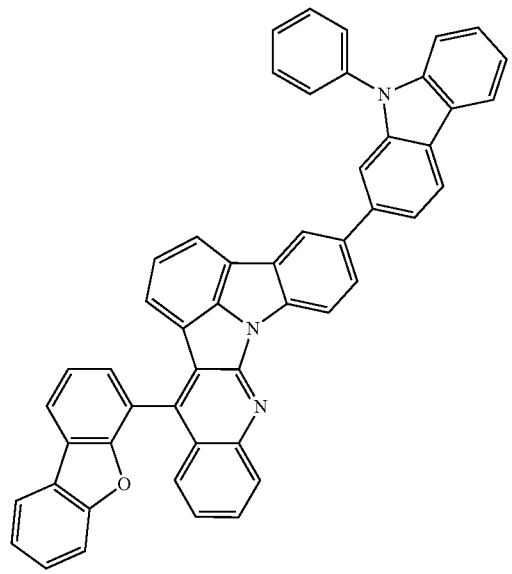
A-236
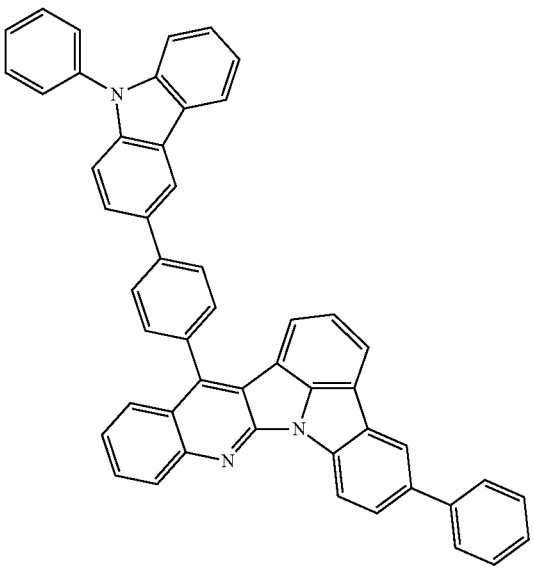
A-237
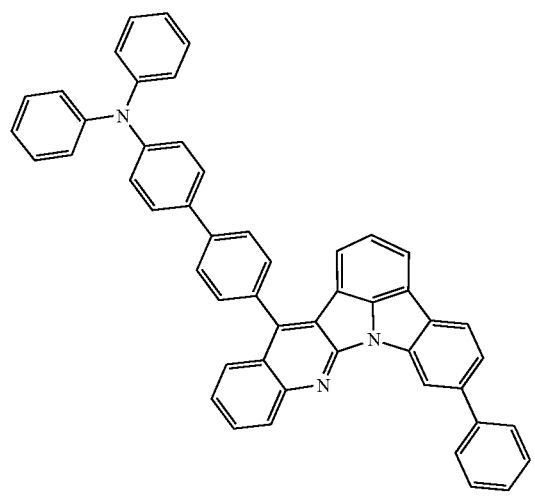
A-238
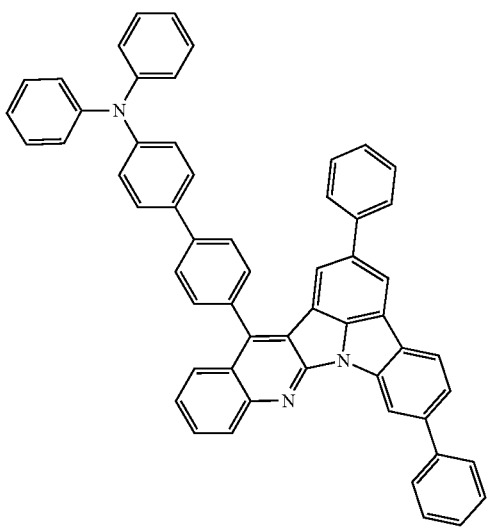

-continued
A-239
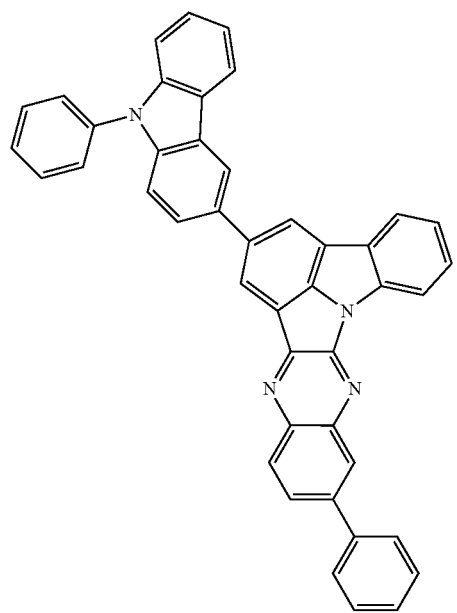
A-240
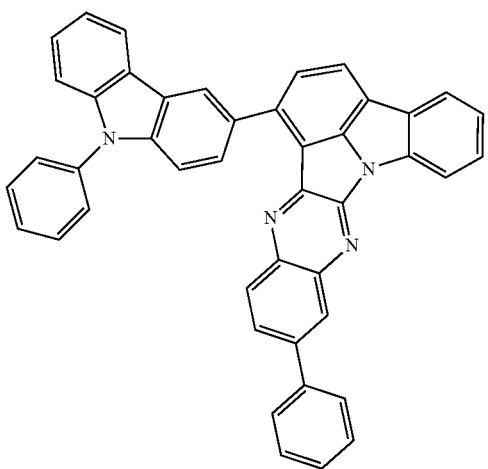
A-241
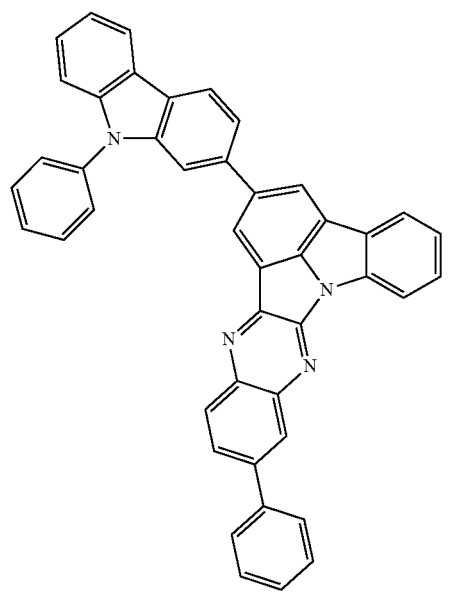
A-242
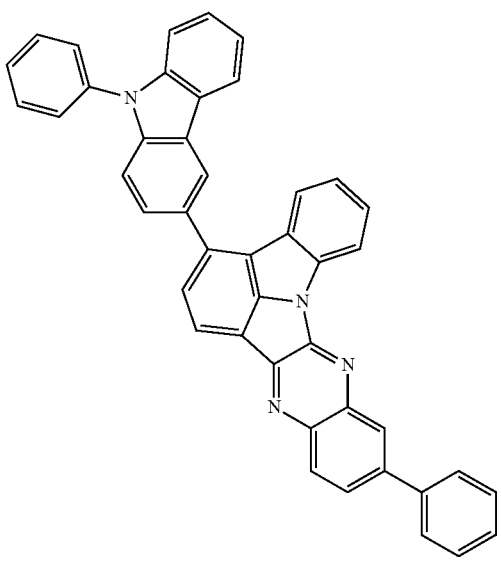

-continued
A-243
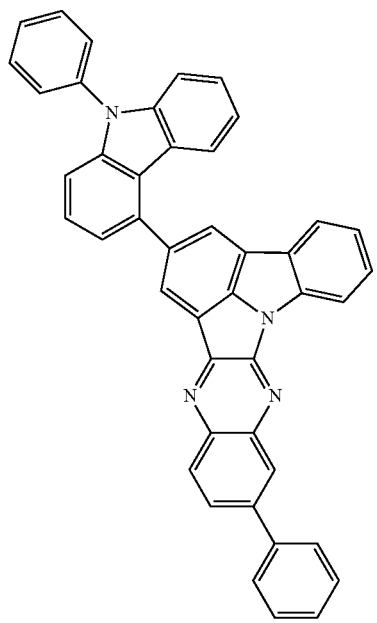
A-244
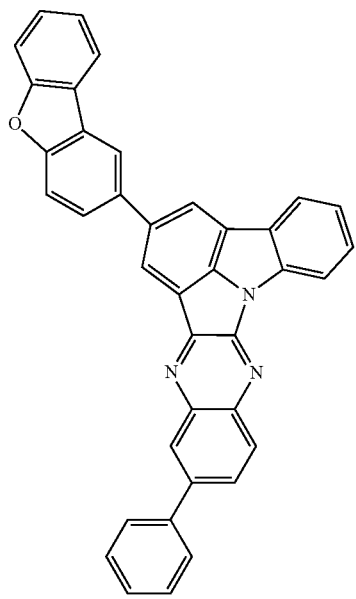
A-245
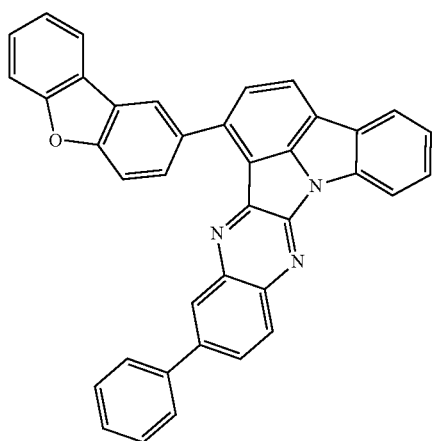
A-246
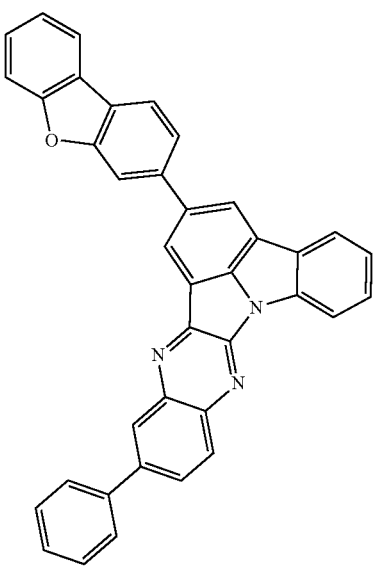

-continued
A-247
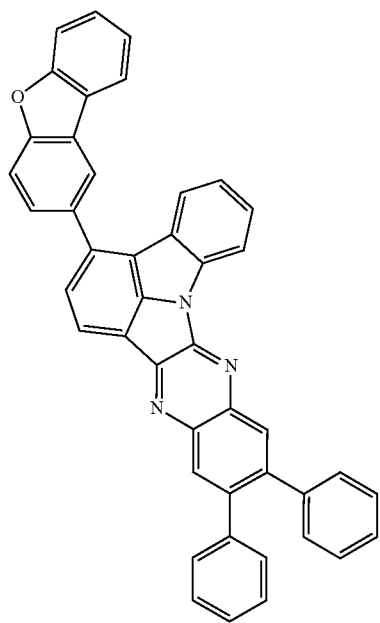
A-248
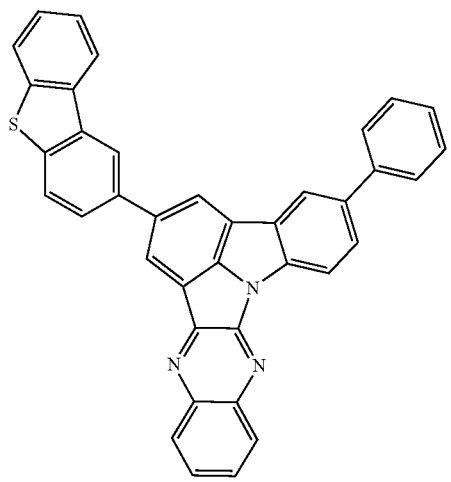
A-249
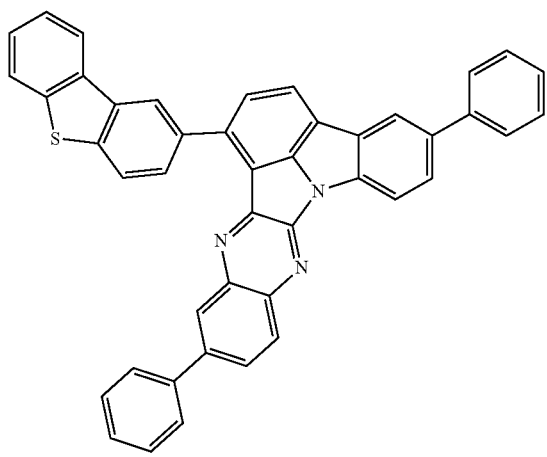
A-250
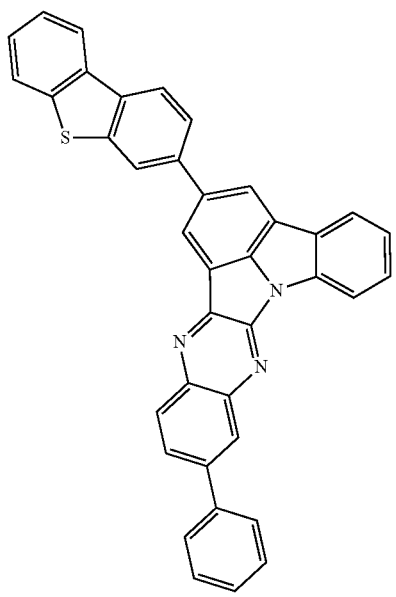

-continued
A-251
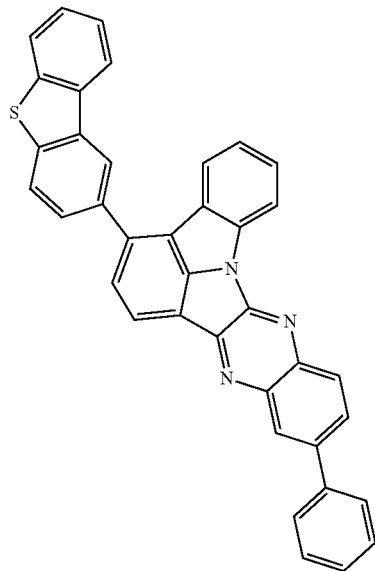
A-252
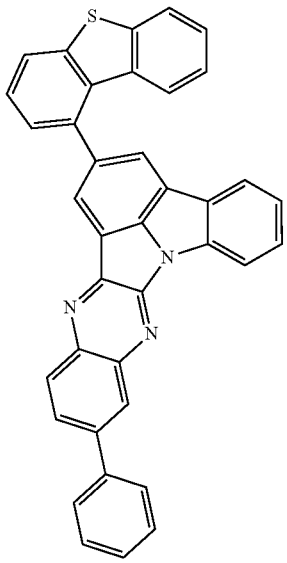
A-253
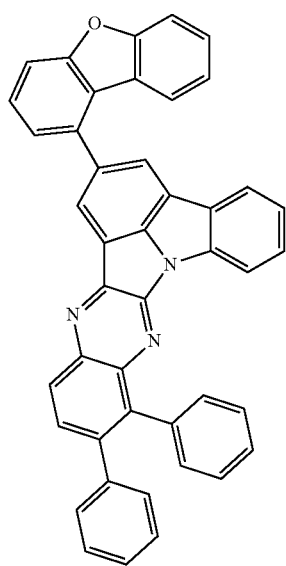
A-254
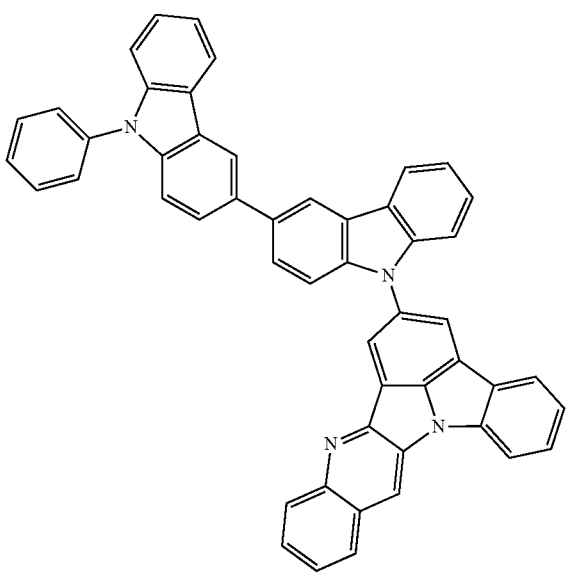

-continued
A-255
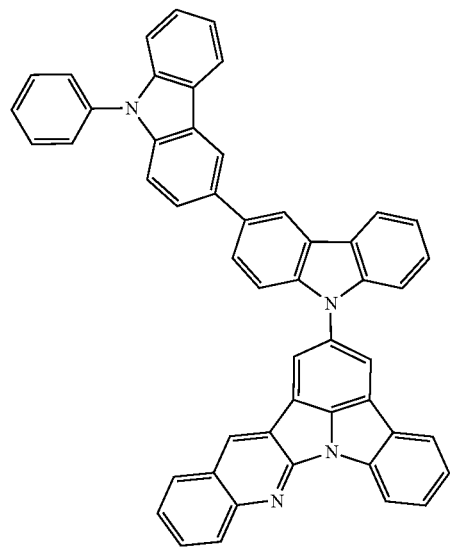
A-256
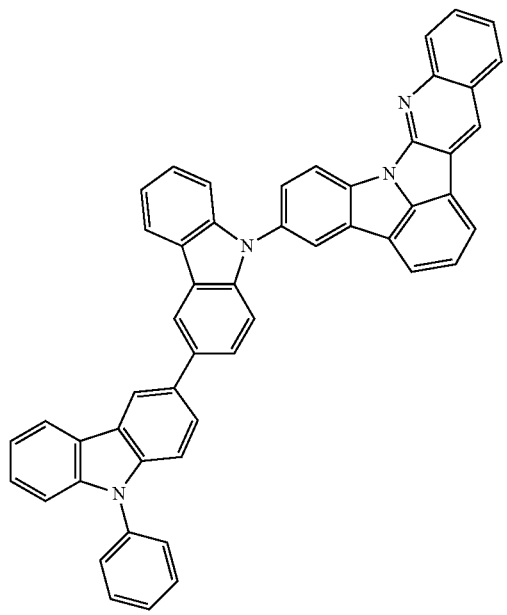
A-257
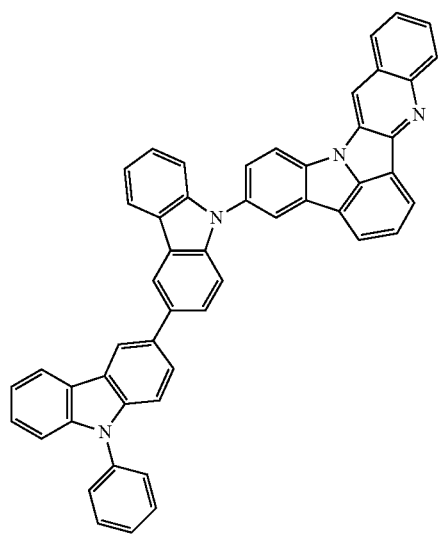
A-258
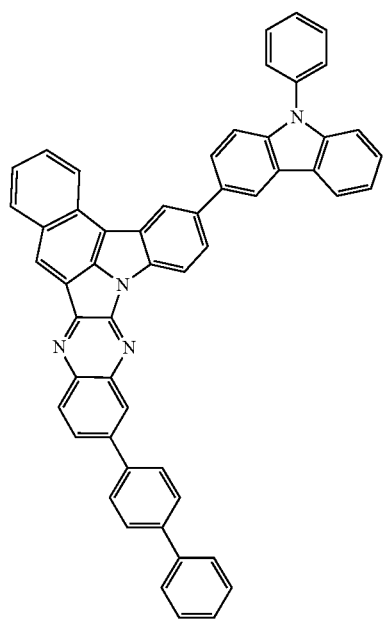

-continued
A-259
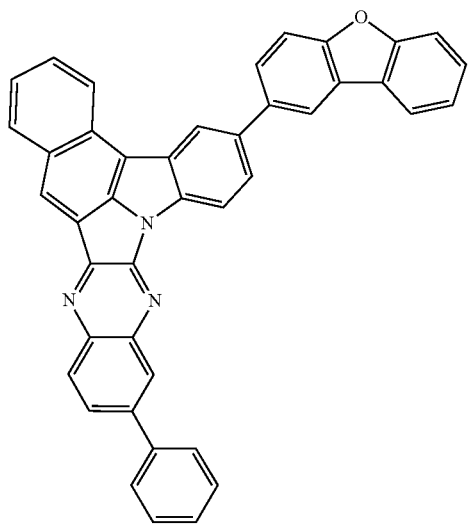
A-260
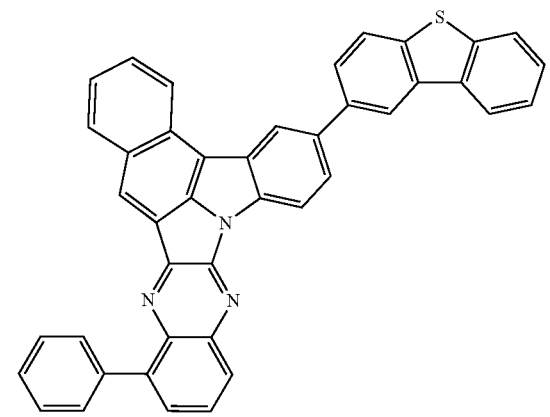
A-261
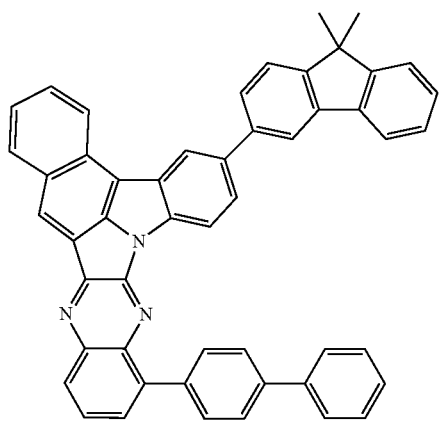
A-262
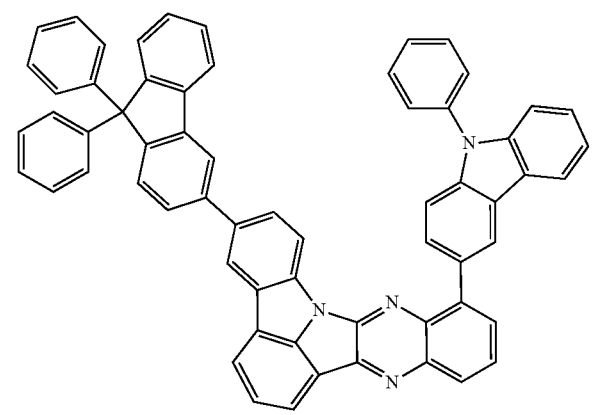
A-263
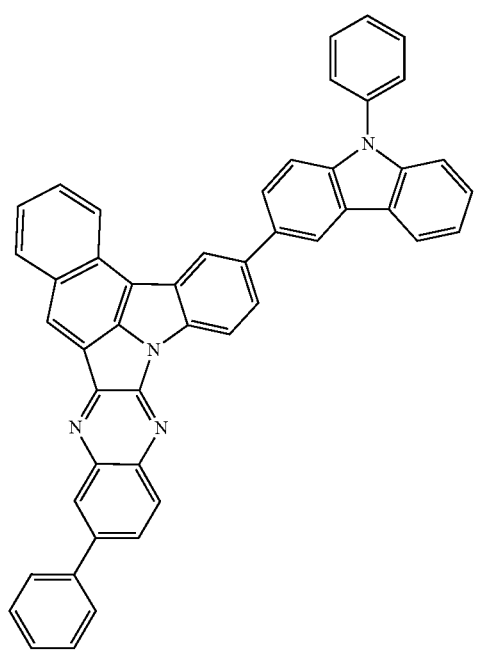
A-264
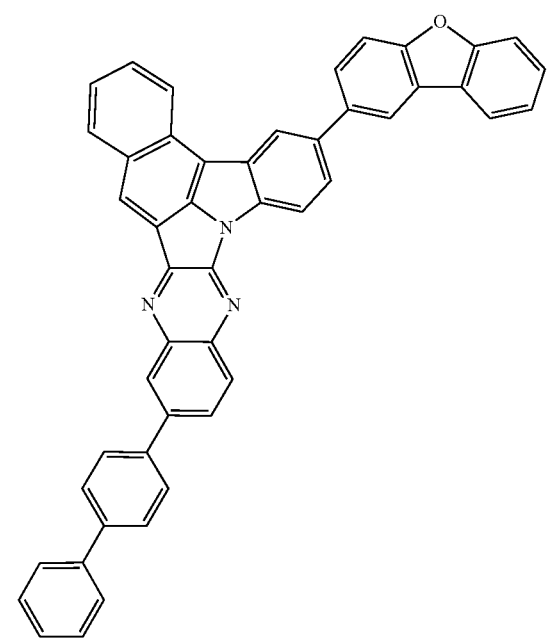

-continued
A-265
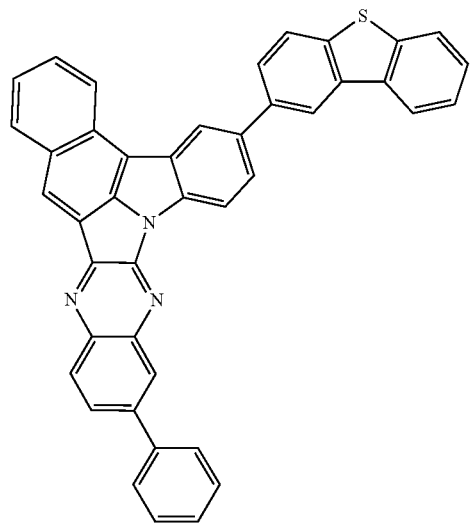
A-266
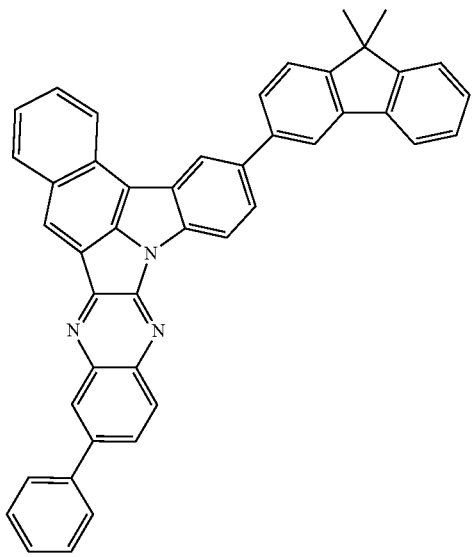
A-267
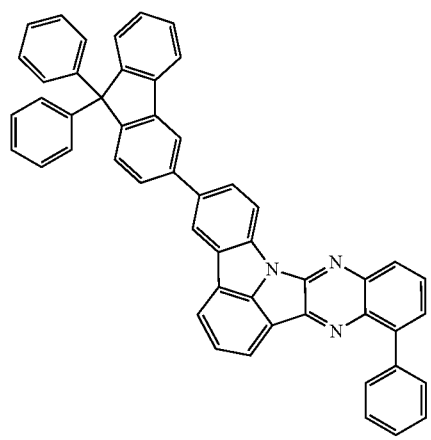
A-268
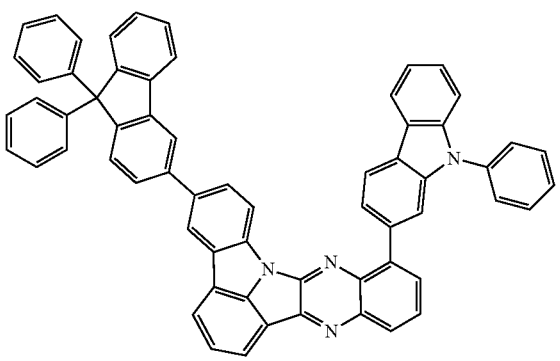
A-269
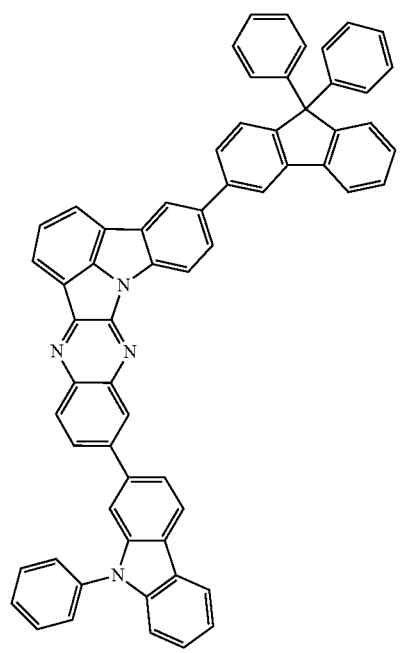
A-270
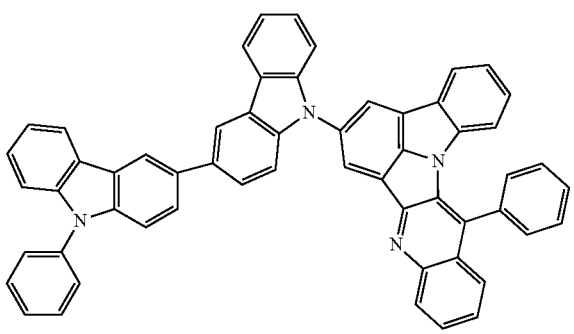

-continued
A-271
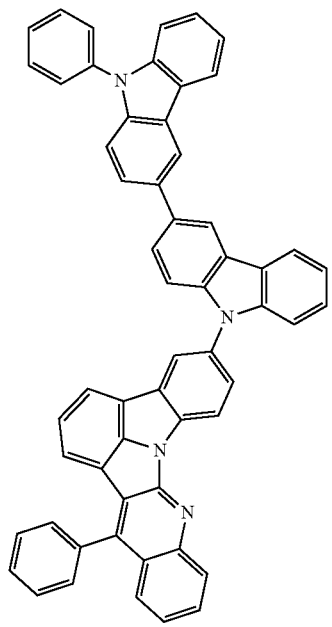
A-272
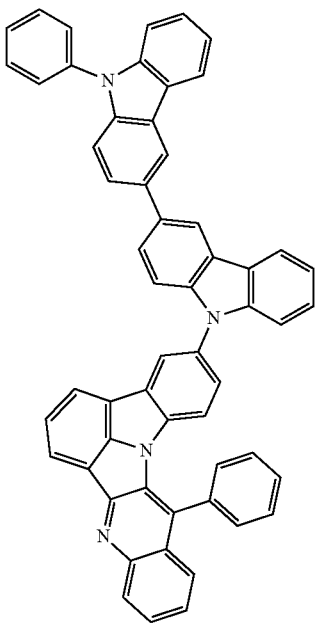
A-273
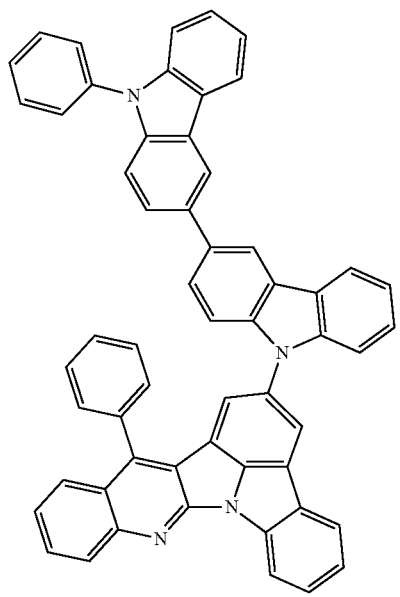
A-274
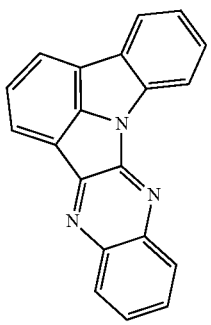
A-275
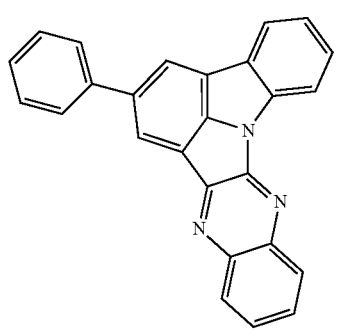
A-276
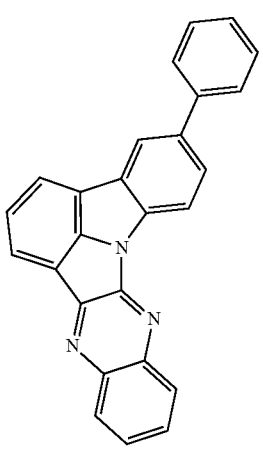

-continued
A-277
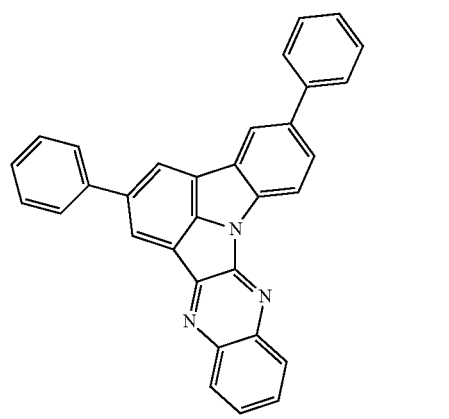
A-278
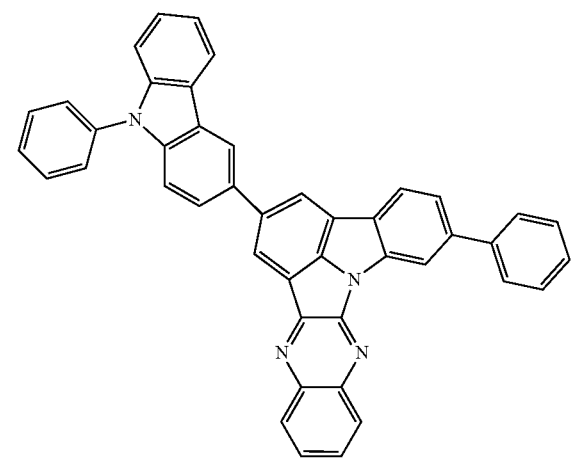
A-279
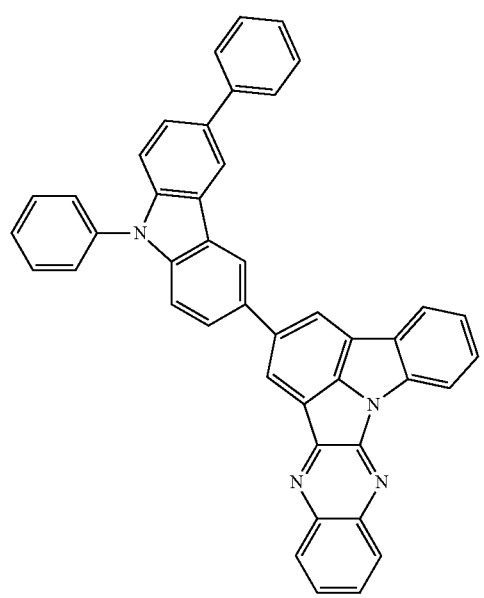
A-280
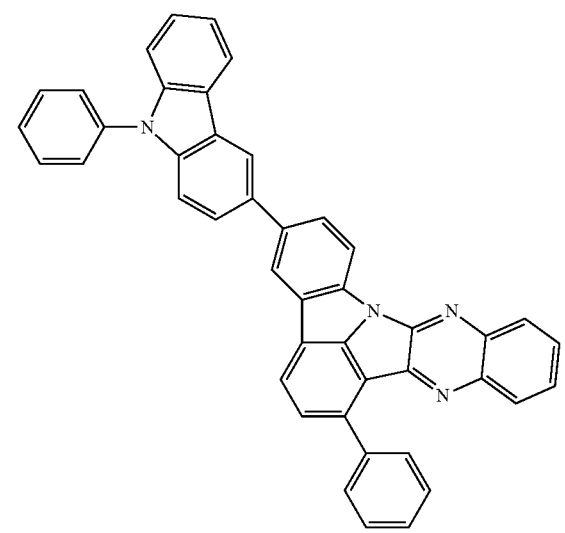
A-281
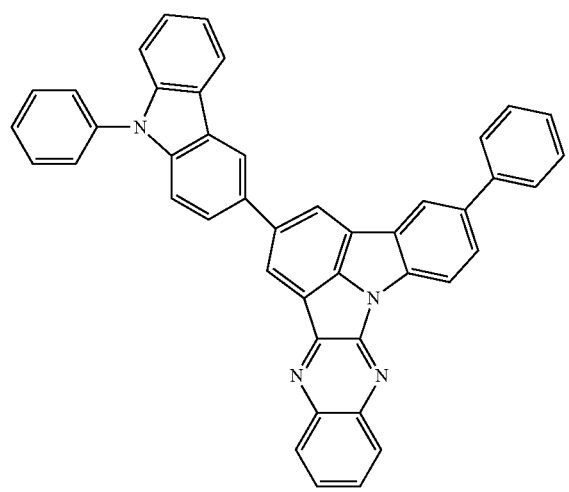
A-282

-continued
A-283
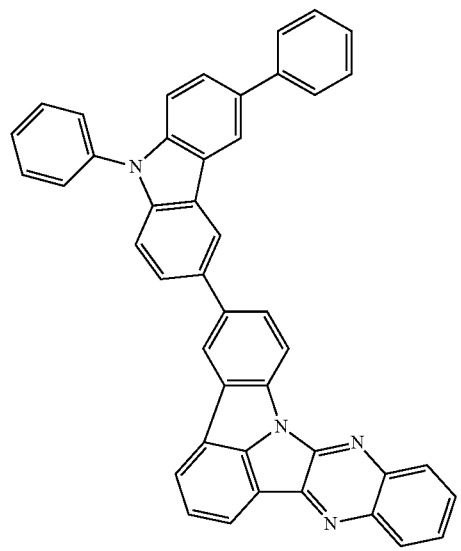
A-284
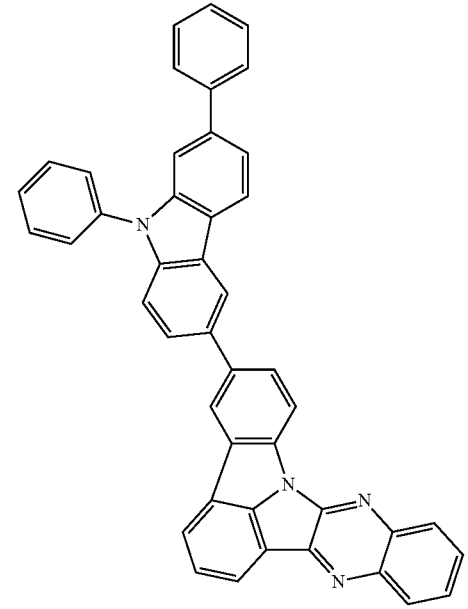
A-285
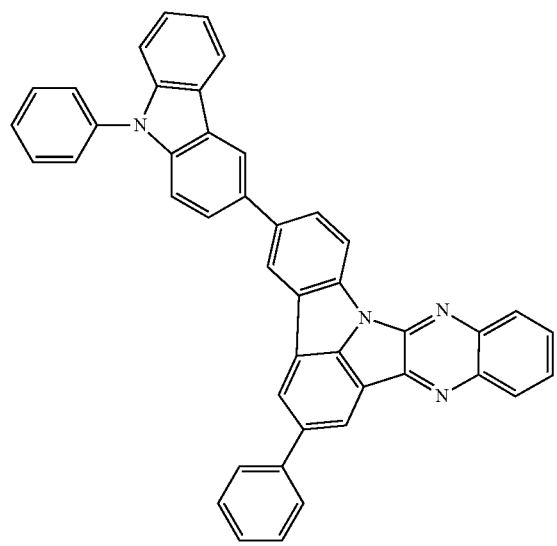
A-286
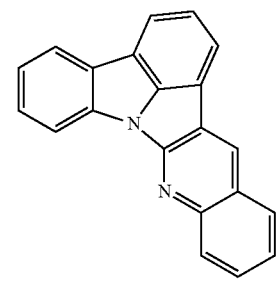
A-287
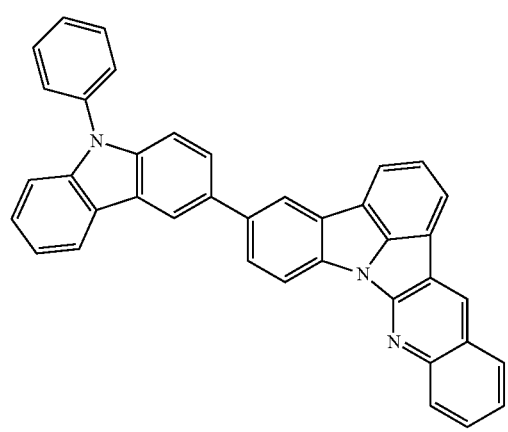
A-288

A-289
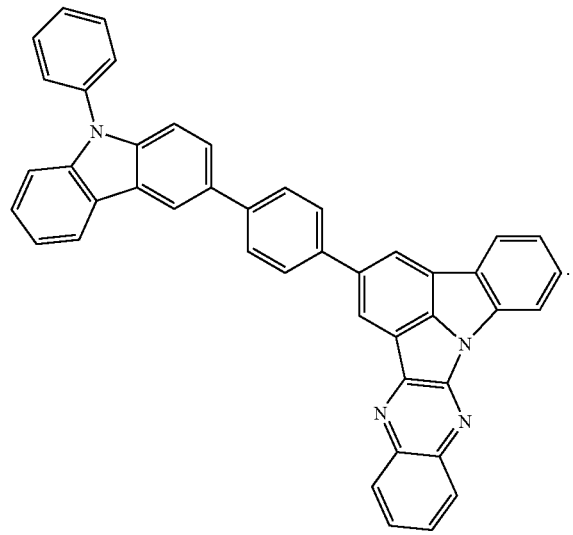
8. An organic electroluminescent device comprising the organic electroluminescent compound according to claim 1.
* * * * *